United States Patent
Whitfill

(10) Patent No.: US 12,208,124 B2
(45) Date of Patent: Jan. 28, 2025

(54) METHODS AND COMPOSITIONS FOR TREATING INFLAMMATORY SKIN DISEASE WITH RECOMBINANT MICROORGANISMS

(71) Applicant: Azitra Inc, Farmington, CT (US)

(72) Inventor: Travis Michael Whitfill, Dallas, TX (US)

(73) Assignee: AZITRA INC., Farmington, CT (US)

( * ) Notice: Subject to any disclaimer, the term of this patent is extended or adjusted under 35 U.S.C. 154(b) by 0 days.

(21) Appl. No.: 16/121,903

(22) Filed: Sep. 5, 2018

(65) Prior Publication Data

US 2019/0298780 A1 Oct. 3, 2019

Related U.S. Application Data

(60) Provisional application No. 62/685,687, filed on Jun. 15, 2018, provisional application No. 62/554,271, filed on Sep. 5, 2017.

(51) Int. Cl.
| | |
|---|---|
| *A61K 39/085* | (2006.01) |
| *A61K 35/74* | (2015.01) |
| *A61K 38/17* | (2006.01) |
| *A61P 17/00* | (2006.01) |
| *C07K 14/71* | (2006.01) |

(52) U.S. Cl.
CPC .......... *A61K 35/74* (2013.01); *A61K 38/179* (2013.01); *A61K 39/085* (2013.01); *A61P 17/00* (2018.01); *C07K 14/71* (2013.01); *C07K 2319/10* (2013.01)

(58) Field of Classification Search
None
See application file for complete search history.

(56) References Cited

U.S. PATENT DOCUMENTS

| | | | |
|---|---|---|---|
| 10,702,558 B2 * | 7/2020 | Munivar | A61K 9/0014 |
| 2011/0236325 A1 | 9/2011 | Mitchell et al. | |
| 2013/0018000 A1 * | 1/2013 | Stout | A61P 29/00 |
| | | | 536/23.4 |
| 2016/0199513 A1 | 7/2016 | Bancel et al. | |
| 2016/0220701 A1 | 8/2016 | March et al. | |
| 2017/0051260 A1 * | 2/2017 | Bermudes | A61K 35/74 |

FOREIGN PATENT DOCUMENTS

| | | |
|---|---|---|
| CN | 106062000 A | 10/2016 |
| JP | 2017-518370 A | 7/2017 |
| WO | 2015/117021 A1 | 8/2015 |
| WO | WO 2015184134 * | 12/2015 |
| WO | 2017/136652 A1 | 8/2017 |

OTHER PUBLICATIONS

Abstract of WO 2009112301 A1, one page, 2009.*
Boguniewicz et al., Atopic dermatitis: a disease of altered skin barrier and immune dysregulation. Immunol Rev. Jul. 2011;242(1):233-46.
Ma et al., Cell-penetrating peptides mediated protein cross-membrane delivery and its use in bacterial vector vaccine. Fish Shellfish Immunol. Jul. 2014;39(1):8-16.
International Search Report and Written Opinion for Application No. PCT/US2018/049477, dated Jan. 16, 2019, 10 pages.
NCBI Accession No. NP_002007, filaggrin [*Homo sapiens*]. 6 pages, Aug. 14, 2017.

* cited by examiner

*Primary Examiner* — S. Devi
(74) *Attorney, Agent, or Firm* — McCarter & English LLP; Jonathan M. Sparks

(57) ABSTRACT

The present invention provides isolated plasmids, recombinant microorganisms, kits, and methods for the treatment of inflammatory skin disease.

6 Claims, 24 Drawing Sheets

Specification includes a Sequence Listing.

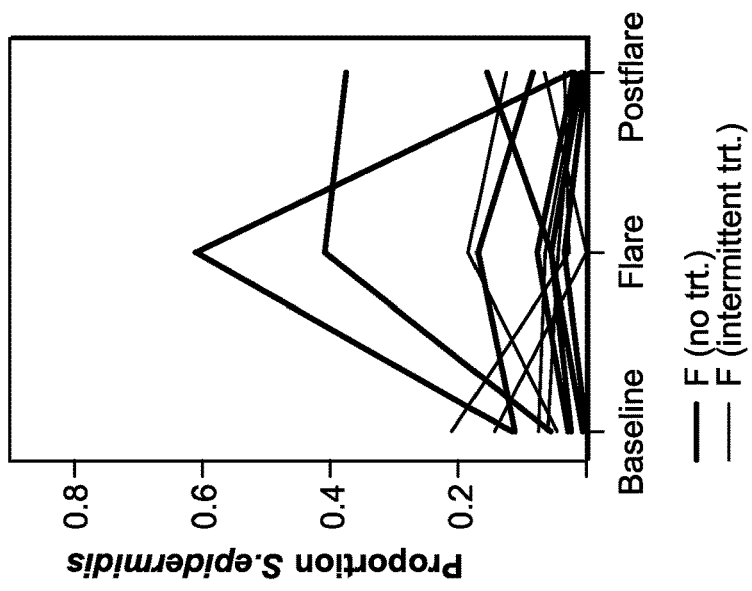
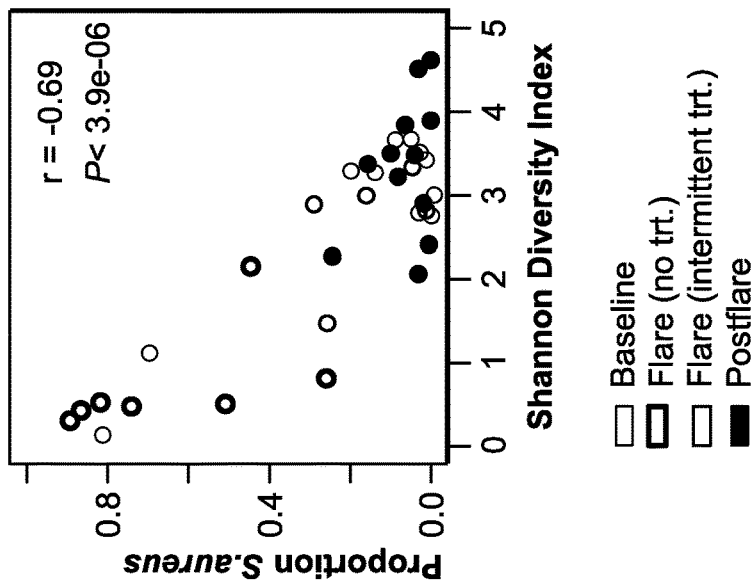
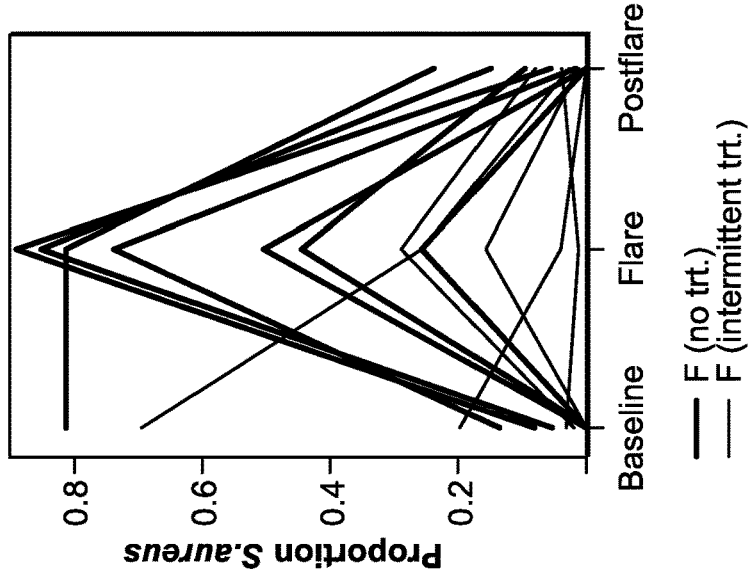

Relationship between staphylococcal species and AD. (A) Longitudinal trend of mean proportion of *S. aureus* in AD in antecubital and popliteal creases (AcPc, n=12) grouped by no-treatment (trt) and intermittent-trt flares. (B) Proportion of *S. aureus* and Shannon diversity index in AcPc. Partial correlation (adjusting for disease state, AcPc). (C) Longitudinal trend of mean proportion of *S. epidermidis* in AcPc.

(D) Correlation of proportion of *S. aureus* versus objective SCORAD for each site (AcPc, Volar forearm [Vf], Nares [N]). Partial correlation (adjusting for disease state.)

(E) Longitudinal Shannon diversity trend in AD grouped by no-treatment (trt) and intermittent-trt flares ($n = 12$, Ac). (F) AD microbiome progression hypothesis. (*) Proposed relationship among shifts in skin microbial diversity, the proportion of *Staphylococcus*, and disease severity.

Figure. Features of a novel, SE-based protein delivery system. (A) Construct design comprised of a promoter, RBS, export signal (B) Characterization of a selection of promoters for tunable control of protein expression (GFP used a reporter). (C) Characterization of export signals for protein export out of SE (GFP used as reporter). (D) Western blots of human filaggrin production from SE, mouse filaggrin production from SE, and whole mouse skin. Anti-mouse filaggrin antibodies were used.

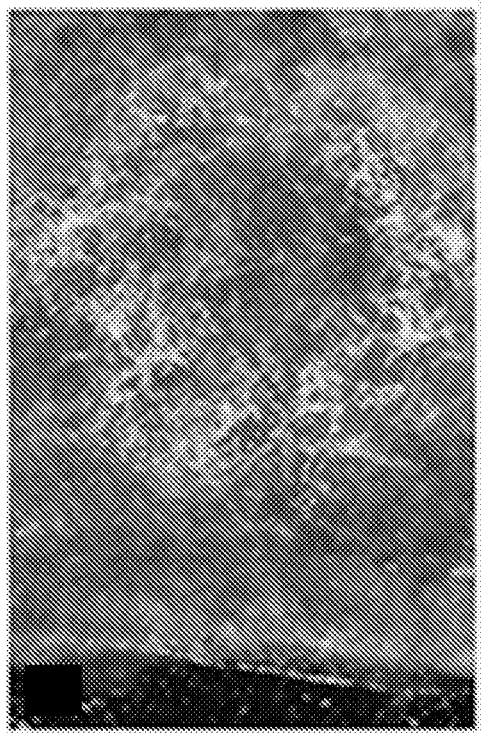
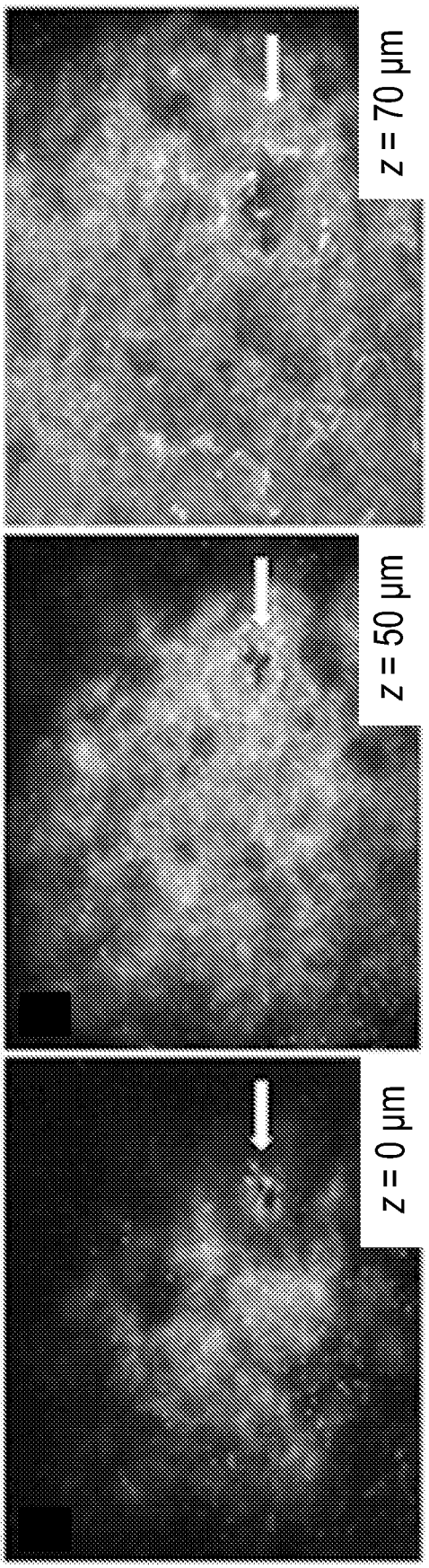
Figure. Characterization of GFP-producing SE in RHE. (A) Fluorescence and light wavelength overlays of RHE at ~25μm at 2 hours past application of SE-GFP. (B-D) Fluorescence and light wavelength overlays of RHE two hours of after dermaroller application then topical SE-GFP application. Depths taken at 0 μm (B), 50 μm (C), and 70 μm (D).
FIG. 3A
FIG. 3B  z = 0 μm
FIG. 3C  z = 50 μm
FIG. 3D  z = 70 μm

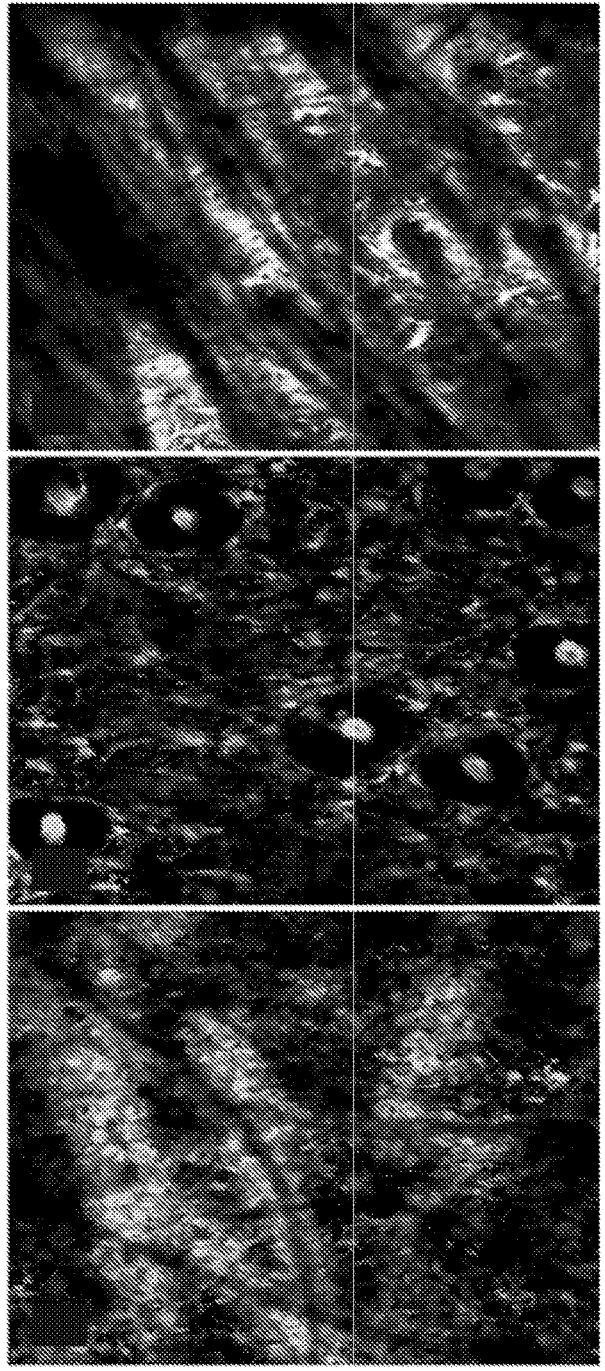
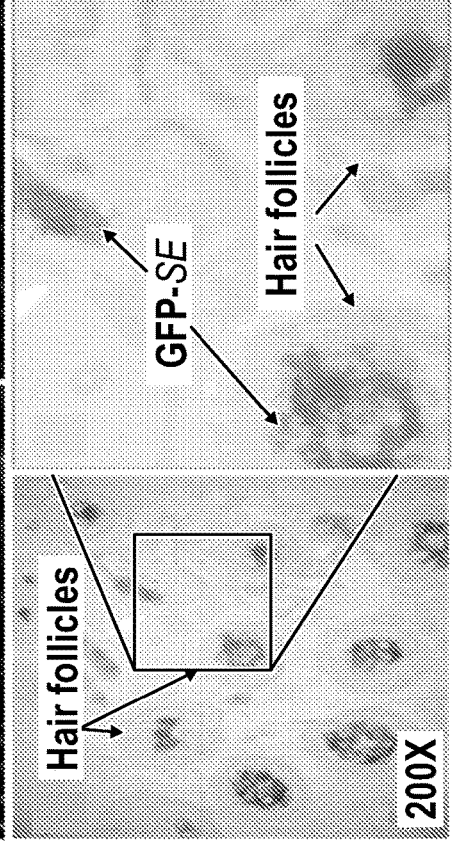
Figure. Characterization of SE-GFP colonization in mice. (A-C) In vivo two-photon microscopy of mouse skin three days following treatment of GFP-expressing S. epidermidis (green). 25 μm (A) and 50 μm (B) depth of unshaved mouse ear skin, and (C) 80 mμ depth on shaved dorsal skin. (D) Light microscopy of dorsal skin of mice following SE-GFP application.

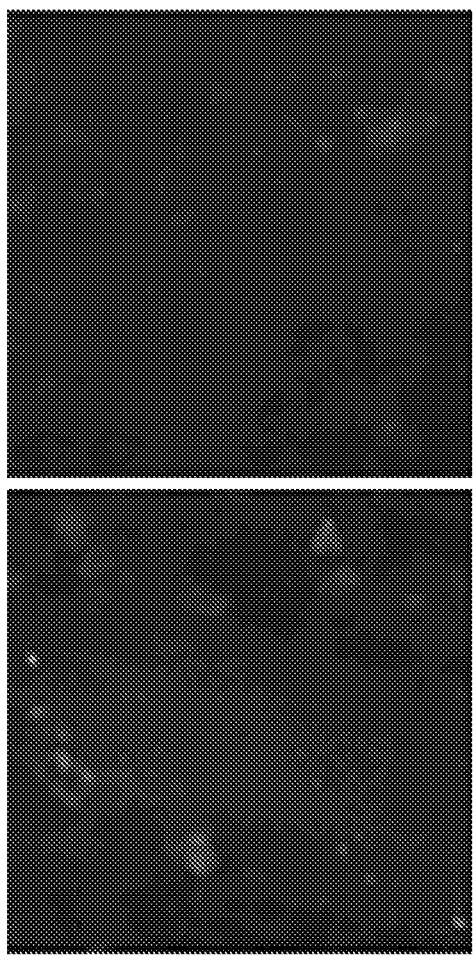

GFP

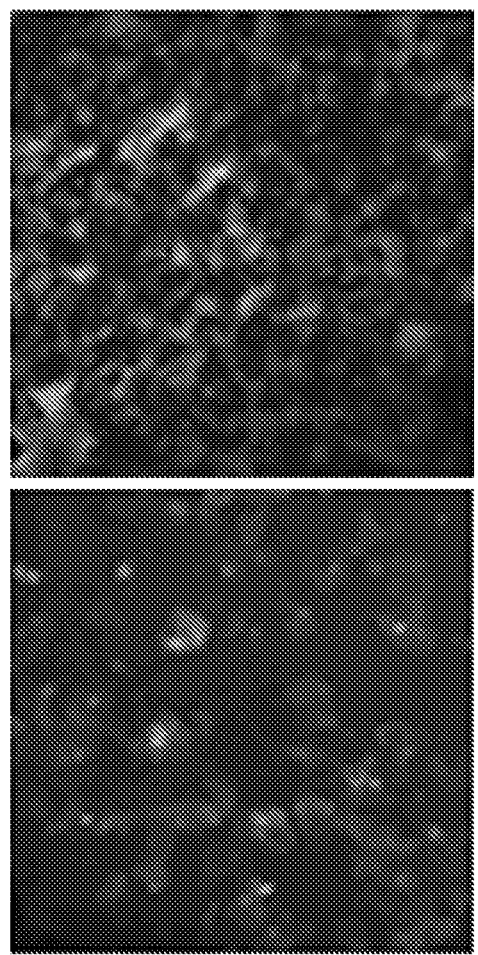

GFP + RMR

Figure. Characterization of protein with and without the RMR signal using 50 μg GFP as a reporter in RHE. (A-D) Two-photon images of topically applied GFP with (C,D) or without (A,B) the RMR signal at 30 minutes (A, C, E, G) or 60 minutes (B, D, F, H). Images are compiled Z-stacks projected onto a 2D plane. (E-H) 3D surface analysis to examine depth of protein penetration into the RHE. (I-N) Confocal images of GFP (K,N), GFP+RMR (J, M), or Vehicle (I, L) using light (L-N) or fluorescent (I-K) wavelengths.

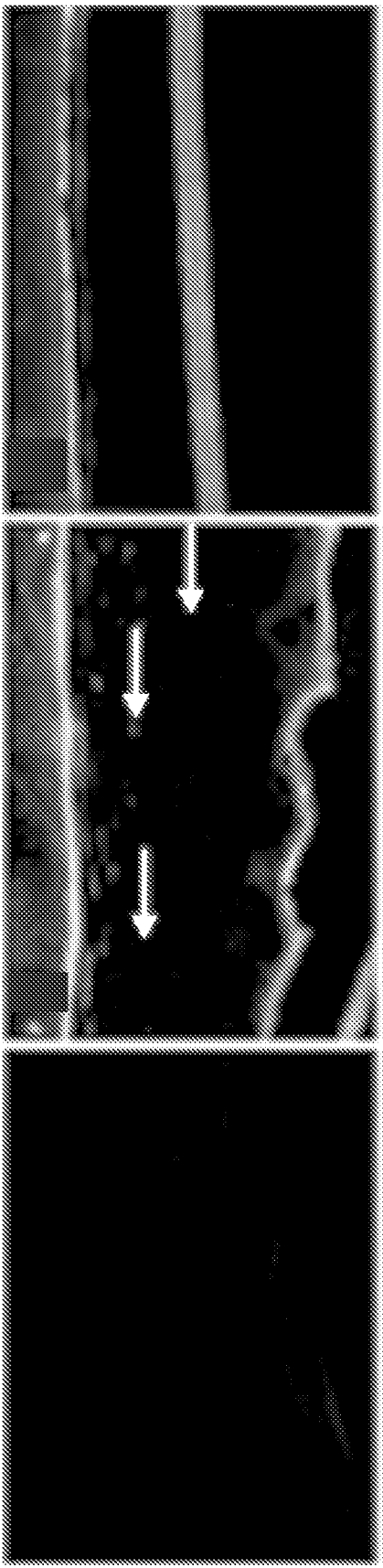

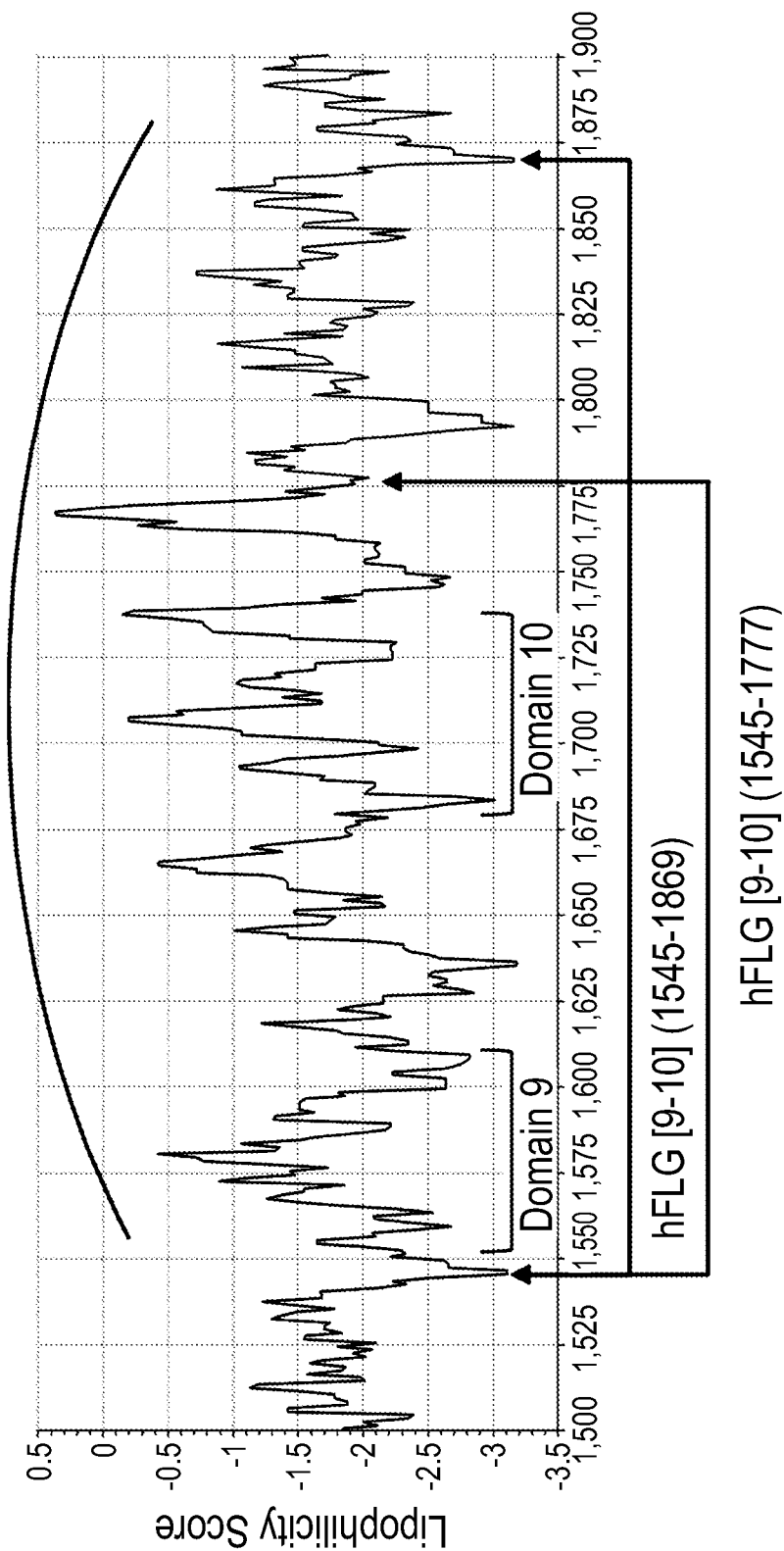

FIG. 13A

```
hFLG[3-4]    SLYQVSTHEQPDSAHGRTGTSTGGRQGSHHEQARDSSRHSASQEGQDTIRGHPGSSRGGR
hFLG[5-6]    FLYQVSTHKQSESSHGWTGPSTGVRQGSHHEQARDNSRHSASQDGQDTIRGHPGSSRRGR
hFLG[7-8]    FIYQVSTHEQSESAHGRTRTSTGRRQGSHHEQARDSSRHSASQDGQDTIRAHPGSRRGGR
hFLG[9-10]   FLYQVSSHEQSESTHGQTAPSTGGRQGSRHEQARNSSRHSASQDGQDTIRGHPGSSRGGR
hFLG[11-12]  FLYQVSTHEQSESAHGRTGPSTGGRQGSRHEQARDSSRHSASQEGQDTIRGHPGSSRGGR
hFLG[13-14]  FLYQVSTHEQSESTHGQSAPSTGGRQRSRHEQARDSSRHSASQEGQDTIRGHPGSSRGGR
hFLG[15-16]  FLYQVSTHEQSESTHGQSAPSTGGRQGSHYDQAQDSSRHKQARDSSRHSTSQEGQDTIHGHPGSSRGGR
hFLG[17-18]  FLYQVSTHEQSESAHGRTGTSTGGRQGSRHEQAQDSSRHSASQDGQDTIRGHPGSSRGGR
hFLG[19-20]  FLYQVSTHEQSESSHGWTGPSTRGRQGSRHEQAQDSSRHSASQYGQDTIRGHPGPSRGGR
hFLG[21-22]  FLYQVSTHEQSESSHGWTGPSTRGRQGSRHEQARDSSRHSASQEGQDTIRGHPGSSRRGR
             * ***:*** :*:  * *  ***:** :*** **:*:****:**  *** :* ***  *
             .                                                            .

hFLG[3-4]    QGSHHEQSVNRSGHSGHSGHSGHHSHHSHTTSQGRSDASHGQSGSRSASRQTRNEEQSGDGTRHSGSR
hFLG[5-6]    QGSHHEQSVDRSGHSGHSGHSGHHSHTTSQGRSDASRGQSGSRSASRTTRNEEQSRDGSRHSGSR
hFLG[7-8]    QGSHHEQSVDRSGHSGHSGHSGHHSHHSHTTSQGRSDASHGQSGSRSASRQTRKDKQSGDGSRHSGSR
hFLG[9-10]   QGSYHEQSVDRSGHSGHSGHSGYHHSHHSHTTPQGRSDASHGQSGPRSASRQTRNEEQSGDGSRHSGSR
hFLG[11-12]  QGSYHEQSVDRSGHSGHSGHSGHHSHHSHTTSQERSDVSRGQSGSRSVSRQTRNEKQSGDGSRHSGSR
hFLG[13-14]  QGSHQEQSVDRSGHSGHSGHSGHHSHHSHTTSQGRSDASRGQSGSRSASRKTYDKEQSGDGSRHSGSH
hFLG[15-16]  QGSHYEQLVDRSGHSGHSGHSGHHSHHSHTTSQGRSDASRGQSGSHSGSRSASRQTRNDEQSGDGSRHSGSR
hFLG[17-18]  QGYHHEHSVDSSGHSGHSGHSGHHSHHSHTTSQGRSDASRGQSGSRSASRTTRNEEQSGDGSRHSVSR
hFLG[19-20]  QGSHYEQSVDRSGHSGHSGHSGHHSHHSHTTSQGRSDASRGQSGSRSASRQTRNDEQSSRHSGSH
hFLG[21-22]  QGSHYEQSVDRSGHSGHSGHSGHHSHHSHTTSQGRSDASRGQSGSRSASRQTRNDEQSGDGSRHSWSH
             ** : *.*  ***** ********  *** ***:***:*****:*:.**::* :*****   
```

FIG. 13B

| | | |
|---|---|---|
| hFLG[3-4]   | HHEASSQADSSRHSQVGQGQSSGPRTSRNQGSSVSQDSDSQGHSEDSERWSGSASRNHHG |
| hFLG[5-6]   | HHEASSHADISRHSQAGQGQSEGSRTSRRQGSSVSQDSDSEGHSEDSERWSGSASRNHRG |
| hFLG[7-8]   | HHEAASWADSSRHSQVGQEQSSGSRTSRHQGSSVSQDSDSERHSDDSERLSGSASRNHRG |
| hFLG[9-10]  | HHEPSTRAGSSRHSQVGQGQESAGSKTSRRQGSSVSQDRDSEGHSEDSERRSESASRNHYG |
| hFLG[11-12] | HHEASSRADSSRHSQVGQGQSSGPRTSRNQGSSVSQDSDSQGHSEDSERWSGSASRNHLG |
| hFLG[13-14] | HHEASSWADSSRHSLVGQGQSSGPRTSRPRGSSVSQDSDSEGHSEDSERRSGSASRNHHG |
| hFLG[15-16] | HHEASSRADSSGHSQVGQGQSEGSRRSRRQGSSFSQDSDSQGHSEDSERWSGSASRNHHG |
| hFLG[17-18] | HHEASTHADISRHSQAVQGQSEGSRRSRRQGSSVSQDSDSEGHSEDSERWSGSASRNHHG |
| hFLG[19-20] | HHEASTHADISRHSQAVQGQSEGSRRSRRQGSSVSQDSDSQGHSEDSERWSGSASRNHRG |
| hFLG[21-22] | HHEASTQADSSRHSQSGQGQSAGPRTSRNQGSSVSQDSDSQGHSEDSERWSGSASRNHRG |
|             | **:*: :. * *..* *::*  *.* *  .:* *  *.**.**: * |

| | | |
|---|---|---|
| hFLG[3-4]   | SAQEQSRDGSRHPRSHHEDRAGHGHSADSSRKSGTRHTQNSSSSGQAASSHEQARSSAGER |
| hFLG[5-6]   | SAQEQSRDGSRHPRSHHEDRAGHGHSADSSRQSGTPHAETSSGGQAASSHEQARSSPGER |
| hFLG[7-8]   | SSREQSRDGSRHPGFHQEDRASHGHSADSSRQSGTHHTESSSHGQAVSSHEQARSSPGER |
| hFLG[9-10]  | SAREQSRHGSRHPRSHQEDRASHGHSAESSRQSGTRHAETSSGGQAASSQEQARSSPGER |
| hFLG[11-12] | SAWEQSRHGSRHPGSHHEDRAGHGHSADSSRQSGTRHTESSSRGQAASSHEQARSSAGER |
| hFLG[13-14] | SAQEQSRDGSRHPRSHHEDRAGHGHSADSSRQSGTHHAENSSGGQAASSHEQARSSAGER |
| hFLG[15-16] | SAQEQLRDGSRHPRSHHEDRAGHGHSADSSRQSGTRHTQISSGGQAASSHEQARSSPGER |
| hFLG[17-18] | SAQEQLRDGSRHPRSHHEDRAGHGHSAESSRQSGTRHTQISSGGQAASSHEQARSSPGER |
| hFLG[19-20] | SVQEQSRHGSRHPRSHHEDRAGHGHSADRSRQSGTRHAETSSGGQAASSHEQARSSPGER |
| hFLG[21-22] | SAQEQSRDGSRHPTSHHEDRAGHGHSAESSRQSGTHHAENSSGGQAASSHEQARSSAGER |
|             | * ** *.****  *:*:*::.*.** *   :..*.*.* |

FIG. 13C

```
hFLG[3-4]    HGSRHQLQSADSSRHSGTGHGQASSAVRDSGHRGSSSGSQATDSEGHSEDSDTQSVSGHGQ
hFLG[5-6]    HGSRHQ-QSADSSRHSGIPRRQASSAVRDSGHWGSSGSQASDSEGHSEESDTQSVSGHGQ
hFLG[7-8]    HGSRHQ-QSADSSRHSGIGHRQASSAVRDSGHRGSSGSQVTNSEGHSEDSDTQSVSAHGQ
hFLG[9-10]   HGSRHQ-QSADSSTDSGTGRRQDSSVVGDSGNRGSSGSQASDSEGHSEESDTQSVSAHGQ
hFLG[11-12]  HGSHHQLQSADSSRHSGIGHGQASSAVRDSGHRGYSGSSGSQASDSEGHSEDSDTQSVAQGK
hFLG[13-14]  HGSHHQ-QSADSSRHSGIGHGQASSAVRDSGHRGSSSGSQASDSEGHSEDSDTQSVSAHGQ
hFLG[15-16]  HGSHHQ-QSADSSRHSGIGHGQASSAVRDSGHRGYSGSSGSQASDNEGHSEDSDTQSVSAHGQ
hFLG[17-18]  HGSRHQ-QSADSSRHSGIGHGQASSAVRDSGHRGYSGSSGSQASDNEGHSEDSDTQSVSAHGQ
hFLG[19-20]  HGSRHQ-QSADSSRHSGIPRGQASSAVRDSRHWGSSGSQASDSEGHSEESDTQSVSGHGQ
hFLG[21-22]  HGSHHQ-QSADSSRHSGIGHGQASSAVRDSGHRGSSSGSQASDSEGHSEDSDTQSVSGHGQ
             *** *  *******  *    * *   *    *   *  * .*** hFLG[3-4]    AGHHQQSHQESARDRSGERSRRSGSFLY
hFLG[5-6]    DGPHQQSHQESARDWSGGRSGRSGSFIY
hFLG[7-8]    AGPHQQSHKESARGQSGESSGRSRSFLY
hFLG[9-10]   AGPHQQSHQESTRGQSGERSGRSGSFLY
hFLG[11-12]  AGPHQQSHKESARGQSGESSGRSGSFLY
hFLG[13-14]  AGPHQQSHQESTRGRSAGRSGRSGSFLY
hFLG[15-16]  AGSHQQSHQESARGRSGETSGHSGSFLY
hFLG[17-18]  AGSHQQSHQESARGRSGETSGHSGSFLY
hFLG[19-20]  AGPHQQSHQESARDRSGGRSGRSGSFLY
hFLG[21-22]  AGPHQQSHQESTRGRSAGRSGRSGSFLY
             * .*:**::*: * * . *  *.*:*:*
```

METHODS AND COMPOSITIONS FOR TREATING INFLAMMATORY SKIN DISEASE WITH RECOMBINANT MICROORGANISMS

RELATED APPLICATIONS

This application claims priority to U.S. Provisional Application 62/554,271 filed on Sep. 5, 2017, and U.S. Provisional Application 62/685,687 filed on Jun. 15, 2018, the entire contents of both of which are incorporated by reference in their entireties herein.

The instant application contains a Sequence Listing which has been submitted electronically in ASCII format and is hereby incorporated by reference in its entirety. Said ASCII copy, created on Oct. 26, 2018 is named 129062-001200_SL.txt and is 309,618 bytes in size.

BACKGROUND OF THE INVENTION

Atopic dermatitis (AD), or eczema, is a chronic, pruritic, inflammatory skin disease that affects 5-20% of children worldwide (Williams, H., et al. J Allergy Clin. Immunol. 1999; 103(1 Pt 1):125-138), and is also prevalent in many adults. The prevalence of atopic dermatitis is increasing, with some form of atopic dermatitis affecting 11% of the U.S. population (Shaw, T. E., et al. J Invest Dermatol. 2011; 131(1):67-73), or about 35 million people, with direct costs of $5 billion in the U.S. alone. The primary features of the disease are dry, scaly, itchy skin. Despite the increasing prevalence of atopic dermatitis worldwide and its significant disease burden, few targeted and effective treatment options are available. Notably, the most commonly used treatment methods include broad, non-specific approaches, including, but not limited to, skin hydration, bleach baths, UV treatment, dietary interventions, antimicrobials, antihistamines, systemic immunomodulatory agents, and the administration of topical corticosteroids (Hoare, C., et al. Health Technol. Assess. 2000; 4(37):1-191). However, despite these numerous options, few provide long-lasting resolution of symptoms, and atopic dermatitis recurrence is common in most individuals. Further, a 2013 National Health and Wellness Survey revealed a significant associated burden on atopic dermatitis patients, who, when compared with non-atopic dermatitis patients, reported higher levels of healthcare resources (healthcare provider/ER visits), lower health-related quality of life, and nearly twice as much lost work productivity. Moreover, atopic dermatitis patients had markedly higher prevalence of allergies (46% vs. 20%), asthma (22% vs. 8%), anxiety (43% vs. 21%), and depression (37% vs. 21%) (Whiteley, J., et al. Current Medical Research and Opinion. 2016:1-32). Accordingly, there is a large unmet need in view of the significant burden atopic dermatitis has on our healthcare system.

Recent research has elucidated the pathophysiology of atopic dermatitis and has revealed that a skin barrier defect is in many cases primarily responsible for the onset of atopic dermatitis, which results in both transepidermal water loss (TEWL or TWL) and increased antigen and pathogen exposure. Concurrently, atopic dermatitis is often characterized by dysbiosis (or a microbial imbalance, the severity of which is associated with disease severity; see Kong, H. H., et al. Genome research. 2012; 22(5):850-859; and FIG. 1), which is a notable feature of atopic dermatitis, and a lack of diversity of the skin microbiome, which is dominated by *Staphylococcus aureus* during atopic dermatitis flares and untreated skin. Finally, there is an activated inflammatory response, particularly driven by, inter alia, IL-4/IL-13, with a predominate T-helper type 2 profile ($T_H2$), existing in lesional and non-lesional skin, indicating a systemic switch to a $T_H2$-weighted profile (Sidbury, R., et al. Current allergy and asthma reports. 2017; 17(7):42). An ideal atopic dermatitis treatment would thus address all of these underlying causes simultaneously, i.e. skin barrier deficiency, dysbiosis, and an activated cutaneous immune response. The present invention addresses these causes.

Engineered probiotics are a novel approach based on leveraging the skin microbiome for therapeutic purposes. Notably, an engineered probiotic has important advantages over other methods of drug delivery, as it will establish residence on the patient's skin and continuously and stably deliver therapeutic proteins in situ. Furthermore, certain strains of *Staphylococcus epidermidis* (SE) have demonstrated important beneficial immuno-modulatory and anti-pathogen effects in the skin, which are relevant to atopic dermatitis disease phenotype and severity. Moreover, the delivery of filaggrin, which is a structural protein derived from profilaggrin, further enhances the therapeutic approach due to filaggrin's role in the skin barrier and ability to reduce transepidermal water loss and improve skin hydration. The present invention has the surprising advantage of providing methods and compositions for treating skin diseases, e.g., atopic dermatitis, using a genetically engineered, recombinant strain of *Staphylococcus epidermidis* as a skin drug delivery system that secretes human filaggrin to address the pathophysiology of atopic dermatitis (e.g., AZT-01). Once applied to the skin, stable colonization of the skin and the subsequent secretion of filaggrin in situ can resolve the disease. The benefits of this invention include its safety as a non-steroidal treatment option, its efficacy due to the invention's combination of benefits from the secretion of filaggrin along with the benefits of the topical application of *Staphylococcus epidermidis*, and its ability to be therapeutically effective at even a low frequency of application (no more than once a day).

The present invention therefore addresses the long-felt need for an effective treatment for inflammatory skin diseases, such as atopic dermatitis. The present invention is also one of the first reported demonstrations of commensal skin bacteria that can secrete therapeutic proteins to treat skin disease.

SUMMARY OF THE INVENTION

The invention refers to methods and compositions for treating inflammatory skin diseases comprising, as an active principle, an engineered microorganism capable of expressing therapeutically relevant recombinant fusion polypeptides (i.e. proteins, peptides, or amino acids).

The present invention features, in a first aspect, a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide. In a related embodiment, the recombinant microorganism further comprising a third coding sequence comprising a gene capable of expressing an export signal. In yet another embodiment, the expression of the first coding sequence, second coding sequence and third coding sequence is under the control of a promoter. In other embodiments, the arrangement of the first coding sequence, second coding sequence and third coding sequences are in-frame. In yet another related embodiment, the first coding sequence, second coding sequence and third coding sequence are operably linked to a promoter. In one embodiment, the recombinant microorganism is bacteria, or a combination of bacteria. In another embodiment, the polypeptide is filaggrin, or a variant thereof. In other embodiments, the microorganism is selected from the group consisting of Bifidobacterium, Brevibacterium, Propionibacterium, Lactococcus, Streptococcus, Staphylococcus, Lactobacillus, Enterococcus, Pediococcus, Leuconostoc, or Oenococcus, or combinations thereof. In yet other embodiments, the recombinant microorganism is Staphylococcus epidermidis. In another embodiment, the microorganism secretes a filaggrin fusion protein. In one embodiment, the polypeptide comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 1. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 2. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 3. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 4. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 5. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 6. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 7. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 8. In one embodiment, the polypeptide has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 9.

The present invention features, in a further aspect, a method for producing a live biotherapeutics composition, the method comprising (a) transfecting a cell with (i) a first coding sequence comprising a nucleic acid sequence capable of expressing a therapeutic polypeptide, and (ii) a second coding sequence comprising a nucleic acid sequence capable of expressing a cell penetrating peptide; and (b) allowing the transfected cell to produce a therapeutic polypeptide fusion protein; and (c) obtaining the live biotherapeutic composition. In a related embodiment, the method further comprises (iii) transfecting the cell with a third coding sequence comprising a nucleic acid sequence capable of expressing an export signal. In another embodiment, the first coding sequence, second coding sequence and third coding sequences are arranged in a single plasmid. In yet another embodiment, the arrangement of the first coding sequence, second coding sequence and third coding sequences are operably linked to a promoter. In other embodiments, the cell is selected from the group consisting of wherein the microorganism is selected from the group consisting of Bifidobacterium, Brevibacterium, Propionibacterium, Lactococcus, Streptococcus, Staphylococcus, Lactobacillus, Enterococcus, Pediococcus, Leuconostoc, or Oenococcus, or combinations thereof. In yet another embodiment, the cell is Staphylococcus epidermidis. In other embodiments, the therapeutic polypeptide fusion protein is a filaggrin fusion protein, or a variant thereof.

The present invention features, in another aspect, a nucleic acid comprising a nucleic acid sequence encoding a polypeptide as set forth any one of the aspects or embodiments herein.

The present invention features, in a further aspect, a composition obtained by any one of the method disclosed or described herein. In a related embodiment, the composition comprises a pharmaceutically acceptable carrier, wherein the pharmaceutically acceptable carrier is selected from the group consisting of an aqueous solution, an emulsion, a cream, a lotion, a gel, or an ointment.

The present invention features, in a further aspect, a live biotherapeutic composition comprising a recombinant microorganism wherein the recombinant microorganism comprises (i) a first coding sequence comprising a nucleic acid sequence capable of expressing a therapeutic polypeptide; (ii) a second coding sequence comprising a nucleic acid sequence capable of expressing a cell penetrating peptide; (iii) a third coding sequence comprising a nucleic acid sequence capable of expressing an export signal; and (iiv) a promoter operably linked to the first coding sequence, the second coding sequence and the third coding sequence; wherein the first coding sequence, second coding sequence and first coding sequence is capable of expressing a filaggrin fusion product, or variant thereof. In a related embodiment, the recombinant microorganism is Staphylococcus epidermidis. In a further embodiment, the export signal exports the filaggrin fusion product, or variant thereof, out of the recombinant microorganism. In yet another embodiment, the cell penetrating peptide facilitates the entry of the filaggrin fusion product, or variant thereof, into a human keratinocyte. In another embodiment, the composition comprises a pharmaceutically acceptable carrier, wherein the pharmaceutically acceptable carrier is selected from the group consisting of an aqueous solution, an emulsion, a cream, a lotion, a gel, or an ointment.

The present invention features, in a further aspect, a kit comprising any one of the compositions disclosed or described herein and instructions for use.

The present invention features, in a further aspect, a method of treating a skin disease comprising administering to a subject in need thereof the composition of any one of the compositions disclosed or described herein. In another embodiment, the skin disease is atopic dermatitis.

BRIEF DESCRIPTION OF THE DRAWINGS

FIG. 1A-F depicts the relationship between staphylococcal species and atopic dermatitis. FIG. 1A shows longitudinal trend of mean proportion of S. aureus in atopic dermatitis in antecubital and popliteal creases (AcPC, n=12) grouped by no-treatment (trt) and intermittent-trt flares. FIG. 1B shows proportion of S. aureus and Shannon diversity index in AcPc. Partial correlation (adjusting for disease state, AcPc). FIG. 1C shows longitudinal trend of mean proportion of S. epidermidis in AcPc. FIG. 1D shows correlation of proportion of S. aureus versus objective SCORAD for each site (AcPc, Volar forearm [Vf], Nares [N]). Partial correlation (adjusting for disease state). FIG. 1E shows longitudinal Shannon diversity trend in atopic dermatitis grouped by no-treatment and intermittent-trt flares (n=12, Ac). FIG. 1F atopic dermatitis microbiome progression hypothesis. (*) Proposed relationship among shifts in skin microbial diversity, the proportion of *Staphylococcus*, and disease severity.

FIGS. 3A-3D depicts the characterization of GFP-producing *Staphylococcus epidermidis* in reconstituted human epidermis (RHE). FIG. 3A shows fluorescence and light wavelength overlays of RHE at ~25 μm at two hours past application of *Staphylococcus epidermidis*-GFP. FIG. 3B-3D shows fluorescence and light wavelength overlays of RHE two hours after dermaroller application then topical *Staphylococcus epidermidis*-GFP application. Depths taken at 0 μm FIG. 3B, 50 μm FIG. 3C, and 70 μm FIG. 3D.

FIGS. 4A-4E depicts the characterization of SE-GFP colonization in mice. FIG. 4A-4C shows in vivo two-photon microscopy of mouse skin three days following treatment of GFP-expressing *S. epidermidis*. FIG. 4A 25 μm; and FIG. 4B 50 μm depth of unshaved mouse ear skin, and FIG. 4C 80 μm depth on shaved dorsal skin. FIG. 4D Light microscopy of dorsal skin of mice following SE-GFP application. FIG. 4E Light microscopy of dorsal skin of mice following SE-GFP application.

FIGS. 5A-5K depicts the characterization of protein with and without the RMR signal using 50 μg GFP as a reporter in RHE. FIG. 5A-5D show two-photon images of topically applied GFP with (FIG. 5C, FIG. 5D) or without (FIG. 5A, FIG. 5B) the RMR signal at 30 minutes (FIG. 5A, FIG. 5C, FIG. 5E, FIG. 5G) or 60 minutes (FIG. 5B, FIG. 5D, FIG. 5F, FIG. 5H). Images are compiled Z-stacks projected onto a 2D plane. (FIG. 5E-FIG. 5H) 3D surface analysis to examine depth of protein penetration into the RHE. (FIG. 5I-FIG. 5N) Confocal images of GFP (FIG. 5K, FIG. N), GFP+RMR (FIG. 5J, FIG. 5M) or vehicle (FIG. 5I, FIG. 5L) using light (FIG. 5L-FIG. 5N) or fluorescent (FIG. 5I-FIG. 5K) wavelengths.

FIGS. 6A-6B discloses SEQ ID NOS 30-33, 33-35, 35-36, and 36-42, respectively, in order of appearance.

FIG. 12 is a graph that shows hydrophobicity score as a function of amino acid position from a point of low hydrophobicity to the next point of low hydrophobicity (indicated by arrows).

FIGS. 13A-13C shows an alignment of human filaggrin dimers hFLG[3-4] (SEQ ID NO: 43), hFLG[5-6] (SEQ ID NO: 44), hFLG[7-8] (SEQ ID NO: 45), hFLG[9-10] (SEQ ID NO: 46), hFLG[11-12] (SEQ ID NO: 47), hFLG[13-14] (SEQ ID NO: 48), hFLG[15-16] (SEQ ID NO: 49), hFLG [17-18] (SEQ ID NO: 50), hFLG[19-20] (SEQ ID NO: 51), hFLG[21-22] (SEQ ID NO: 52).

DETAILED DESCRIPTION OF THE INVENTION

I. Overview and Definitions

Figure 1D:
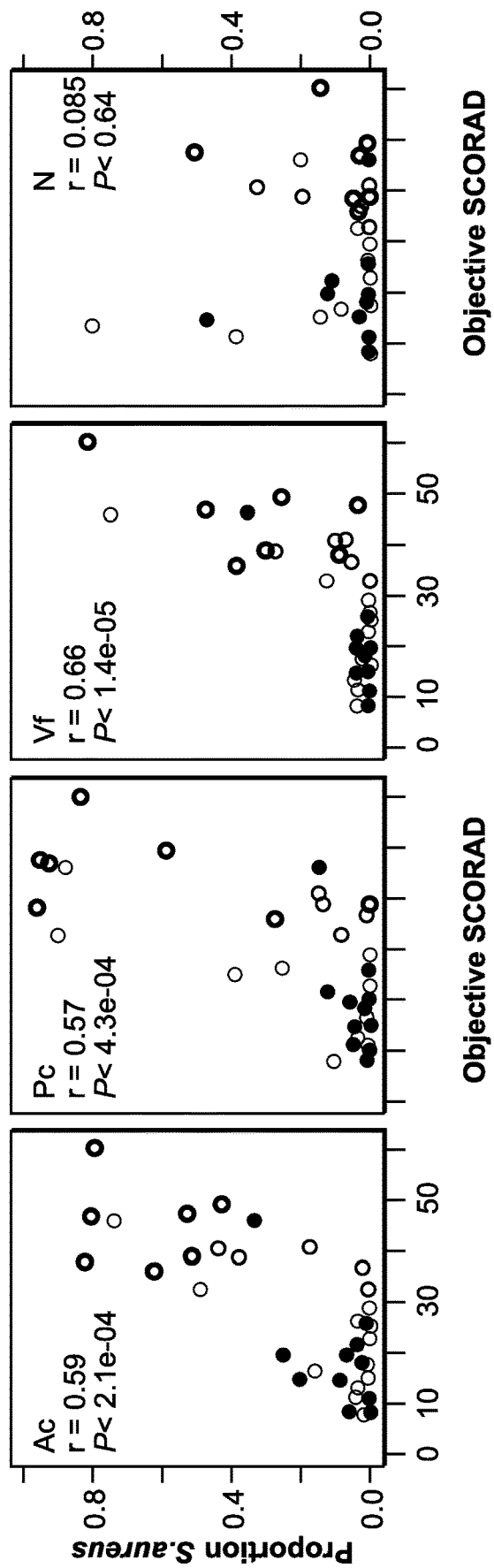
Figure 1E:
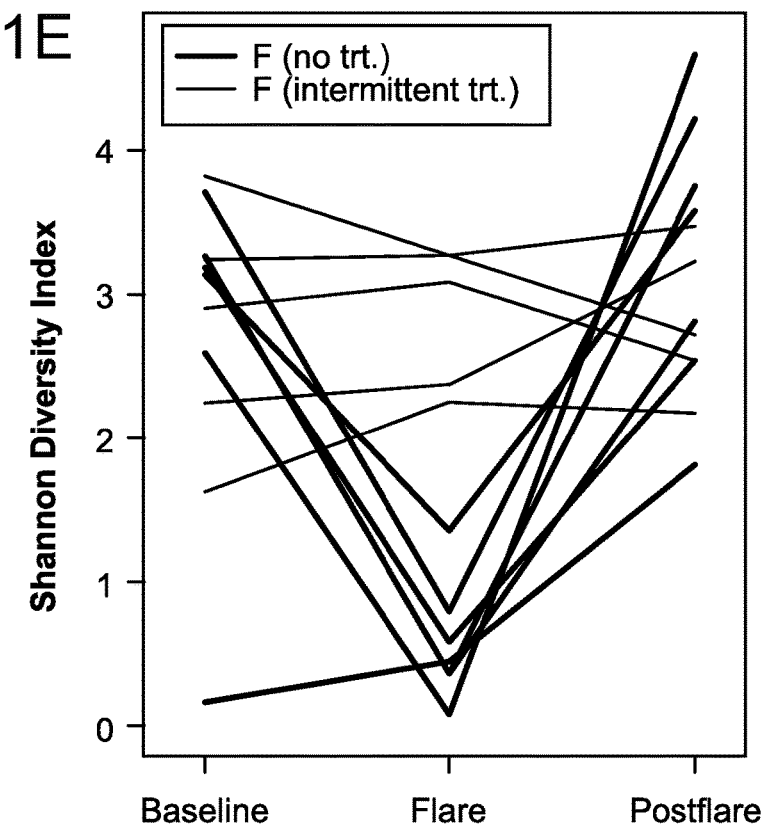
Figure 1F:
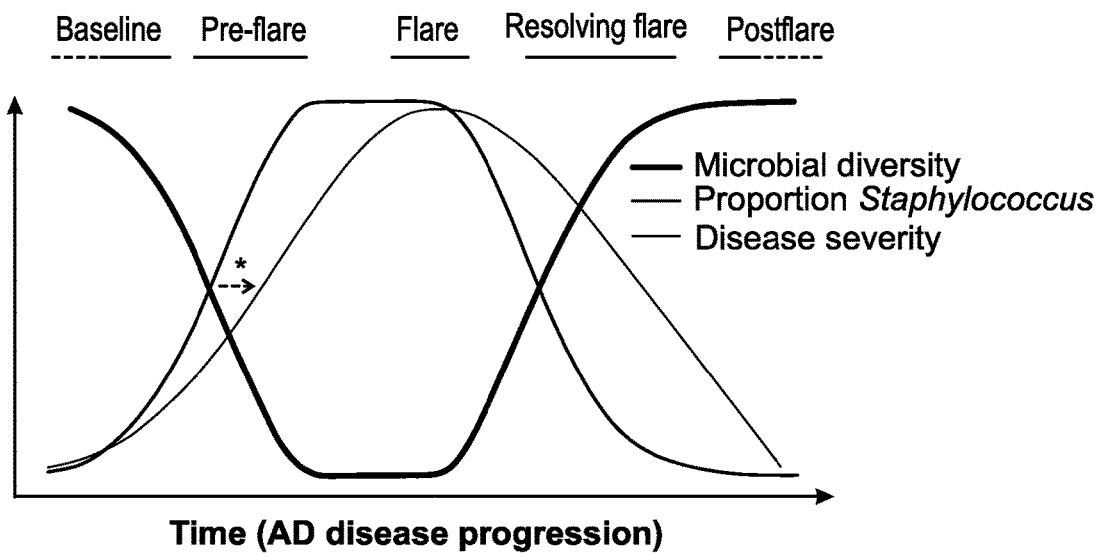
Figure 2A:
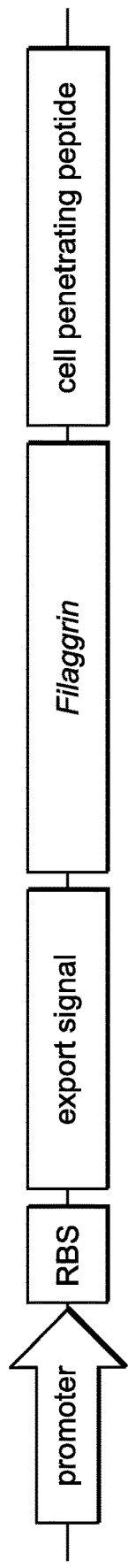
FIG. 2A depicts a schematic drawing of a *Staphylococcus epidermidis*-based protein delivery system, as described herein. The construct design comprises a promoter, a ribosome binding site (RBS), an export signal, a filaggrin expression sequence, and a cell-penetrating peptide sequence.
Figure 2B:
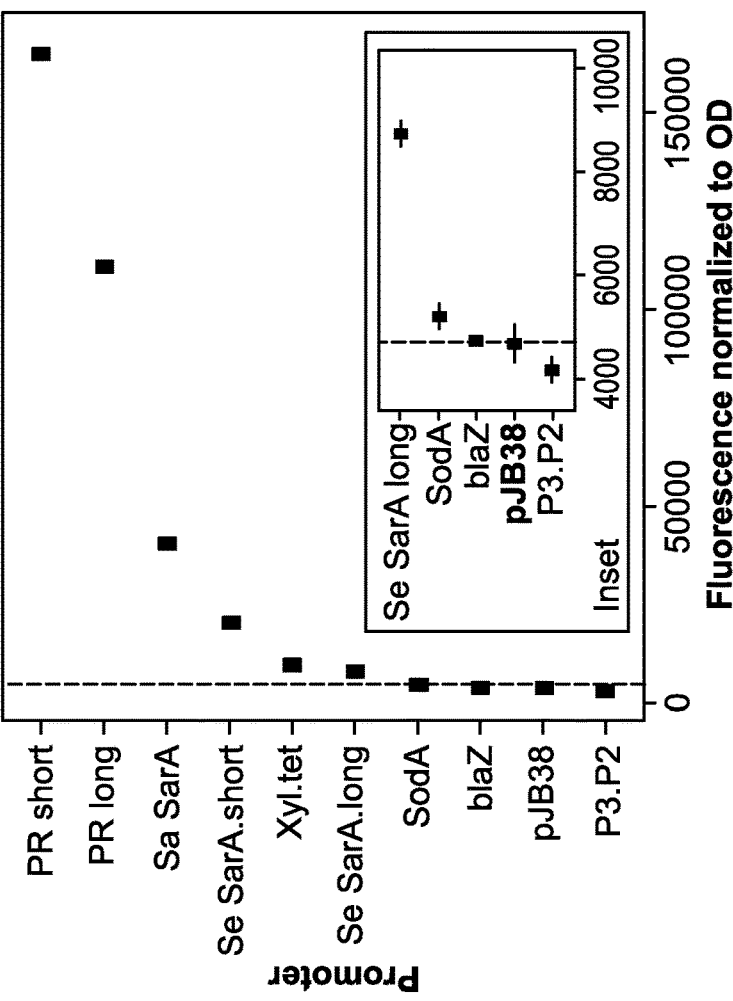
FIG. 2B displays the characterization of certain promoters for tunable control of protein expression (using GFP as a reporter).
Figure 2D:
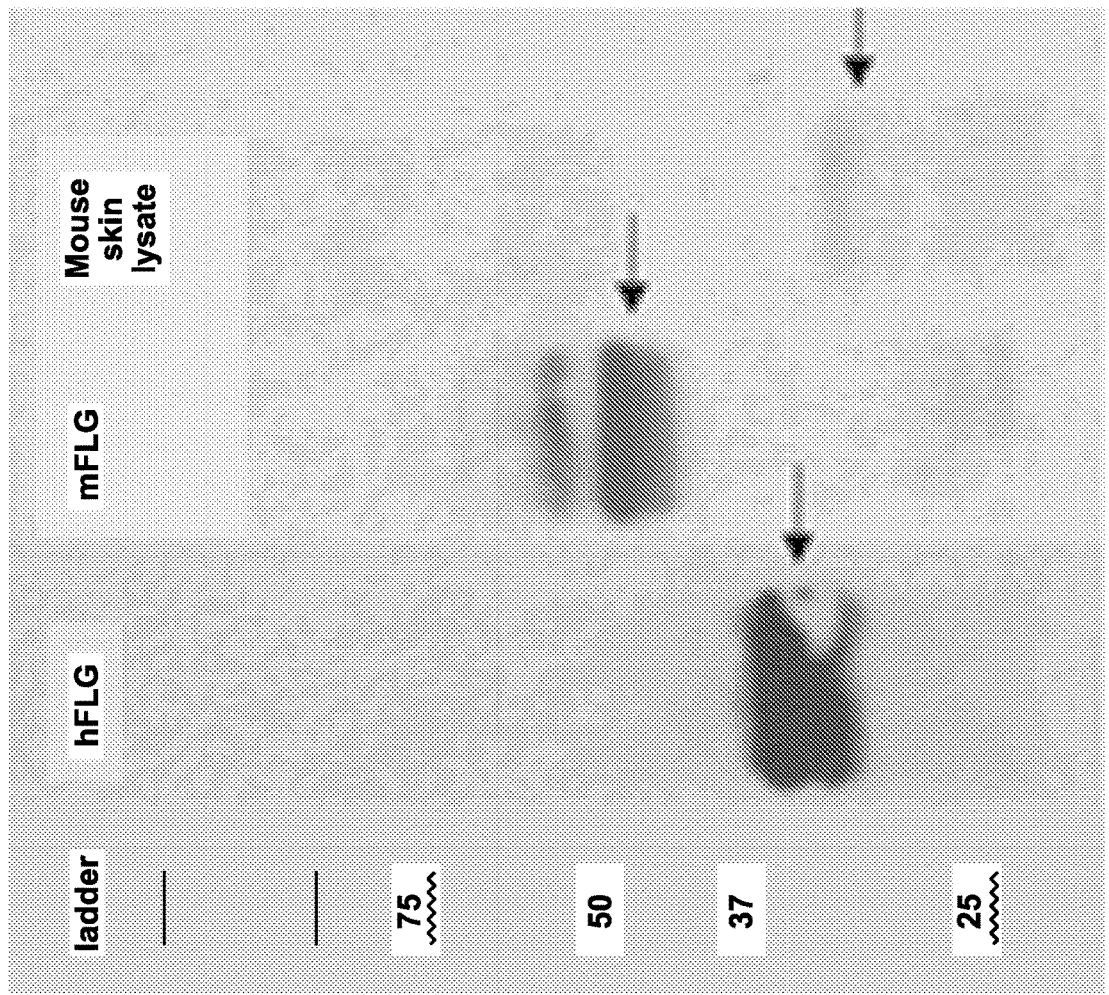
FIG. 2D shows Western blot analysis of human filaggrin produced from *Staphylococcus epidermidis*, mouse filaggrin produced from *Staphylococcus epidermidis*, and whole mouse skin (anti-mouse flaggrin antibodies were used).
Figure 2C:
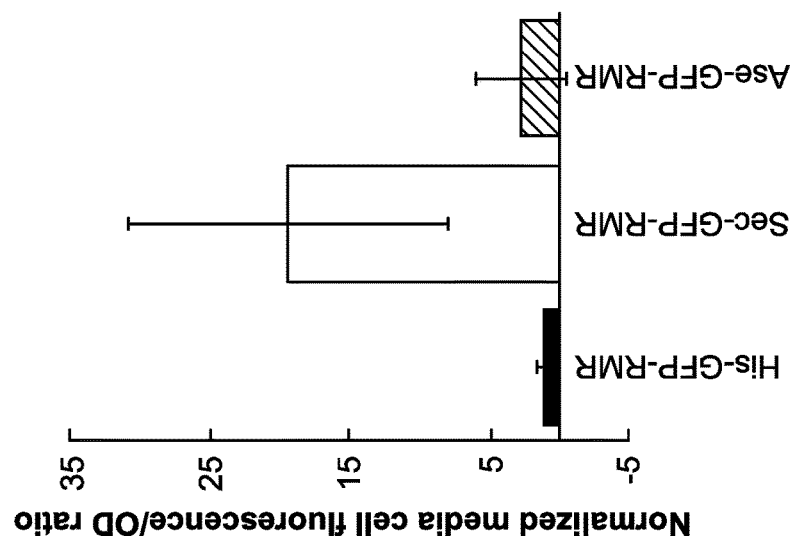
FIG. 2C shows characterization of export signals for protein export out of SE (GFP used as reporter).
Figure 5F:
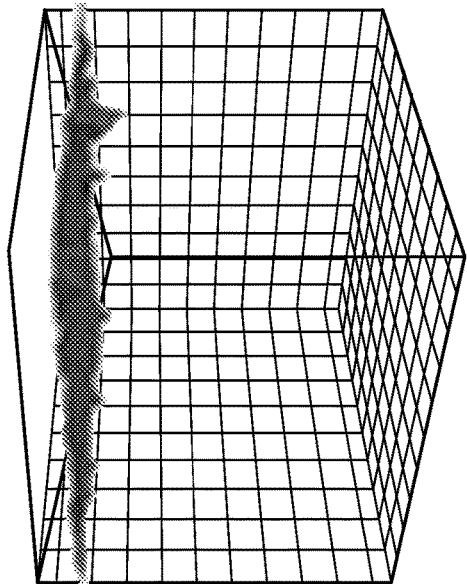
Figure 5H:
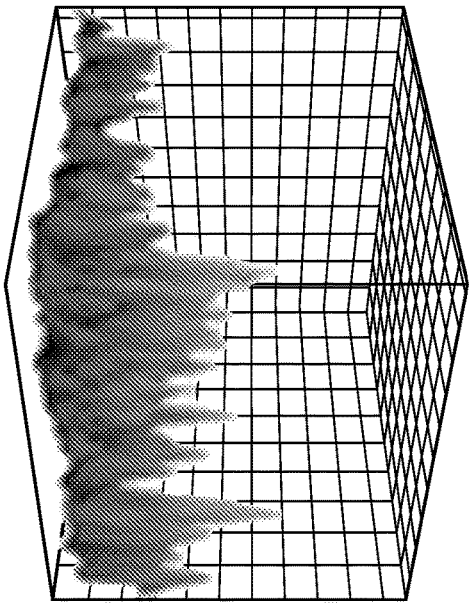
Figure 5E:
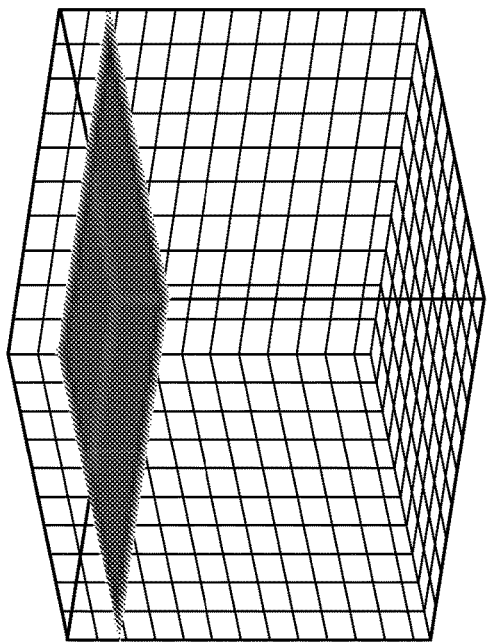
Figure 5G:
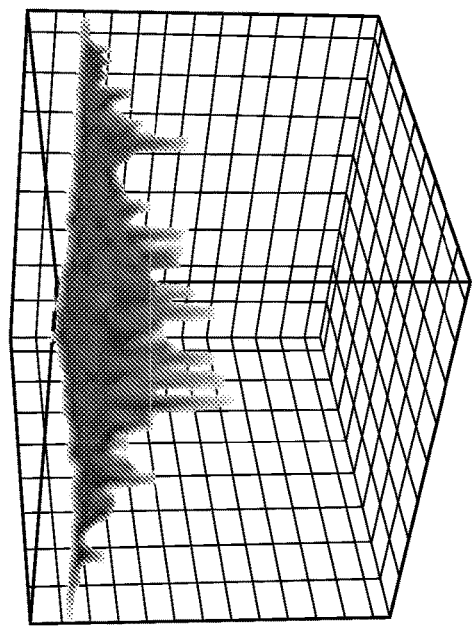

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The articles "a" and "an" are used herein to refer to one or to more than one (i.e. to at least one) of the grammatical object of the article. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

As used herein, the following terms have the following meanings unless expressly stated to the contrary: As used herein, the term "abnormal skin condition" or a "skin disease" (e.g., an inflammatory skin disease) refers to a skin state or condition that is generally undesirable or deleterious compared to the normal or baseline condition of human skin. Examples of abnormal skin conditions include: psoriasis, acne, atopic dermatitis, allergic contact dermatitis, epidermolytic hyperkeratosis, seborrheic dermatitis, eczema, dry skin, allergy, rashes, UV-irritated skin, detergent irritated skin (including irritation caused by enzymes and molecules used in washing detergents and sodium lauryl sulfate), thinning skin (e.g. skin from the elderly and children), bullous pemphigoid, pemphigus vulgaris, impetigo, vitiligio, baldness, and hirsutism.

As used herein, the terms "patient" or "subject", refers to a human or animal (in the case of an animal, more typically a mammal such as domesticated mammals, or animals such as poultry animals and fish and other seafood or freshwater food creatures), that would be subjected to the treatments and compositions of the present invention. Such patient or subject would be considered to be in need of the pharmaceutical compositions of the present invention or of the methods of treating, preventing, or reducing the risk of an abnormal skin condition or a skin disease (e.g., an inflammatory skin disease).

As used herein, the term "therapeutically effective amount" refers to an amount of a pharmaceutical active compound, a live biotherapeutic composition, a combination of compounds or compositions, or an amount of pharmaceutical active compound delivered by an engineered bacterial strain or strains, for example a skin treatment agent or agents, when administered alone or in combination, to treat, prevent, or reduce the risk of a disease state or condition, for example an abnormal skin condition or a skin disease (e.g., an inflammatory skin disease). The term also refers to an amount of a pharmaceutical composition containing an active compound or combination of compounds or an engineered bacterial strain or strains that delivers a pharmaceutical active compound. For example, an effective amount refers to an amount of the compound or an amount of the compound delivered by an engineered bacterial strain (or a recombinant bacterial strain) or strains present in a formulation given to a recipient patient or subject sufficient to elicit biological activity, for example, activity for treating or preventing an abnormal skin condition or a skin disease (e.g., an inflammatory skin disease).

As used herein, the phrase "pharmaceutically acceptable" refers to those active compounds, materials, engineered bacterial strain or strains, compositions, carriers, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio. As used herein, the term "treating" refers to providing a therapeutic intervention to cure or ameliorate an abnormal skin condition.

As used herein, the term "preventing", refers to completely or almost completely stopping an abnormal skin condition from occurring, for example when the patient or subject is predisposed to an abnormal skin condition or at risk of contracting an abnormal skin condition. Preventing can also include inhibiting, i.e. arresting the development, of an abnormal skin condition.

As used herein, the term "reducing the risk of," refers to lowering the likelihood or probability of an abnormal skin condition from occurring, for example when the patient or subject is predisposed to an abnormal skin condition or at risk of contracting an abnormal skin condition.

As used herein, the term "engineered bacterial strain," or a "recombinant bacterial strain" refers to a strain of bacteria that has been "genetically modified" or "engineered" by the introduction of DNA prepared outside the organism into the bacterial strain. For example, the introduction of a plasmid containing new genes or other nucleic acid sequence(s) into bacteria will allow the bacteria to express those genes or other nucleic acid sequence(s). Alternatively, the plasmid containing new genes or other nucleic acid sequence(s) can be introduced to the bacteria and then integrated into the bacteria's genome, where the bacteria will express those genes or other nucleic acid sequence(s).

As used herein, the terms "carriers", "carrier system" or "vehicles" refer to compatible substances that are suitable for delivering, containing, or "carrying" a pharmaceutical active ingredient or other materials for administration in a topically applied composition to a patient or subject. Carriers useful herein should be pharmaceutically acceptable. Carriers and vehicles useful herein include any such materials known in the art, which are non-toxic and do not interact with other components of the formulation in which it is contained in a deleterious manner. The term "aqueous" refers to a formulation that contains water or that becomes water-containing following application to the skin or mucosal tissue. Further examples of "carriers" include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers.

As used herein, the terms "polypeptide" or "protein" refer to biological molecules, or macromolecules composed of amino-acid residues bonding together in a chain. The definition of polypeptides used herein is intended to encompass proteins (generally higher molecular weight) composed of one or more long chains of amino acid residues and small peptides (generally lower molecular weight) of a few amino acids. In other embodiments, a single amino acid, although not technically a polypeptide, is also considered within the scope of the invention.

As used here, the term "live biotherapeutic product" (or LBP) refers to a product candidate(s) containing bacteria, yeast, and/or other microorganisms.

The term "isolated" for the purposes of the present invention designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

An "isolated nucleic acid molecule" (such as, for example, an isolated promoter) is one which is separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule in the genomic DNA of the organism from which the nucleic acid molecule is derived.

The present invention provides skin-colonizing bacteria that are genetically altered to express recombinant therapeutic polypeptides for the treatment or prevention of skin disease (FIG. 2). Using genetically engineered protein-producing bacteria has several advantages over the prior art method of treating skin disease. Therapeutic proteins are able to treat the underlying cause of defects leading to the skin condition. Further, bacteria are able to self-replicate while retaining the inserted gene to continuously produce the therapeutic protein.

The present invention provides skin-colonizing bacteria, such as for example, *Staphylococcus epidermidis*, that are genetically altered to express human filaggrin. Using genetically engineered filaggrin-producing bacteria has several advantages over using filaggrin supplementation. First, bacteria are able to self-replicate while retaining the inserted filaggrin gene. Second, *S. epidermidis* is normally present on the skin and has been shown to inhibit growth of *Staphylococcus aureus*, a bacterial species of the same genre that dominates the skin flora in AD flares.

II. Methods and Compositions of the Invention

The present invention provides skin-colonizing microorganisms, e.g., bacteria, that are genetically altered to express recombinant therapeutic polypeptides for the treatment or prevention of skin disease (FIG. 2). Using genetically engineered protein-producing microorganisms, e.g., bacteria, has several advantages over the prior art method of treating skin disease. Therapeutic proteins are able to treat the underlying cause of defects leading to the skin condition. Further, microorganisms, e.g., bacteria, are able to self-replicate while retaining the inserted nucleic acid (e.g., a gene) to continuously produce the therapeutic protein.

The present invention provides skin-colonizing microorganisms, e.g., bacteria, such as for example, *Staphylococcus epidermidis*, that are genetically altered to express therapeutic proteins, e.g., human filaggrin. Using genetically engineered filaggrin-producing microorganisms, e.g., bacteria, has several advantages over using filaggrin supplementation. First, microorganisms, e.g., bacteria, are able to self-replicate while retaining the inserted filaggrin nucleic acid sequence (e.g., a gene). Second, *S. epidermidis* is normally present on the skin and has been shown to inhibit growth of *Staphylococcus aureus*, a bacterial species of the same genre that dominates the skin flora in atopic dermatitis flares.

Bacterial Strains

The present invention provides genetically altered microorganisms, e.g., bacteria, capable of expressing recombinant therapeutic proteins. A wide range of microorganisms are suitable for use in the present invention. Examples include, but are not limited to, non-pathogenic and commensal bacteria. Bacteria suitable for use in the present invention include, but are not limited to, *Bifidobacterium, Brevibacterium, Propionibacterium, Lactococcus, Streptococcus, Staphylococcus* (e.g., *S. epidermidis*), *Lactobacillus* (e.g., *L. acidophilus*), *Pediococcus, Leuconostoc,* or *Oenococcus*. In certain embodiments of the invention, the bacterium is *Staphylococcus epidermidis*. In preferred embodiments of the invention, the strain of *S. epidermidis* to be used is incapable of producing biofilms. One such example of a strain of *S. epidermidis* incapable of producing biofilms is *S. epidermidis* strain ATCC 12228. However, in yet other embodiments of the invention, other related or similar species found on the skin can be used.

Therapeutic Proteins

The present invention provides genetically altered microorganisms, e.g., bacteria, capable of expressing recombinant therapeutic proteins.

In some embodiments, the disclosure is directed to therapeutic proteins that include a filaggrin polypeptide amino acid sequence. In some embodiments, the disclosure is directed to therapeutic proteins that include a filaggrin polypeptide amino acid sequence and a cell penetrating polypeptide amino acid sequence. In some embodiments, the disclosure is directed to therapeutic proteins that include a filaggrin polypeptide amino acid sequence, a cell penetrating polypeptide amino acid sequence and a secretion signal or export signal polypeptide sequence. As used herein, a "polypeptide" generally is defined herein to refer to a peptide sequence of about 2 to about 10,000 or more amino acid residues. The term "amino acid" not only encompasses the 20 common amino acids in naturally synthesized proteins, but also includes any modified, unusual, or synthetic amino acid. One of ordinary skill in the art would be familiar with modified, unusual, or synthetic amino acids.

The polypeptides of the present invention may possess deletions and/or substitutions of amino acids relative to the native sequence; thus, sequences with a deletion, sequences with a substitution, and sequences with a deletion and a substitution are contemplated for inclusion in the polypeptides of the present invention. In some embodiments, these polypeptides may further include insertions or added amino acids, such as linkers.

Substitutional or replacement variants typically contain the exchange of one amino acid for another at one or more sites within the protein and may be designed to modulate one or more properties of the polypeptide, particularly to increase its efficacy or specificity. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In addition to a deletion or substitution, the polypeptides may possess an insertion one or more residues. This may include the addition of one or more amino acid residues.

Amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Filaggrin

In some embodiments, the disclosure is directed to therapeutic proteins that include a filaggrin polypeptide amino acid sequence. In preferred embodiments of the invention, the therapeutic protein comprises human filaggrin. Human filaggrin is expressed by a human gene encoding filaggrin (FLG). Filaggrin is a protein produced by differentiating keratinocytes and functions to aggregate keratin filaments into a cytoskeleton, which, in combination with other components, comprises the cornified cell envelope. FLG is a large gene located on chromosome lq21 that produces profilaggrin, an insoluble polyprotein that is proteolyzed to release functional filaggrin monomers (Armengot-Carbo et al. 2014). The therapeutic protein (and, i.e., the gene from which the protein is expressed) of the invention may be from any mammal. Non-limiting examples include, but are not limited to, mouse, rat, rabbit, goat, sheep, horse, cow, dog, primate, or human gene sequence.

The filaggrin amino acid sequences contemplated for inclusion in the polypeptides, compositions, and methods of the present invention may be obtained from any source. For example, the filaggrin amino acid may be obtained from a natural source or may be chemically synthesized. The filaggrin amino acid sequence may be from any species. For example, it may be a mammalian filaggrin amino acid sequence. Non-limiting examples include mouse, rat, rabbit, goat, sheep, horse, cow, dog, cat, primate, or human amino acid sequence. In preferred embodiments, the filaggrin amino acid sequence is a human amino acid sequence. Non-limiting examples of filaggrin proteins are set forth in Table 1, below.

TABLE 1

| Sequence | GenBank Accession No. | SEQ ID NO. |
| --- | --- | --- |
| Filaggrin, *Homo sapiens* | NP_002007.1 | 1 |
| Filaggrin, *Homo sapiens* | AAA52454 | 10 |
| Filaggrin, *Homo sapiens* | P20930.3 | 11 |
| Filaggrin, *Mus musculus* | XP_017175331.1 | 12 |
| Filaggrin, *Mus musculus* | AAM23016 | 13 |
| Filaggrin, *Mus musculus* | AAA75559 | 14 |
| Filaggrin, *Mus musculus* | AAA37626 | 15 |
| Filaggrin, *Mus musculus* | XP_485270 | 16 |
| Filaggrin, *Mus musculus* | P11088 | 17 |
| Filaggrin, *Mus musculus* | EDL00668.1 | 18 |
| Filaggrin, *Rattus norvegicus* | EDL87862 | 19 |
| Filaggrin, *Pan troglodytes* | XP_001134714 | 20 |
| Filaggrin, *Pan troglodytes* | XP_513808 | 21 |
| Filaggrin, *Bos taurus* | XP_001255583 | 22 |
| Filaggrin, *Macaca mulatta* | XP_001101725.1 | 23 |
| Filaggrin, *Macaca mulatta* | XP_001109011.1 | 24 |

In some embodiments, the filaggrin amino acid sequence includes any of the amino acid sequences set forth in Table 1. In particular embodiments, the filaggrin amino acid sequence includes Gen Bank Accession No. NP_002007.1 (SEQ ID NO:1).

In some embodiments, the filaggrin amino acid sequence includes 20, 30, 40, 50, 60, 70, 80, 90, 100, 120, 130, 150, 150, 160, 170, 180, 190, 200, 210, 220, 230, 240, 250, 260, 270, 280, 290, 300, 310, 320, 330, 340 or more consecutive amino acids of any of the amino acid sequences set forth in Table 1, or any range of amino acids derivable therein, so long as the filaggrin amino acid sequence when conjugated to a cell penetrating peptide and/or export or secretion signal retains at least some of the function of a native filaggrin amino acid sequence conjugated to the same cell penetration peptide and/or export or secretion signal.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with a native filaggrin amino acid sequence, or any range of percent sequence identify derivable therein. In one embodiments, the filaggrin amino acid sequence is an amino acid sequence selected from Table 1. In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 1.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 2.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 3.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 4.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 5.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 6.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 7.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 8.

In some embodiments, the human filaggrin consensus sequence is a consensus sequence shown as SEQ ID NO: 9, and refers to a sequence formed from the most frequently occurring amino acids in hFLG[3-4], hFLG[5-6], hFLG[7-8], hFLG[9-10], hFLG[11-12], hFLG[13-14], hFLG[15-16], hFLG[17-18], hFLG[19-20], hFLG[21-22].

```
                                              SEQ ID NO: 9
XLYQVSTHXQXDSXHGXTXXSTXXRQXSHXXQAXXXSRHSXSQXG       100
QDTIRGHPGXXXXGRQGXXXEXXVXXSGHSGXHHSHTTXQXRSDA
SHGXSGXRSA

SRXTXXXXQSXDXTRHSXSRHHEXXSXAXXSXHSXXGQXXSXGXR       200
XSRXXGSSXSQDXDSXXHSEDSERXSXSASRNHXGSXXEQXRXGS
RXPXXHXEDR

AXHGHSADXSRKSGTXHXXXSSXGQAASSXEQARSSXGERHGSRH       300
QXQSADSSXXSGXXHXQXSSAVXDSXXXGXSGSQATXXEGHSEDS
DTQSVSGXGX

XGXHQQSHXESXRXXSGXXSXRSXSFLY.                       328
```

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO: 9.

"Sequence identity" is defined as the percentage of amino acid residues in a candidate sequence that are identical with the amino acid residues at corresponding positions in a native polypeptide sequence, after aligning the sequences and introducing gaps if necessary, to achieve the maximum percent sequence identity, and not considering any conservative substitutions as part of the sequence identity. The % sequence identity values may be generated by the NCBI BLAST2.0 software as defined by Altschul et al. (1997). The parameters are set to default values, with the exception of Penalty for mismatch, which is set to −1.

In preferred embodiments of the invention, the therapeutic protein comprises a recombinant fusion protein comprising filaggrin operably linked to a cell penetrating protein (CPP). In other embodiments of the invention, the therapeutic protein comprises a recombinant fusion protein comprising filaggrin operably linked to an export or secretion signal, which allows the recombinant filaggrin to be exported out of the microorganism (e.g., bacteria). In another embodiment, the therapeutic protein comprises a recombinant fusion protein comprising filaggrin operably linked to a cell penetrating protein (CPP) and to an export or secretion signal.

Furthermore, the polypeptides set forth herein may comprises a sequence of any number of additional amino acid residues at either the N-terminus or C-terminus of the amino acid sequence that includes the filaggrin amino acid sequence and the cell penetrating protein (CPP) and/or export or secretion signal. For example, there may be an amino acid sequence of about 3 to about 10,000 or more amino acid residues at either the N-terminus, the C-terminus, or both the N-terminus and C-terminus of the amino acid sequence that includes the filaggrin amino acid sequence and the cell penetrating peptide and/or export or secretion signal.

Secretion Signals

Secretion signals or export signals are peptide sequences on a protein that facilitate the export of the protein through the secretory pathway, which ultimately results in the protein being secreted from the cell. In the present invention, any secretion signal that facilitates the export of a protein, such as a protein comprising filaggrin, out of a microorganism (e.g., a bacterial cell) is contemplated as a secretion signal.

Cell Penetrating Peptides

A cell penetrating peptide is a peptide sequence that facilitates or mediates the delivery of a biomolecule (e.g., a protein) in vivo without using any receptors and without causing any significant membrane damage. Cell penetrating peptides that facilitate entry into the skin keratinocytes are contemplated as a cell penetrating peptides of the present invention.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises a filaggrin polypeptide amino acid sequence.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 1.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 2.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 3.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 4.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 5.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 6.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 7.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 8.

According to some embodiments, the present disclosure provides a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide, where the polypeptide comprises an amino acid sequence at least 95%, 96%, 97%, 98%, or 99% identical to SEQ ID NO: 9.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 2.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 3.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 4.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 5.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 6.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 7.

According to some embodiments, the present disclosure provides a recombinant microorganism capable of secreting a polypeptide, wherein the recombinant microorganism comprises an expression vector comprising an amino acid sequence at least 95%, 96%, 97%, 98%, or 99% identical to SEQ ID NO: 8.

Nucleic Acids

The present invention includes nucleic acids that include a nucleic acid sequence that encodes a recombinant polypeptide of the present invention. Some embodiments of the present invention include a nucleic acid that includes a nucleic acid sequence that encodes a polypeptide as set forth above. Further embodiments include a nucleic acid that encodes a filaggrin amino acid sequence. The filaggrin amino acid sequence is any filaggrin amino acid sequence as set forth herein. In some embodiments, the nucleic acid is comprised in an expression vector. The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between 3 and about 100 nucleobases in length. The term "polynucleotide" refers to at least one molecule of greater than about 100 nucleobases in length.

These definitions refer to a single-stranded or double-stranded nucleic acid molecule. Double stranded nucleic acids are formed by fully complementary binding, although in some embodiments a double stranded nucleic acid may formed by partial or substantial complementary binding. Thus, a nucleic acid may encompass a double-stranded molecule that comprises one or more complementary strand(s) or "complement(s)" of a particular sequence, typically comprising a molecule. As used herein, a single stranded nucleic acid may be denoted by the prefix "ss" and a double stranded nucleic acid by the prefix "ds".

Genetic Construct

The present invention utilizes standard molecular biology techniques, e.g., those described in (Sambrook et al. 2001). An example of the genetic construct used for this invention is pAZT, which is based on pJB38, an allelic exchange *E. coli*-staphylococcal shuttle vector, further comprising additional design features on the plasmid to improve functionality (Bose, J. L., et al. *Applied and environmental microbiology*. 2013; 79(7):2218-2224). The plasmid is constructed by inserting cDNA of a gene encoding a therapeutic protein into a restriction site, using standard molecular biology techniques (FIG. 2). The insert further comprises a coding sequence driven by a promoter. Such a promoter can be either constitutive or inducible. Examples of inducible promoters include those that are activated by chemical compounds such as alcohols, sugars, metals, or tetracycline, or by physical factors such as light or high temperatures.

The mRNA sequence of human FLG has a Genebank accession No. NM_002016. A plasmid pAZT was constructed by inserting part of the FLG cDNA into a restriction site of pJB38. The insert contains a nucleic acid coding sequence driven by a promoter. The construct further comprises a nucleic acid sequence encoding a secretion signal and a cell penetrating peptide, thus resulting in a recombinant filaggrin fusion protein.

Uses of Recombinant Bacterial Strain

It will be understood that the skin disease to be treated can be any disease or disorder associated with skin. In preferred embodiments the disorder is selected from the group consisting of atopic dermatitis, psoriasis, acne, allergic contact dermatitis, epidermolytic hyperkeratosis, seborrheic dermatitis, eczema, dry skin, allergy, rashes, UV-irritated skin, detergent irritated skin (including irritation caused by enzymes and compounds used in washing detergents and sodium lauryl sulfate), thinning skin (e.g. skin from the elderly and children), bullous pemphigoid, pemphigus vulgaris, impetigo, vitiligio, baldness, and hirsutism, Examples of proteins that can be administered according to the invention are preferably eukaryotic proteins. These proteins include, but are not limited to, single amino acids, small peptides, and large proteins. More particularly, genes encoding proteins that are useful in the invention as recombinant therapeutic proteins include, but are not limited to, the following: members of the interleukin family of genes, including, but not limited to, IL-2, IL-3, IL-4, IL-5, IL-6, IL-7, IL-8, IL-9, IL-10, IL-11, IL-12, IL-13, IL-14 and IL-15 and genes encoding receptor antagonists thereof. Genes which encode hematopoietic growth factors, including but not limited to, erythropoietin, granulocyte colony stimulating factor, granulocyte macrophage colony stimulating factor, macrophage colony stimulating factor, stem cell factor, leukemia inhibitory factor and thrombopoietin are also contemplated in the invention. Genes encoding neurotropic factors are also contemplated, including but not limited to, nerve growth factor, brain derived neurotropic factor and ciliary neurotropic factor. In addition, genes which encode interferons, including, but not limited, to IFN-alpha, IFN-beta and IFN-gamma are included. Further contemplated in the present invention are genes encoding chemokines such as the C-C family and the C-X-C family of cytokines, genes encoding hormones, such as proinsulin and growth hormone, and genes encoding thrombolytic enzymes, including tissue plasminogen activator, streptokinase, urokinase or other enzymes such as trypsin inhibitor. The invention further includes genes which encode tissue repair factors, growth and regulatory factors including, but not limited to, oncostatine M, platelet-derived growth factors, fibroblast growth factors, epidermal growth factor, hepatocyte growth factor, bone morphogenic proteins, insulin-like growth factors, calcitonin and transforming growth factor alpha and beta. Further contemplated genes include genes encoding structural proteins including filaggrin, actin, collagen, fibrillin, elastin, or scleroprotein.

Formulations

It will be further apparent that a formulation for use according to the present invention may comprise any pharmaceutically effective amount of a genetically engineered microorganism, e.g., bacteria, to produce a therapeutically effective amount of a desired polypeptide, for example, at least about 0.01%, about 0.05%, about 0.1%, about 0.2%, about 0.3%, about 0.4%, about 0.5%, about 0.6%, about 0.7%, about 0.8%, about 0.9%, about 1.0%, about. 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% or more by weight of the genetically engineered microorganism, e.g., bacteria, the upper limit of which is about 90.0% by weight of the genetically engineered microorganism, e.g., bacteria.

In an alternative embodiment, the formulation for use according to the present invention can comprise, for example, at least about 0,01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5%, or more by weight of a genetically engineered microorganism, e.g., bacteria.

The topical formulation for use in the present invention can be in any form suitable for application to the body surface, such as a cream, lotion, sprays, solution, gel, ointment, paste, plaster, paint, bioadhesive, suspensions, emulsions, or the like, and/or can be prepared so as to contain liposomes, micelles, and/or microspheres. Such a formulation can be used in combination with an occlusive overlayer so that moisture evaporating from the body surface is maintained within the formulation upon application to the body surface and thereafter. The formulation can include a living biotherapeutic composition and can comprise at least one a genetically engineered microorganism, e.g., an engineered bacterial strain, that produces a recombinant polypeptide. This engineered living biotherapeutic composition can deliver the polypeptide directly to the skin for treating or preventing abnormal skin conditions, and/or skin diseases (e.g., inflammatory skin diseases).

Topical formulations include those in which any other active ingredients are dissolved or dispersed in a dermatological vehicle known in the art, e.g. aqueous or nonaqueous gels, ointments, water-in-oil or oil-in-water emulsions. Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as MIGLYOL, or silicone oils such as dimethicone). Depending upon the nature of the formulation as well as its intended use and site of application, the dermatological vehicle employed can contain one or more components (e.g., when the formulation is an aqueous gel, components in addition to water) selected from the following: a solubilizing agent or solvent (e.g. a β-cyclodextrin, such as bydroxypropyl β-cyclodextrin, or an alcohol or polyol such as ethanol, propylene glycol or glycerol); a thickening agent (e.g. hydroxyethylceliulose, hydroxypropylcellulose, carboxymethylcellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (such as a mixture of dihydrogen phosphate and hydrogen phosphate salts, or a mixture of citric acid and a hydrogen phosphate salt).

A pharmaceutically acceptable carrier can also be incorporated in the formulation of the present invention and can be any carrier conventionally used in the art. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers. The term "pharmaceutically acceptable" or "pharmaceutically acceptable carrier" is used herein to refer to a compound or composition that can be incorporated into a pharmaceutical formulation without causing undesirable biological effects or unwanted, interaction with other components of the formulation, "carriers" or "vehicles" as used herein refer to carrier materials suitable for incorporation in a topically applied composition. Carriers and vehicles useful herein include any such materials known in the art, which are non-toxic and do not interact with other components of the formulation in which it is contained in a deleterious manner. The term "aqueous" refers to a formulation that contains water or that becomes water-containing following application to the skin or mucosal tissue.

Cream bases are water-washable, and contain an oil phase, an emulsifier, and an aqueous phase. The oil phase, also called the "internal" phase, is generally comprised of petrolatum and a fatty alcohol such ascetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions are preparations to be applied to the skin surface without friction, and are typically liquid or semiliquid preparations in which particles, including the active agent, are present in a water or alcohol base. Lotions are usually suspensions of solids, and preferably, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like. Solutions are homogeneous mixtures prepared by dissolving one or more chemical substances (solutes) in a liquid such that the molecules of the dissolved substance are dispersed among those of the solvent. The solution can contain other pharmaceutically or cosmetically acceptable chemicals to buffer, stabilize or preserve the solute. Common examples of solvents used in preparing solutions are ethanol, water, propylene glycol or any other acceptable vehicles. As is of course well known, gels are semisolid, suspension-type systems. Single-phase gels contain organic macromolecules distributed substantially uniformly throughout the carrier liquid, which is typically aqueous, but also, preferably, contain an alcohol, and, optionally, an oil. Preferred organic macromolecules, i.e., gelling agents, are cross-linked acrylic acid polymers such as the "carbomer" family of polymers, e.g., carboxypolyalkylenes that can be obtained commercially under the Carbopol trademark. Also preferred are hydrophilic polymers such as polyethylene oxides, polyoxyethylene-polyoxypropylene copolymers and polyvinylalcohol; cellulosic polymers such as hydroxy-propyl cellulose, hydroxyethyl cellulose, hydroxypropyl methylcellulose, hydroxy-propyl methylcellulose phthaiate, and methylcellulose; gums such as tragacanth and xanthan gum; sodium alginate; and gelatin, In order to prepare a uniform gel, dispersing agents such as alcohol or glycerin can be added, or the gelling agent can be dispersed by trituration, mechanical mixing or stirring, or combinations thereof. Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19th Ed. (Easton, PA: Mack Publishing Co., 1995), at pages 1399-1404, ointment bases can be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum.

Emulsifiable ointment bases, also known as absorbent ointment bases, contain little or no water and include, for example, hydroxystearin sulfate, anhydrous lanolin, and hydrophilic petrolatum.

Emulsion ointment bases are either water-in-oil (W/O) emulsions or oil-in-water (O/W) emulsions, and include, for example, acetyl alcohol, glyceryl monostearate, lanolin, and stearic acid. Preferred water-soluble ointment bases are prepared from polyethylene glycols of varying molecular weight; see Remington: The Science and Practice of Pharmacy for further information.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Enhancers are lipophilic co-enhancers typically referred to as "plasticizing" enhancers, i.e., enhancers that have a molecular weight in the range of about 150 to 1000, an aqueous solubility of less than about 1 wt. %, preferably less than about 0.5 wt. %, and most preferably less than about 0.2 wt. %. The Hildebrand solubility parameter 6 of plasticizing enhancers is in the range of about 2.5 to about 10, preferably in the range of about 5 to about 10. Preferred lipophilic enhancers are fatty esters, fatty alcohols, and fatty ethers. Examples of specific and most preferred fatty acid esters include methyl laurate, ethyl oleate, propylene glycol nionolaurace, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$-$C_4$ alkane diol or triol, are substituted with one or two fatty ether substituents. Additional permeation enhancers will be known to those of ordinary skill in the art of topical drag delivery, and/or are described in the pertinent texts and literature. See, e.g., Percutaneous Penetration Enhancers, eds. Smith et al. (CRC Press, 1995)(incorporated herein by reference herein in its entirety).

Various other additives can be included in the compositions of the present invention in addition to those identified above. These include, but are not limited to, antioxidants, astringents, perfumes, preservatives, emollients, pigments, dyes, humectants, propellants, and sunscreen agents, as well as other classes of materials whose presence can be pharmaceutically or otherwise desirable. Typical examples of optional additives for inclusion in the formulations of the present invention are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylaury 1 ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), a-tocopherol (Vitamin E), β-tocopherol, γ-tocopherol, δ-tocopherol, ε-tocopherol, $ζ_1$-tocopherol, $Z^Λ$-tocopherol, η-tocopherol, and retinol (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that can be obtained commercially under the Carbopol trademark. Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Further additional active agents including, for example, alpha hydroxyacids, alpha ketoacids, polymeric hydroxyacids, moisturizers, collagen, marine extract, and antioxidants such as ascorbic acid (Vitamin C), a-tocopherol (Vitamin E), β-tocopherol, γ-tocopherol, 6-tocopherol, ε-tocopherol, $ζ_1$-tocopherol, $ζ_2$-tocopherol, η-tocopherol, and retinol (Vitamin A), and/or pharmaceutically acceptable salts, esters, amides, or other derivatives thereof. A preferred tocopherol compound is α-tocopherol. Additional agents include those that are capable of improving oxygen supply in skin tissue, as described, for example, in Gross, et al., WO 94/00098 and Gross, et al., WO 94/00109, both assigned to Lancaster Group AG (incorporated herein by reference in their entirety). Sunscreens and UV absorbing compounds can also be included. Non-limiting examples of such sunscreens and UV absorbing compounds include aminobenzoic acid (PABA), avobenzone, cinoxate, dioxybenzone, homosalate, menthyl anthranilate, oxtocrylene, octyl methoxycmnamate, octyl salicylate, oxybenzone, padirnate O, phenylbenzirmdazole sulfonic acid, sulisobenzone, titanium dioxide, trolamine salicylate, zinc oxide, ensulizole, meradiraate, octinoxate, octisalate, and octocrylene. See Title 21. Chapter 1. Subchapter D. Part 352. "Sunscreen drug products for over-the-counter human use" incorporated herein in its entirety. Other embodiments can include a variety of non-carcinogenic, non-irritating healing materials that facilitate treatment with the formulations of the invention. Such healing materials can include nutrients, minerals, vitamins, electrolytes, enzymes, herbs, plant extracts, glandular or animal extracts, or safe therapeutic agents that can be added to the formulation to facilitate the healing of dermal disorders.

The present invention contemplates amounts of these various additives equivalent to those conventionally used in the cosmetics field, and range, for example, from about 0.01% to about 20% of the total weight of the topical formulation.

The formulations of the invention can also include conventional additives such as opacifiers, fragrance, colorant, stabilizers, surfactants, and the like. In certain embodiments, other agents can also be added, such as antimicrobial agents, to prevent spoilage upon storage, i.e., to inhibit growth of microbes such as yeasts and molds.

Suitable antimicrobial agents for the present invention include, but are not limited to the following selected from the group consisting of the methyl and propyl esters of p-hydroxybenzoic acid (i.e., methyl and propyl paraben), sodium benzoate, sorbic acid, imidurea, and combinations thereof. In other embodiments, other agents can also be added, such as repressors and inducers, i.e., to inhibit (i.e., glycose) or induce (i.e. xylose) the production of the polypeptide of interest. Such additives can be employed provided they are compatible with and do not interfere with the function of the formulations.

The formulations can also contain irritation-mitigating additives to minimize or eliminate the possibility of skin irritation or skin damage resulting from the chemical entity to be administered, or other components of the composition.

Suitable irritation-mitigating additives include, for example: α-tocopherol; monoamine oxidase inhibitors, particularly phenyl alcohols such as 2-phenyl-1-ethanol; glycerin; salicylates; ascorbates; ionophores such as monensin; amphophilic amines; ammonium chloride; N-acetylcysteine; capsaicin; and chloroquine. The irritation-mitigating additive, if present, can be incorporated into the compositions at a concentration effective to mitigate irritation or skin damage, typically representing not more than about 20 wt. %, more typically not more than about 5 wt. %, of the formulation. Further suitable pharmacologically active agents that can be incorporated into the present formulations in certain embodiments and thus topically applied along with the active agent include, but are not limited to, the following: agents that improve or eradicate pigmented or non-pigmented age spots, keratoses, and wrinkles; antimicrobial agents; antibacterial agents; antipruritic and antixerotic agents; anti-inflammatory agents; local anesthetics and analgesics; corticosteroids; retinoids; vitamins; hormones; and antimetabolites. Some examples of topical pharmacologically active agents include acyclovir, amphotericins, chlorhexidine, clotrimazole, ketoconazole, econazole, miconazole, metronidazole, minocycline, nystatin, neomycin, kanamycin, phenytoin, para-amino benzoic acid esters, octyl methoxycmnamate, octyl salicylate, oxybenzone, dioxybenzone, tocopherol, tocopheryl acetate, selenium sulfide, zinc pyrithione, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, and 5-fluorouracil. A cream, lotion, gel, ointment, paste or the like can be spread on the affected surface and gently rubbed in. A solution can be applied in the same way, but more typically will be applied with a dropper, swab, or the like, and carefully applied to the affected areas.

The application regimen will depend on a number of factors that can readily be determined, such as the severity of the condition and its responsiveness to initial treatment, but will normally not involve more than one application per day. One of ordinary skill can readily determine the optimum amount of the formulation to be administered, administration methodologies and repetition rates. In general, it is contemplated that the formulations of the invention will be applied in the range of once or twice weekly up to once daily.

III. Methods and Kits of the Invention

Methods of Treatment

The invention provides methods for treating a skin disease, wherein the methods comprise administering to a subject in need of such treatment a genetically engineered microorganism, e.g., genetically engineered bacteria, capable of expressing a recombinant therapeutic fusion protein of the invention, thereby treating the subject. In a preferred embodiment, the disease is atopic dermatitis. In yet another preferred embodiment, the recombinant therapeutic fusion protein comprises filaggrin. In other embodiments, the recombinant therapeutic fusion protein comprises filaggrin operably linked to a cell penetrating peptide. In further embodiments, the recombinant therapeutic fusion protein is operably linked to an export signal.

Kits

The present invention also provides kits. In one aspect, a kit of the invention comprises (a) a composition of the invention and (b) instructions for use thereof. In another aspect, a kit of the invention comprises (a) any one of the live biotherapeutic compositions of the invention, and (b) instructions for use thereof. Instructions can include an explanation of how to apply, administer, use, and maintain the compositions. The compositions of the invention are described supra. In some embodiments, a composition of the invention is an engineered microorganism capable of expressing therapeutically relevant recombinant fusion polypeptides, as described supra. In preferred embodiments, the composition comprises engineered bacteria (e.g., *S. epidermidis*) capable of expressing a recombinant fusion polypeptide comprising filaggrin.

In some embodiments, a kit can include a sealed container. Non-limiting examples of containers include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. Other examples of containers include glass or plastic vials or bottles. The kit and/or container can include indicia on its surface. The indicia, for example, can be a word, a phrase, an abbreviation, a picture, or a symbol.

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Example 1: Development of a Nucleic Acid Construct that can Encode a Protein Capable of being Exported Out of the *S. epidermidis* Cell and then Imported into Human Keratinocytes The invention describes in one embodiment the generation of a recombinant *S. epidermidis* strains that is capable of heterologous protein secretion, therefore overcoming the intractability of genetic modification of *S. epidermidis*. Functional genetic analyses of the common skin colonizers *S. aureus* and *S. epidermidis* have previously been limited due to the presence of Type I and IV restriction systems in virtually all strains of these bacteria. These restriction systems recognize methylated cytosine bases in DNA from standard clone expansion systems such as DH10B *E. coli*. However, using a methylation deficient *E. coli* strain, DC10B, several constructs have been created in *S. epidermidis* strain ATCC12228[5], which is a commensal, non-pathogenic isolate lacking ica operons implicated in *S. epidermidis*-associated catheter bloodstream infections. Accordingly, the invention describes the first known reported heterologous protein expression in *S. epidermidis*. The present invention thus provides, in one embodiment, a nucleic acid plasmid capable of encoding a protein that is exported out of the *S. epidermidis* cell and subsequently imported into human keratinocytes. This plasmid, pAZT, is based on pJB38 (Bose, J. L., et al. Applied and environmental microbiology. 2013; 79(7):2218-2224), an allelic exchange *E. coli*-staphylococcal shuttle vector, which has been specifically re-engineered to possess features that improve functionality. The present invention provides, in one embodiment, an engineered *S. epidermidis* capable of effectively colonizing reconstituted epidermis and that is capable of producing 50 µg of protein per mL of ~$10^9$ CFU/mL (FIG. 2).

Cell Penetrating Peptides (CPP).

Despite the formidable barrier properties of the epidermis, protein delivery through the stratum corneum has been demonstrated by employing transduction peptides or cell penetrating peptides (CPP). This challenge arises due to the diffusion impediments from the hydrophobic surface and the layers of linked corneocytes comprising the stratum corneum. However, by attaching a CPP sequence to the N-terminal end of a protein of interest, successful delivery of the fusion protein into the deeper epidermis is possible, in addition to the facilitation of intracellular localization and endosomal/lysosomal escape of the target protein. The present invention, in one embodiment, provides a construct that utilizes such an approach, and comprises an HIV trans-activator of a transcription-derived cell-penetration peptide (RMR) protein motif (FIG. 2). This approach is foundational to delivering protein into deeper layers of the skin for higher therapeutic effect.

Safety and "Kill Switches"

A key requirement for nearly all recombinant microorganisms for clinical use is the ability to prevent undesired introduction to other individuals or environments. In order to ensure safety of the engineered strain, the present invention, in one embodiment, uses an auxotrophic strain, which requires supplementation of key amino acids (D-ala) or a certain metabolic gene (AlaR) for survival, and simultaneously replaces the need for an antibiotic resistant strain for selection, the latter of which is not commercially viable. In another embodiment, the present invention integrates a "kill switch", which is based on CRISPR/Cas9 self-cleavage upon induction of a dual xylose-riboswitch promoter. In yet another embodiment, the present invention provides cell counters, which recombine out the AZT locus after a defined number of divisions, although this method would necessitate reapplication of the vehicle. To ensure the safety of the engineered *S. epidermidis* of the present invention, a CRISPR/Cas9-based kill switch, which is xylose-inducible and doubly regulated with a theophylline riboswitch, was developed. The basis of this approach is that Cas9 is extremely efficient at chromosomal cleavage given a targeting guide, and since staphylococci lack canonical non-homologous end joining repair pathways, genomic cleavage results in death in the absence of a homologous recombination template. The use of a CRISPR-based system also confers great specificity, since comparative genomics can be used to design guides unique to the engineered *S. epidermidis* strain of the present invention, such that the construct is inactive if spread to other microbes by horizontal gene transfer. Finally, in one embodiment, the present invention provides a construct designed to express multiple CRISPR spacers to simultaneously target multiple genomic regions to ensure cleavage and minimize survival by reversion.

Example 2: Determine the Persistence and Localization of Topically Applied *S. epidermidis* Using In Vitro Model Systems Materials and Methods Create Reporter Bacteria.

In order to facilitate tracking of the topically applied bacteria, an sGFP-expressing strain of *S. epidermidis* (SE) was employed. The SecA and RMR peptides was removed such that the sGFP protein was not shuttled to the secretion system and free sGFP did not penetrate the stratum corneum. This construct is referred to as SE-sGFP.

Quantify and Compare Growth Characteristics of Transformed Bacteria in Liquid Media.

A basic understanding of the ability of transformed (recombinant) *S. epidermidis* to compete against wild type *S. epidermidis* was required. In order to understand the growth characteristics of the transformed bacteria and the growth dynamics of recombinant, protein-producing bacteria, standard techniques were used to quantify colony forming units (CFU) in liquid media. In order to determine growth differences between *S. epidermidis*-sGFP, *S. epidermidis*-chl and wild-type *S. epidermidis*, each strain was grown separately in two triplicate 100 mL cultures each for 12 hours. Every hour, a 1 mL sample was taken and measured at 395 nm and 600 nm to obtain measurements of both the signal of sGFP and the total concentration of bacteria, respectively. Fluorescence and optical density were compared across all samples to understand growth characteristics and sGFP production. The results indicated that protein production only slightly diminished the competitive growth of *S. epidermidis*-GFP relative to *S. epidermidis*-Chl as determined by fluorescence and CFU measurements.

Quantification of the Growth of *S. epidermidis*-GFP and Control Strains on RHE.

In order to characterize the feasibility of applying bacteria to the skin, the growth dynamics of externally applied bacteria on an in vitro skin model was determined, with the understanding that this is only a first approximation of the ecological competition these bacteria would encounter on the skin of a human. Assays began two days after receiving the differentiated culture, in order to allow the culture to achieve stability after shipment. RHE cultures were established and maintained in antibiotic- and antifungal-free media (supplemented with Chl as needed) that were replaced every two days. Bacteria suspended in 50% glycerol were applied with a pipette to the center 3 mm diameter of the RHE. Control RHE with *S. epidermidis*-chl and *S. epidermidis*-WT bacteria were also applied and removed alongside the experimental arms. Upon removal from culture, the tissue inserts were homogenized and passed through a 5 µm filter to allow for collection of bacteria flow through. The bacterial suspensions were spun down, resuspended in media, and serially diluted and plated to determine the CFUs of bacteria in the insert. All measurements were normalized by the maximum recovery of bacteria as determined by the CFUs recovered 15 minutes after application.

Qualitative Characterization of the Growth of SE-GFP and Control Strains on RHE.

Assays were designed to obtain spatial and temporal information about *S. epidermidis*-GFP colonization using RHE and the Vivascope. *S. epidermidis*-GFP was applied to RHE, and samples were imaged in reflectance and fluorescence modes in three standardized regions 2 mm×2 mm wide and 100 µm deep using 10 µm steps and linear increase in laser power. Ultrasound gel (Parker Laboratories) was used to preserve the refractive index between the objective and the glass sample plate. Images were analyzed in ImageJ using 'Grid/Collection Stitching' (FIG. 3).

The results indicated that bacteria home to the surface and deep grooves of the stratum corneum layer and are maintained at a constant presence over the course of the experiment.

Importantly, in order to mimic the hyperstructure of damaged skin in atopic dermatitis patients, the RHE was intentionally punctured with a Derma Microneedle device to determine localization of the bacteria in the presence of damaged skin. The results indicated that the bacteria localized to the puncture at depths up to 70 µm (arrows, FIG. 3 (B)-(D)). This suggests that the topically applied bacteria are able to hone to areas of damaged skin.

These studies were repeated in vivo. Specifically, SE-GFP was applied, to which light and in vivo two-photon microscopy was performed three days following application. At different depths, ranging from 25 µm in the mouse ear to 80 µm in shaved mouse dorsal skin (FIG. 4), the results indicated that there was sustained and pervasive GFP expression, demonstrating *S. epidermidis*-GFP's ability to colonize to the deepest layers of the stratum corneum (10-40 µm), and further colonize the hair follicles of the mice.

Example 3: The Characterization of the Delivery of Bacterially Secreted sGFP to the Skin Using an In Vitro Model System Characterization of the Production of sGFP in SE.

Characterization of the Delivery of Bulk Purified sGFP and sGFP+RMR to RHE.

Data regarding the localization of purified sGFP and sGFP+RMR would facilitate an understanding of: (i) whether sGFP+RMR penetrates the stratum corneum; (ii) if there is penetration, how deeply the penetration can be detected; and; (iii) the kinetic characteristics of penetration. Here, 5.0 µg/µL of GFP+/−RMR was applied at time points 0, 2, 6, 12, 18, and 24 hours to determine the effect of dosage on the penetration and time. The results indicated that GFP was detected as deep as the epidermal-dermal junction within 30 minutes after application.

Characterization of the Cellular Compartment and Depth of Penetration of In Situ Secreted sGFP Protein from SE-GFP Reporter and Control Strains.

The goal of this assay is similar to that as described above, except for the critical difference that the protein is being made in situ by SE-sGFP$^{RMR/SecA}$ and SE-sGFP$^{SecA}$, and compared to controls strains on the RHE. The same methods described herein were used to characterize the dynamics of sGFP penetration into the RHE. The Vivascope provided useful information on the penetration of sGFP over larger surface areas, while the use of IHC allowed for finer discrimination. IHC methods can detect GFP-positive regions relative to SE peptidoglycan-positive regions, so that secreted sGFP can be discriminated from the sGFP signal in the bacteria. (FIG. 5)

Non fluorescence based detection of therapeutic proteins. The therapeutic proteins ultimately delivered are not be fluorescent, and further, suitable antibodies to characterize their delivery to epidermis may not be available. Proteomic analysis of tape strips of the stratum corneum has been used to characterize differences in in vivo protein profiles from patients with atopic dermatitis (Sakabe, J., et al. *The Journal of allergy and clinical immunology*. 2014; 134(4):957-960 e958) and ichthyosis (Rice, R. H., et al. *PloS one*. 2013; 8(10):e75355). Moreover, inside-out, horizontal sections of skin biopsies may be used to demonstrate that low abundance molecules can be identified after penetrating the stratum corneum.

Example 4: Evaluate Pharmacokinetics (PK) and Pharmacodynamics (PD) of AZT-01 in Mice (Non-GLP)

A genetic atopic dermatitis mouse construct (flaky tail mice) was used to assess the PK/PD of AZT-01, while the PK of AZT-01 was assessed in healthy mice. In order to evaluate the PD, AZT-01 was topically applied to mice and the PD was assessed via phenotypic (erythema, edema, excoriation, dryness, and transepidermal water loss) and histological changes (skin barrier recapitulation, fibrosis, CD4+ T cells, etc.). To evaluate the PK, the distribution of AZT-01 and filaggrin was examined, and the colonization patterns were characterized. Changes in the skin microbiome were assessed.

Atopic dermatitis mouse models. In order to investigate the applicability of the approach, two model mouse systems were used: the filaggrin knockout mouse (flg−/−) and the flaky tail mouse (ft/ft). A thorough review of atopic the dermatitis model mice is presented by Geha et. al. (Vavrova K., et al. The Journal of Invest. Dermat. 2014; 134(3):746-

753.). Briefly, flg−/− mice exhibit dry, scaly skin. Despite marked decreases in natural moisturizing factor levels, which are filaggrin degradation products, stratum corneum (SC) hydration and transepidermal water loss (TEWL) were normal in flg−/− mice. Antigens penetrated the flg−/− SC more efficiently, leading to enhanced responses in hapten-induced contact hypersensitivity and higher serum levels of anti-ovalbumin IgG(1) and IgE. As such, the mouse ear was sensitized using OVA antigen.

Ft/ft mice possess two distinct autosomal recessive mutations, hair abnormality (matted: ma) and SC layer abnormality (flaky tail: ft). These mice developed dermatitis spontaneously with high serum IgE even under specific pathogen free conditions. Flaky tail mice also possess the loss of function mutation in Filaggrin (Flg) and demonstrated skin barrier abnormality as well as increased TEWL and SC hydration.

Study design. The study was conducted for four weeks using four arms in both types of mice (Flg−/− and ft/ft). Mice were randomized into the following treatment groups: topical vehicle control (50% glycerol, 50% sterilized BHI medium), topical recombinant filaggrin (purified recombinant filaggrin in 50 μg/ml), topical wild type *Staphylococcus Epidermidis* (SE) ($1.0 \times 10^9$ CFU in 50% glycerol), and topical SE FLG ($1.0 \times 10^9$ CFU in 50% glycerol). Each solution was applied to the same ear on each mouse on days 0, 7, 14, and 21, and mice were also assessed on these days before application of the appropriate solution. Final assessment occurred on day 28 after which point the mice was sacrificed according to the appropriate animal protocols. The primary outcome (described in detail below) is the change in clinical disease score, which assessed macroscopic changes in disease presentation.

Based on a sample size estimate using standard deviation of 2.5, power of 90%, and type I error of 0.05, 8 mice per arm per genotype was required in order to detect a mean change of 4 points in the clinical disease score between groups. This means that a total of 32 mice per genotype (for a total of 64 mice) were needed for the study.

TABLE 2

Clinical outcome measures

| Component | Values | Description |
| --- | --- | --- |
| Primary outcome: composite clinical disease score (macroscopic observations) | | |
| Erythema | 0 to 4 | 0 - not visible, 2 - mild, |
| Edema | 0 to 4 | 2 - moderate, 3 - evere |
| Excoriation | 0 to 4 | |
| Dryness | 0 to 4 | |
| Total: | 0 to 16 | Sum of four components |
| Secondary outcomes | | |
| Infiltrated lymphocytes | Qualitative | Cell types will be indicated via histology |
| Fibrosis | 0 to 4 | 0 - not visible, 2 - mild, 2 - moderate, 3 - severe |
| TEWL | Continuous | Measured by TEWL meter |
| Skin barrier permeability | Continuous | Measured by calcein assay |

Primary outcome: Clinical disease score. In order to measure the effect of treatment on the macroscopic and microscopic changes associated with treatment of $SE^{FLG}$, a clinical score based on previous studies was used (see, e.g., Matsuoka H., et al. *Allergy*. 2003; 58(2):139-145, and Kim, M. C., et al. *Journal of acupuncture and meridian studies*. 2013; 6(2):98-109). The composite clinical disease score is the sum of the degree of severity of erythema, edema, excoriation and dryness on the ear surface was scored as 0 (not visible), 1 (mild), 2 (moderate) and 3 (severe), accordingly. Scoring was performed by individual who was blinded to treatment status of each group. Skin was photographed every 7 days. Additionally, TEWL was measured by a TEWL meter (Khazaka Electronic). Finally, the methods described in Kawasaki (i.e., Kawasaki, H. et al. *The Journal of allergy and clinical immunology*. 2012; 129(6):1538-1546.e1536) were used to assess the resolution of the skin barrier and its ability to prevent the permeation of foreign material past the *Stratum corneum* (SC). Calcein Bis[N,Nbis (carboxymethyl)aminomethyl] fluorescein (Sigma-Aldrich) was mixed with liposome prepared from Presome CSII-101 (Nippon Fine Chemical, Osaka, Japan) and topically applied to regions of the 6- to 8-week-old mice for 3 hours. The tails were then removed and rapidly freeze embedded.

Figure 6A:
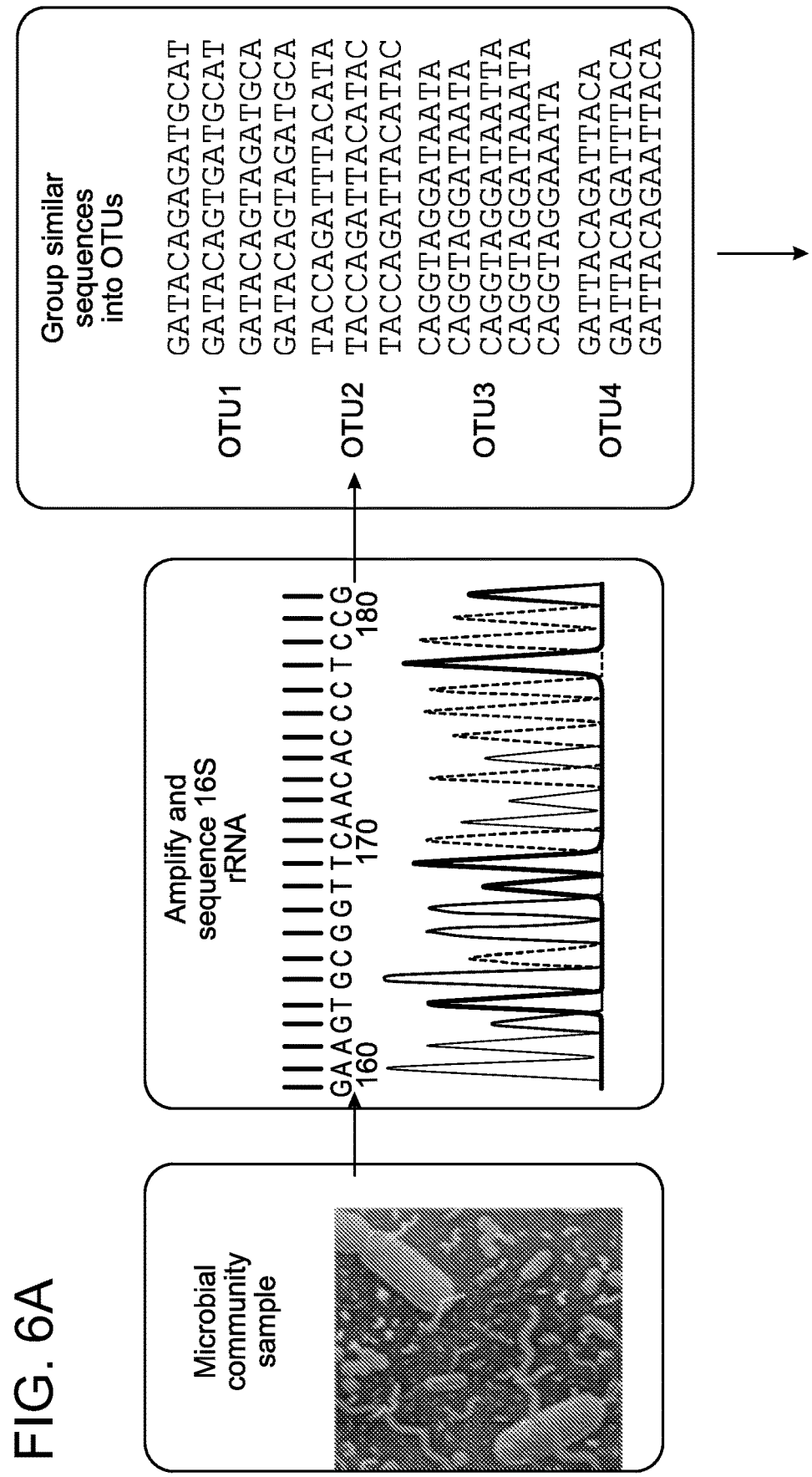
FIGS. 6A-6B depicts the experimental outline of 16S rRNA sequencing.
Figure 6B:
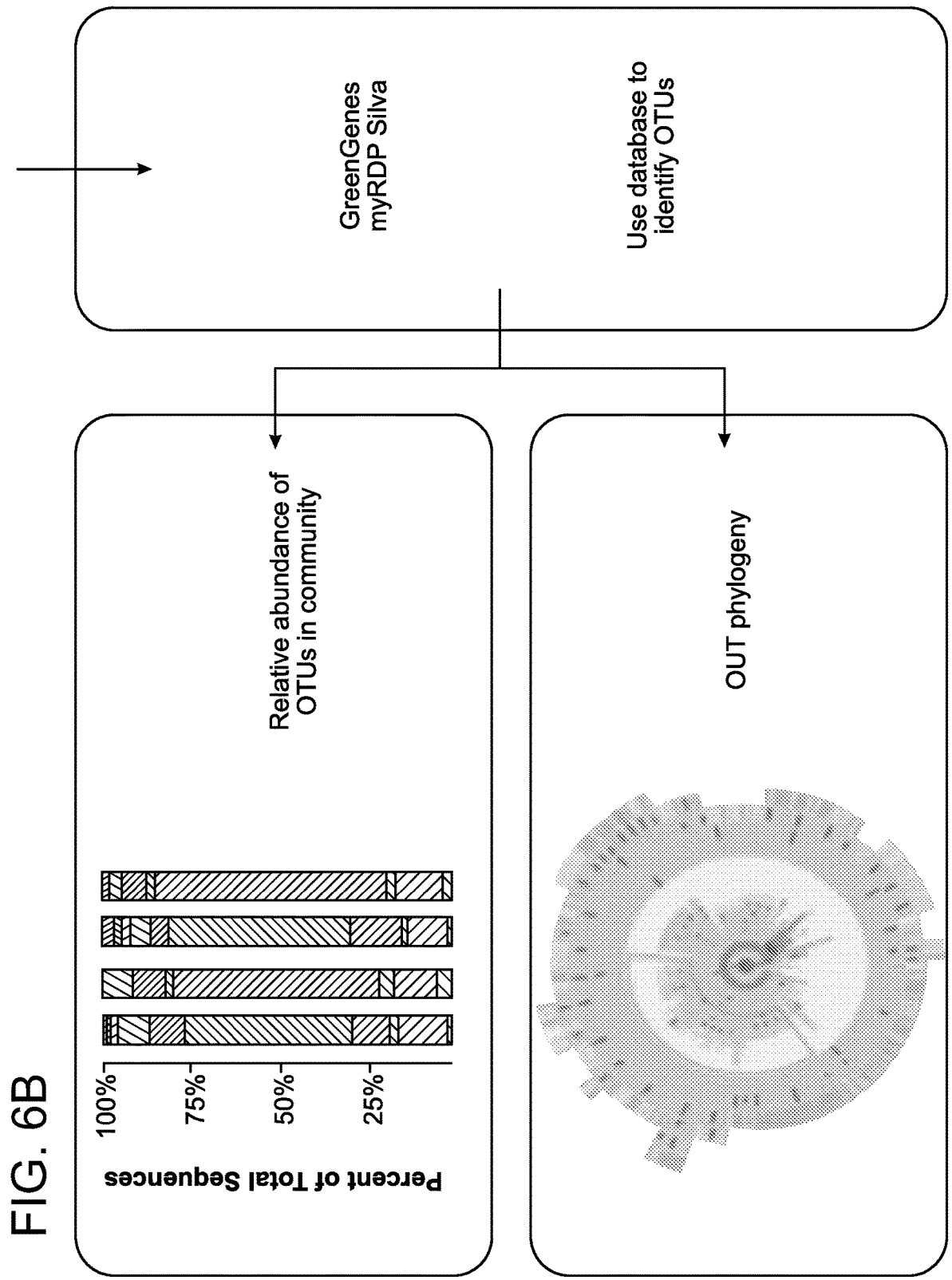

Microbiome characterization after application of AZT-01. In order to understand the influence of the addition of SE on the microbial diversity of the skin microbiome, a combined 16S rRNA was used to measure the changes in the microbial community. This was done using qPCR for RT-PCR and sequencing using the Illumina MiSeq platform at the JAX Genomic Medicine Facility at the Jackson Laboratory. The methods described in Caporaso et al. (Caporaso, J. G., et al. *The ISME journal*. 2012; 6(8):1621-1624) were used to measure the changes in relative abundance of bacteria in the community. Briefly, samples were collected from the skin using cotton swabs and the rRNA was extracted using an rRNA extraction kit (Qiagen), which was then amplified, analyzed with qPCR and sequenced. Subsequently, bioinformatic and statistical methods were used to group similar sequences into operational taxonomic units (OTUs) (FIG. 6).

Dysbiosis was measured using ecological metrics and community structure analyses. First, dysbiosis was assessed as a function of diversity using the Shannon Diversity Index, which is an ecological measure of microbial communities that considers and was compared before and after application. Additionally, community structures of the local microbiome was compared before and after treatment. Dysbiosis was then measured as % overall deviation from (i) the baseline microbiome, and (ii) deviation from the mean community structure across our controls using statistics such as the Yue-Clayton index that compares community structures. Finally, microbiome trends was analyzed on a per-species level. The longitudinal dynamics of each species was also tracked over the treatments, to identify whether species are being lost from the community.

Immunohistochemistry studies. Filaggrin was visualized and quantified using immunocytochemistry by comparing AZT-01 to a vehicle control. Keratinocytes cells were fixed with 70% ethanol, 50 mM glycine for 1 hour. Immunofluorescence staining was performed by incubation of anti-filaggrin primary antibody at 1:200 for 2 hours, followed by incubation with rat anti-goat rhodamine secondary antibody (Jackson Laboratory) at 1:200 dilutions in the presence of Hoechst Stain Solution (Sigma). Slides were mounted with coverslips in Gel/Mount (Biomed). In addition, alternative sequences was created and tested in the place of the RMR signal (e.g., endosomal escape peptides such as those described in Appelbaum et al. 2012, incorporated by reference herein in its entirety (Appelbaum, J. S., et al. *Chemistry & biology*. 2012; 19(7):819-830).

Statistical analyses. The differences between groups for the primary outcome and/or the macroscopic clinical disease score, were assessed using two-sided student T-tests. The differences across groups were assessed using ANOVA. The same technique will be used for assessing the TEWL and the thickening of the epidermis. The differences in non-parametric continuous variables were assessed using Mann-Whitney U tests. Finally, the differences in ordinal variables were assessed using Chi-square tests.

For analyses of the microbiome, community variation among samples were calculated using the quantitative, taxonomy-based Canberra distance. Discriminant analysis of within-group similarity were conducted using permutational MANOVA. To determine whether skin microbial communities became more similar to one another, we used a 0-dispersion test with the betadisper function in vegan. This test is a multivariate analog of Levene's test for homogeneity of variances, and tests for a significant difference in sample heterogeneity between groups (Anderson, M. J., et al. *Ecology Letters*. 2006; 9(6):683-693). P-values for significant indicators were adjusted for multiple comparisons using Holm's correction (Holm S. *Scandinavian Journal of Statistics*. 1979; 6(2):65-70).

Immunofluorescence Microscopy. Immunofluorescence microscopy was used to visualize filaggrin localization. Mouse skin samples were fixed in 10% formalin and paraffin embedded. Paraffin sections were dewaxed and washed with 95% ethanol followed by methanol hydrogen peroxide. The sections were then treated with a heat induced epitope retrieval (HIER) procedure using rodent Decloaker solution (Biocare Medical, RD913) and the Biocare decloaking chamber. After being washed in Tris pH 7.4, sections were incubated in the presence of rat serum and FcBlock (24G2) followed by rabbit anti-*Escherichia coli* B (DAKO, B0357) diluted in the blocking solution. Samples were washed in Tris and then incubated with goat anti-rabbit IgG-Texas Red antibody (Invitrogen, T2767). The tissue was then counterstained with HOECSHT, and imaged using a Leica DM IRBE fluorescent microscope.

Example 5: AZT-01 and its Effects on Local and Systemic Inflammation and Immunity in Rats (Non-GLP)

To evaluate toxicology, local tissue samples, serum samples, and lymph node samples of euthanized topically treated rats at specified time points were analyzed. The tissues were analyzed for histologic changes in inflammatory activity (e.g., quantification CD4+ T cells, Langerhans cells, IgE, IL-4, IFN-γ, etc.) as well as activity and changes in the cutaneous immune response (e.g., quantitation of IL-4, IL-10, IL-13, etc.). Clinical signs of potential side effects related to the use of therapy including erythema, skin temperature changes, edema, blistering, and ulcerations were also monitored.

Histological evaluation. Excised ears of each group were fixed in 4% paraformaldehyde for 16 h and were embedded in paraffin. Subsequently, 6 μm sections were stained with hematoxylin (Sigma Aldrich, St Louis, MO, USA) and eosin (Sigma Aldrich, St Louis, MO, USA) (H&E). Infiltrated lymphocytes and fibrosis in the dermis were observed by microscope (100×, 200×).

Disease-relevant mRNA transcript quantification. Variable expression of genes associated with atopic dermatitis development, progression, and maintenance (AD-associated pathogenic cytokines (e.g., IL-4, IL-5, IL-13, INF-γ, IL-17, IL-10 and TNF-α)) were measured by standard qPCR assays. Briefly, total RNA from the skin samples were isolated using the Qiagen RNeasy Mini Kit (Qiagen, Valencia, CA) following the manufacturer's instructions. The respective cDNA were synthesized using reverse transcriptase PCR (RT-PCR). Real-time PCR was performed using the comparative 2-ΔΔCT method and was normalized to Glyceraldehyde 3-phosphate dehydrogenase (GAPDH) transcript levels.

Immunological changes after application of AZT-01. Cells from areas of bacterial application as well as areas in which bacteria were not applied were isolated to study immunological changes. Keratinocytes, epidermal cells, cells from the lymph nodes, and small intestine lamina propria were isolated. Single cell suspensions were stained with either LIVE/DEAD Fixable Blue Dead Cell Stain Kit (Invitrogen) or with 4', 6-diamidino-2-phenylindol (DAPI, Sigma) in HBSS to exclude dead cells. For detection of transcription factors, cells were stained using the Foxp3 staining set (eBioscience) according to the manufacturer's protocol. For detection of intracellular cytokines, cells were fixed and permeabilized with BD Cytofix/Cytoperm and stained in BD Perm Wash buffer (BD Biosciences). Cells were stained with the following antibodies purchased from either eBioscience, BD Biosciences, or Dendritics Ccorp: CD4, IL-10, IL-17A, IFN-γ, TNF-α, Foxp3, CD34, CD44 and/or CD25. Staining was performed in the presence of FcBlock (eBioscience), 0.2 mg/ml purified rat IgG and 1 mg/ml of normal mouse serum (Jackson Immunoresearch). Stain for skin homing markers was performed as previously described (Lopes, L. B., et al. Pharm Res. 2005; 22(5):750-757). As a measure of safety, signs of AZT-01 becoming blood-borne was monitored by taking samples of skin-draining lymph nodes (DLNs) and the spleen of one mouse after two weeks of application of AZT-01. Briefly, the mouse was placed in 70% EtOH and moved to a laminar flow hood. After 1-2 minutes in EtOH, DLNs and spleen was isolated in a 50-mL conical tube with a 70 μm strainer and was processed as separate samples. The organs were dissociated with 500 μl of sterile PBS, and 50-100 μl of cell suspension was cultured on BHI agar media.

Example 6: Conduct Initial Formulation and Analytical Method Development to Evaluate a Proposed Set of Specifications for the Active Pharmaceutical Ingredient (API) and the Drug Product (DP)

Critical to the clinical development of a live biotherapeutic product (LBP; e.g., AZT-01) is developing a useful formulation and practical analytical assays given the unique nature of LBPs as active pharmaceutical ingredient (API) or drug product (DP) over traditional small molecules. A formulation will be developed for the API to produce the DP, and analytical methods will be developed for both the API and the DP stability to establish the specifications of GMP material for clinical studies.

Statistical analyses. Unless otherwise indicated, experiments were performed in triplicates, and means and standard deviations were be reported. For comparisons between groups, two-sided t-test or analysis of variance was used. If data were not normally distributed, the data were replaced with non-parametric equivalents (Wilcoxon-rank sum and Kruskal-Wallis tests).

Example 7: Hydrophobicity Analysis

Figure 7:
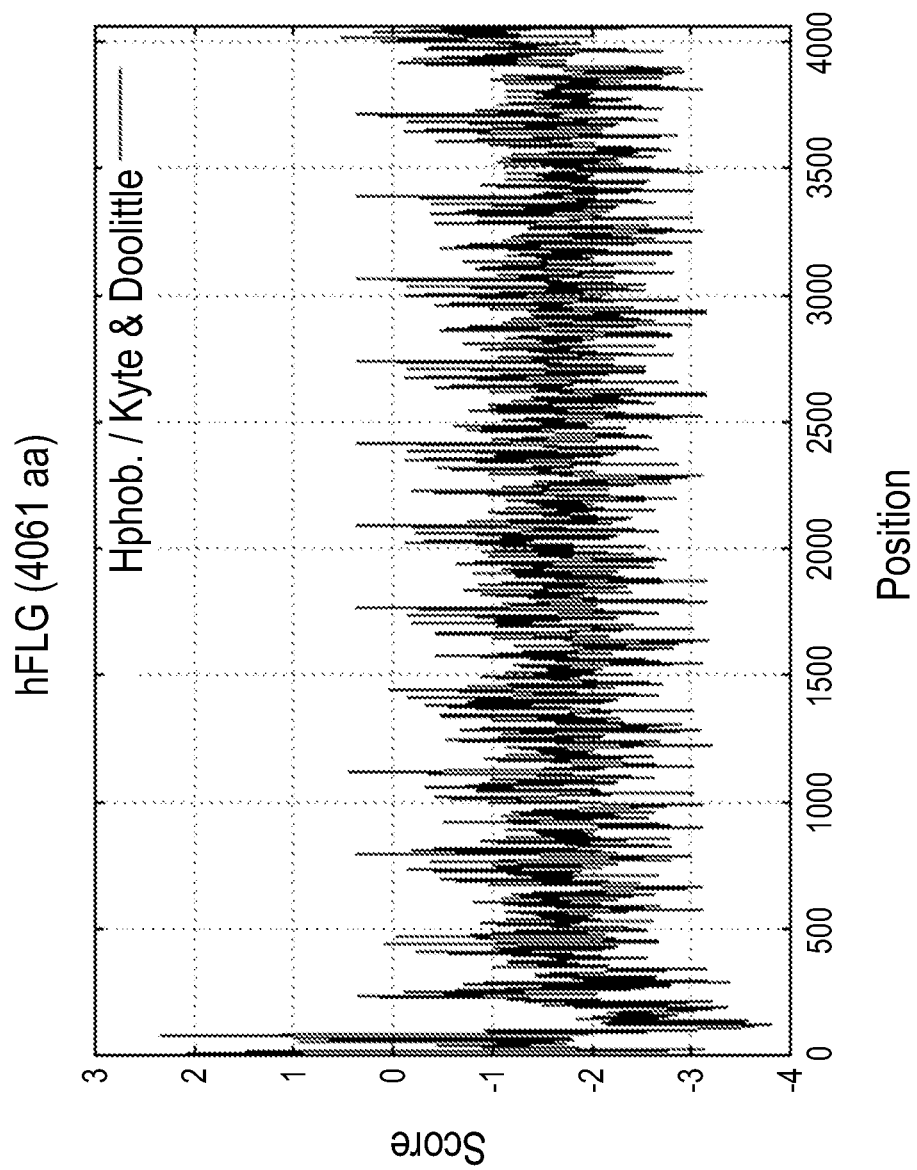
FIG. 7 is a graph that shows hydrophobicity score as a function of amino acid position for the entire human filaggrin (hFLG) sequence (Uniprot P20930).
Figure 8:
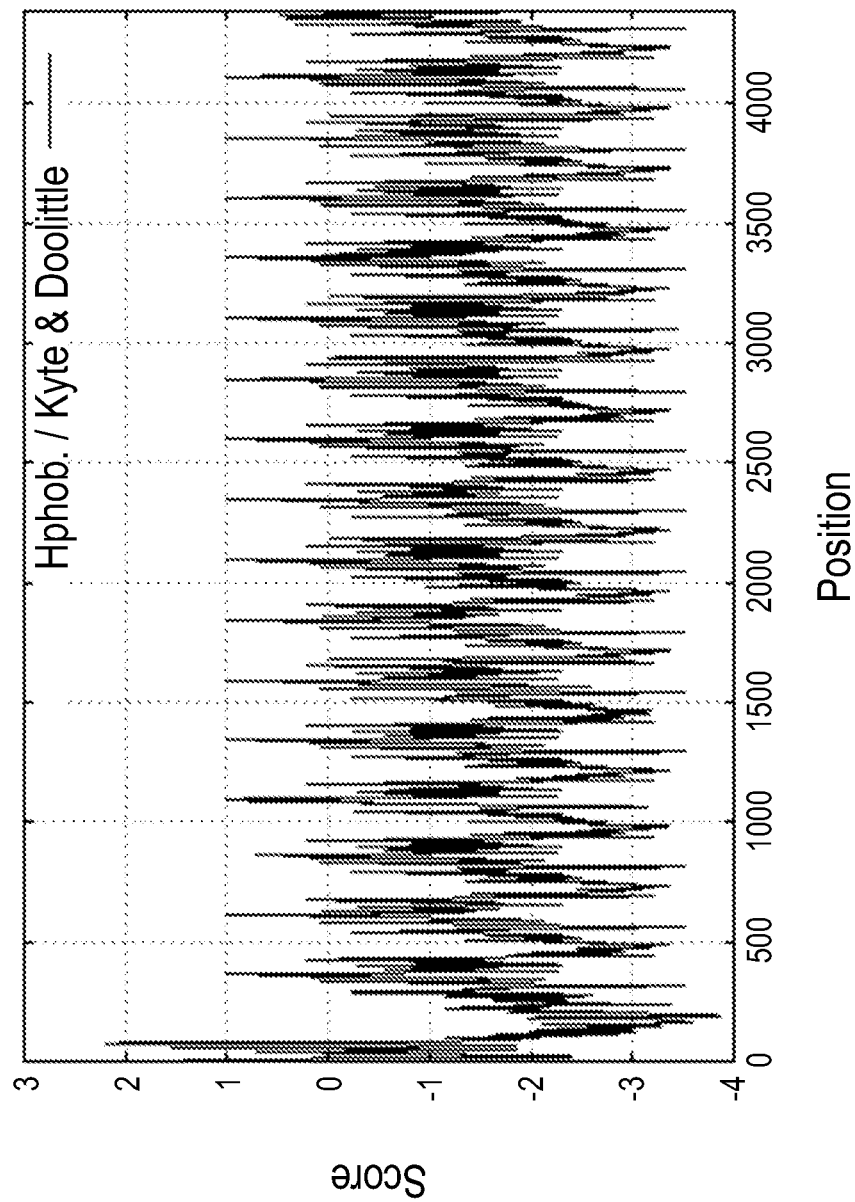
FIG. 8 is a graph that shows hydrophobicity score as a function of amino acid position for the entire mouse filaggrin (mFLG) sequence (NCBI Reference Sequence: XP_017175331.1).

Human filaggrin (hFLG) is comprised of 12 repeating units and is processed by intracellular proteases to release the individual units. The sequences within these units are highly homologous. It has been proposed that the units are cleaved at "linker regions." The segments between these linker regions are the individual units, with each unit containing a pair of sub-domains. The entire human filaggrin (hFLG) sequence (Uniprot P20930) was analyzed using the on-line Kite-Doolittle calculation tool, available at (web.expasy.org/protscale/. The hydrophobicity score as a function of amino acid position graph is shown in FIG. 7. As shown in FIG. 7, there is a periodic increase in hydrophobicity. The Kite-Doolittle score gave the highest differential between the highest and lowest values. When compared to the mouse filaggrin (mFLG) sequence (NCBI Reference Sequence: XP_017175331.1) shown in FIG. 8, a much higher differential of hydrophobicity scores is seen. This is due to the nature of the proteins from the different organisms.

The molecular regions of interest were examined further. It was found that the distance between the crests which correspond to the more hydrophobic regions was farther in the human filaggrin than in the mouse. Also, the maximum hydrophobicity was found to be higher in the mouse than in human.

Figure 9:
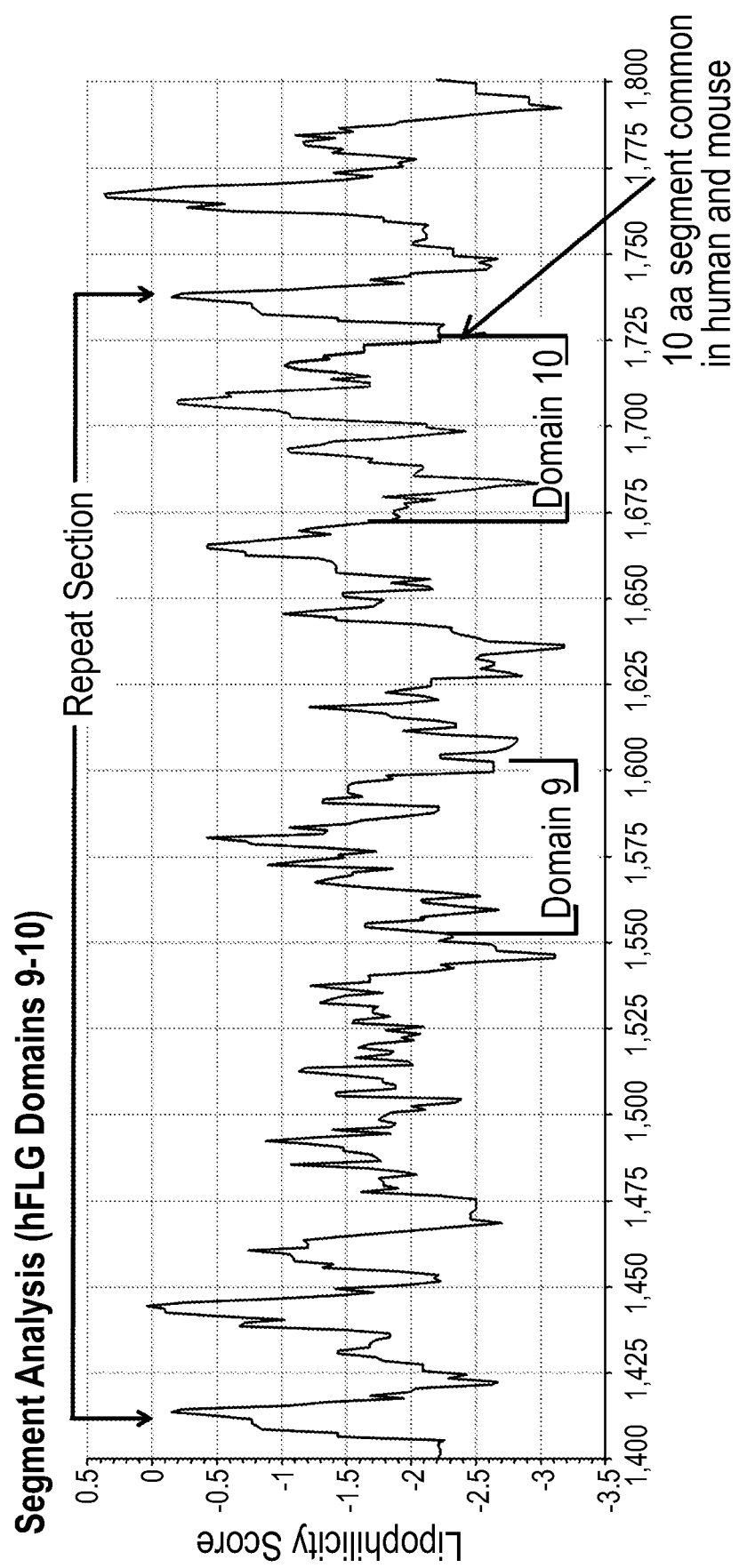
FIG. 9 is a graph that shows hydrophobicity score as a function of amino acid position for the hFLG region starting at amino acid 1400 to 1800 with the unit segment of domains 9 and 10.

Two particular domains of hFLG were of interest, hFLG [domains 5-6] and [domains 9-10]. FIG. 9 shows the region of hFLG starting at amino acid 1400 to 1800, with the unit segment of domains 9 and 10 shown. The repeat end at a peak that comes right after the 10 amino acid segment that is common to human and mouse filaggrin (SGSQASD-SEGHS) (SEQ ID NO: 25) is also shown. The high peaks at positions 1444 and 1767 of the graph correspond to the FLY segments. The peaks at 1679 and 1929 are regions containing poly-tyrosines.

Figure 10:
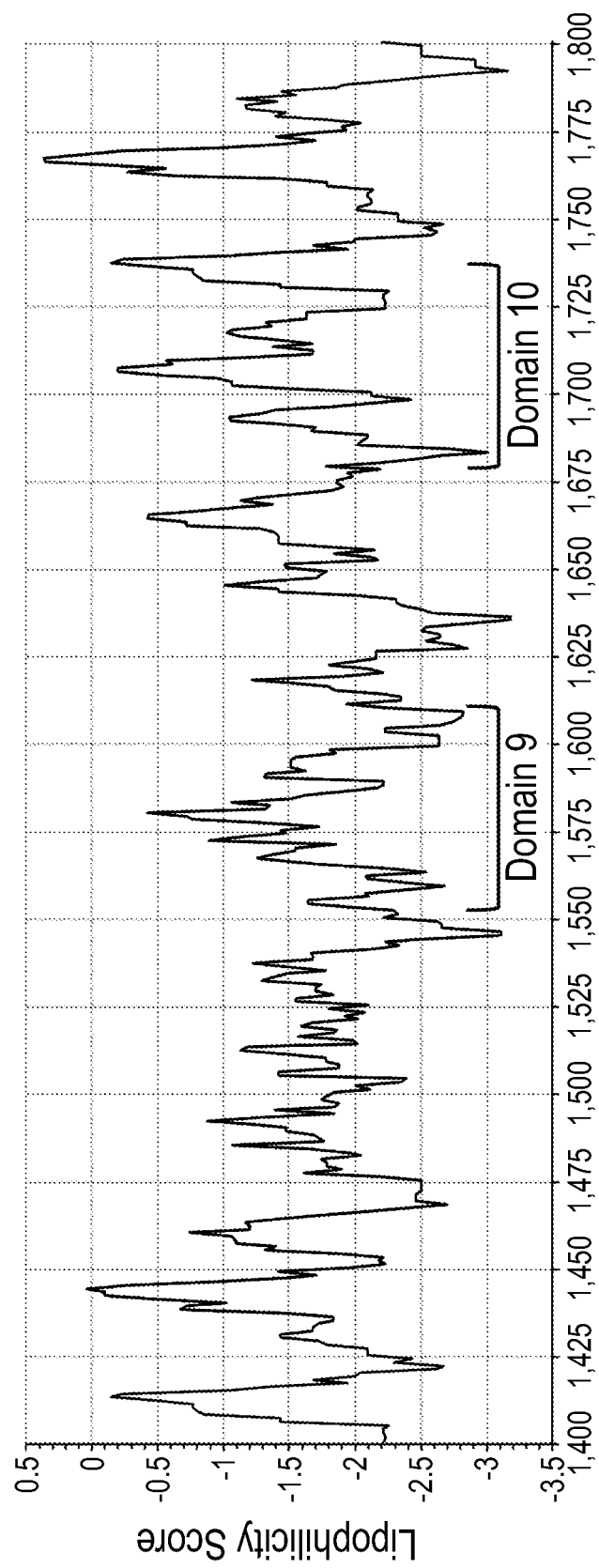
FIG. 10 is a graph that shows hydrophobicity score as a function of amino acid position for hFLG[9-10](1429-1774) from amino acid position 1400 to amino acid position 1800 in hFLG.

The protein hFLG (Domains 9-10) (1429-1774) (SEQ ID NO: 2) represents the high-to-high hydrophobicity segments. The segment is shown in FIG. 10. It contains the FLY segments at both ends of the protein.

```
hFLG[9-10](M-1429-1774)
                                                    SEQ ID NO: 2
                                              1430        1440
                                              MQ SGESSGRSRS 1450       1460       1470       1480       1490       1500
   FLYQVSSHEQ SESTHGQTAP STGGRQGSRH EQARNSSRHS ASQDGQDTIR GHPGSSRGGR 1510       1520       1530       1540       1550       1560
   QGSYHEQSVD RSGHSGYHHS HTTPQGRSDA SHGQSGPRSA SRQTRNEEQS GDGSRHSGSR 1570       1580       1590       1600       1610       1620
   HHEPSTRAGS SRHSQVGQGE SAGSKTSRRQ GSSVSQDRDS EGHSEDSERR SESASRNHYG 1630       1640       1650       1660       1670       1680
   SAREQSRHGS RNPRSHQEDR ASHGHSAESS RQSGTRHAET SSGGQAASSQ EQARSSPGER 1690       1700       1710       1720       1730       1740
   HGSRHQQSAD SSTDSGTGRR QDSSVVGDSG NRGSSGSQAS DSEGHSEESD TQSVSAHGQA 1750       1760       1770       1780
   GPHQQSHQES TRGQSGERSG RSGSFLYQVS THEQ
```

The complete sequence of the protein hFLG (Domains 9-10) (1429-1774) with N-terminus methionine and an RMR segment at C-terminus is shown in SEQ ID NO: 3 (M and RMR are underlined). The repeated sequence QSGEXS-GRSXSFLYQVSXHEQSES (SEQ ID NO: 26) is shown in bold below.

```
hFLG[9-10](M-1429-1774-RMR)
                                                    SEQ ID NO: 3
                                              1430        1440
                                              MQ SGESSGRSRS 1450       1460       1470       1480       1490       1500
   FLYQVSSHEQ SESTHGQTAP STGGRQGSRH EQARNSSRHS ASQDGQDTIR GHPGSSRGGR 1510       1520       1530       1540       1550       1560
   QGSYHEQSVD RSGHSGYHHS HTTPQGRSDA SHGQSGPRSA SRQTRNEEQS GDGSRHSGSR 1570       1580       1590       1600       1610       1620
   HHEPSTRAGS SRHSQVGQGE SAGSKTSRRQ GSSVSQDRDS EGHSEDSERR SESASRNHYG 1630       1640       1650       1660       1670       1680
   SAREQSRHGS RNPRSHQEDR ASHGHSAESS RQSGTRHAET SSGGQAASSQ EQARSSPGER 1690       1700       1710       1720       1730       1740
   HGSRHQQSAD SSTDSGTGRR QDSSVVGDSG NRGSSGSQAS DSEGHSEESD TQSVSAHGQA 1750       1760       1770       1780
   GPHQQSHQES TRGQSGERSG RSGSFLYQVS THEQRMPRMR PMRR
```

It was found that repeating the FLY segments may not be required for activity, and further, it may be a burden for bacteria and may be the source of the lack of production in a Gram positive organism.

FIG. 10 is a graph that shows hydrophobicity score as a function of amino acid position for hFLG[9-10](1429-1774) from amino acid position 1400 to amino acid position 1800 in hFLG.

Example 8. New Protein Structures Based on Hydrophobicity Analysis hFLG [Domains 9-10]

Next, hFLG [domain 9-10] proteins with systematically shaved off regions of the N-terminus were produced.
Selection of Segment Based on "U" Shape ("High-Low-High")

Figure 11:
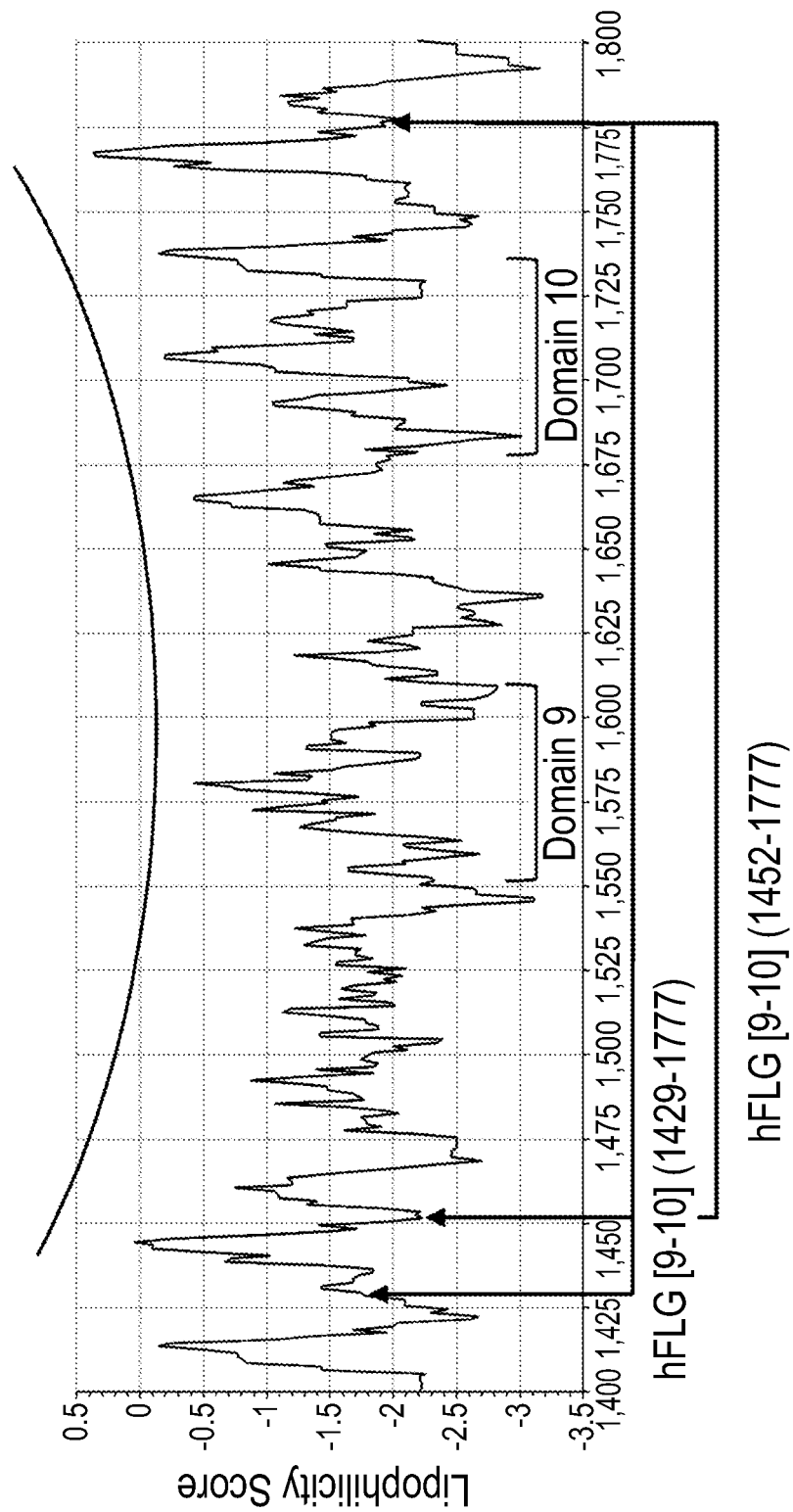
FIG. 11 is a graph that shows hydrophobicity score as a function of amino acid position for the start and end positions of the hFLG [9-10] (1429-1777).

The graph in FIG. 11 shows that the start and end positions of the hFLG [9-10] 1429-1777) (SEQ ID NO: 2) may be too long. Therefore, the N-terminal FLY segment was cut to make hFLG [9-10] (1452-1777) (SEQ ID NO: 4) to prevent unwanted recombination events.

```
hFLG[9-10](1452-1777)-RMR
                                                    SEQ ID NO: 4
            1460       1470       1480       1490       1500
         MESTHGQTAP STGGRQGSRH EQARNSSRHS ASQDGQDTIR GHPGSSRGGF 1510       1520       1530       1540       1550       1560
QGSYHEQSVD RSGHSGYHHS HTTPQGRSDA SHGQSGPRSA SRQTRNEEQS GDGSRHSGSR 1570       1580       1590       1600       1610       1620
HHEPSTRAGS SRHSQVGQGE SAGSKTSRRQ GSSVSQDRDS EGHSEDSERR SESASRNHYG 1630       1640       1650       1660       1670       1680
SAREQSRHGS RNPRSHQEDR ASHGHSAESS RQSGTRHAET SSGGQAASSQ EQARSSPGER 1690       1700       1710       1720       1730       1740
HGSRHQQSAD SSTDSGTGRR QDSSVVGDSG NRGSSGSQAS DSEGHSEESD TQSVSAHGQA 1750       1760       1770
GPHQQSHQES TRGQSGERSG RSGSFLYQVS THEQSESRMR RMPPMKR
```

Theoretical pI/Mw: 10.65/36162.11
Selection of Segment Based on "Λ" Shape ("Low-High-Low")

Next, the selection of a repeat sequence from a point of low hydrophobicity to the next point of low hydrophobicity was carried out. This segment has the two domains at the N-terminus with the FLY region close to the middle of the sequence. Thus, the "core" sequence containing the domains 9-10 are at an end, rather than in the middle of the sequence. Further, the long intersection repeat sequence is toward the C-terminus of the sequence. This is shown in FIG. 12.

Based on the aforementioned analyses, a protein based on the low-to-low segment hFLG[9-10](1545-1869) was made, shown below as SEQ ID NO: 5.

```
hFLG[9-10](1545-1869)-RMR
                                                    SEQ ID NO: 5
                                                  1550       1560
                                               MRNEEQS GDGSRHSGSR 1570       1580       1590       1600       1610       1620
       HHEPSTRAGS SRHSQVGQGE SAGSKTSRRQ GSSVSQDRDS EGHSEDSERR SESASRNHYG 1630       1640       1650       1660       1670       1680
       SAREQSRHGS RNPRSHQEDR ASHGHSAESS RQSGTRHAET SSGGQAASSQ EQARSSPGER 1690       1700       1710       1720       1730       1740
       HGSRHQQSAD SSTDSGTGRR QDSSVVGDSG NRGSSGSQAS DSEGHSEESD TQSVSAHGQA 1750       1760       1770       1780       1790       1800
       GPHQQSHQES TRGQSGERSG RSGSFLYQVS THEQSESAHG RTGPSTGGRQ RSRHEQARDS
```

-continued

```
        1810       1820       1830       1840       1850       1860
SRHSASQEGQ DTIRGHPGSS RGGRQGSHYE QSVDSSGHSG SHHSHTTSQE RSDVSRGQSG

1870
SRSVSRQTRP MKRMPRMRR
```

Theoretical pI/Mw: 11.00/36182.19

The importance of the segment that has no known function will be evaluated by removing it in hFLG[9-10] (1545-1777), shown below as SEQ ID NO: 6.

```
hFLG[9-10](1545-1777)-RMR
                                                   SEQ ID NO: 6
                                              1550       1560
                                              MRNEEQS GDGSRHSGSR 1570       1580       1590       1600       1610       1620
HHEPSTRAGS SRHSQVGQGE SAGSKTSRRQ GSSVSQDRDS EGHSEDSERR SESASRNHYG 1630       1640       1650       1660       1670       1680
SAREQSRHGS RNPRSHQEDR ASHGHSAESS RQSGTRHAET SSGGQAASSQ EQARSSPGER 1690       1700       1710       1720       1730       1740
HGSRHQQSAD SSTDSGTGRR QDSSVVGDSG NRGSSGSQAS DSEGHSEESD TQSVSAHGQA 1750       1760       1770
GPHQQSHQES TRGQSGERSG RSGSFLYQVS THEQSESRMR RMRRMRR
```

Theoretical pI/Mw: 10.07/26329.02

It is further contemplated that on hFLG[9-10](1452-1777) (SEQ ID NO: 2), the N-terminus region would be knocked off.

Example 9. Filaggrin (M-AZT-Mutein-RMR)

The hFLG[9-10] sequence (SEQ ID NO: 1) was subjected to a BLAST analysis:
Filaggrin [*Homo sapiens*]
Sequence ID: NP_002007.1
Length: 4061 Number of Matches: 16
Range 1: 1430 to 1774

| Alignment statistics for match #1 | | | | | |
|---|---|---|---|---|---|
| Score | Expect | Method | Identities | Positives | Gaps |
| 625 bits(1611) | 0.0 | Compositional matrix adjust. | 345/345(100%) | 345/345(100%) | 0/345(0%) |

```
Query     1  QSGESSGRSRSFLYQVSSHEQSESTHGQTAPSTGGRQGSRHEQARNSSRHSASQDGQDTI    60
             QSGESSGRSRSFLYQVSSHEQSESTHGQTAPSTGGRQGSRHEQARNSSRHSASQDGQDTI
Sbjct  1430  QSGESSGRSRSFLYQVSSHEQSESTHGQTAPSTGGRQGSRHEQARNSSRHSASQDGQDTI  1489

Query    61  RGHPGSSRGGRQGSYHEQSVDRSGHSGYHHSHTTPQGRSDASHGQSGPRSASRQTRNEEQ   120
             RGHPGSSRGGRQGSYHEQSVDRSGHSGYHHSHTTPQGRSDASHGQSGPRSASRQTRNEEQ
Sbjct  1490  RGHPGSSRGGRQGSYHEQSVDRSGHSGYHHSHTTPQGRSDASHGQSGPRSASRQTRNEEQ  1549

Query   121  SGDGSRHSGSRHHEPSTRAGSSRHSQVGQGESAGSKTSRRQGSSVSQDRDSEGHSEDSER   180
             SGDGSRHSGSRHHEPSTRAGSSRHSQVGQGESAGSKTSRRQGSSVSQDRDSEGHSEDSER
Sbjct  1550  SGDGSRHSGSRHHEPSTRAGSSRHSQVGQGESAGSKTSRRQGSSVSQDRDSEGHSEDSER  1609

Query   181  RSESASRNHYGSAREQSRHGSRNPRSHQEDRASHGHSAESSRQSGTRHAETSSGGQAASS   240
             RSESASRNHYGSAREQSRHGSRNPRSHQEDRASHGHSAESSRQSGTRHAETSSGGQAASS
```

| Alignment statistics for match #1 | | | |
|---|---|---|---|
| Sbjct | 1610 | RSESASRNHYGSAREQSRHGSRNPRSHQEDRASHGHSAESSRQSGTRHAETSSGGQAASS | 1669 |
| Query | 241 | QEQARSSPGERHGSRHQQSADSSTDSGTGRRQDSSVVGDSGNRGSSGSQASDSEGHSEES | 300 |
|  |  | QEQARSSPGERHGSRHQQSADSSTDSGTGRRQDSSVVGDSGNRGSSGSQASDSEGHSEES |  |
| Sbjct | 1670 | QEQARSSPGERHGSRHQQSADSSTDSGTGRRQDSSVVGDSGNRGSSGSQASDSEGHSEES | 1729 |
| Query | 301 | DTQSVSAHGQAGPHQQSHQESTRGQSGERSGRSGSFLYQVSTHEQ (SEQ ID NO: 27) | 345 |
|  |  | DTQSVSAHGQAGPHQQSHQESTRGQSGERSGRSGSFLYQVSTHEQ (SEQ ID NO: 28) |  |
| Sbjct | 1730 | DTQSVSAHGQAGPHQQSHQESTRGQSGERSGRSGSFLYQVSTHEQ (SEQ ID NO: 27) | 177 |

This sequence was compared to the other hFLG units (FLG[3-4], hFLG[5-6], hFLG[7-8], hFLG[11-12], hFLG [13-14], hFLG[15-16], hFLG[17-18], hFLG[19-20], hFLG [21-22]). The amino acids that were variable were compared and the most common ones were replaced into the [9-10] sequence.

The new sequence (S-FLG) was compared to the original hFLG[9-10] sequence by multiple alignment, shown below:

```
hFLG[9-10]   MQSGESSGRSRSFLYQVSSHEQSESTHGQTAPSTGGRQGSRHEQARNSSRHSASQDGQDT
S-FLG        M------RSRSFLYQVSSHEQSESTHGQTAPSTGGRQGSRHEQARNSSRHSASQDGQDT
                    ******************************************************** hFLG[9-10]   IRGHPGSSRGGRQGSYHEQSVDRSGHSGYHHSHTTPQGRSDASHGQSGPRSASRQTRNEE
S-FLG        IRGHPGSSRGGRQGSYHEQSVDRSGHSGYHHSHTTPQGRSDASHGQSGPRSASRQTRNEE
             ************************************************************ hFLG[9-10]   QSGDGSRHSGSRHHEPSTRAGSSRHSQVGQGESAGSKTSRRQGSSVSQDRDSEGHSEDSE
S-FLG        QSGDGSRHSGSRHHEASTRADSSRHSQVGQGQSSGSRTSRRQGSSVSQDSDSEGHSEDSE
             *************  ****** : :  *********** ******** hFLG[9-10]   RRSGSASRNHYGSAREQSRHGSRNPRSHQEDRASHGHSAESSRQSGTRHAETSSGGQAAS
S-FLG        RRSGSASRNHYGSAQEQSRDGSRHPRSHQEDRASHGHSAESSRQSGTRHAETSSGGQAAS
             * ******:  *:************************************* hFLG[9-10]   SQEQARSSPGERHGSRHQQSADSSTDSGTGRRQDSSVVGDSGNRGSSGSQASDSEGHSEE
S-FLG        SHEQARSSPGERHGSRHQQSADSSRHSGIGHGQASSAVRDSGHRGSSGSQASDSEGHSED
             *:********************** ** *: * **.* ***.*****************:

hFLG[9-10]   SDTQSVSAHGQAGPHQQSHQESTRGQSGERSGRSGSFLYQVSTHEQ---RMRRMRRMRR  (SEQ ID NO: 3)
S-FLG        SDTQSVSAHGQAGPHQQSHQESARGRSGERSGRSGSFLYQVSTHEQSESRMRRMRRMRR  (SEQ ID NO: 8)
             **********************:**:********************   **********
``` hFLG[M-AZT-mutein-RMR](1-352) was created, shown below as SEQ ID NO: 8.

```
hFLG[M-AZT-mutein-RMR](1-352)
         10         20         30         40         50         60
MRSRSFLYQV SSHEQSESTH GQTAPSTGGR QGSRHEQARN SSRHSASQDG QDTIRGHPGS 70         80         90        100        110        120
SRGGRQGSYH EQSVDRSGHS GYHHSHTTPQ GRSDASHGQS GPRSASRQTR NEEQSGDGSR 130        140        150        160        170        180
HSGSRHHEAS TRADSSRHSQ VGQGQSSGSR TSRRQGSSVS QDSDSEGHSE DSERRSGSAS 190        200        210        220        230        240
RNHYGSAQEQ SRDGSRHPRS HQEDRASHGH SAESSRQSGT RHAETSSGGQ AASSHEQARS 250        260        270        280        290        300
SPGERHGSRH QQSADSSRHS GIGHGQASSA VRDSGHRGSS GSQASDSEGH SEDSDTQSVS 310        320        330        340        350
AHGQAGPHQQ SHQESARGRS GERSGRSGSF LYQVSTHEQS ESRMRRMRRM RR
```

The amino acids shown in bold in SEQ ID NO: 8 were modified to the most prevalent amino acid when comparing every FLG unit. Table 3 below shows the amino acid residue in hFLG[9-10] and the corresponding modified amino acid in hFLG[AZT-mutein]. The Ser-Glu-Ser (SES) was re-introduced in the sequence to align with the Kite-Doolittle analysis. The QSGESSG (SEQ ID NO: 29) sequence was removed for the same reason as the SES and was calculated to be frivolous.

TABLE 3

| Position | Amino Acid in hFLG[9-10] | Amino Acid in hFLG[AZT-mutein] |
|---|---|---|
| 130 | P | S |
| 134 | G | D |
| 145 | E | Q |
| 147 | A | S |
| 150 | K | R |
| 163 | R | S |
| 177 | E | G |
| 188 | R | Q |
| 193 | H | D |
| 197 | N | H |
| 235 | Q | H |
| 258 | T | R |
| 259 | D | H |
| 262 | T | I |
| 264 | R | H |
| 265 | R | G |
| 267 | D | A |
| 270 | V | A |
| 272 | G | R |
| 276 | N | H |
| 293 | E | D |
| 316 | T | A |
| 319 | Q | R |
| 340 | S (absent) | S |
| 341 | E (absent) | E |
| 342 | S (absent) | S |

Example 10. Filaggrin Consensus Sequence

A human filaggrin consensus sequence was generated by alignment of filaggrin dimers hFLG[3-4], hFLG[5-6], hFLG[7-8], hFLG[9-10], hFLG[11-12], hFLG[13-14], hFLG[15-16], hFLG[17-18], hFLG[19-20], hFLG[21-22] as shown in FIG. 13. The consensus sequence shown as SEQ ID NO: 9 refers to the sequence formed from the most frequently occurring amino acids shown in the alignment in FIG. 13.

```
                                                 SEQ ID NO: 9
XLYQVSTHXQXDSXHGXTXXSTXXRQXSHXXQAXXXSRHSXSQXGQ   100
DTIRGHPGXXXXGRQGXXXEXXVXXSGHSGXHHSHTTXQXRSDASH
GXSGXRSA

SRXTXXXXQSXDXTRHSXSRHHEXXSXAXXSXHSXXGQXXSXGXRX   200
SRXXGSSXSQDXDSXXHSEDSERXSXSASRNHXGSXXEQXRXGSRX
PXXHXEDR

AXHGHSADXSRKSGTXHXXXSSXGQAASSXEQARSSXGERHGSRHQ   300
XQSADSSXXSGXXHXQXSSAVXDSXXXGXSGSQATXXEGHSEDSDT
QSVSGXGX

XGXHQQSHXESXRXXSGXXSXRSXSFLY                     328
```

Example 11. Keratin Binding Assay to Measure Activity of Filaggrin

A keratin binding assay was used to measure activity of various hFLG[9-10] sequences set forth in SEQ ID NOs 1-9.

Keratin Extraction from Human Callus:
Keratins were extracted from human callus. One to two grams of callus was homogenized in 10 mL 5 mM Tris pH 7.4 with protease inhibitors using a BULLET BLENDER bead beater. Homogenized tissue was centrifuged 10 000 rpm for 20 minutes at 4° C. The resulting pellet was resuspended in 0.05M tris pH 7.4 containing 8 M urea and 0.025 mM β-mercaptoethanol and mixed gently for 2 h at 37° C. The urea lysate was centrifuged 10 000 rpm for 10 minutes. The supernatant was dialyzed against 5 mM Tris pH7.4 overnight at 4° C. allowing the gradual assembly of keratin filaments.

Filaggrin—Keratin Binding Assay:
An aliquot of assembled callus keratin filaments (above section) was centrifuged minutes at 10 000 RPM to remove insoluble contaminants. Wells were coated overnight at 4° C. with specified amount of keratin extract diluted in coating buffer to a final volume of 200 μL. Coating buffer was removed, wells were blocked with 200 μl 5% non-fat dry milk in PBST (PBS+0.05% TWEEN20) and incubated at 37° C. for 2 h. Blocking buffer was removed and a pre-determined amount (1 μg) of the appropriate human recombinant filaggrin protein, diluted in PBST to a final volume of 200 μL, was added and plates were incubated at 37° C. for 2 h. Plates were washed 3 times with 200 μL per well of PBST. For the detection of filaggrin binding, an anti-filaggrin IgY chicken antibody (RL-012-001B antibody 1/1000 in PBST) was added to the wells. For the detection of keratin (controls) 200 μL of a mouse pan-keratin antibody (Type II AE3 Ab at a dilution of 1/500 in PBST) was added to indicated wells. Primary antibodies were incubated at room temperature with shaking for 1 h. Primary antibodies were removed and plates washed 3 times with PBST. To all the wells containing the anti-chicken antibody a secondary alpaca anti-chicken antibody conjugated with horse radish peroxidase (HRP) was added at a dilution of 1/2000 in PBST. Wells containing the anti-keratin antibody received a goat anti-mouse antibody conjugated with HRP at a dilution of 1/500 in PBST. Plates were incubated at room temperature with shaking for 1 h. Plates were washed 3 times with PBST and 100 ul of 1-Step Ultra TMB substrate was added. Plates were incubated at room temperature until the appearance of blue color subsided, 15-20 minutes. The reaction was stopped by adding 100 μL of 2M HCL and absorbances were read on a spectrophotometer at 450-550 nm.

Figure 14:
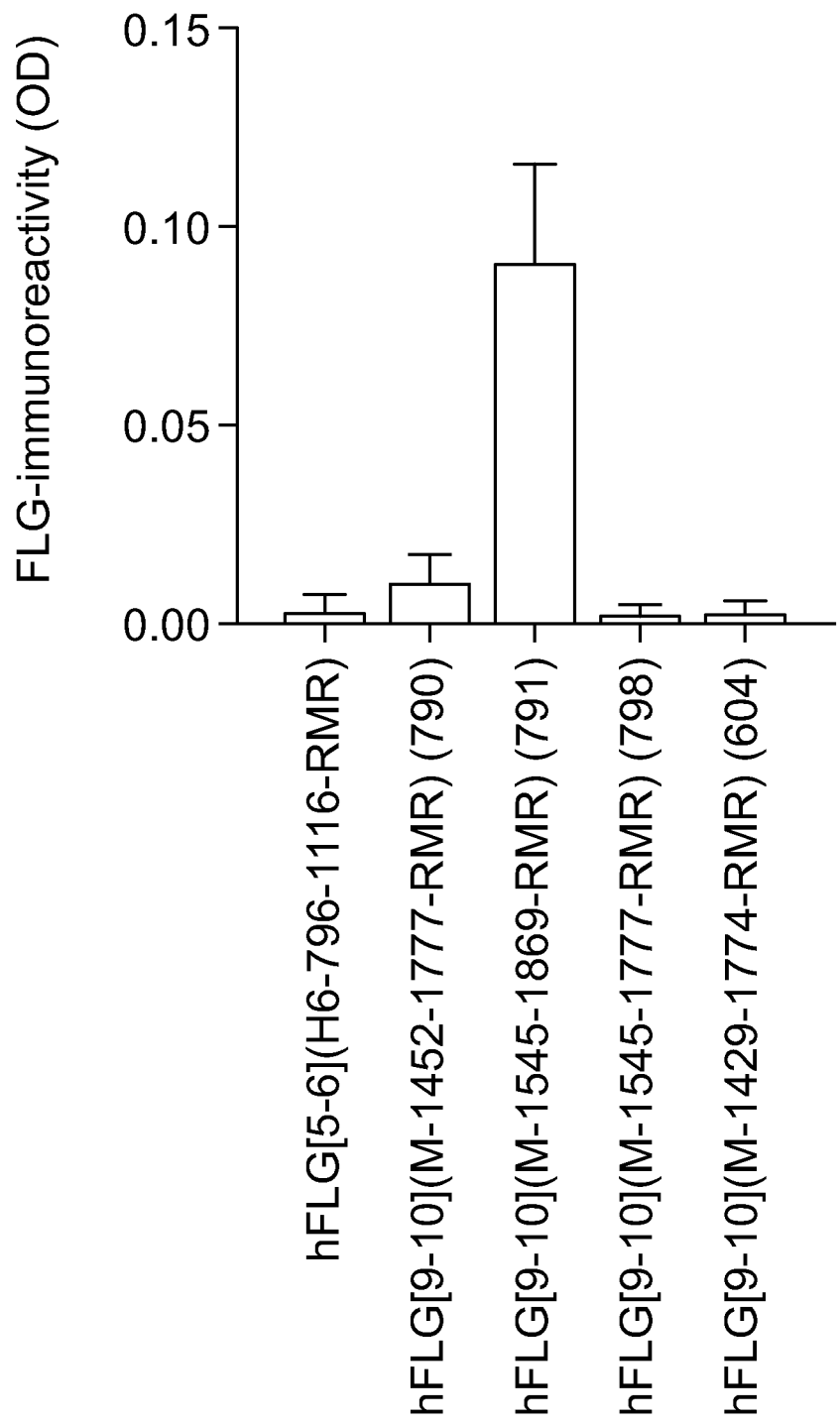
FIG. 14 is a graph that shows background FLG binding at 1 μg/well for 2 h at 37° C. (non specific binding—NSB).
Figure 15:
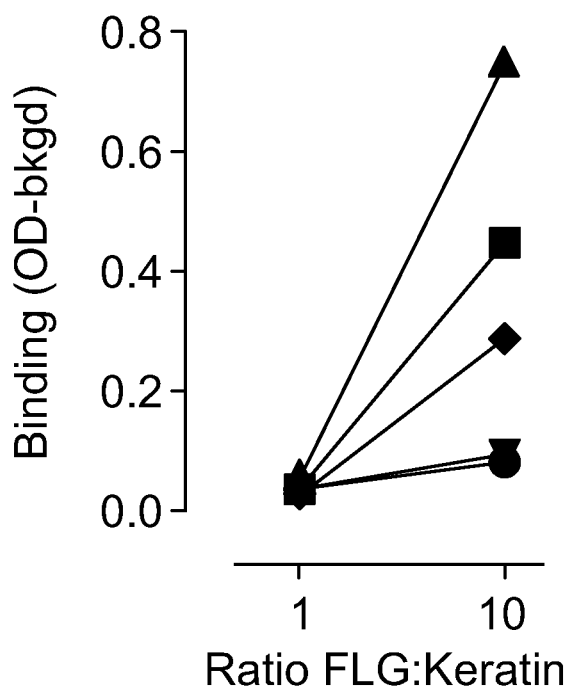
FIG. 15 is a graph that shows binding of hFLG segments to human callus keratin (NSB removed).
Figure 16:
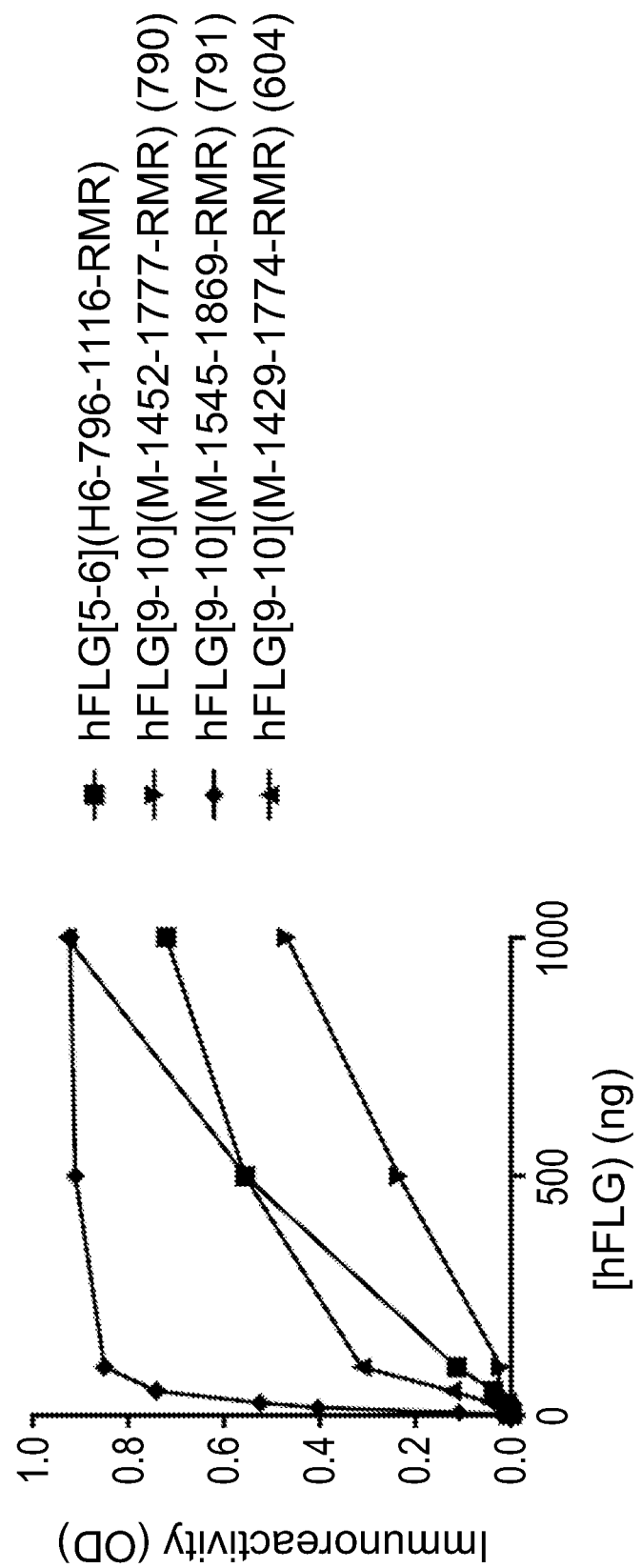
FIG. 16 is a graph that shows titration of IgY anti-hFLG.

The results are shown in FIGS. 14-16, and demonstrate that there was differential binding to keratin among the hFLG sequences tested. FIG. 14 is a graph that shows background FLG binding at 1 μg/well for 2 h at 37° C. The results shown in FIG. 14 include non specific binding (NSB). FIG. 15 is a graph that shows the binding of various hFLG segments to human callus keratin (with NSB removed). FIG. 16 is a graph that shows titration of IgY anti-hFLG. As shown in FIGS. 14-16, hFLG[5-6] did not bind keratin, while the various hFLG[9-10] sequences that were tested showed binding to keratin.

Example 12. Activity of hFLG[9-10]-Secreting SE in Mice

A genetic IV mouse model (Flg−/−) will be used, as well as wild type mice to assess colonization dynamics of FLG-producing SE in vivo. Flg−/− mice are filaggrin deficient and exhibit dry, scaly skin. Despite marked decreases in natural moisturizing factor levels, which are filaggrin degradation products, stratum corneum (SC) hydration and TEWL are normal in Flg−/− mice. Antigens penetrate the Flg−/− SC more efficiently, leading to enhanced responses in hapten-induced contact hypersensitivity and higher serum levels of anti-ovalbumin (OVA) IgG(1) and IgE. Flg−/− mice are obtained from RIKEN BioResource Research Center (RIKEN BRC, Tsukuba, Ibaraki, Japan). Wild type mice (BALB/c) will also be used in this experiment.

The hFLG[9-10] sequences set forth in SEQ ID NOs 1-9 will be used in SE to Flg−/− and BALB/c mice. The study will be conducted for four weeks using five groups in each mouse type. Mice will be assigned into the following treatment groups: topical vehicle control (50% glycerol, 50% sterilized BHI medium), topical wild type SE ($1.0 \times 10^8$ CFU/cm 2 in 50% glycerol), and three doses of each of each filaggrin-secreting SE constructs (SE FLG) ($10^6$, $10^7$, and $10^8$ CFU/cm 2 in 50% glycerol). Each solution will be applied to the same ear and tail on each mouse daily for seven days, and mice be assessed on days 7, 14, 30, and 60 for microbiome analyses to assess colonization dynamics and on days 7 and 14 for microscopy and histology to assess localization and macroscopic changes in the skin (e.g., any signs of adverse events such as inflammation), etc. 12 mice in each arm per mouse type will be used.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant *Staphylococcus epidermidis* bacterium capable of secreting a filaggrin (FLG) polypeptide, wherein the recombinant *Staphylococcus epidermidis* bacterium comprises an expression vector comprising a first coding sequence comprising a gene capable of expressing the filaggrin polypeptide, wherein the filaggrin polypeptide consists of: SEQ ID NO: 46 and a second coding sequence comprising a gene capable of expressing a cell penetrating peptide.

2. The recombinant *Staphylococcus epidermidis* bacterium of claim 1, further comprising a third coding sequence comprising a gene capable of expressing an export signal.

3. The recombinant *Staphylococcus epidermidis* bacterium of claim 1, wherein the *Staphylococcus epidermidis* bacterium secretes a filaggrin fusion protein.

4. A biotherapeutic composition comprising a live recombinant *Staphylococcus epidermidis* bacterium wherein the recombinant *Staphylococcus epidermidis* bacterium comprises (i) a first coding sequence comprising a nucleic acid sequence capable of expressing a therapeutic polypeptide, wherein the therapeutic polypeptide consists of SEQ ID NO: 46;
(ii) a second coding sequence comprising a nucleic acid sequence capable of expressing a cell penetrating peptide;
(iii) a third coding sequence comprising a nucleic acid sequence capable of expressing an export signal; and
(iv) a promoter operably linked to the first coding sequence, the second coding sequence and the third coding sequence, wherein the first coding sequence, the second coding sequence and the third-coding sequence are capable of expressing a filaggrin fusion product.

5. The composition of claim 4, wherein the export signal exports the filaggrin fusion product out of the recombinant bacterium.

6. The composition of claim 4, wherein the cell penetrating peptide facilitates the entry of the filaggrin fusion product into a human keratinocyte.

* * * * *

SEQUENCE LISTING

```
<160> NUMBER OF SEQ ID NOS: 52

<210> SEQ ID NO 1
<211> LENGTH: 4061
<212> TYPE: PRT
<213> ORGANISM: Homo sapiens

<400> SEQUENCE: 1

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Gln Ile Leu Lys Asn Pro
        35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His His Asp Lys His Glu Asp
            100                 105                 110

Asn Lys Gln Glu Glu Asn Lys Glu Asn Arg Lys Arg Pro Ser Ser Leu
        115                 120                 125

Glu Arg Arg Asn Asn Arg Lys Gly Asn Lys Gly Arg Ser Lys Ser Pro
    130                 135                 140

Arg Glu Thr Gly Gly Lys Arg His Glu Ser Ser Ser Glu Lys Lys Glu
145                 150                 155                 160

Arg Lys Gly Tyr Ser Pro Thr His Arg Glu Glu Glu Tyr Gly Lys Asn
                165                 170                 175

His His Asn Ser Ser Lys Lys Glu Lys Asn Lys Thr Glu Asn Thr Arg
            180                 185                 190

Leu Gly Asp Asn Arg Lys Arg Leu Ser Glu Arg Leu Glu Glu Lys Glu
        195                 200                 205

Asp Asn Glu Glu Gly Val Tyr Asp Tyr Glu Asn Thr Gly Arg Met Thr
    210                 215                 220

Gln Lys Trp Ile Gln Ser Gly His Ile Ala Thr Tyr Tyr Thr Ile Gln
225                 230                 235                 240

Asp Glu Ala Tyr Asp Thr Thr Asp Ser Leu Leu Glu Glu Asn Lys Ile
                245                 250                 255

Tyr Glu Arg Ser Arg Ser Ser Asp Gly Lys Ser Ser Ser Gln Val Asn
            260                 265                 270
```

```
Arg Ser Arg His Glu Asn Thr Ser Gln Val Pro Leu Gln Glu Ser Arg
            275                 280                 285

Thr Arg Lys Arg Arg Gly Ser Arg Val Ser Gln Asp Arg Asp Ser Glu
            290                 295                 300

Gly His Ser Glu Asp Ser Glu Arg His Ser Gly Ser Ala Ser Arg Asn
305                 310                 315                 320

His His Gly Ser Ala Trp Glu Gln Ser Arg Asp Gly Ser Arg His Pro
                325                 330                 335

Arg Ser His Asp Glu Asp Arg Ala Ser His Gly His Ser Ala Asp Ser
            340                 345                 350

Ser Arg Gln Ser Gly Thr Arg His Ala Glu Thr Ser Ser Arg Gly Gln
            355                 360                 365

Thr Ala Ser Ser His Glu Gln Ala Arg Ser Ser Pro Gly Glu Arg His
370                 375                 380

Gly Ser Gly His Gln Gln Ser Ala Asp Ser Ser Arg His Ser Ala Thr
385                 390                 395                 400

Gly Arg Gly Gln Ala Ser Ser Ala Val Ser Asp Arg Gly His Arg Gly
                405                 410                 415

Ser Ser Gly Ser Gln Ala Ser Asp Ser Glu Gly His Ser Glu Asn Ser
            420                 425                 430

Asp Thr Gln Ser Val Ser Gly His Gly Lys Ala Gly Leu Arg Gln Gln
            435                 440                 445

Ser His Gln Glu Ser Thr Arg Gly Arg Ser Gly Glu Arg Ser Gly Arg
            450                 455                 460

Ser Gly Ser Ser Leu Tyr Gln Val Ser Thr His Glu Gln Pro Asp Ser
465                 470                 475                 480

Ala His Gly Arg Thr Gly Thr Ser Thr Gly Gly Arg Gln Gly Ser His
                485                 490                 495

His Glu Gln Ala Arg Asp Ser Ser Arg His Ser Ala Ser Gln Glu Gly
            500                 505                 510

Gln Asp Thr Ile Arg Gly His Pro Gly Ser Ser Arg Gly Gly Arg Gln
            515                 520                 525

Gly Ser His His Glu Gln Ser Val Asn Arg Ser Gly His Ser Gly Ser
530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
                565                 570                 575

Ser Gly Asp Gly Thr Arg His Ser Gly Ser Arg His His Glu Ala Ser
            580                 585                 590

Ser Gln Ala Asp Ser Ser Arg His Ser Gln Val Gly Gln Gly Gln Ser
            595                 600                 605

Ser Gly Pro Arg Thr Ser Arg Asn Gln Gly Ser Ser Val Ser Gln Asp
610                 615                 620

Ser Asp Ser Gln Gly His Ser Glu Asp Ser Glu Arg Trp Ser Gly Ser
625                 630                 635                 640

Ala Ser Arg Asn His His Gly Ser Ala Gln Glu Gln Ser Arg Asp Gly
                645                 650                 655

Ser Arg His Pro Arg Ser His His Glu Asp Arg Ala Gly His Gly His
            660                 665                 670

Ser Ala Asp Ser Ser Arg Lys Ser Gly Thr Arg His Thr Gln Asn Ser
            675                 680                 685
```

-continued

```
Ser Ser Gly Gln Ala Ala Ser His Glu Gln Ala Arg Ser Ser Ala
    690                 695                 700
Gly Glu Arg His Gly Ser Arg His Gln Leu Gln Ser Ala Asp Ser Ser
705                 710                 715                 720
Arg His Ser Gly Thr Gly His Gly Gln Ala Ser Ser Ala Val Arg Asp
                725                 730                 735
Ser Gly His Arg Gly Ser Ser Gly Ser Gln Ala Thr Asp Ser Glu Gly
            740                 745                 750
His Ser Glu Asp Ser Asp Thr Gln Ser Val Ser Gly His Gly Gln Ala
        755                 760                 765
Gly His His Gln Gln Ser His Gln Glu Ser Ala Arg Asp Arg Ser Gly
    770                 775                 780
Glu Arg Ser Arg Arg Ser Gly Ser Phe Leu Tyr Gln Val Ser Thr His
785                 790                 795                 800
Lys Gln Ser Glu Ser Ser His Gly Trp Thr Gly Pro Ser Thr Gly Val
                805                 810                 815
Arg Gln Gly Ser His His Glu Gln Ala Arg Asp Asn Ser Arg His Ser
            820                 825                 830
Ala Ser Gln Asp Gly Gln Asp Thr Ile Arg Gly His Pro Gly Ser Ser
        835                 840                 845
Arg Arg Gly Arg Gln Gly Ser His His Glu Gln Ser Val Asp Arg Ser
    850                 855                 860
Gly His Ser Gly Ser His His Ser His Thr Thr Ser Gln Gly Arg Ser
865                 870                 875                 880
Asp Ala Ser Arg Gly Gln Ser Gly Ser Arg Ser Ala Ser Arg Thr Thr
                885                 890                 895
Arg Asn Glu Glu Gln Ser Arg Asp Gly Ser Arg His Ser Gly Ser Arg
            900                 905                 910
His His Glu Ala Ser Ser His Ala Asp Ile Ser Arg His Ser Gln Ala
        915                 920                 925
Gly Gln Gly Gln Ser Glu Gly Ser Arg Thr Ser Arg Arg Gln Gly Ser
    930                 935                 940
Ser Val Ser Gln Asp Ser Asp Ser Glu Gly His Ser Glu Asp Ser Glu
945                 950                 955                 960
Arg Trp Ser Gly Ser Ala Ser Arg Asn His Arg Gly Ser Ala Gln Glu
                965                 970                 975
Gln Ser Arg His Gly Ser Arg His Pro Arg Ser His His Glu Asp Arg
            980                 985                 990
Ala Gly His Gly His Ser Ala Asp Ser Ser Arg Gln Ser Gly Thr Pro
        995                 1000                1005
His Ala Glu Thr Ser Ser Gly Gly Gln Ala Ala Ser Ser His Glu
        1010                1015                1020
Gln Ala Arg Ser Ser Pro Gly Glu Arg His Gly Ser Arg His Gln
        1025                1030                1035
Gln Ser Ala Asp Ser Ser Arg His Ser Gly Ile Pro Arg Arg Gln
        1040                1045                1050
Ala Ser Ser Ala Val Arg Asp Ser Gly His Trp Gly Ser Ser Gly
        1055                1060                1065
Ser Gln Ala Ser Asp Ser Glu Gly His Ser Glu Ser Asp Thr
        1070                1075                1080
Gln Ser Val Ser Gly His Gly Gln Asp Gly Pro His Gln Gln Ser
        1085                1090                1095
His Gln Glu Ser Ala Arg Asp Trp Ser Gly Gly Arg Ser Gly Arg
```

-continued

```
            1100                1105                1110
Ser Gly Ser Phe Ile Tyr Gln Val Ser Thr His Glu Gln Ser Glu
    1115                1120                1125
Ser Ala His Gly Arg Thr Arg Thr Ser Thr Gly Arg Arg Gln Gly
    1130                1135                1140
Ser His His Glu Gln Ala Arg Asp Ser Ser Arg His Ser Ala Ser
    1145                1150                1155
Gln Glu Gly Gln Asp Thr Ile Arg Ala His Pro Gly Ser Arg Arg
    1160                1165                1170
Gly Gly Arg Gln Gly Ser His His Glu Gln Ser Val Asp Arg Ser
    1175                1180                1185
Gly His Ser Gly Ser His His Ser His Thr Thr Ser Gln Gly Arg
    1190                1195                1200
Ser Asp Ala Ser His Gly Gln Ser Gly Ser Arg Ser Ala Ser Arg
    1205                1210                1215
Gln Thr Arg Lys Asp Lys Gln Ser Gly Asp Gly Ser Arg His Ser
    1220                1225                1230
Gly Ser Arg His His Glu Ala Ala Ser Trp Ala Asp Ser Ser Arg
    1235                1240                1245
His Ser Gln Val Gly Gln Glu Gln Ser Ser Gly Ser Arg Thr Ser
    1250                1255                1260
Arg His Gln Gly Ser Ser Val Ser Gln Asp Ser Asp Ser Glu Arg
    1265                1270                1275
His Ser Asp Asp Ser Glu Arg Leu Ser Gly Ser Ala Ser Arg Asn
    1280                1285                1290
His His Gly Ser Ser Arg Glu Gln Ser Arg Asp Gly Ser Arg His
    1295                1300                1305
Pro Gly Phe His Gln Glu Asp Arg Ala Ser His Gly His Ser Ala
    1310                1315                1320
Asp Ser Ser Arg Gln Ser Gly Thr His His Thr Glu Ser Ser Ser
    1325                1330                1335
His Gly Gln Ala Val Ser Ser His Glu Gln Ala Arg Ser Ser Pro
    1340                1345                1350
Gly Glu Arg His Gly Ser Arg His Gln Gln Ser Ala Asp Ser Ser
    1355                1360                1365
Arg His Ser Gly Ile Gly His Arg Gln Ala Ser Ser Ala Val Arg
    1370                1375                1380
Asp Ser Gly His Arg Gly Ser Gly Ser Gln Val Thr Asn Ser
    1385                1390                1395
Glu Gly His Ser Glu Asp Ser Asp Thr Gln Ser Val Ser Ala His
    1400                1405                1410
Gly Gln Ala Gly Pro His Gln Gln Ser His Lys Glu Ser Ala Arg
    1415                1420                1425
Gly Gln Ser Gly Glu Ser Ser Gly Arg Ser Arg Ser Phe Leu Tyr
    1430                1435                1440
Gln Val Ser Ser His Glu Gln Ser Glu Ser Thr His Gly Gln Thr
    1445                1450                1455
Ala Pro Ser Thr Gly Gly Arg Gln Gly Ser Arg His Glu Gln Ala
    1460                1465                1470
Arg Asn Ser Ser Arg His Ser Ala Ser Gln Asp Gly Gln Asp Thr
    1475                1480                1485
Ile Arg Gly His Pro Gly Ser Ser Arg Gly Gly Arg Gln Gly Ser
    1490                1495                1500
```

```
Tyr His Glu Gln Ser Val Asp Arg Ser Gly His Ser Gly Tyr His
1505                1510                1515

His Ser His Thr Thr Pro Gln Gly Arg Ser Asp Ala Ser His Gly
1520                1525                1530

Gln Ser Gly Pro Arg Ser Ala Ser Arg Gln Thr Arg Asn Glu Glu
1535                1540                1545

Gln Ser Gly Asp Gly Ser Arg His Ser Gly Ser Arg His His Glu
1550                1555                1560

Pro Ser Thr Arg Ala Gly Ser Ser Arg His Ser Gln Val Gly Gln
1565                1570                1575

Gly Glu Ser Ala Gly Ser Lys Thr Ser Arg Arg Gln Gly Ser Ser
1580                1585                1590

Val Ser Gln Asp Arg Asp Ser Glu Gly His Ser Glu Asp Ser Glu
1595                1600                1605

Arg Arg Ser Glu Ser Ala Ser Arg Asn His Tyr Gly Ser Ala Arg
1610                1615                1620

Glu Gln Ser Arg His Gly Ser Arg Asn Pro Arg Ser His Gln Glu
1625                1630                1635

Asp Arg Ala Ser His Gly His Ser Ala Glu Ser Ser Arg Gln Ser
1640                1645                1650

Gly Thr Arg His Ala Glu Thr Ser Ser Gly Gly Gln Ala Ala Ser
1655                1660                1665

Ser Gln Glu Gln Ala Arg Ser Ser Pro Gly Glu Arg His Gly Ser
1670                1675                1680

Arg His Gln Gln Ser Ala Asp Ser Ser Thr Asp Ser Gly Thr Gly
1685                1690                1695

Arg Arg Gln Asp Ser Ser Val Val Gly Asp Ser Gly Asn Arg Gly
1700                1705                1710

Ser Ser Gly Ser Gln Ala Ser Asp Ser Glu Gly His Ser Glu Glu
1715                1720                1725

Ser Asp Thr Gln Ser Val Ser Ala His Gly Gln Ala Gly Pro His
1730                1735                1740

Gln Gln Ser His Gln Glu Ser Thr Arg Gly Gln Ser Gly Glu Arg
1745                1750                1755

Ser Gly Arg Ser Gly Ser Phe Leu Tyr Gln Val Ser Thr His Glu
1760                1765                1770

Gln Ser Glu Ser Ala His Gly Arg Thr Gly Pro Ser Thr Gly Gly
1775                1780                1785

Arg Gln Arg Ser Arg His Glu Gln Ala Arg Asp Ser Ser Arg His
1790                1795                1800

Ser Ala Ser Gln Glu Gly Gln Asp Thr Ile Arg Gly His Pro Gly
1805                1810                1815

Ser Ser Arg Gly Gly Arg Gln Gly Ser His Tyr Glu Gln Ser Val
1820                1825                1830

Asp Ser Ser Gly His Ser Gly Ser His His Ser His Thr Thr Ser
1835                1840                1845

Gln Glu Arg Ser Asp Val Ser Arg Gly Gln Ser Gly Ser Arg Ser
1850                1855                1860

Val Ser Arg Gln Thr Arg Asn Glu Lys Gln Ser Gly Asp Gly Ser
1865                1870                1875

Arg His Ser Gly Ser Arg His His Glu Ala Ser Ser Arg Ala Asp
1880                1885                1890
```

```
Ser Ser Arg His Ser Gln Val Gly Gln Gly Gln Ser Ser Gly Pro
1895                1900                1905

Arg Thr Ser Arg Asn Gln Gly Ser Ser Val Ser Gln Asp Ser Asp
1910                1915                1920

Ser Gln Gly His Ser Glu Asp Ser Glu Arg Trp Ser Gly Ser Ala
1925                1930                1935

Ser Arg Asn His Leu Gly Ser Ala Trp Glu Gln Ser Arg Asp Gly
1940                1945                1950

Ser Arg His Pro Gly Ser His His Glu Asp Arg Ala Gly His Gly
1955                1960                1965

His Ser Ala Asp Ser Ser Arg Gln Ser Gly Thr Arg His Thr Glu
1970                1975                1980

Ser Ser Ser Arg Gly Gln Ala Ala Ser Ser His Glu Gln Ala Arg
1985                1990                1995

Ser Ser Ala Gly Glu Arg His Gly Ser His His Gln Leu Gln Ser
2000                2005                2010

Ala Asp Ser Ser Arg His Ser Gly Ile Gly His Gly Gln Ala Ser
2015                2020                2025

Ser Ala Val Arg Asp Ser Gly His Arg Gly Tyr Ser Gly Ser Gln
2030                2035                2040

Ala Ser Asp Ser Glu Gly His Ser Glu Asp Ser Asp Thr Gln Ser
2045                2050                2055

Val Ser Ala Gln Gly Lys Ala Gly Pro His Gln Gln Ser His Lys
2060                2065                2070

Glu Ser Ala Arg Gly Gln Ser Gly Glu Ser Ser Gly Arg Ser Gly
2075                2080                2085

Ser Phe Leu Tyr Gln Val Ser Thr His Glu Gln Ser Glu Ser Thr
2090                2095                2100

His Gly Gln Ser Ala Pro Ser Thr Gly Gly Arg Gln Gly Ser His
2105                2110                2115

Tyr Asp Gln Ala Gln Asp Ser Ser Arg His Ser Ala Ser Gln Glu
2120                2125                2130

Gly Gln Asp Thr Ile Arg Gly His Pro Gly Pro Ser Arg Gly Gly
2135                2140                2145

Arg Gln Gly Ser His Gln Glu Gln Ser Val Asp Arg Ser Gly His
2150                2155                2160

Ser Gly Ser His His Ser His Thr Thr Ser Gln Gly Arg Ser Asp
2165                2170                2175

Ala Ser Arg Gly Gln Ser Gly Ser Arg Ser Ala Ser Arg Lys Thr
2180                2185                2190

Tyr Asp Lys Glu Gln Ser Gly Asp Gly Ser Arg His Ser Gly Ser
2195                2200                2205

His His His Glu Ala Ser Ser Trp Ala Asp Ser Ser Arg His Ser
2210                2215                2220

Leu Val Gly Gln Gly Gln Ser Ser Gly Pro Arg Thr Ser Arg Pro
2225                2230                2235

Arg Gly Ser Ser Val Ser Gln Asp Ser Asp Ser Glu Gly His Ser
2240                2245                2250

Glu Asp Ser Glu Arg Arg Ser Gly Ser Ala Ser Arg Asn His His
2255                2260                2265

Gly Ser Ala Gln Glu Gln Ser Arg Asp Gly Ser Arg His Pro Arg
2270                2275                2280

Ser His His Glu Asp Arg Ala Gly His Gly His Ser Ala Glu Ser
```

-continued

```
                2285                2290                2295
Ser Arg Gln Ser Gly Thr His His Ala Glu Asn Ser Ser Gly Gly
    2300                2305                2310
Gln Ala Ala Ser Ser His Glu Gln Ala Arg Ser Ser Ala Gly Glu
    2315                2320                2325
Arg His Gly Ser His His Gln Gln Ser Ala Asp Ser Ser Arg His
    2330                2335                2340
Ser Gly Ile Gly His Gly Gln Ala Ser Ser Ala Val Arg Asp Ser
    2345                2350                2355
Gly His Arg Gly Ser Ser Gly Ser Gln Ala Ser Asp Ser Glu Gly
    2360                2365                2370
His Ser Glu Asp Ser Asp Thr Gln Ser Val Ser Ala His Gly Gln
    2375                2380                2385
Ala Gly Pro His Gln Gln Ser His Gln Glu Ser Thr Arg Gly Arg
    2390                2395                2400
Ser Ala Gly Arg Ser Gly Arg Ser Gly Ser Phe Leu Tyr Gln Val
    2405                2410                2415
Ser Thr His Glu Gln Ser Glu Ser Ala His Gly Arg Thr Gly Thr
    2420                2425                2430
Ser Thr Gly Gly Arg Gln Gly Ser His His Lys Gln Ala Arg Asp
    2435                2440                2445
Ser Ser Arg His Ser Thr Ser Gln Glu Gly Gln Asp Thr Ile His
    2450                2455                2460
Gly His Pro Gly Ser Ser Ser Gly Gly Arg Gln Gly Ser His Tyr
    2465                2470                2475
Glu Gln Leu Val Asp Arg Ser Gly His Ser Gly Ser His His Ser
    2480                2485                2490
His Thr Thr Ser Gln Gly Arg Ser Asp Ala Ser His Gly His Ser
    2495                2500                2505
Gly Ser Arg Ser Ala Ser Arg Gln Thr Arg Asn Asp Glu Gln Ser
    2510                2515                2520
Gly Asp Gly Ser Arg His Ser Gly Ser Arg His His Glu Ala Ser
    2525                2530                2535
Ser Arg Ala Asp Ser Ser Gly His Ser Gln Val Gly Gln Gly Gln
    2540                2545                2550
Ser Glu Gly Pro Arg Thr Ser Arg Asn Trp Gly Ser Ser Phe Ser
    2555                2560                2565
Gln Asp Ser Asp Ser Gln Gly His Ser Glu Asp Ser Glu Arg Trp
    2570                2575                2580
Ser Gly Ser Ala Ser Arg Asn His His Gly Ser Ala Gln Glu Gln
    2585                2590                2595
Leu Arg Asp Gly Ser Arg His Pro Arg Ser His Gln Glu Asp Arg
    2600                2605                2610
Ala Gly His Gly His Ser Ala Asp Ser Ser Arg Gln Ser Gly Thr
    2615                2620                2625
Arg His Thr Gln Thr Ser Ser Gly Gly Gln Ala Ala Ser Ser His
    2630                2635                2640
Glu Gln Ala Arg Ser Ser Ala Gly Glu Arg His Gly Ser His His
    2645                2650                2655
Gln Gln Ser Ala Asp Ser Ser Arg His Ser Gly Ile Gly His Gly
    2660                2665                2670
Gln Ala Ser Ser Ala Val Arg Asp Ser Gly His Arg Gly Tyr Ser
    2675                2680                2685
```

```
Gly Ser Gln Ala Ser Asp Asn Glu Gly His Glu Asp Ser Asp
    2690            2695            2700

Thr Gln Ser Val Ser Ala His Gly Gln Ala Gly Ser His Gln Gln
    2705            2710            2715

Ser His Gln Glu Ser Ala Arg Gly Arg Ser Gly Glu Thr Ser Gly
    2720            2725            2730

His Ser Gly Ser Phe Leu Tyr Gln Val Ser Thr His Glu Gln Ser
    2735            2740            2745

Glu Ser Ser His Gly Trp Thr Gly Pro Ser Thr Arg Gly Arg Gln
    2750            2755            2760

Gly Ser Arg His Glu Gln Ala Gln Asp Ser Ser Arg His Ser Ala
    2765            2770            2775

Ser Gln Asp Gly Gln Asp Thr Ile Arg Gly His Pro Gly Ser Ser
    2780            2785            2790

Arg Gly Gly Arg Gln Gly Tyr His His Glu His Ser Val Asp Ser
    2795            2800            2805

Ser Gly His Ser Gly Ser His His Ser His Thr Thr Ser Gln Gly
    2810            2815            2820

Arg Ser Asp Ala Ser Arg Gly Gln Ser Gly Ser Arg Ser Ala Ser
    2825            2830            2835

Arg Thr Thr Arg Asn Glu Glu Gln Ser Gly Asp Gly Ser Arg His
    2840            2845            2850

Ser Gly Ser Arg His His Glu Ala Ser Thr His Ala Asp Ile Ser
    2855            2860            2865

Arg His Ser Gln Ala Val Gln Gly Gln Ser Glu Gly Ser Arg Arg
    2870            2875            2880

Ser Arg Arg Gln Gly Ser Ser Val Ser Gln Asp Ser Asp Ser Glu
    2885            2890            2895

Gly His Ser Glu Asp Ser Glu Arg Trp Ser Gly Ser Ala Ser Arg
    2900            2905            2910

Asn His His Gly Ser Ala Gln Glu Gln Leu Arg Asp Gly Ser Arg
    2915            2920            2925

His Pro Arg Ser His Gln Glu Asp Arg Ala Gly His Gly His Ser
    2930            2935            2940

Ala Asp Ser Ser Arg Gln Ser Gly Thr Arg His Thr Gln Thr Ser
    2945            2950            2955

Ser Gly Gly Gln Ala Ala Ser Ser His Glu Gln Ala Arg Ser Ser
    2960            2965            2970

Ala Gly Glu Arg His Gly Ser His His Gln Gln Ser Ala Asp Ser
    2975            2980            2985

Ser Arg His Ser Gly Ile Gly His Gly Gln Ala Ser Ser Ala Val
    2990            2995            3000

Arg Asp Ser Gly His Arg Gly Tyr Ser Gly Ser Gln Ala Ser Asp
    3005            3010            3015

Asn Glu Gly His Ser Glu Asp Ser Asp Thr Gln Ser Val Ser Ala
    3020            3025            3030

His Gly Gln Ala Gly Ser His Gln Gln Ser His Gln Glu Ser Ala
    3035            3040            3045

Arg Gly Arg Ser Gly Glu Thr Ser Gly His Ser Gly Ser Phe Leu
    3050            3055            3060

Tyr Gln Val Ser Thr His Glu Gln Ser Glu Ser Ser His Gly Trp
    3065            3070            3075
```

```
Thr Gly Pro Ser Thr Arg Gly Arg Gln Gly Ser Arg His Glu Gln
    3080            3085            3090

Ala Gln Asp Ser Ser Arg His Ser Ala Ser Gln Tyr Gly Gln Asp
    3095            3100            3105

Thr Ile Arg Gly His Pro Gly Ser Ser Arg Gly Gly Arg Gln Gly
    3110            3115            3120

Tyr His His Glu His Ser Val Asp Ser Ser Gly His Ser Gly Ser
    3125            3130            3135

His His Ser His Thr Thr Ser Gln Gly Arg Ser Asp Ala Ser Arg
    3140            3145            3150

Gly Gln Ser Gly Ser Arg Ser Ala Ser Arg Thr Thr Arg Asn Glu
    3155            3160            3165

Glu Gln Ser Gly Asp Ser Ser Arg His Ser Val Ser Arg His His
    3170            3175            3180

Glu Ala Ser Thr His Ala Asp Ile Ser Arg His Ser Gln Ala Val
    3185            3190            3195

Gln Gly Gln Ser Glu Gly Ser Arg Arg Ser Arg Arg Gln Gly Ser
    3200            3205            3210

Ser Val Ser Gln Asp Ser Asp Ser Glu Gly His Ser Glu Asp Ser
    3215            3220            3225

Glu Arg Trp Ser Gly Ser Ala Ser Arg Asn His Arg Gly Ser Val
    3230            3235            3240

Gln Glu Gln Ser Arg His Gly Ser Arg His Pro Arg Ser His His
    3245            3250            3255

Glu Asp Arg Ala Gly His Gly His Ser Ala Asp Arg Ser Arg Gln
    3260            3265            3270

Ser Gly Thr Arg His Ala Glu Thr Ser Ser Gly Gly Gln Ala Ala
    3275            3280            3285

Ser Ser His Glu Gln Ala Arg Ser Ser Pro Gly Glu Arg His Gly
    3290            3295            3300

Ser Arg His Gln Gln Ser Ala Asp Ser Ser Arg His Ser Gly Ile
    3305            3310            3315

Pro Arg Gly Gln Ala Ser Ser Ala Val Arg Asp Ser Arg His Trp
    3320            3325            3330

Gly Ser Ser Gly Ser Gln Ala Ser Asp Ser Glu Gly His Ser Glu
    3335            3340            3345

Glu Ser Asp Thr Gln Ser Val Ser Gly His Gly Gln Ala Gly Pro
    3350            3355            3360

His Gln Gln Ser His Gln Glu Ser Ala Arg Asp Arg Ser Gly Gly
    3365            3370            3375

Arg Ser Gly Arg Ser Gly Ser Phe Leu Tyr Gln Val Ser Thr His
    3380            3385            3390

Glu Gln Ser Glu Ser Ala His Gly Arg Thr Arg Thr Ser Thr Gly
    3395            3400            3405

Arg Arg Gln Gly Ser His His Glu Gln Ala Arg Asp Ser Ser Arg
    3410            3415            3420

His Ser Ala Ser Gln Glu Gly Gln Asp Thr Ile Arg Gly His Pro
    3425            3430            3435

Gly Ser Ser Arg Arg Gly Arg Gln Gly Ser His Tyr Glu Gln Ser
    3440            3445            3450

Val Asp Arg Ser Gly His Ser Gly Ser His His Ser His Thr Thr
    3455            3460            3465

Ser Gln Gly Arg Ser Asp Ala Ser Arg Gly Gln Ser Gly Ser Arg
```

```
            3470            3475            3480
Ser Ala Ser Arg Gln Thr Arg Asn Asp Glu Gln Ser  Gly Asp Gly
        3485            3490            3495

Ser Arg His Ser Trp Ser His His His Glu Ala Ser  Thr Gln Ala
        3500            3505            3510

Asp Ser Ser Arg His Ser Gln Ser Gly Gln Gly Gln  Ser Ala Gly
        3515            3520            3525

Pro Arg Thr Ser Arg Asn Gln Gly Ser Ser Val Ser  Gln Asp Ser
        3530            3535            3540

Asp Ser Gln Gly His Ser Glu Asp Ser Glu Arg Trp  Ser Gly Ser
        3545            3550            3555

Ala Ser Arg Asn His Arg Gly Ser Ala Gln Glu Gln  Ser Arg Asp
        3560            3565            3570

Gly Ser Arg His Pro Thr Ser His His Glu Asp Arg  Ala Gly His
        3575            3580            3585

Gly His Ser Ala Glu Ser Ser Arg Gln Ser Gly Thr  His His Ala
        3590            3595            3600

Glu Asn Ser Ser Gly Gly Gln Ala Ala Ser Ser His  Glu Gln Ala
        3605            3610            3615

Arg Ser Ser Ala Gly Glu Arg His Gly Ser His His  Gln Gln Ser
        3620            3625            3630

Ala Asp Ser Ser Arg His Ser Gly Ile Gly His Gly  Gln Ala Ser
        3635            3640            3645

Ser Ala Val Arg Asp Ser Gly His Arg Gly Ser Ser  Gly Ser Gln
        3650            3655            3660

Ala Ser Asp Ser Glu Gly His Ser Glu Asp Ser Asp  Thr Gln Ser
        3665            3670            3675

Val Ser Ala His Gly Gln Ala Gly Pro His Gln Gln  Ser His Gln
        3680            3685            3690

Glu Ser Thr Arg Gly Arg Ser Ala Gly Arg Ser Gly  Arg Ser Gly
        3695            3700            3705

Ser Phe Leu Tyr Gln Val Ser Thr His Glu Gln Ser  Glu Ser Ala
        3710            3715            3720

His Gly Arg Ala Gly Pro Ser Thr Gly Gly Arg Gln  Gly Ser Arg
        3725            3730            3735

His Glu Gln Ala Arg Asp Ser Ser Arg His Ser Ala  Ser Gln Glu
        3740            3745            3750

Gly Gln Asp Thr Ile Arg Gly His Pro Gly Ser Arg  Arg Gly Gly
        3755            3760            3765

Arg Gln Gly Ser Tyr His Glu Gln Ser Val Asp Arg  Ser Gly His
        3770            3775            3780

Ser Gly Ser His His Ser His Thr Thr Ser Gln Gly  Arg Ser Asp
        3785            3790            3795

Ala Ser His Gly Gln Ser Gly Ser Arg Ser Ala Ser  Arg Glu Thr
        3800            3805            3810

Arg Asn Glu Glu Gln Ser Gly Asp Gly Ser Arg His  Ser Gly Ser
        3815            3820            3825

Arg His His Glu Ala Ser Thr Gln Ala Asp Ser Ser  Arg His Ser
        3830            3835            3840

Gln Ser Gly Gln Gly Glu Ser Ala Gly Ser Arg Arg  Ser Arg Arg
        3845            3850            3855

Gln Gly Ser Ser Val Ser Gln Asp Ser Asp Ser Glu  Ala Tyr Pro
        3860            3865            3870
```

```
Glu Asp Ser Glu Arg Arg Ser Glu Ser Ala Ser Arg Asn His His
    3875            3880                3885

Gly Ser Ser Arg Glu Gln Ser Arg Asp Gly Ser Arg His Pro Gly
    3890            3895                3900

Ser Ser His Arg Asp Thr Ala Ser His Val Gln Ser Ser Pro Val
    3905            3910                3915

Gln Ser Asp Ser Ser Thr Ala Lys Glu His Gly His Phe Ser Ser
    3920            3925                3930

Leu Ser Gln Asp Ser Ala Tyr His Ser Gly Ile Gln Ser Arg Gly
    3935            3940                3945

Ser Pro His Ser Ser Ser Ser Tyr His Tyr Gln Ser Glu Gly Thr
    3950            3955                3960

Glu Arg Gln Lys Gly Gln Ser Gly Leu Val Trp Arg His Gly Ser
    3965            3970                3975

Tyr Gly Ser Ala Asp Tyr Asp Tyr Gly Glu Ser Gly Phe Arg His
    3980            3985                3990

Ser Gln His Gly Ser Val Ser Tyr Asn Ser Asn Pro Val Val Phe
    3995            4000                4005

Lys Glu Arg Ser Asp Ile Cys Lys Ala Ser Ala Phe Gly Lys Asp
    4010            4015                4020

His Pro Arg Tyr Tyr Ala Thr Tyr Ile Asn Lys Asp Pro Gly Leu
    4025            4030                4035

Cys Gly His Ser Ser Asp Ile Ser Lys Gln Leu Gly Phe Ser Gln
    4040            4045                4050

Ser Gln Arg Tyr Tyr Tyr Tyr Glu
    4055            4060

<210> SEQ ID NO 2
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gln Ser Gly Glu Ser Ser Gly Arg Ser Arg Ser Phe Leu Tyr Gln
1               5                   10                  15

Val Ser Ser His Glu Gln Ser Glu Ser Thr His Gly Gln Thr Ala Pro
                20                  25                  30

Ser Thr Gly Gly Arg Gln Gly Ser Arg His Glu Gln Ala Arg Asn Ser
            35                  40                  45

Ser Arg His Ser Ala Ser Gln Asp Gly Gln Asp Thr Ile Arg Gly His
        50                  55                  60

Pro Gly Ser Ser Arg Gly Gly Arg Gln Gly Ser Tyr His Glu Gln Ser
65                  70                  75                  80

Val Asp Arg Ser Gly His Ser Gly Tyr His His Ser His Thr Thr Pro
                85                  90                  95

Gln Gly Arg Ser Asp Ala Ser His Gly Gln Ser Gly Pro Arg Ser Ala
            100                 105                 110

Ser Arg Gln Thr Arg Asn Glu Gln Ser Gly Asp Gly Ser Arg His
        115                 120                 125

Ser Gly Ser Arg His His Glu Pro Ser Thr Arg Ala Gly Ser Ser Arg
    130                 135                 140

His Ser Gln Val Gly Gln Gly Glu Ser Ala Gly Ser Lys Thr Ser Arg
```

```
                145                 150                 155                 160
Arg Gln Gly Ser Ser Val Ser Gln Asp Arg Asp Ser Glu Gly His Ser
                    165                 170                 175
Glu Asp Ser Glu Arg Arg Ser Glu Ser Ala Ser Arg Asn His Tyr Gly
                    180                 185                 190
Ser Ala Arg Glu Gln Ser Arg His Gly Ser Arg Asn Pro Arg Ser His
                    195                 200                 205
Gln Glu Asp Arg Ala Ser His Gly His Ser Ala Glu Ser Ser Arg Gln
                    210                 215                 220
Ser Gly Thr Arg His Ala Glu Thr Ser Ser Gly Gly Gln Ala Ala Ser
225                 230                 235                 240
Ser Gln Glu Gln Ala Arg Ser Ser Pro Gly Glu Arg His Gly Ser Arg
                    245                 250                 255
His Gln Gln Ser Ala Asp Ser Ser Thr Asp Ser Gly Thr Gly Arg Arg
                    260                 265                 270
Gln Asp Ser Ser Val Val Gly Asp Ser Gly Asn Arg Gly Ser Ser Gly
                    275                 280                 285
Ser Gln Ala Ser Asp Ser Glu Gly His Ser Glu Glu Ser Asp Thr Gln
                    290                 295                 300
Ser Val Ser Ala His Gly Gln Ala Gly Pro His Gln Gln Ser His Gln
305                 310                 315                 320
Glu Ser Thr Arg Gly Gln Ser Gly Glu Arg Ser Gly Arg Ser Gly Ser
                    325                 330                 335
Phe Leu Tyr Gln Val Ser Thr His Glu Gln
                    340                 345

<210> SEQ ID NO 3
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gln Ser Gly Glu Ser Gly Arg Ser Arg Ser Phe Leu Tyr Gln
1                   5                   10                  15
Val Ser Ser His Glu Gln Ser Gly Ser Thr His Gly Gln Thr Ala Pro
                    20                  25                  30
Ser Thr Gly Gly Arg Gln Gly Ser Arg His Glu Gln Ala Arg Asn Ser
                    35                  40                  45
Ser Arg His Ser Ala Ser Gln Asp Gly Gln Asp Thr Ile Arg Gly His
50                  55                  60
Pro Gly Ser Ser Arg Gly Gly Arg Gln Gly Ser Tyr His Glu Gln Ser
65                  70                  75                  80
Val Asp Arg Ser Gly His Ser Gly Tyr His His Ser His Thr Thr Pro
                    85                  90                  95
Gln Gly Arg Ser Asp Ala Ser His Gly Gln Ser Gly Pro Arg Ser Ala
                    100                 105                 110
Ser Arg Gln Thr Arg Asn Glu Glu Gln Ser Gly Asp Gly Ser Arg His
                    115                 120                 125
Ser Gly Ser Arg His His Glu Pro Ser Thr Arg Ala Gly Ser Ser Arg
                    130                 135                 140
His Ser Gln Val Gly Gln Gly Glu Ser Ala Gly Ser Lys Thr Ser Arg
145                 150                 155                 160
```

```
Arg Gln Gly Ser Ser Val Ser Gln Asp Arg Asp Ser Glu Gly His Ser
                165                 170                 175

Glu Asp Ser Glu Arg Arg Ser Glu Ser Ala Ser Arg Asn His Tyr Gly
            180                 185                 190

Ser Ala Arg Glu Gln Ser Arg His Gly Ser Arg Asn Pro Arg Ser His
            195                 200                 205

Gln Glu Asp Arg Ala Ser His Gly His Ser Ala Glu Ser Ser Arg Gln
        210                 215                 220

Ser Gly Thr Arg His Ala Glu Thr Ser Ser Gly Gln Ala Ala Ser
225                 230                 235                 240

Ser Gln Glu Gln Ala Arg Ser Ser Pro Gly Glu Arg His Gly Ser Arg
            245                 250                 255

His Gln Gln Ser Ala Asp Ser Ser Thr Asp Ser Gly Thr Gly Arg Arg
            260                 265                 270

Gln Asp Ser Ser Val Val Gly Asp Ser Gly Asn Arg Gly Ser Ser Gly
        275                 280                 285

Ser Gln Ala Ser Asp Ser Glu Gly His Ser Glu Ser Asp Thr Gln
        290                 295                 300

Ser Val Ser Ala His Gly Gln Ala Gly Pro His Gln Ser His Gln
305                 310                 315                 320

Glu Ser Thr Arg Gly Gln Ser Gly Glu Arg Ser Gly Arg Ser Gly Ser
            325                 330                 335

Phe Leu Tyr Gln Val Ser Thr His Glu Gln Arg Met Arg Met Arg
            340                 345                 350

Arg Met Arg Arg
        355

<210> SEQ ID NO 4
<211> LENGTH: 337
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Glu Ser Thr His Gly Gln Thr Ala Pro Ser Thr Gly Gly Arg Gln
1               5                   10                  15

Gly Ser Arg His Glu Gln Ala Arg Asn Ser Ser Arg His Ser Ala Ser
            20                  25                  30

Gln Asp Gly Gln Asp Thr Ile Arg Gly His Pro Gly Ser Ser Arg Gly
        35                  40                  45

Gly Arg Gln Gly Ser Tyr His Glu Gln Ser Val Asp Arg Ser Gly His
    50                  55                  60

Ser Gly Tyr His His Ser His Thr Thr Pro Gln Gly Arg Ser Asp Ala
65                  70                  75                  80

Ser His Gly Gln Ser Gly Pro Arg Ser Ala Ser Arg Gln Thr Arg Asn
                85                  90                  95

Glu Glu Gln Ser Gly Asp Gly Ser Arg His Ser Gly Ser Arg His His
            100                 105                 110

Glu Pro Ser Thr Arg Ala Gly Ser Ser Arg His Ser Gln Val Gly Gln
        115                 120                 125

Gly Glu Ser Ala Gly Ser Lys Thr Ser Arg Arg Gln Gly Ser Ser Val
    130                 135                 140

Ser Gln Asp Arg Asp Ser Glu Gly His Ser Glu Asp Ser Glu Arg Arg
145                 150                 155                 160
```

Ser Glu Ser Ala Ser Arg Asn His Tyr Gly Ser Ala Arg Glu Gln Ser
            165                 170                 175

Arg His Gly Ser Arg Asn Pro Arg Ser His Gln Glu Asp Arg Ala Ser
            180                 185                 190

His Gly His Ser Ala Glu Ser Ser Arg Gln Ser Gly Thr Arg His Ala
            195                 200                 205

Glu Thr Ser Ser Gly Gly Gln Ala Ala Ser Ser Gln Glu Gln Ala Arg
            210                 215                 220

Ser Ser Pro Gly Glu Arg His Gly Ser Arg His Gln Gln Ser Ala Asp
225                 230                 235                 240

Ser Ser Thr Asp Ser Gly Thr Gly Arg Arg Gln Asp Ser Ser Val Val
            245                 250                 255

Gly Asp Ser Gly Asn Arg Gly Ser Ser Gly Ser Gln Ala Ser Asp Ser
            260                 265                 270

Glu Gly His Ser Glu Glu Ser Asp Thr Gln Ser Val Ser Ala His Gly
            275                 280                 285

Gln Ala Gly Pro His Gln Gln Ser His Gln Glu Ser Thr Arg Gly Gln
            290                 295                 300

Ser Gly Glu Arg Ser Gly Arg Ser Gly Ser Phe Leu Tyr Gln Val Ser
305                 310                 315                 320

Thr His Glu Gln Ser Glu Ser Arg Met Arg Arg Met Arg Arg Met Arg
            325                 330                 335

Arg

<210> SEQ ID NO 5
<211> LENGTH: 336
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 5

Met Arg Asn Glu Glu Gln Ser Gly Asp Gly Ser Arg His Ser Gly Ser
1               5                   10                  15

Arg His His Glu Pro Ser Thr Arg Ala Gly Ser Ser Arg His Ser Gln
            20                  25                  30

Val Gly Gln Gly Glu Ser Ala Gly Ser Lys Thr Ser Arg Arg Gln Gly
            35                  40                  45

Ser Ser Val Ser Gln Asp Arg Asp Ser Glu Gly His Ser Glu Asp Ser
            50                  55                  60

Glu Arg Arg Ser Glu Ser Ala Ser Arg Asn His Tyr Gly Ser Ala Arg
65                  70                  75                  80

Glu Gln Ser Arg His Gly Ser Arg Asn Pro Arg Ser His Gln Glu Asp
            85                  90                  95

Arg Ala Ser His Gly His Ser Ala Glu Ser Ser Arg Gln Ser Gly Thr
            100                 105                 110

Arg His Ala Glu Thr Ser Ser Gly Gly Gln Ala Ala Ser Ser Gln Glu
            115                 120                 125

Gln Ala Arg Ser Ser Pro Gly Glu Arg His Gly Ser Arg His Gln Gln
            130                 135                 140

Ser Ala Asp Ser Ser Thr Asp Ser Gly Thr Gly Arg Arg Gln Asp Ser
145                 150                 155                 160

Ser Val Val Gly Asp Ser Gly Asn Arg Gly Ser Ser Gly Ser Gln Ala
            165                 170                 175

```
Ser Asp Ser Glu Gly His Ser Glu Glu Ser Asp Thr Gln Ser Val Ser
            180                 185                 190

Ala His Gly Gln Ala Gly Pro His Gln Gln Ser His Gln Glu Ser Thr
        195                 200                 205

Arg Gly Gln Ser Gly Glu Arg Ser Gly Arg Ser Gly Ser Phe Leu Tyr
    210                 215                 220

Gln Val Ser Thr His Glu Gln Ser Glu Ser Ala His Gly Arg Thr Gly
225                 230                 235                 240

Pro Ser Thr Gly Gly Arg Gln Arg Ser Arg His Glu Gln Ala Arg Asp
                245                 250                 255

Ser Ser Arg His Ser Ala Ser Gln Glu Gly Gln Asp Thr Ile Arg Gly
            260                 265                 270

His Pro Gly Ser Ser Arg Gly Gly Arg Gln Gly Ser His Tyr Glu Gln
        275                 280                 285

Ser Val Asp Ser Ser Gly His Ser Gly Ser His Ser His Thr Thr
    290                 295                 300

Ser Gln Glu Arg Ser Asp Val Ser Arg Gly Gln Ser Gly Ser Arg Ser
305                 310                 315                 320

Val Ser Arg Gln Thr Arg Arg Met Arg Arg Met Arg Arg Met Arg Arg
                325                 330                 335

<210> SEQ ID NO 6
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Arg Asn Glu Glu Gln Ser Gly Asp Gly Ser Arg His Ser Gly Ser
1               5                   10                  15

Arg His His Glu Pro Ser Thr Arg Ala Gly Ser Ser Arg His Ser Gln
            20                  25                  30

Val Gly Gln Gly Glu Ser Ala Gly Ser Lys Thr Ser Arg Arg Gln Gly
        35                  40                  45

Ser Ser Val Ser Gln Asp Arg Asp Ser Glu Gly His Ser Glu Asp Ser
    50                  55                  60

Glu Arg Arg Ser Glu Ser Ala Ser Arg Asn His Tyr Gly Ser Ala Arg
65                  70                  75                  80

Glu Gln Ser Arg His Gly Ser Arg Asn Pro Arg Ser His Gln Glu Asp
                85                  90                  95

Arg Ala Ser His Gly His Ser Ala Glu Ser Ser Arg Gln Ser Gly Thr
            100                 105                 110

Arg His Ala Glu Thr Ser Ser Gly Gly Gln Ala Ala Ser Ser Gln Glu
        115                 120                 125

Gln Ala Arg Ser Ser Pro Gly Glu Arg His Gly Ser Arg His Gln Gln
    130                 135                 140

Ser Ala Asp Ser Ser Thr Asp Ser Gly Thr Gly Arg Arg Gln Asp Ser
145                 150                 155                 160

Ser Val Val Gly Asp Ser Gly Asn Arg Gly Ser Ser Gly Ser Gln Ala
                165                 170                 175

Ser Asp Ser Glu Gly His Ser Glu Glu Ser Asp Thr Gln Ser Val Ser
            180                 185                 190

Ala His Gly Gln Ala Gly Pro His Gln Gln Ser His Gln Glu Ser Thr
```

```
            195                 200                 205
Arg Gly Gln Ser Gly Glu Arg Ser Gly Arg Ser Gly Ser Phe Leu Tyr
    210                 215                 220

Gln Val Ser Thr His Glu Gln Ser Glu Ser Arg Met Arg Met Arg
225                 230                 235                 240

Arg Met Arg Arg

<210> SEQ ID NO 7

<400> SEQUENCE: 7

000

<210> SEQ ID NO 8
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Arg Ser Arg Ser Phe Leu Tyr Gln Val Ser Ser His Glu Gln Ser
1               5                   10                  15

Glu Ser Thr His Gly Gln Thr Ala Pro Ser Thr Gly Gly Arg Gln Gly
                20                  25                  30

Ser Arg His Glu Gln Ala Arg Asn Ser Ser Arg His Ser Ala Ser Gln
            35                  40                  45

Asp Gly Gln Asp Thr Ile Arg Gly His Pro Gly Ser Ser Arg Gly Gly
        50                  55                  60

Arg Gln Gly Ser Tyr His Glu Gln Ser Val Asp Arg Ser Gly His Ser
65                  70                  75                  80

Gly Tyr His His Ser His Thr Thr Pro Gln Gly Arg Ser Asp Ala Ser
                85                  90                  95

His Gly Gln Ser Gly Pro Arg Ser Ala Ser Arg Gln Thr Arg Asn Glu
            100                 105                 110

Glu Gln Ser Gly Asp Gly Ser Arg His Ser Gly Ser Arg His His Glu
        115                 120                 125

Ala Ser Thr Arg Ala Asp Ser Ser Arg His Ser Gln Val Gly Gln Gly
    130                 135                 140

Gln Ser Ser Gly Ser Arg Thr Ser Arg Arg Gln Gly Ser Ser Val Ser
145                 150                 155                 160

Gln Asp Ser Asp Ser Glu Gly His Ser Glu Asp Ser Glu Arg Arg Ser
                165                 170                 175

Gly Ser Ala Ser Arg Asn His Tyr Gly Ser Ala Gln Glu Gln Ser Arg
            180                 185                 190

Asp Gly Ser Arg His Pro Arg Ser His Gln Glu Asp Arg Ala Ser His
        195                 200                 205

Gly His Ser Ala Glu Ser Ser Arg Gln Ser Gly Thr Arg His Ala Glu
    210                 215                 220

Thr Ser Ser Gly Gly Gln Ala Ala Ser Ser His Glu Gln Ala Arg Ser
225                 230                 235                 240

Ser Pro Gly Glu Arg His Gly Ser Arg His Gln Gln Ser Ala Asp Ser
                245                 250                 255

Ser Arg His Ser Gly Ile Gly His Gly Gln Ala Ser Ser Ala Val Arg
            260                 265                 270
```

```
                    -continued

Asp Ser Gly His Arg Gly Ser Gly Ser Gln Ala Ser Asp Ser Glu
            275                 280                 285

Gly His Ser Glu Asp Ser Asp Thr Gln Ser Val Ser Ala His Gly Gln
        290                 295                 300

Ala Gly Pro His Gln Gln Ser His Gln Glu Ser Ala Arg Gly Arg Ser
305                 310                 315                 320

Gly Glu Arg Ser Gly Arg Ser Gly Ser Phe Leu Tyr Gln Val Ser Thr
                325                 330                 335

His Glu Gln Ser Glu Ser Arg Met Arg Arg Met Arg Arg Met Arg Arg
            340                 345                 350

<210> SEQ ID NO 9
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (19)..(20)
<223> OTHER INFORMATION: Any amino acid
<220> FEATURE:
<221> NAME/KEY: MOD_RES
<222> LOCATION: (23)..(24)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (30)..(31)
<223> OTHER INFORMATION: Any amino acid
<220> FEATURE:
<221> NAME/KEY: MOD_RES
<222> LOCATION: (34)..(36)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
<221> NAME/KEY: MOD_RES
<222> LOCATION: (44)..(44)
<223> OTHER INFORMATION: Any amino acid
<220> FEATURE:
<221> NAME/KEY: MOD_RES
<222> LOCATION: (55)..(58)
<223> OTHER INFORMATION: Any amino acid
<220> FEATURE:
<221> NAME/KEY: MOD_RES
<222> LOCATION: (63)..(65)
<223> OTHER INFORMATION: Any amino acid
```

```
<220> FEATURE:
<221> NAME/KEY: MOD_RES
<222> LOCATION: (67)..(68)
<223> OTHER INFORMATION: Any amino acid
<220> FEATURE:
<221> NAME/KEY: MOD_RES
<222> LOCATION: (70)..(71)
<223> OTHER INFORMATION: Any amino acid
<220> FEATURE:
<221> NAME/KEY: MOD_RES
<222> LOCATION: (77)..(77)
<223> OTHER INFORMATION: Any amino acid
<220> FEATURE:
<221> NAME/KEY: MOD_RES
<222> LOCATION: (84)..(84)
<223> OTHER INFORMATION: Any amino acid
<220> FEATURE:
<221> NAME/KEY: MOD_RES
<222> LOCATION: (86)..(86)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (97)..(97)
<223> OTHER INFORMATION: Any amino acid
<220> FEATURE:
<221> NAME/KEY: MOD_RES
<222> LOCATION: (103)..(103)
<223> OTHER INFORMATION: Any amino acid
<220> FEATURE:
<221> NAME/KEY: MOD_RES
<222> LOCATION: (105)..(108)
<223> OTHER INFORMATION: Any amino acid
<220> FEATURE:
<221> NAME/KEY: MOD_RES
<222> LOCATION: (111)..(111)
<223> OTHER INFORMATION: Any amino acid
<220> FEATURE:
<221> NAME/KEY: MOD_RES
<222> LOCATION: (113)..(113)
<223> OTHER INFORMATION: Any amino acid
<220> FEATURE:
<221> NAME/KEY: MOD_RES
<222> LOCATION: (118)..(118)
<223> OTHER INFORMATION: Any amino acid
<220> FEATURE:
<221> NAME/KEY: MOD_RES
<222> LOCATION: (124)..(125)
<223> OTHER INFORMATION: Any amino acid
<220> FEATURE:
<221> NAME/KEY: MOD_RES
<222> LOCATION: (127)..(127)
<223> OTHER INFORMATION: Any amino acid
<220> FEATURE:
<221> NAME/KEY: MOD_RES
<222> LOCATION: (129)..(130)
<223> OTHER INFORMATION: Any amino acid
<220> FEATURE:
<221> NAME/KEY: MOD_RES
<222> LOCATION: (132)..(132)
<223> OTHER INFORMATION: Any amino acid
<220> FEATURE:
<221> NAME/KEY: MOD_RES
<222> LOCATION: (135)..(136)
<223> OTHER INFORMATION: Any amino acid
<220> FEATURE:
<221> NAME/KEY: MOD_RES
<222> LOCATION: (139)..(140)
<223> OTHER INFORMATION: Any amino acid
<220> FEATURE:
<221> NAME/KEY: MOD_RES
<222> LOCATION: (142)..(142)
<223> OTHER INFORMATION: Any amino acid
<220> FEATURE:
<221> NAME/KEY: MOD_RES
<222> LOCATION: (144)..(144)
```

```
<223> OTHER INFORMATION: Any amino acid
<220> FEATURE:
<221> NAME/KEY: MOD_RES
<222> LOCATION: (146)..(146)
<223> OTHER INFORMATION: Any amino acid
<220> FEATURE:
<221> NAME/KEY: MOD_RES
<222> LOCATION: (149)..(150)
<223> OTHER INFORMATION: Any amino acid
<220> FEATURE:
<221> NAME/KEY: MOD_RES
<222> LOCATION: (154)..(154)
<223> OTHER INFORMATION: Any amino acid
<220> FEATURE:
<221> NAME/KEY: MOD_RES
<222> LOCATION: (158)..(158)
<223> OTHER INFORMATION: Any amino acid
<220> FEATURE:
<221> NAME/KEY: MOD_RES
<222> LOCATION: (161)..(162)
<223> OTHER INFORMATION: Any amino acid
<220> FEATURE:
<221> NAME/KEY: MOD_RES
<222> LOCATION: (170)..(170)
<223> OTHER INFORMATION: Any amino acid
<220> FEATURE:
<221> NAME/KEY: MOD_RES
<222> LOCATION: (172)..(172)
<223> OTHER INFORMATION: Any amino acid
<220> FEATURE:
<221> NAME/KEY: MOD_RES
<222> LOCATION: (179)..(179)
<223> OTHER INFORMATION: Any amino acid
<220> FEATURE:
<221> NAME/KEY: MOD_RES
<222> LOCATION: (182)..(183)
<223> OTHER INFORMATION: Any amino acid
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (188)..(188)
<223> OTHER INFORMATION: Any amino acid
<220> FEATURE:
<221> NAME/KEY: MOD_RES
<222> LOCATION: (192)..(192)
<223> OTHER INFORMATION: Any amino acid
<220> FEATURE:
<221> NAME/KEY: MOD_RES
<222> LOCATION: (194)..(195)
<223> OTHER INFORMATION: Any amino acid
<220> FEATURE:
<221> NAME/KEY: MOD_RES
<222> LOCATION: (197)..(197)
<223> OTHER INFORMATION: Any amino acid
<220> FEATURE:
<221> NAME/KEY: MOD_RES
<222> LOCATION: (202)..(202)
<223> OTHER INFORMATION: Any amino acid
<220> FEATURE:
<221> NAME/KEY: MOD_RES
<222> LOCATION: (209)..(209)
<223> OTHER INFORMATION: Any amino acid
<220> FEATURE:
<221> NAME/KEY: MOD_RES
<222> LOCATION: (216)..(216)
<223> OTHER INFORMATION: Any amino acid
<220> FEATURE:
<221> NAME/KEY: MOD_RES
<222> LOCATION: (218)..(220)
<223> OTHER INFORMATION: Any amino acid
<220> FEATURE:
<221> NAME/KEY: MOD_RES
<222> LOCATION: (223)..(223)
<223> OTHER INFORMATION: Any amino acid
<220> FEATURE:
<221> NAME/KEY: MOD_RES
```

```
<222> LOCATION: (230)..(230)
<223> OTHER INFORMATION: Any amino acid
<220> FEATURE:
<221> NAME/KEY: MOD_RES
<222> LOCATION: (237)..(237)
<223> OTHER INFORMATION: Any amino acid
<220> FEATURE:
<221> NAME/KEY: MOD_RES
<222> LOCATION: (247)..(247)
<223> OTHER INFORMATION: Any amino acid
<220> FEATURE:
<221> NAME/KEY: MOD_RES
<222> LOCATION: (254)..(255)
<223> OTHER INFORMATION: Any amino acid
<220> FEATURE:
<221> NAME/KEY: MOD_RES
<222> LOCATION: (258)..(259)
<223> OTHER INFORMATION: Any amino acid
<220> FEATURE:
<221> NAME/KEY: MOD_RES
<222> LOCATION: (261)..(261)
<223> OTHER INFORMATION: Any amino acid
<220> FEATURE:
<221> NAME/KEY: MOD_RES
<222> LOCATION: (263)..(263)
<223> OTHER INFORMATION: Any amino acid
<220> FEATURE:
<221> NAME/KEY: MOD_RES
<222> LOCATION: (268)..(268)
<223> OTHER INFORMATION: Any amino acid
<220> FEATURE:
<221> NAME/KEY: MOD_RES
<222> LOCATION: (271)..(273)
<223> OTHER INFORMATION: Any amino acid
<220> FEATURE:
<221> NAME/KEY: MOD_RES
<222> LOCATION: (275)..(275)
<223> OTHER INFORMATION: Any amino acid
<220> FEATURE:
<221> NAME/KEY: MOD_RES
<222> LOCATION: (282)..(283)
<223> OTHER INFORMATION: Any amino acid
<220> FEATURE:
<221> NAME/KEY: MOD_RES
<222> LOCATION: (298)..(298)
<223> OTHER INFORMATION: Any amino acid
<220> FEATURE:
<221> NAME/KEY: MOD_RES
<222> LOCATION: (300)..(301)
<223> OTHER INFORMATION: Any amino acid
<220> FEATURE:
<221> NAME/KEY: MOD_RES
<222> LOCATION: (303)..(303)
<223> OTHER INFORMATION: Any amino acid
<220> FEATURE:
<221> NAME/KEY: MOD_RES
<222> LOCATION: (309)..(309)
<223> OTHER INFORMATION: Any amino acid
<220> FEATURE:
<221> NAME/KEY: MOD_RES
<222> LOCATION: (312)..(312)
<223> OTHER INFORMATION: Any amino acid
<220> FEATURE:
<221> NAME/KEY: MOD_RES
<222> LOCATION: (314)..(315)
<223> OTHER INFORMATION: Any amino acid
<220> FEATURE:
<221> NAME/KEY: MOD_RES
<222> LOCATION: (318)..(319)
<223> OTHER INFORMATION: Any amino acid
<220> FEATURE:
<221> NAME/KEY: MOD_RES
<222> LOCATION: (321)..(321)
<223> OTHER INFORMATION: Any amino acid
<220> FEATURE:
<221> NAME/KEY: MOD_RES
<222> LOCATION: (324)..(324)
<223> OTHER INFORMATION: Any amino acid
```

<400> SEQUENCE: 9

```
Xaa Leu Tyr Gln Val Ser Thr His Xaa Gln Xaa Asp Ser Xaa His Gly
1               5                   10                  15

Xaa Thr Xaa Xaa Ser Thr Xaa Xaa Arg Gln Xaa Ser His Xaa Xaa Gln
            20                  25                  30

Ala Xaa Xaa Xaa Ser Arg His Ser Xaa Ser Gln Xaa Gly Gln Asp Thr
        35                  40                  45

Ile Arg Gly His Pro Gly Xaa Xaa Xaa Gly Arg Gln Gly Xaa Xaa
50                  55                  60

Xaa Glu Xaa Xaa Val Xaa Xaa Ser Gly His Ser Gly Xaa His His Ser
65                  70                  75                  80

His Thr Thr Xaa Gln Xaa Arg Ser Asp Ala Ser His Gly Xaa Ser Gly
            85                  90                  95

Xaa Arg Ser Ala Ser Arg Xaa Thr Xaa Xaa Xaa Xaa Gln Ser Xaa Asp
            100                 105                 110

Xaa Thr Arg His Ser Xaa Ser Arg His His Glu Xaa Xaa Ser Xaa Ala
            115                 120                 125

Xaa Xaa Ser Xaa His Ser Xaa Xaa Gly Gln Xaa Xaa Ser Xaa Gly Xaa
130                 135                 140

Arg Xaa Ser Arg Xaa Xaa Gly Ser Ser Xaa Ser Gln Asp Xaa Asp Ser
145                 150                 155                 160

Xaa Xaa His Ser Glu Asp Ser Glu Arg Xaa Ser Xaa Ser Ala Ser Arg
            165                 170                 175

Asn His Xaa Gly Ser Xaa Xaa Glu Gln Xaa Arg Xaa Gly Ser Arg Xaa
            180                 185                 190

Pro Xaa Xaa His Xaa Glu Asp Arg Ala Xaa His Gly His Ser Ala Asp
        195                 200                 205

Xaa Ser Arg Lys Ser Gly Thr Xaa His Xaa Xaa Ser Ser Xaa Gly
210                 215                 220

Gln Ala Ala Ser Xaa Glu Gln Ala Arg Ser Ser Xaa Gly Glu Arg
225                 230                 235                 240

His Gly Ser Arg His Gln Xaa Gln Ser Ala Asp Ser Ser Xaa Xaa Ser
            245                 250                 255

Gly Xaa Xaa His Xaa Gln Xaa Ser Ser Ala Val Xaa Asp Ser Xaa Xaa
            260                 265                 270

Xaa Gly Xaa Ser Gly Ser Gln Ala Thr Xaa Xaa Glu Gly His Ser Glu
            275                 280                 285

Asp Ser Asp Thr Gln Ser Val Ser Gly Xaa Gly Xaa Xaa Gly Xaa His
            290                 295                 300

Gln Gln Ser His Xaa Glu Ser Xaa Arg Xaa Xaa Ser Gly Xaa Xaa Ser
305                 310                 315                 320

Xaa Arg Ser Xaa Ser Phe Leu Tyr
                325
```

<210> SEQ ID NO 10
<211> LENGTH: 416
<212> TYPE: PRT
<213> ORGANISM: Homo sapiens

<400> SEQUENCE: 10

```
Ala Gly Pro His Gln Gln Ser His Gln Glu Ser Thr Arg Gly Arg Ser
1               5                   10                  15

Ala Gly Arg Ser Gly Arg Ser Gly Ser Phe Leu Tyr Gln Val Ser Thr
            20                  25                  30
```

```
His Glu Gln Ser Glu Ser Ala His Gly Arg Thr Gly Thr Ser Thr Gly
             35                  40                  45

Gly Arg Gln Gly Ser His His Gln Gln Ala Arg Asp Ser Ser Arg His
 50                  55                  60

Ser Thr Ser Gln Glu Gly Gln Asp Thr Ile His Gly His Arg Gly Ser
 65                  70                  75                  80

Ser Ser Gly Gly Arg Gln Gly Ser His Tyr Glu Gln Leu Val Asp Arg
                 85                  90                  95

Ser Gly His Ser Gly Ser His His Ser His Thr Thr Ser Gln Gly Arg
                100                 105                 110

Ser Asp Ala Ser His Gly His Ser Gly Ser Arg Ser Ala Ser Arg Gln
            115                 120                 125

Thr Arg Asn Asp Glu Gln Ser Gly Asp Gly Ser Arg His Ser Gly Ser
130                 135                 140

Arg His His Glu Ala Ser Ser Arg Ala Asp Ser Ser Gly His Ser Gln
145                 150                 155                 160

Val Gly Gln Gly Gln Ser Glu Gly Pro Arg Thr Ser Arg Asn Trp Gly
                165                 170                 175

Ser Ser Phe Ser Gln Asp Ser Asp Ser Gln Gly His Ser Glu Asp Ser
            180                 185                 190

Glu Arg Trp Ser Gly Ser Ala Ser Arg Asn His His Gly Ser Ala Gln
            195                 200                 205

Glu Gln Leu Arg Asp Gly Ser Arg His Pro Arg Ser His Gln Glu Asp
        210                 215                 220

Arg Ala Gly His Gly His Ser Ala Asp Ser Ser Arg Gln Ser Gly Thr
225                 230                 235                 240

Arg His Thr Gln Thr Ser Ser Gly Gly Gln Ala Ala Ser Ser His Glu
                245                 250                 255

Gln Ala Arg Ser Ser Ala Gly Asp Arg His Gly Ser His His Gln Gln
            260                 265                 270

Ser Ala Asp Ser Ser Arg His Ser Gly Ile Gly His Gly Gln Ala Ser
            275                 280                 285

Ser Ala Val Arg Asp Ser Gly His Arg Gly Tyr Ser Gly Ser Gln Ala
        290                 295                 300

Ser Asp Asn Glu Gly His Ser Glu Asp Ser Asp Thr Gln Ser Val Ser
305                 310                 315                 320

Ala His Gly Gln Ala Gly Ser His Gln Gln Ser His Gln Glu Ser Ala
                325                 330                 335

Arg Gly Arg Ser Gly Glu Thr Ser Gly His Ser Gly Ser Phe Leu Tyr
            340                 345                 350

Gln Val Ser Thr His Glu Gln Ser Glu Ser Ser His Gly Trp Thr Gly
            355                 360                 365

Pro Ser Thr Arg Gly Arg Gln Gly Ser Arg His Glu Gln Ala Gln Asp
        370                 375                 380

Ser Ser Arg His Ser Ala Ser Gln Asp Gly Asp Thr Ile Arg Gly
385                 390                 395                 400

His Pro Gly Ser Ser Arg Gly Gly Arg Gln Gly Tyr His His Glu Gln
                405                 410                 415

<210> SEQ ID NO 11
<211> LENGTH: 4061
<212> TYPE: PRT
<213> ORGANISM: Homo sapiens

<400> SEQUENCE: 11
```

```
Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
                20                  25                  30

Leu Lys Glu Leu Leu Glu Lys Glu Phe Arg Gln Ile Leu Lys Asn Pro
            35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His His Asp Lys His Glu Asp
            100                 105                 110

Asn Lys Gln Glu Glu Asn Lys Glu Asn Arg Lys Arg Pro Ser Ser Leu
        115                 120                 125

Glu Arg Arg Asn Asn Arg Lys Gly Asn Lys Gly Arg Ser Lys Ser Pro
    130                 135                 140

Arg Glu Thr Gly Gly Lys Arg His Glu Ser Ser Ser Glu Lys Lys Glu
145                 150                 155                 160

Arg Lys Gly Tyr Ser Pro Thr His Arg Glu Glu Glu Tyr Gly Lys Asn
                165                 170                 175

His His Asn Ser Ser Lys Lys Glu Lys Asn Lys Thr Glu Asn Thr Arg
            180                 185                 190

Leu Gly Asp Asn Arg Lys Arg Leu Ser Glu Arg Leu Glu Glu Lys Glu
        195                 200                 205

Asp Asn Glu Glu Gly Val Tyr Asp Tyr Glu Asn Thr Gly Arg Met Thr
    210                 215                 220

Gln Lys Trp Ile Gln Ser Gly His Ile Ala Thr Tyr Tyr Thr Ile Gln
225                 230                 235                 240

Asp Glu Ala Tyr Asp Thr Thr Asp Ser Leu Leu Glu Glu Asn Lys Ile
                245                 250                 255

Tyr Glu Arg Ser Arg Ser Ser Asp Gly Lys Ser Ser Ser Gln Val Asn
            260                 265                 270

Arg Ser Arg His Glu Asn Thr Ser Gln Val Pro Leu Gln Glu Ser Arg
        275                 280                 285

Thr Arg Lys Arg Arg Gly Ser Arg Val Ser Gln Asp Arg Asp Ser Glu
    290                 295                 300

Gly His Ser Glu Asp Ser Glu Arg His Ser Gly Ser Ala Ser Arg Asn
305                 310                 315                 320

His His Gly Ser Ala Trp Glu Gln Ser Arg Asp Gly Ser Arg His Pro
                325                 330                 335

Arg Ser His Asp Glu Asp Arg Ala Ser His Gly His Ser Ala Asp Ser
            340                 345                 350

Ser Arg Gln Ser Gly Thr Arg His Ala Glu Thr Ser Ser Arg Gly Gln
        355                 360                 365

Thr Ala Ser Ser His Glu Gln Ala Arg Ser Ser Pro Gly Glu Arg His
    370                 375                 380

Gly Ser Gly His Gln Gln Ser Ala Asp Ser Ser Arg His Ser Ala Thr
385                 390                 395                 400

Gly Arg Gly Gln Ala Ser Ser Ala Val Ser Asp Arg Gly His Arg Gly
                405                 410                 415
```

-continued

Ser Ser Gly Ser Gln Ala Ser Asp Ser Glu Gly His Ser Glu Asn Ser
            420                 425                 430

Asp Thr Gln Ser Val Ser Gly His Gly Lys Ala Gly Leu Arg Gln Gln
            435                 440                 445

Ser His Gln Glu Ser Thr Arg Gly Arg Ser Gly Glu Arg Ser Gly Arg
450                 455                 460

Ser Gly Ser Ser Leu Tyr Gln Val Ser Thr His Glu Gln Pro Asp Ser
465                 470                 475                 480

Ala His Gly Arg Thr Gly Thr Ser Thr Gly Gly Arg Gln Gly Ser His
            485                 490                 495

His Glu Gln Ala Arg Asp Ser Ser Arg His Ser Ala Ser Gln Glu Gly
            500                 505                 510

Gln Asp Thr Ile Arg Gly His Pro Gly Ser Ser Arg Gly Gly Arg Gln
            515                 520                 525

Gly Ser His His Glu Gln Ser Val Asn Arg Ser Gly His Ser Gly Ser
            530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
            565                 570                 575

Ser Gly Asp Gly Thr Arg His Ser Gly Ser Arg His His Glu Ala Ser
            580                 585                 590

Ser Gln Ala Asp Ser Ser Arg His Ser Gln Val Gly Gln Gly Gln Ser
            595                 600                 605

Ser Gly Pro Arg Thr Ser Arg Asn Gln Gly Ser Ser Val Ser Gln Asp
610                 615                 620

Ser Asp Ser Gln Gly His Ser Glu Asp Ser Glu Arg Trp Ser Gly Ser
625                 630                 635                 640

Ala Ser Arg Asn His His Gly Ser Ala Gln Glu Gln Ser Arg Asp Gly
            645                 650                 655

Ser Arg His Pro Arg Ser His His Glu Asp Arg Ala Gly His Gly His
            660                 665                 670

Ser Ala Asp Ser Ser Arg Lys Ser Gly Thr Arg His Thr Gln Asn Ser
            675                 680                 685

Ser Gly Gln Ala Ala Ser Ser His Glu Gln Ala Arg Ser Ser Ala
690                 695                 700

Gly Glu Arg His Gly Ser Arg His Gln Leu Gln Ser Ala Asp Ser Ser
705                 710                 715                 720

Arg His Ser Gly Thr Gly His Gly Gln Ala Ser Ser Ala Val Arg Asp
            725                 730                 735

Ser Gly His Arg Gly Ser Ser Gly Ser Gln Ala Thr Asp Ser Glu Gly
            740                 745                 750

His Ser Glu Asp Ser Asp Thr Gln Ser Val Ser Gly His Gly Gln Ala
            755                 760                 765

Gly His His Gln Gln Ser His Gln Glu Ser Ala Arg Asp Arg Ser Gly
770                 775                 780

Glu Arg Ser Arg Arg Ser Gly Ser Phe Leu Tyr Gln Val Ser Thr His
785                 790                 795                 800

Lys Gln Ser Glu Ser Ser His Gly Trp Thr Gly Pro Ser Thr Gly Val
            805                 810                 815

Arg Gln Gly Ser His His Glu Gln Ala Arg Asp Asn Ser Arg His Ser
            820                 825                 830

Ala Ser Gln Asp Gly Gln Asp Thr Ile Arg Gly His Pro Gly Ser Ser

```
            835                 840                 845
Arg Arg Gly Arg Gln Gly Ser His His Glu Gln Ser Val Asp Arg Ser
            850                 855                 860
Gly His Ser Gly Ser His His Ser His Thr Thr Ser Gln Gly Arg Ser
865                 870                 875                 880
Asp Ala Ser Arg Gly Gln Ser Gly Ser Arg Ser Ala Ser Arg Thr Thr
                        885                 890                 895
Arg Asn Glu Glu Gln Ser Arg Asp Gly Ser Arg His Ser Gly Ser Arg
                        900                 905                 910
His His Glu Ala Ser Ser His Ala Asp Ile Ser Arg His Ser Gln Ala
                        915                 920                 925
Gly Gln Gly Gln Ser Glu Gly Ser Arg Thr Ser Arg Arg Gln Gly Ser
            930                 935                 940
Ser Val Ser Gln Asp Ser Asp Ser Glu Gly His Ser Glu Asp Ser Glu
945                 950                 955                 960
Arg Trp Ser Gly Ser Ala Ser Arg Asn His Arg Gly Ser Ala Gln Glu
                        965                 970                 975
Gln Ser Arg His Gly Ser Arg His Pro Arg Ser His His Glu Asp Arg
                        980                 985                 990
Ala Gly His Gly His Ser Ala Asp Ser Ser Arg Gln Ser Gly Thr Pro
                        995                     1000                1005
His Ala Glu Thr Ser Ser Gly Gly Gln Ala Ala Ser Ser His Glu
            1010                1015                1020
Gln Ala Arg Ser Ser Pro Gly Glu Arg His Gly Ser Arg His Gln
            1025                1030                1035
Gln Ser Ala Asp Ser Ser Arg His Ser Gly Ile Pro Arg Arg Gln
            1040                1045                1050
Ala Ser Ser Ala Val Arg Asp Ser Gly His Trp Gly Ser Ser Gly
            1055                1060                1065
Ser Gln Ala Ser Asp Ser Glu Gly His Ser Glu Glu Ser Asp Thr
            1070                1075                1080
Gln Ser Val Ser Gly His Gly Gln Asp Gly Pro His Gln Gln Ser
            1085                1090                1095
His Gln Glu Ser Ala Arg Asp Trp Ser Gly Gly Arg Ser Gly Arg
            1100                1105                1110
Ser Gly Ser Phe Ile Tyr Gln Val Ser Thr His Glu Gln Ser Glu
            1115                1120                1125
Ser Ala His Gly Arg Thr Arg Thr Ser Thr Gly Arg Arg Gln Gly
            1130                1135                1140
Ser His His Glu Gln Ala Arg Asp Ser Ser Arg His Ser Ala Ser
            1145                1150                1155
Gln Glu Gly Gln Asp Thr Ile Arg Ala His Pro Gly Ser Arg Arg
            1160                1165                1170
Gly Gly Arg Gln Gly Ser His His Glu Gln Ser Val Asp Arg Ser
            1175                1180                1185
Gly His Ser Gly Ser His Ser His Thr Thr Ser Gln Gly Arg
            1190                1195                1200
Ser Asp Ala Ser His Gly Gln Ser Gly Ser Arg Ser Ala Ser Arg
            1205                1210                1215
Gln Thr Arg Lys Asp Lys Gln Ser Gly Asp Gly Ser Arg His Ser
            1220                1225                1230
Gly Ser Arg His His Glu Ala Ala Ser Trp Ala Asp Ser Ser Arg
            1235                1240                1245
```

```
His Ser Gln Val Gly Gln Glu Gln Ser Ser Gly Ser Arg Thr Ser
1250                1255                1260

Arg His Gln Gly Ser Ser Val Ser Gln Asp Ser Asp Ser Glu Arg
1265                1270                1275

His Ser Asp Asp Ser Glu Arg Leu Ser Gly Ser Ala Ser Arg Asn
1280                1285                1290

His His Gly Ser Ser Arg Glu Gln Ser Arg Asp Gly Ser Arg His
1295                1300                1305

Pro Gly Phe His Gln Glu Asp Arg Ala Ser His Gly His Ser Ala
1310                1315                1320

Asp Ser Ser Arg Gln Ser Gly Thr His His Thr Glu Ser Ser Ser
1325                1330                1335

His Gly Gln Ala Val Ser Ser His Glu Gln Ala Arg Ser Ser Pro
1340                1345                1350

Gly Glu Arg His Gly Ser Arg His Gln Gln Ser Ala Asp Ser Ser
1355                1360                1365

Arg His Ser Gly Ile Gly His Arg Gln Ala Ser Ser Ala Val Arg
1370                1375                1380

Asp Ser Gly His Arg Gly Ser Ser Gly Ser Gln Val Thr Asn Ser
1385                1390                1395

Glu Gly His Ser Glu Asp Ser Asp Thr Gln Ser Val Ser Ala His
1400                1405                1410

Gly Gln Ala Gly Pro His Gln Gln Ser His Lys Glu Ser Ala Arg
1415                1420                1425

Gly Gln Ser Gly Glu Ser Ser Gly Arg Ser Arg Ser Phe Leu Tyr
1430                1435                1440

Gln Val Ser Ser His Glu Gln Ser Glu Ser Thr His Gly Gln Thr
1445                1450                1455

Ala Pro Ser Thr Gly Gly Arg Gln Gly Ser Arg His Glu Gln Ala
1460                1465                1470

Arg Asn Ser Ser Arg His Ser Ala Ser Gln Asp Gly Gln Asp Thr
1475                1480                1485

Ile Arg Gly His Pro Gly Ser Ser Arg Gly Gly Arg Gln Gly Ser
1490                1495                1500

Tyr His Glu Gln Ser Val Asp Arg Ser Gly His Ser Gly Tyr His
1505                1510                1515

His Ser His Thr Thr Pro Gln Gly Arg Ser Asp Ala Ser His Gly
1520                1525                1530

Gln Ser Gly Pro Arg Ser Ala Ser Arg Gln Thr Arg Asn Glu Glu
1535                1540                1545

Gln Ser Gly Asp Gly Ser Arg His Ser Gly Ser Arg His His Glu
1550                1555                1560

Pro Ser Thr Arg Ala Gly Ser Ser Arg His Ser Gln Val Gly Gln
1565                1570                1575

Gly Glu Ser Ala Gly Ser Lys Thr Ser Arg Arg Gln Gly Ser Ser
1580                1585                1590

Val Ser Gln Asp Arg Asp Ser Glu Gly His Ser Glu Asp Ser Glu
1595                1600                1605

Arg Arg Ser Glu Ser Ala Ser Arg Asn His Tyr Gly Ser Ala Arg
1610                1615                1620

Glu Gln Ser Arg His Gly Ser Arg Asn Pro Arg Ser His Gln Glu
1625                1630                1635
```

```
Asp Arg Ala Ser His Gly His  Ser Ala Glu Ser Ser  Arg Gln Ser
    1640            1645                1650

Gly Thr Arg His Ala Glu Thr  Ser Ser Gly Gly Gln  Ala Ala Ser
    1655            1660                1665

Ser Gln Glu Gln Ala Arg Ser  Ser Pro Gly Glu Arg  His Gly Ser
    1670            1675                1680

Arg His Gln Gln Ser Ala Asp  Ser Ser Thr Asp Ser  Gly Thr Gly
    1685            1690                1695

Arg Arg Gln Asp Ser Ser Val  Val Gly Asp Ser Gly  Asn Arg Gly
    1700            1705                1710

Ser Ser Gly Ser Gln Ala Ser  Asp Ser Glu Gly His  Ser Glu Glu
    1715            1720                1725

Ser Asp Thr Gln Ser Val Ser  Ala His Gly Gln Ala  Gly Pro His
    1730            1735                1740

Gln Gln Ser His Gln Glu Ser  Thr Arg Gly Gln Ser  Gly Glu Arg
    1745            1750                1755

Ser Gly Arg Ser Gly Ser Phe  Leu Tyr Gln Val Ser  Thr His Glu
    1760            1765                1770

Gln Ser Glu Ser Ala His Gly  Arg Thr Gly Pro Ser  Thr Gly Gly
    1775            1780                1785

Arg Gln Arg Ser Arg His Glu  Gln Ala Arg Asp Ser  Ser Arg His
    1790            1795                1800

Ser Ala Ser Gln Glu Gly Gln  Asp Thr Ile Arg Gly  His Pro Gly
    1805            1810                1815

Ser Ser Arg Gly Gly Arg Gln  Gly Ser His Tyr Glu  Gln Ser Val
    1820            1825                1830

Asp Ser Ser Gly His Ser Gly  Ser His His Ser His  Thr Thr Ser
    1835            1840                1845

Gln Glu Arg Ser Asp Val Ser  Arg Gly Gln Ser Gly  Ser Arg Ser
    1850            1855                1860

Val Ser Arg Gln Thr Arg Asn  Glu Lys Gln Ser Gly  Asp Gly Ser
    1865            1870                1875

Arg His Ser Gly Ser Arg His  His Glu Ala Ser Ser  Arg Ala Asp
    1880            1885                1890

Ser Ser Arg His Ser Gln Val  Gly Gln Gly Gln Ser  Ser Gly Pro
    1895            1900                1905

Arg Thr Ser Arg Asn Gln Gly  Ser Ser Val Ser Gln  Asp Ser Asp
    1910            1915                1920

Ser Gln Gly His Ser Glu Asp  Ser Glu Arg Trp Ser  Gly Ser Ala
    1925            1930                1935

Ser Arg Asn His Leu Gly Ser  Ala Trp Glu Gln Ser  Arg Asp Gly
    1940            1945                1950

Ser Arg His Pro Gly Ser His  His Glu Asp Arg Ala  Gly His Gly
    1955            1960                1965

His Ser Ala Asp Ser Ser Arg  Gln Ser Gly Thr Arg  His Thr Glu
    1970            1975                1980

Ser Ser Ser Arg Gly Gln Ala  Ala Ser Ser His Glu  Gln Ala Arg
    1985            1990                1995

Ser Ser Ala Gly Glu Arg His  Gly Ser His His Gln  Leu Gln Ser
    2000            2005                2010

Ala Asp Ser Ser Arg His Ser  Gly Ile Gly His Gly  Gln Ala Ser
    2015            2020                2025

Ser Ala Val Arg Asp Ser Gly  His Arg Gly Tyr Ser  Gly Ser Gln
```

```
                2030                2035                2040
Ala Ser Asp Ser Glu Gly His Ser Glu Asp Ser Asp Thr Gln Ser
        2045                2050                2055

Val Ser Ala Gln Gly Lys Ala Gly Pro His Gln Gln Ser His Lys
        2060                2065                2070

Glu Ser Ala Arg Gly Gln Ser Gly Glu Ser Ser Gly Arg Ser Gly
        2075                2080                2085

Ser Phe Leu Tyr Gln Val Ser Thr His Glu Gln Ser Glu Ser Thr
        2090                2095                2100

His Gly Gln Ser Ala Pro Ser Thr Gly Gly Arg Gln Gly Ser His
        2105                2110                2115

Tyr Asp Gln Ala Gln Asp Ser Ser Arg His Ser Ala Ser Gln Glu
        2120                2125                2130

Gly Gln Asp Thr Ile Arg Gly His Pro Gly Pro Ser Arg Gly Gly
        2135                2140                2145

Arg Gln Gly Ser His Gln Glu Gln Ser Val Asp Arg Ser Gly His
        2150                2155                2160

Ser Gly Ser His His Ser His Thr Thr Ser Gln Gly Arg Ser Asp
        2165                2170                2175

Ala Ser Arg Gly Gln Ser Gly Ser Arg Ser Ala Ser Arg Lys Thr
        2180                2185                2190

Tyr Asp Lys Glu Gln Ser Gly Asp Gly Ser Arg His Ser Gly Ser
        2195                2200                2205

His His His Glu Ala Ser Ser Trp Ala Asp Ser Ser Arg His Ser
        2210                2215                2220

Leu Val Gly Gln Gly Gln Ser Ser Gly Pro Arg Thr Ser Arg Pro
        2225                2230                2235

Arg Gly Ser Ser Val Ser Gln Asp Ser Asp Ser Glu Gly His Ser
        2240                2245                2250

Glu Asp Ser Glu Arg Arg Ser Gly Ser Ala Ser Arg Asn His His
        2255                2260                2265

Gly Ser Ala Gln Glu Gln Ser Arg Asp Gly Ser Arg His Pro Arg
        2270                2275                2280

Ser His His Glu Asp Arg Ala Gly His Gly His Ser Ala Glu Ser
        2285                2290                2295

Ser Arg Gln Ser Gly Thr His His Ala Glu Asn Ser Ser Gly Gly
        2300                2305                2310

Gln Ala Ala Ser Ser His Glu Gln Ala Arg Ser Ser Ala Gly Glu
        2315                2320                2325

Arg His Gly Ser His His Gln Gln Ser Ala Asp Ser Ser Arg His
        2330                2335                2340

Ser Gly Ile Gly His Gly Gln Ala Ser Ser Ala Val Arg Asp Ser
        2345                2350                2355

Gly His Arg Gly Ser Ser Gly Ser Gln Ala Ser Asp Ser Glu Gly
        2360                2365                2370

His Ser Glu Asp Ser Asp Thr Gln Ser Val Ser Ala His Gly Gln
        2375                2380                2385

Ala Gly Pro His Gln Gln Ser His Gln Glu Ser Thr Arg Gly Arg
        2390                2395                2400

Ser Ala Gly Arg Ser Gly Arg Ser Gly Ser Phe Leu Tyr Gln Val
        2405                2410                2415

Ser Thr His Glu Gln Ser Glu Ser Ala His Gly Arg Thr Gly Thr
        2420                2425                2430
```

```
Ser Thr Gly Gly Arg Gln Gly Ser His His Lys Gln Ala Arg Asp
2435            2440                2445

Ser Ser Arg His Ser Thr Ser Gln Glu Gly Gln Asp Thr Ile His
2450            2455                2460

Gly His Pro Gly Ser Ser Ser Gly Gly Arg Gln Gly Ser His Tyr
2465            2470                2475

Glu Gln Leu Val Asp Arg Ser Gly His Ser Gly Ser His His Ser
2480            2485                2490

His Thr Thr Ser Gln Gly Arg Ser Asp Ala Ser His Gly His Ser
2495            2500                2505

Gly Ser Arg Ser Ala Ser Arg Gln Thr Arg Asn Asp Glu Gln Ser
2510            2515                2520

Gly Asp Gly Ser Arg His Ser Gly Ser Arg His His Glu Ala Ser
2525            2530                2535

Ser Arg Ala Asp Ser Ser Gly His Ser Gln Val Gly Gln Gly Gln
2540            2545                2550

Ser Glu Gly Pro Arg Thr Ser Arg Asn Trp Gly Ser Ser Phe Ser
2555            2560                2565

Gln Asp Ser Asp Ser Gln Gly His Ser Glu Asp Ser Glu Arg Trp
2570            2575                2580

Ser Gly Ser Ala Ser Arg Asn His His Gly Ser Ala Gln Glu Gln
2585            2590                2595

Leu Arg Asp Gly Ser Arg His Pro Arg Ser His Gln Glu Asp Arg
2600            2605                2610

Ala Gly His Gly His Ser Ala Asp Ser Ser Arg Gln Ser Gly Thr
2615            2620                2625

Arg His Thr Gln Thr Ser Ser Gly Gly Gln Ala Ala Ser Ser His
2630            2635                2640

Glu Gln Ala Arg Ser Ser Ala Gly Glu Arg His Gly Ser His His
2645            2650                2655

Gln Gln Ser Ala Asp Ser Ser Arg His Ser Gly Ile Gly His Gly
2660            2665                2670

Gln Ala Ser Ser Ala Val Arg Asp Ser Gly His Arg Gly Tyr Ser
2675            2680                2685

Gly Ser Gln Ala Ser Asp Asn Glu Gly His Ser Glu Asp Ser Asp
2690            2695                2700

Thr Gln Ser Val Ser Ala His Gly Gln Ala Gly Ser His Gln Gln
2705            2710                2715

Ser His Gln Glu Ser Ala Arg Gly Arg Ser Gly Glu Thr Ser Gly
2720            2725                2730

His Ser Gly Ser Phe Leu Tyr Gln Val Ser Thr His Glu Gln Ser
2735            2740                2745

Glu Ser Ser His Gly Trp Thr Gly Pro Ser Thr Arg Gly Arg Gln
2750            2755                2760

Gly Ser Arg His Glu Gln Ala Gln Asp Ser Ser Arg His Ser Ala
2765            2770                2775

Ser Gln Asp Gly Gln Asp Thr Ile Arg Gly His Pro Gly Ser Ser
2780            2785                2790

Arg Gly Gly Arg Gln Gly Tyr His His Glu His Ser Val Asp Ser
2795            2800                2805

Ser Gly His Ser Gly Ser His His Ser His Thr Thr Ser Gln Gly
2810            2815                2820
```

```
Arg Ser Asp Ala Ser Arg Gly Gln Ser Gly Ser Arg  Ser Ala Ser
    2825                2830                     2835

Arg Thr Thr Arg Asn Glu Glu Gln Ser Gly Asp Gly  Ser Arg His
    2840                2845                     2850

Ser Gly Ser Arg His His Glu Ala Ser Thr His Ala  Asp Ile Ser
    2855                2860                     2865

Arg His Ser Gln Ala Val Gln Gly Gln Ser Glu Gly  Ser Arg Arg
    2870                2875                     2880

Ser Arg Arg Gln Gly Ser Ser Val Ser Gln Asp Ser  Asp Ser Glu
    2885                2890                     2895

Gly His Ser Glu Asp Ser Glu Arg Trp Ser Gly Ser  Ala Ser Arg
    2900                2905                     2910

Asn His His Gly Ser Ala Gln Glu Gln Leu Arg Asp  Gly Ser Arg
    2915                2920                     2925

His Pro Arg Ser His Gln Glu Asp Arg Ala Gly His  Gly His Ser
    2930                2935                     2940

Ala Asp Ser Ser Arg Gln Ser Gly Thr Arg His Thr  Gln Thr Ser
    2945                2950                     2955

Ser Gly Gly Gln Ala Ala Ser Ser His Glu Gln Ala  Arg Ser Ser
    2960                2965                     2970

Ala Gly Glu Arg His Gly Ser His His Gln Gln Ser  Ala Asp Ser
    2975                2980                     2985

Ser Arg His Ser Gly Ile Gly His Gly Gln Ala Ser  Ser Ala Val
    2990                2995                     3000

Arg Asp Ser Gly His Arg Gly Tyr Ser Gly Ser Gln  Ala Ser Asp
    3005                3010                     3015

Asn Glu Gly His Ser Glu Asp Ser Asp Thr Gln Ser  Val Ser Ala
    3020                3025                     3030

His Gly Gln Ala Gly Ser His Gln Gln Ser His Gln  Glu Ser Ala
    3035                3040                     3045

Arg Gly Arg Ser Gly Glu Thr Ser Gly His Ser Gly  Ser Phe Leu
    3050                3055                     3060

Tyr Gln Val Ser Thr His Glu Gln Ser Glu Ser Ser  His Gly Trp
    3065                3070                     3075

Thr Gly Pro Ser Thr Arg Gly Arg Gln Gly Ser Arg  His Glu Gln
    3080                3085                     3090

Ala Gln Asp Ser Ser Arg His Ser Ala Ser Gln Tyr  Gly Gln Asp
    3095                3100                     3105

Thr Ile Arg Gly His Pro Gly Ser Ser Arg Gly Gly  Arg Gln Gly
    3110                3115                     3120

Tyr His His Glu His Ser Val Asp Ser Ser Gly His  Ser Gly Ser
    3125                3130                     3135

His His Ser His Thr Thr Ser Gln Gly Arg Ser Asp  Ala Ser Arg
    3140                3145                     3150

Gly Gln Ser Gly Ser Arg Ser Ala Ser Arg Thr Thr  Arg Asn Glu
    3155                3160                     3165

Glu Gln Ser Gly Asp Ser Ser Arg His Ser Val Ser  Arg His His
    3170                3175                     3180

Glu Ala Ser Thr His Ala Asp Ile Ser Arg His Ser  Gln Ala Val
    3185                3190                     3195

Gln Gly Gln Ser Glu Gly Ser Arg Arg Ser Arg Arg  Gln Gly Ser
    3200                3205                     3210

Ser Val Ser Gln Asp Ser Asp Ser Glu Gly His Ser  Glu Asp Ser
```

-continued

```
                3215                3220                3225
Glu Arg Trp Ser Gly Ser Ala Ser Arg Asn His Arg Gly Ser Val
        3230                3235                3240
Gln Glu Gln Ser Arg His Gly Ser Arg His Pro Arg Ser His His
        3245                3250                3255
Glu Asp Arg Ala Gly His Gly His Ser Ala Asp Arg Ser Arg Gln
        3260                3265                3270
Ser Gly Thr Arg His Ala Glu Thr Ser Ser Gly Gly Gln Ala Ala
        3275                3280                3285
Ser Ser His Glu Gln Ala Arg Ser Ser Pro Gly Glu Arg His Gly
        3290                3295                3300
Ser Arg His Gln Gln Ser Ala Asp Ser Ser Arg His Ser Gly Ile
        3305                3310                3315
Pro Arg Gly Gln Ala Ser Ser Ala Val Arg Asp Ser Arg His Trp
        3320                3325                3330
Gly Ser Ser Gly Ser Gln Ala Ser Asp Ser Glu Gly His Ser Glu
        3335                3340                3345
Glu Ser Asp Thr Gln Ser Val Ser Gly His Gly Gln Ala Gly Pro
        3350                3355                3360
His Gln Gln Ser His Gln Glu Ser Ala Arg Asp Arg Ser Gly Gly
        3365                3370                3375
Arg Ser Gly Arg Ser Gly Ser Phe Leu Tyr Gln Val Ser Thr His
        3380                3385                3390
Glu Gln Ser Glu Ser Ala His Gly Arg Thr Arg Thr Ser Thr Gly
        3395                3400                3405
Arg Arg Gln Gly Ser His His Glu Gln Ala Arg Asp Ser Ser Arg
        3410                3415                3420
His Ser Ala Ser Gln Glu Gly Gln Asp Thr Ile Arg Gly His Pro
        3425                3430                3435
Gly Ser Ser Arg Arg Gly Arg Gln Gly Ser His Tyr Glu Gln Ser
        3440                3445                3450
Val Asp Arg Ser Gly His Ser Gly Ser His His Ser His Thr Thr
        3455                3460                3465
Ser Gln Gly Arg Ser Asp Ala Ser Arg Gly Gln Ser Gly Ser Arg
        3470                3475                3480
Ser Ala Ser Arg Gln Thr Arg Asn Asp Glu Gln Ser Gly Asp Gly
        3485                3490                3495
Ser Arg His Ser Trp Ser His His Glu Ala Ser Thr Gln Ala
        3500                3505                3510
Asp Ser Ser Arg His Ser Gln Ser Gly Gln Gly Gln Ser Ala Gly
        3515                3520                3525
Pro Arg Thr Ser Arg Asn Gln Gly Ser Ser Val Ser Gln Asp Ser
        3530                3535                3540
Asp Ser Gln Gly His Ser Glu Asp Ser Glu Arg Trp Ser Gly Ser
        3545                3550                3555
Ala Ser Arg Asn His Arg Gly Ser Ala Gln Glu Gln Ser Arg Asp
        3560                3565                3570
Gly Ser Arg His Pro Thr Ser His His Glu Asp Arg Ala Gly His
        3575                3580                3585
Gly His Ser Ala Glu Ser Ser Arg Gln Ser Gly Thr His His Ala
        3590                3595                3600
Glu Asn Ser Ser Gly Gly Gln Ala Ala Ser Ser His Glu Gln Ala
        3605                3610                3615
```

```
Arg Ser Ser Ala Gly Glu Arg His Gly Ser His His Gln Gln Ser
    3620            3625            3630

Ala Asp Ser Ser Arg His Ser Gly Ile Gly His Gly Gln Ala Ser
    3635            3640            3645

Ser Ala Val Arg Asp Ser Gly His Arg Gly Ser Ser Gly Ser Gln
    3650            3655            3660

Ala Ser Asp Ser Glu Gly His Ser Glu Asp Ser Asp Thr Gln Ser
    3665            3670            3675

Val Ser Ala His Gly Gln Ala Gly Pro His Gln Gln Ser His Gln
    3680            3685            3690

Glu Ser Thr Arg Gly Arg Ser Ala Gly Arg Ser Gly Arg Ser Gly
    3695            3700            3705

Ser Phe Leu Tyr Gln Val Ser Thr His Glu Gln Ser Glu Ser Ala
    3710            3715            3720

His Gly Arg Ala Gly Pro Ser Thr Gly Gly Arg Gln Gly Ser Arg
    3725            3730            3735

His Glu Gln Ala Arg Asp Ser Ser Arg His Ser Ala Ser Gln Glu
    3740            3745            3750

Gly Gln Asp Thr Ile Arg Gly His Pro Gly Ser Arg Arg Gly Gly
    3755            3760            3765

Arg Gln Gly Ser Tyr His Glu Gln Ser Val Asp Arg Ser Gly His
    3770            3775            3780

Ser Gly Ser His His Ser His Thr Thr Ser Gln Gly Arg Ser Asp
    3785            3790            3795

Ala Ser His Gly Gln Ser Gly Ser Arg Ser Ala Ser Arg Glu Thr
    3800            3805            3810

Arg Asn Glu Glu Gln Ser Gly Asp Gly Ser Arg His Ser Gly Ser
    3815            3820            3825

Arg His His Glu Ala Ser Thr Gln Ala Asp Ser Ser Arg His Ser
    3830            3835            3840

Gln Ser Gly Gln Gly Glu Ser Ala Gly Ser Arg Arg Ser Arg Arg
    3845            3850            3855

Gln Gly Ser Ser Val Ser Gln Asp Ser Asp Ser Glu Ala Tyr Pro
    3860            3865            3870

Glu Asp Ser Glu Arg Arg Ser Glu Ser Ala Ser Arg Asn His His
    3875            3880            3885

Gly Ser Ser Arg Glu Gln Ser Arg Asp Gly Ser Arg His Pro Gly
    3890            3895            3900

Ser Ser His Arg Asp Thr Ala Ser His Val Gln Ser Ser Pro Val
    3905            3910            3915

Gln Ser Asp Ser Ser Thr Ala Lys Glu His Gly His Phe Ser Ser
    3920            3925            3930

Leu Ser Gln Asp Ser Ala Tyr His Ser Gly Ile Gln Ser Arg Gly
    3935            3940            3945

Ser Pro His Ser Ser Ser Ser Tyr His Tyr Gln Ser Glu Gly Thr
    3950            3955            3960

Glu Arg Gln Lys Gly Gln Ser Gly Leu Val Trp Arg His Gly Ser
    3965            3970            3975

Tyr Gly Ser Ala Asp Tyr Asp Tyr Gly Glu Ser Gly Phe Arg His
    3980            3985            3990

Ser Gln His Gly Ser Val Ser Tyr Asn Ser Asn Pro Val Val Phe
    3995            4000            4005
```

-continued

```
Lys Glu Arg Ser Asp Ile Cys Lys Ala Ser Ala Phe Gly Lys Asp
    4010                4015                4020

His Pro Arg Tyr Tyr Ala Thr Tyr Ile Asn Lys Asp Pro Gly Leu
    4025                4030                4035

Cys Gly His Ser Ser Asp Ile Ser Lys Gln Leu Gly Phe Ser Gln
    4040                4045                4050

Ser Gln Arg Tyr Tyr Tyr Glu
    4055                4060

<210> SEQ ID NO 12
<211> LENGTH: 4384
<212> TYPE: PRT
<213> ORGANISM: Mus musculus
<220> FEATURE:
<221> NAME/KEY: MOD_RES
<222> LOCATION: (1045)..(1045)
<223> OTHER INFORMATION: Any amino acid
<220> FEATURE:
<221> NAME/KEY: MOD_RES
<222> LOCATION: (1048)..(1048)
<223> OTHER INFORMATION: Any amino acid

<400> SEQUENCE: 12

Met Ser Ala Leu Leu Glu Ser Ile Thr Ser Met Ile Glu Ile Phe Gln
1               5                   10                  15

Gln Tyr Ser Thr Ser Asp Lys Glu Glu Glu Thr Leu Ser Lys Glu Glu
                20                  25                  30

Leu Lys Glu Leu Leu Glu Gly Gln Leu Gln Ala Val Leu Lys Asn Pro
            35                  40                  45

Asp Asp Gln Asp Ile Ala Glu Val Phe Met Gln Met Leu Asp Val Asp
        50                  55                  60

His Asp Asp Lys Leu Asp Phe Ala Glu Tyr Leu Leu Leu Val Leu Lys
    65                  70                  75                  80

Leu Ala Lys Ala Tyr Tyr Glu Ala Ser Lys Asn Glu Ser Phe Gln Thr
                85                  90                  95

His Gly Ser Asn Gly Arg Ser Lys Thr Asp Tyr Lys Gly Leu Glu Glu
                100                 105                 110

Glu Gly Glu Gly Asn Lys Gln Asn Leu Arg Arg Arg His Gly Gly
            115                 120                 125

Thr Asp Gly Lys Arg Lys Ser Asp Arg Thr Arg Ser Pro Asn Gly Lys
        130                 135                 140

Arg Gly Lys Arg Gln Glu Ser Arg Cys Arg Ser Glu Gly Lys Asp Lys
145                 150                 155                 160

His Arg Arg Glu Pro Glu Lys His Arg His Gln Asp Ser Lys Arg
                165                 170                 175

Lys Gln Arg His Gly Ser Gly Ser Thr Glu Arg Lys Asp Asn Arg Asn
                180                 185                 190

Lys Lys Asn Arg Gln Ser Lys Glu Arg Asn Tyr Asp Glu Ile Tyr Asp
            195                 200                 205

Asn Gly Lys Tyr Asn Glu Asp Trp Glu Ala Ser Tyr Asn Asn Cys Tyr
        210                 215                 220

Tyr Lys Thr Gln Asn Thr Thr Leu Asp Gln Arg Glu Gly Asn Arg Arg
225                 230                 235                 240

Pro Arg Ala Asp Ser Gln Lys Glu Pro Gln Ser Ser His Gly Gln Ala
                245                 250                 255

Asp Asn Ser Asp Ser Glu Gly Gly Arg Gln Gln Ser His Ser Lys Pro
                260                 265                 270
```

```
Ser Pro Val Arg Ala Asp Gln Arg Ser Arg Ala Gly Gln Ala Gly
        275                 280                 285

Ser Ser Lys Val Ser Ala Arg Ser Gly Ser Gly Gly Arg Gly Gln Ser
        290                 295                 300

Pro Asp Gly Ser Gly Arg Ser Ser Asn Arg Arg Asp Arg Pro Arg Gln
305                 310                 315                 320

Pro Ser Pro Ser Gln Ser Ser Asp Ser Gln Val His Ser Gly Val Gln
                325                 330                 335

Val Glu Gly Arg Arg Gly Gln Ser Ser Ala Asn Arg Arg Ala Gly
            340                 345                 350

Ser Ser Ser Gly Ser Gly Val Gln Gly Ala Ser Ala Gly Gly Leu Ala
        355                 360                 365

Ala Asp Ala Ser Arg Arg Ser Gly Ala Arg Gln Gly Gln Ala Ser Ala
        370                 375                 380

Gln Gly Arg Ala Gly Ser Gln Gly Gln Ala Gln Gly Arg Val Gly Ser
385                 390                 395                 400

Ser Ala Asp Arg Gln Gly Arg Arg Gly Val Ser Glu Ser Gln Ala Ser
                405                 410                 415

Asp Ser Glu Gly His Ser Asp Phe Ser Glu Gly Gln Ala Val Gly Ala
                420                 425                 430

His Arg Gln Ser Gly Ala Gly Gln Arg His Glu Gln Arg Ser Ser Arg
        435                 440                 445

Gly Gln His Gly Ser Arg Tyr Tyr Glu Gln Glu His Ser Glu Glu
        450                 455                 460

Glu Ser Asp Ser Gln His Gln His Gly His Gln His Glu Gln Gln Arg
465                 470                 475                 480

Gly His Gln His Gln His Glu His Glu Gln Pro Glu Ser Gly His Arg
                485                 490                 495

Gln Gln Gln Ser Ser Gly Arg Gly His Gln Gly Ala His Gln Glu Gln
                500                 505                 510

Gly Arg Asp Ser Ala Arg Ser Arg Gly Ser Asn Gln Gly His Ser Ser
        515                 520                 525

Ser Arg His Gln Ala Asp Ser Pro Arg Val Ser Ala Arg Ser Gly Ser
        530                 535                 540

Gly Gly Arg Gly Gln Ser Pro Asp Ala Ser Gly Arg Ser Ser Asn Arg
545                 550                 555                 560

Arg Asp Arg Pro Arg Gln Pro Ser Pro Ser Gln Ser Ser Asp Ser Gln
                565                 570                 575

Val His Ser Gly Val Gln Val Glu Gly Arg Arg Gly Gln Ser Ser Ser
                580                 585                 590

Ala Asn Arg Arg Ala Gly Ser Ser Gly Ser Gly Val Gln Gly Ala
        595                 600                 605

Ser Ala Gly Gly Leu Ala Ala Asp Ala Ser Arg Arg Ser Gly Ala Leu
        610                 615                 620

Gln Gly Gln Ala Ser Ala Gln Gly Arg Ala Gly Ser Gln Gly Gln Ala
625                 630                 635                 640

Gln Gly Arg Val Gly Ser Ser Ala Asp Arg Gln Gly Arg Arg Gly Val
                645                 650                 655

Ser Glu Ser Gln Ala Ser Asp Ser Glu Gly His Ser Asp Phe Ser Glu
                660                 665                 670

Gly Gln Ala Val Gly Ala His Arg Gln Ser Gly Ala Gly Gln Arg His
        675                 680                 685

Glu Gln Arg Ser Ser Arg Gly Gln His Gly Ser Gly Tyr Tyr Tyr Glu
```

```
                690             695             700
Gln Glu His Ser Glu Glu Ser Asp Ser Gln His Gln His Gly His
705             710             715             720

Gln His Glu Gln Gln Arg Gly His Gln His Gln His Gln His
        725             730             735

Glu His Glu Gln Pro Glu Ser Gly His Arg Gln Gln Ser Ser Gly
        740             745             750

Arg Gly His Gln Gly Ala His Gln Glu Gln Gly Arg Asp Ser Ala Arg
        755             760             765

Ser Arg Gly Ser Asn Gln Gly His Ser Ser Arg His Gln Ala Asp
770             775             780

Ser Pro Arg Val Ser Ala Arg Ser Gly Ser Gly Arg Gly Gln Ser
785             790             795             800

Pro Asp Ala Ser Gly Arg Ser Ser Asn Arg Arg Asp Arg Pro Arg Gln
            805             810             815

Pro Ser Pro Ser Gln Ser Ser Asp Ser Gln Val His Ser Gly Val Gln
820             825             830

Val Glu Gly Arg Arg Gly Gln Ser Ser Ser Ala Asn Arg Arg Ala Gly
        835             840             845

Ser Ser Ser Gly Ser Gly Val Gln Gly Thr Ser Ala Gly Gly Leu Ala
850             855             860

Ala Asp Ala Ser Arg Arg Ser Gly Ala Arg Gln Gly Gln Ala Ser Ala
865             870             875             880

Gln Gly Arg Ala Gly Ser Gln Gly Gln Ala Gln Gly Arg Val Gly Ser
            885             890             895

Ser Ala Asp Arg Gln Gly Arg Arg Gly Val Ser Glu Ser Gln Ala Ser
        900             905             910

Asp Ser Glu Gly His Ser Asp Phe Ser Glu Gly Gln Ala Val Gly Ala
        915             920             925

His Arg Gln Ser Gly Ala Gly Gln Arg His Glu Gln Arg Ser Ser Arg
930             935             940

Gly Gln His Gly Ser Gly Tyr Tyr Tyr Glu Gln Glu His Ser Glu Glu
945             950             955             960

Glu Ser Asp Ser Gln His Gln His Gly His Gln His Glu Gln Gln Arg
            965             970             975

Gly His Gln His Gln His Gln His Gln His Glu His Glu Gln Pro Glu
        980             985             990

Ser Gly His Arg Gln Gln Ser  Ser Gly Arg Gly Asn  Gln Gly Ala
        995             1000              1005

His Gln Lys Gln Gly Arg Asp  Ser Ala Arg Ser Arg  Gly Ser Asn
    1010             1015              1020

Gln Gly His Ser Ser Arg  His Gln Ala Asp Ser  Pro Arg Val
    1025             1030              1035

Ser Ala Arg Ser Gly Ser Xaa  Gly Arg Xaa Gln Ser  Pro Asp Ala
    1040             1045              1050

Ser Gly Arg Asn Ser Thr Lys  Arg Asp Arg Pro Arg  Gln Pro Ser
    1055             1060              1065

Pro Ser Gln Ser Ser Asp Ser  His Val His Ser Gly  Lys Ala Gly
    1070             1075              1080

Ser Ile Ser Gly Ser Gly Val  Gln Gly Ala Ser Ala  Gly Gly Leu
    1085             1090              1095

Ala Ala Asp Ala Ser Arg Arg  Ser Gly Ala Arg Gln  Gly Gln Ala
    1100             1105              1110
```

```
Ser Ala Gln Gly Arg Ala Gly Ser Gln Gly Gln Ala Gln Gly Arg
1115                1120                1125

Val Gly Ser Ser Ala Asp Arg Gln Gly Arg Arg Gly Val Ser Glu
1130                1135                1140

Ser Gln Ala Ser Asp Ser Glu Gly His Ser Asp Phe Ser Glu Gly
1145                1150                1155

Gln Ala Val Gly Ala His Arg Gln Ser Gly Ala Gly Gln Arg His
1160                1165                1170

Glu Gln Arg Ser Ser Arg Gly Gln His Gly Ser Arg Tyr Tyr Tyr
1175                1180                1185

Glu Gln Glu His Ser Glu Glu Ser Asp Ser Gln His Gln His
1190                1195                1200

Gly His Gln His Glu Gln Gln Arg Gly His Gln His Gln His Glu
1205                1210                1215

His Glu Gln Pro Glu Ser Gly His Arg Gln Gln Gln Ser Ser Gly
1220                1225                1230

Arg Gly His Gln Gly Ala His Gln Glu Gln Gly Arg Asp Ser Ala
1235                1240                1245

Arg Ser Arg Gly Ser Asn Gln Gly His Ser Ser Ser Arg His Gln
1250                1255                1260

Ala Asp Ser Pro Arg Val Ser Ala Arg Ser Gly Ser Gly Gly Arg
1265                1270                1275

Gly Gln Ser Pro Asp Ala Ser Gly Arg Ser Ser Asn Arg Arg Asp
1280                1285                1290

Arg Pro Arg Gln Pro Ser Pro Ser Gln Ser Ser Asp Ser Gln Val
1295                1300                1305

His Ser Gly Val Gln Val Glu Gly Arg Arg Gly Gln Ser Ser Ser
1310                1315                1320

Ala Asn Arg Arg Ala Gly Ser Ser Ser Gly Ser Gly Val Gln Gly
1325                1330                1335

Ala Ser Ala Gly Gly Leu Ala Ala Asp Ala Ser Arg Arg Ser Gly
1340                1345                1350

Ala Arg Gln Gly Gln Ala Ser Ala Gln Gly Arg Ala Gly Ser Gln
1355                1360                1365

Gly Gln Ala Gln Gly Arg Ile Gly Ser Ser Ala Asp Arg Gln Gly
1370                1375                1380

Arg Arg Gly Val Ser Glu Ser Gln Ala Ser Asp Ser Glu Gly His
1385                1390                1395

Ser Asp Phe Ser Glu Gly Gln Ala Val Gly Ala His Arg Gln Ser
1400                1405                1410

Glu Ala Gly Gln Arg His Glu Gln Arg Ser Ser Arg Gly Gln His
1415                1420                1425

Gly Ser Gly Tyr Tyr Tyr Glu Gln Glu His Ser Glu Glu Glu Ser
1430                1435                1440

Asp Ser Gln His Gln His Gly His Gln His Glu Gln Gln Arg Gly
1445                1450                1455

Thr Gln His Gln His Glu His Glu Gln Pro Glu Ser Gly His Arg
1460                1465                1470

Gln Gln Gln Ser Ser Gly Arg Gly His Gln Gly Thr His Gln Glu
1475                1480                1485

Gln Gly Arg Asp Ser Ala Arg Ser Arg Gly Ser Asn Gln Gly His
1490                1495                1500
```

```
Ser Ser Ser Arg His Gln Ala Asp Ser Pro Arg Val Ser Ala Arg
    1505                1510                1515

Ser Gly Ser Gly Gly Arg Gly Gln Ser Pro Asp Ala Ser Gly Arg
    1520                1525                1530

Ser Ser Asn Arg Arg Asp Arg Pro Arg Gln Pro Ser Pro Ser Gln
    1535                1540                1545

Ser Ser Asp Ser Gln Val His Ser Gly Val Gln Val Glu Gly Arg
    1550                1555                1560

Arg Arg Gln Ser Ser Ser Ala Asn Arg Arg Ala Gly Ser Ser Ser
    1565                1570                1575

Gly Ser Gly Val Gln Gly Ala Ser Ala Gly Gly Leu Ala Ala Asp
    1580                1585                1590

Ala Ser Arg Arg Ser Gly Ala Arg Gln Gly Gln Ala Ser Ala Gln
    1595                1600                1605

Gly Arg Ala Gly Ser Gln Gly Gln Ala Gln Gly Arg Val Gly Ser
    1610                1615                1620

Ser Ala Asp Arg Gln Gly Arg Arg Gly Val Ser Glu Ser Gln Ala
    1625                1630                1635

Ser Asp Ser Glu Gly His Ser Asp Phe Ser Glu Gly Gln Ala Val
    1640                1645                1650

Gly Ala His Arg Gln Ser Gly Ala Gly Gln Arg His Glu Gln Arg
    1655                1660                1665

Ser Ser Arg Gly Gln His Gly Ser Gly Phe Tyr Pro Val Tyr Tyr
    1670                1675                1680

Tyr Tyr Glu Gln Glu His Ser Glu Glu Ser Asp Ser Gln His
    1685                1690                1695

Gln His Gly His Gln His Glu Gln Gln Arg Gly His Gln His Gln
    1700                1705                1710

His Gln His Glu His Glu Gln Pro Glu Ser Gly His Arg Gln Gln
    1715                1720                1725

Gln Ser Ser Gly Arg Gly His Gln Gly Ala His Gln Glu Gln Gly
    1730                1735                1740

Arg Asp Ser Ala Arg Ser Arg Gly Ser Asn Gln Gly His Ser Ser
    1745                1750                1755

Ser Arg His Gln Ala Asp Ser Pro Arg Val Ser Ala Arg Ser Gly
    1760                1765                1770

Ser Gly Gly Arg Gly Gln Ser Pro Asp Ala Ser Gly Arg Ser Ser
    1775                1780                1785

Asn Arg Arg Asp Arg Pro Arg Gln Pro Ser Pro Ser Gln Ser Ser
    1790                1795                1800

Asp Ser Gln Val His Ser Gly Val Gln Val Glu Gly Arg Arg Gly
    1805                1810                1815

Gln Ser Ser Ser Ala Asn Arg Arg Ala Gly Ser Ser Ser Gly Ser
    1820                1825                1830

Gly Val Gln Gly Ala Ser Ala Gly Gly Leu Ala Ala Asp Ala Ser
    1835                1840                1845

Arg Arg Ser Gly Ala Leu Gln Gly Gln Ala Ser Ala Gln Gly Arg
    1850                1855                1860

Ala Gly Ser Gln Gly Gln Ala Gln Gly Arg Val Gly Ser Ser Ala
    1865                1870                1875

Asp Arg Gln Gly Arg Arg Gly Val Ser Gly Ser Gln Ala Ser Asp
    1880                1885                1890

Ser Glu Gly His Ser Asp Phe Ser Glu Gly Gln Ala Val Gly Ala
```

-continued

```
            1895                1900                1905
His Arg Gln Ser Gly Ala Gly Gln Arg His Glu Gln Arg Ser Ser
    1910                1915                1920
Arg Gly Gln His Gly Ser Gly Tyr Tyr Tyr Glu Gln Glu His Ser
    1925                1930                1935
Glu Glu Glu Ser Asp Ser Gln His Gln His Gly His Gln His Glu
    1940                1945                1950
Gln Gln Arg Gly His Gln His Gln His Gln His Gln His Glu His
    1955                1960                1965
Glu Gln Pro Glu Ser Gly His Arg Gln Gln Gln Phe Ser Gly Arg
    1970                1975                1980
Gly His Gln Gly Ala His Gln Glu Gln Gly Arg Asp Ser Ala Arg
    1985                1990                1995
Ser Arg Gly Ser Asn Gln Gly His Ser Ser Ser Arg His Gln Ala
    2000                2005                2010
Asp Ser Pro Arg Val Ser Ala Arg Ser Gly Ser Gly Arg Gly
    2015                2020                2025
Gln Ser Pro Asp Ala Ser Gly Arg Ser Ser Asn Arg Arg Asp Arg
    2030                2035                2040
Pro Arg Gln Pro Ser Pro Ser Gln Ser Ser Asp Ser Gln Val His
    2045                2050                2055
Ser Gly Val Gln Val Glu Gly Arg Arg Gly Gln Ser Ser Ser Ala
    2060                2065                2070
Asn Arg Arg Ala Gly Ser Ser Ser Gly Ser Gly Val Gln Gly Ala
    2075                2080                2085
Ser Ala Gly Gly Leu Ala Ala Asp Ala Ser Arg Arg Ser Gly Ala
    2090                2095                2100
Arg Gln Gly Gln Ala Ser Ala Gln Gly Arg Ala Gly Ser Gln Gly
    2105                2110                2115
Gln Ala Gln Gly Arg Val Gly Ser Ser Ala Asp Arg Gln Gly Arg
    2120                2125                2130
Arg Gly Val Ser Glu Ser Gln Ala Ser Asp Ser Glu Gly His Ser
    2135                2140                2145
Asp Phe Ser Glu Gly Gln Ala Val Gly Ala His Arg Gln Ser Gly
    2150                2155                2160
Ala Gly Gln Arg His Glu Gln Arg Ser Ser Arg Gly Gln His Gly
    2165                2170                2175
Ser Gly Phe Tyr Pro Val Tyr Tyr Tyr Glu Gln Glu His Ser
    2180                2185                2190
Glu Glu Glu Ser Asp Ser Gln His Gln His Gly His Gln His Glu
    2195                2200                2205
Gln Gln Arg Gly His Gln His Gln His Gln His Gln His Glu His
    2210                2215                2220
Glu Gln Pro Glu Ser Gly His Arg Gln Gln Gln Ser Ser Gly Arg
    2225                2230                2235
Gly His Gln Gly Ala His Gln Glu Gln Gly Arg Asp Ser Ala Arg
    2240                2245                2250
Ser Arg Gly Ser Asn Gln Gly His Ser Ser Ser Arg His Gln Ala
    2255                2260                2265
Asp Ser Pro Arg Val Ser Ala Arg Ser Gly Ser Gly Gly Arg Gly
    2270                2275                2280
Gln Ser Pro Asp Ala Ser Gly Arg Ser Ser Asn Arg Arg Asp Arg
    2285                2290                2295
```

-continued

```
Pro Arg Gln Pro Ser Pro Ser Gln Ser Ser Asp Ser Gln Val His
    2300            2305                2310
Ser Gly Val Gln Val Glu Gly Arg Arg Gly Gln Ser Ser Ser Ala
    2315            2320                2325
Asn Arg Arg Ala Gly Ser Ser Ser Gly Ser Gly Val Gln Gly Ala
    2330            2335                2340
Ser Ala Gly Gly Leu Ala Ala Asp Ala Ser Arg Arg Ser Gly Ala
    2345            2350                2355
Arg Gln Gly Gln Ala Ser Ala Gln Gly Arg Ala Gly Ser Gln Gly
    2360            2365                2370
Gln Ala Gln Gly Arg Val Gly Ser Ser Ala Asp Arg Gln Gly Arg
    2375            2380                2385
Arg Gly Val Ser Glu Ser Gln Ala Ser Asp Ser Glu Gly His Ser
    2390            2395                2400
Asp Phe Ser Glu Gly Gln Ala Val Gly Ala His Arg Gln Ser Gly
    2405            2410                2415
Ala Gly Gln Arg His Glu Gln Arg Ser Ser Arg Gly Gln His Gly
    2420            2425                2430
Ser Gly Tyr Tyr Tyr Glu Glu His Ser Glu Glu Glu Ser Asp
    2435            2440                2445
Ser Gln His Gln His Gly His Gln His Glu Gln Gln Arg Gly His
    2450            2455                2460
Gln His Gln His Gln His Gln His Glu His Glu Gln Pro Glu Ser
    2465            2470                2475
Gly His Arg Gln Gln Gln Ser Ser Gly Arg Gly His Gln Gly Ala
    2480            2485                2490
His Gln Glu Gln Gly Arg Asp Ser Ala Arg Ser Arg Gly Ser Asn
    2495            2500                2505
Gln Gly His Ser Ser Ser Arg His Gln Ala Asp Ser Pro Arg Val
    2510            2515                2520
Ser Ala Arg Ser Gly Ser Gly Gly Arg Gly Gln Ser Pro Asp Ala
    2525            2530                2535
Ser Gly Arg Ser Ser Asn Arg Arg Asp Arg Pro Arg Gln Pro Ser
    2540            2545                2550
Pro Ser Gln Ser Ser Asp Ser Gln Val His Ser Gly Val Gln Val
    2555            2560                2565
Glu Gly Arg Arg Gly Gln Ser Ser Ser Ala Asn Arg Arg Ala Gly
    2570            2575                2580
Ser Ser Gly Ser Gly Val Gln Gly Ala Ser Ala Gly Gly Leu
    2585            2590                2595
Ala Ala Asp Ala Ser Arg Arg Ser Gly Ala Arg Gln Gly Gln Ala
    2600            2605                2610
Ser Ala Gln Gly Arg Ala Gly Ser Gln Gly Gln Ala Gln Gly Arg
    2615            2620                2625
Val Gly Ser Ser Ala Asp Arg Gln Gly Arg Arg Gly Val Ser Glu
    2630            2635                2640
Ser Gln Ala Ser Asp Ser Glu Gly His Ser Asp Phe Ser Glu Gly
    2645            2650                2655
Gln Ala Val Gly Ala His Arg Gln Ser Gly Ala Gly Gln Arg His
    2660            2665                2670
Glu Gln Arg Ser Ser Arg Ser Gln His Gly Ser Gly Tyr Tyr Tyr
    2675            2680                2685
```

```
Glu Gln Glu His Ser Glu Glu Ser Asp Ser Gln His Gln His
        2690            2695            2700

Ser His Gln His Glu Gln Gln Arg Gly His Gln His Gln His Gln
        2705            2710            2715

His Gln His Glu His Glu Gln Pro Glu Ser Gly His Arg Gln Gln
        2720            2725            2730

Gln Ser Ser Gly Arg Gly Asn Gln Gly Ala His Gln Glu Gln Gly
        2735            2740            2745

Arg Asp Ser Ala Arg Ser Arg Gly Ser Asn Gln Gly His Ser Ser
        2750            2755            2760

Ser Arg His Gln Ala Asp Ser Pro Arg Val Ser Ala Arg Ser Gly
        2765            2770            2775

Ser Gly Gly Arg Gly Gln Ser Pro Asp Ala Ser Gly Arg Ser Ser
        2780            2785            2790

Asn Arg Arg Asp Arg Pro Arg Gln Pro Ser Pro Ser Gln Ser Ser
        2795            2800            2805

Asp Ser His Val His Ser Gly Val Gln Val Glu Gly Arg Arg Gly
        2810            2815            2820

Gln Ser Ser Ser Ala Asn Arg Arg Ala Gly Ser Ser Ser Gly Ser
        2825            2830            2835

Gly Val Gln Gly Ala Ser Ala Gly Gly Leu Ala Ala Asp Ala Ser
        2840            2845            2850

Arg Arg Ser Gly Ala Arg Gln Gly Gln Ala Ser Ala Gln Gly Arg
        2855            2860            2865

Ala Gly Ser Gln Gly Gln Ala Gln Gly Arg Val Gly Ser Ser Ala
        2870            2875            2880

Asp Arg Gln Gly Arg Arg Gly Val Ser Glu Ser Gln Ala Ser Asp
        2885            2890            2895

Ser Glu Gly His Ser Asp Phe Ser Glu Gly Gln Ala Val Gly Ala
        2900            2905            2910

His Arg Gln Ser Gly Ala Gly Gln Arg His Glu Gln Arg Ser Ser
        2915            2920            2925

Arg Gly Gln His Gly Ser Gly Phe Tyr Pro Val Tyr Tyr Tyr Tyr
        2930            2935            2940

Glu Gln Glu His Ser Glu Glu Ser Asp Ser Gln His Gln His
        2945            2950            2955

Gly His Gln His Glu Gln Gln Arg Gly His Gln His Gln His Gln
        2960            2965            2970

His Gln His Glu His Glu Gln Pro Glu Ser Gly His Arg Gln Gln
        2975            2980            2985

Gln Ser Ser Gly Arg Gly His Gln Gly Ala His Gln Glu Gln Gly
        2990            2995            3000

Arg Asp Ser Ala Arg Ser Arg Gly Ser Asn Gln Gly His Ser Ser
        3005            3010            3015

Ser Arg His Gln Ala Asp Ser Pro Arg Val Ser Ala Arg Ser Gly
        3020            3025            3030

Ser Gly Gly Arg Gly Gln Ser Pro Asp Ala Ser Gly Arg Ser Ser
        3035            3040            3045

Asn Arg Arg Asp Arg Ser Arg Gln Pro Ser Pro Ser Gln Ser Ser
        3050            3055            3060

Asp Ser Gln Val His Ser Gly Val Gln Val Glu Gly Arg Arg Gly
        3065            3070            3075

Gln Ser Ser Ser Ala Asn Arg Arg Ala Gly Ser Ser Ser Gly Ser
```

-continued

```
              3080              3085              3090
Gly Val Gln Gly Ala Ser Ala Gly Gly Leu Ala Ala Asp Ala Ser
    3095              3100              3105
Arg Arg Ser Gly Ala Arg Gln Gly Gln Ala Ser Ala Gln Gly Arg
    3110              3115              3120
Ala Gly Ser Gln Gly Gln Ala Gln Gly Arg Val Gly Ser Ser Ala
    3125              3130              3135
Asp Arg Gln Gly Arg Arg Gly Val Ser Glu Ser Gln Ala Ser Asp
    3140              3145              3150
Ser Glu Gly His Ser Asp Phe Ser Glu Gly Gln Ala Val Gly Ala
    3155              3160              3165
His Arg Gln Ser Gly Ala Gly Gln Arg His Glu Gln Arg Ser Ser
    3170              3175              3180
Arg Gly Gln His Gly Ser Gly Phe Tyr Pro Val Tyr Tyr Tyr Tyr
    3185              3190              3195
Glu Gln Glu His Ser Glu Glu Ser Asp Ser Gln His Gln His
    3200              3205              3210
Gly His Gln His Glu Gln Gln Arg Gly His Gln His Gln His Gln
    3215              3220              3225
His Glu His Glu Gln Pro Glu Ser Gly His Arg Gln Gln Gln Ser
    3230              3235              3240
Ser Gly Arg Gly His Gln Gly Ala His Gln Glu Gln Gly Arg Asp
    3245              3250              3255
Ser Ala Arg Ser Arg Gly Ser Asn Gln Gly His Ser Ser Ser Arg
    3260              3265              3270
His Gln Ala Asp Ser Pro Arg Val Ser Ala Arg Ser Gly Ser Gly
    3275              3280              3285
Gly Arg Gly Gln Ser Pro Asp Ala Ser Gly Arg Ser Ser Asn Arg
    3290              3295              3300
Arg Asp Arg Pro Arg Gln Pro Ser Pro Ser Gln Ser Ser Asp Ser
    3305              3310              3315
Gln Val His Ser Gly Val Gln Val Glu Gly Arg Arg Gly Gln Ser
    3320              3325              3330
Ser Ser Ala Asn Arg Arg Ala Gly Ser Ser Ser Gly Ser Gly Val
    3335              3340              3345
Gln Gly Ala Ser Ala Gly Gly Leu Ala Ala Asp Ala Ser Arg Arg
    3350              3355              3360
Ser Gly Ala Leu Gln Gly Gln Ala Ser Ala Gln Gly Arg Ala Gly
    3365              3370              3375
Ser Gln Gly Gln Ala Gln Gly Arg Val Gly Ser Ser Ala Asp Arg
    3380              3385              3390
Gln Gly Arg Arg Gly Val Ser Glu Ser Gln Ala Ser Asp Ser Glu
    3395              3400              3405
Gly His Ser Asp Phe Ser Glu Gly Gln Ala Val Gly Ala His Arg
    3410              3415              3420
Gln Ser Gly Ala Gly Gln Arg His Glu Gln Arg Ser Ser Arg Gly
    3425              3430              3435
Gln His Gly Ser Gly Tyr Tyr Tyr Glu Gln Glu His Ser Glu Glu
    3440              3445              3450
Glu Ser Asp Ser Gln His Gln His Gly His Gln His Glu Gln Gln
    3455              3460              3465
Arg Gly His Gln His Gln His Gln His Gln His Glu His Glu Gln
    3470              3475              3480
```

-continued

```
Pro Glu Ser Gly His Arg Gln Gln Ser Ser Gly Arg Gly His
    3485                3490                3495

Gln Gly Ala His Gln Glu Gln Gly Arg Asp Ser Ala Arg Ser Arg
    3500                3505                3510

Gly Ser Asn Gln Gly His Ser Ser Ser Arg His Gln Ala Asp Ser
    3515                3520                3525

Pro Arg Val Ser Ala Arg Ser Gly Ser Gly Gly Arg Gly Gln Ser
    3530                3535                3540

Pro Asp Ala Ser Gly Arg Ser Ser Asn Arg Arg Asp Arg Pro Arg
    3545                3550                3555

Gln Pro Ser Pro Ser Gln Ser Ser Asp Ser Gln Val His Ser Gly
    3560                3565                3570

Val Gln Val Glu Gly Arg Arg Gly Gln Ser Ser Ala Asn Arg
    3575                3580                3585

Arg Ala Gly Ser Ser Ser Gly Ser Gly Val Gln Gly Ala Ser Ala
    3590                3595                3600

Gly Gly Leu Ala Ala Asp Ala Ser Arg Arg Ser Gly Ala Arg Gln
    3605                3610                3615

Gly Gln Ala Ser Ala Gln Gly Arg Ala Gly Ser Gln Gly Gln Ala
    3620                3625                3630

Gln Gly Arg Val Gly Ser Ser Ala Asp Arg Gln Gly Arg Arg Gly
    3635                3640                3645

Val Ser Gly Ser Gln Ala Ser Asp Ser Glu Gly His Ser Asp Phe
    3650                3655                3660

Ser Glu Gly Gln Ala Val Gly Ala His Arg Gln Ser Gly Ala Gly
    3665                3670                3675

Gln Arg His Glu Gln Arg Ser Ser Arg Gly Gln His Gly Ser Gly
    3680                3685                3690

Tyr Tyr Tyr Glu Gln Glu His Ser Glu Glu Glu Ser Asp Ser Gln
    3695                3700                3705

His Gln His Gly His Gln His Glu Gln Gln Arg Gly His Gln His
    3710                3715                3720

Gln His Gln His Gln His Glu His Glu Gln Pro Glu Ser Gly His
    3725                3730                3735

Arg Gln Gln Gln Phe Ser Gly Arg Gly His Gln Gly Ala His Gln
    3740                3745                3750

Glu Gln Gly Arg Asp Ser Ala Arg Ser Arg Gly Ser Asn Gln Gly
    3755                3760                3765

His Ser Ser Ser Arg His Gln Ala Asp Ser Pro Arg Val Ser Ala
    3770                3775                3780

Arg Ser Gly Ser Gly Gly Arg Gly Gln Ser Pro Asp Ala Ser Gly
    3785                3790                3795

Arg Ser Ser Asn Arg Arg Asp Arg Pro Arg Gln Pro Ser Pro Ser
    3800                3805                3810

Gln Ser Ser Asp Ser Gln Val His Ser Gly Val Gln Val Glu Gly
    3815                3820                3825

Arg Arg Gly Gln Ser Ser Ser Ala Asn Arg Arg Ala Gly Ser Ser
    3830                3835                3840

Ser Ser Ser Gly Val Gln Gly Ala Ser Ala Gly Gly Leu Ala Ala
    3845                3850                3855

Asp Ala Ser Arg Arg Ser Gly Ala Arg Gln Gly Gln Ala Ser Ala
    3860                3865                3870
```

```
Gln Gly Arg Ala Gly Ser Gln Gly Gln Ala Gln Gly Arg Val Gly
3875                 3880                 3885

Ser Ser Ala Asp Arg Gln Gly Arg Arg Gly Val Ser Glu Ser Gln
3890                 3895                 3900

Ala Ser Asp Ser Glu Gly His Ser Asp Phe Ser Glu Gly Gln Ala
3905                 3910                 3915

Val Gly Ala His Arg Gln Ser Gly Ala Gly Gln Arg His Glu Gln
3920                 3925                 3930

Arg Ser Ser Arg Gly Gln His Gly Ser Gly Phe Tyr Pro Val Tyr
3935                 3940                 3945

Tyr Tyr Tyr Glu Gln Glu His Ser Glu Glu Glu Ser Asp Ser Gln
3950                 3955                 3960

His Gln His Gly His Gln His Glu Gln Gln Arg Gly His Gln His
3965                 3970                 3975

Gln His Gln His Gln His Glu His Glu Gln Pro Glu Ser Gly His
3980                 3985                 3990

Arg Gln Gln Gln Phe Ser Gly Arg Gly His Gln Gly Ala His Gln
3995                 4000                 4005

Glu Gln Gly Arg Asp Ser Ala Arg Ser Arg Gly Ser Asn Gln Gly
4010                 4015                 4020

His Ser Ser Ser Arg His Gln Ala Asp Ser Pro Arg Val Ser Ala
4025                 4030                 4035

Arg Ser Gly Ser Gly Gly Arg Gly Gln Ser Pro Asp Ala Ser Gly
4040                 4045                 4050

Arg Ser Ser Asn Arg Arg Asp Arg Pro Arg Gln Pro Ser Pro Ser
4055                 4060                 4065

Gln Ser Ser Asp Ser Gln Val His Ser Gly Val Gln Val Glu Gly
4070                 4075                 4080

Arg Arg Gly Gln Ser Ser Ser Ala Asn Arg Arg Ala Gly Ser Ser
4085                 4090                 4095

Ser Gly Ser Gly Val Gln Gly Ala Ser Ala Gly Gly Leu Ala Ala
4100                 4105                 4110

Asp Ala Ser Arg Arg Ser Gly Ala Arg Gln Gly Gln Ala Ser Ala
4115                 4120                 4125

Gln Gly Arg Ala Gly Ser Gln Gly Gln Ala Gln Gly Arg Val Gly
4130                 4135                 4140

Ser Ser Ala Asp Arg Gln Gly Arg Arg Gly Val Ser Glu Ser Gln
4145                 4150                 4155

Ala Ser Asp Ser Glu Gly His Ser Asp Phe Ser Glu Gly Gln Ala
4160                 4165                 4170

Val Gly Ala His Arg Gln Ser Gly Ala Gly Gln Arg His Glu Gln
4175                 4180                 4185

Arg Ser Ser Arg Gly Gln His Gly Ser Gly Tyr Tyr Tyr Glu Gln
4190                 4195                 4200

Glu His Ser Glu Glu Glu Ser Asp Ser Gln His Gln Gln Gly His
4205                 4210                 4215

Gln His Glu Gln Gln Arg Gly His Gln His Gln His Gln His Gln
4220                 4225                 4230

His Glu His Glu Gln Pro Glu Ser Gly His Arg Gln Gln Gln Ser
4235                 4240                 4245

Ser Gly Arg Gly His Gln Gly Ala His Gln Glu Gln Gly Arg Asp
4250                 4255                 4260

Ser Ala Arg Ser Arg Gly Ser Asn Gln Gly His Ser Ser Ser Arg
```

4265                4270                4275

His Gln Ala Asp Ser Pro Arg Val Ser Ala Arg Ser Gly Ser Gly
              4280                4285                4290

Gly Arg Gly Gln Ser Pro Asp Gly Ser Gly Arg Ser Ser Asn Arg
              4295                4300                4305

Arg Asp Arg Pro Arg Gln Pro Ser Ala Ser Gln Ser Ser Asp Ser
    4310                4315                4320

Gln Val His Ser Gly Val Gln Val Glu Ala Gln Arg Gly Gln Ser
    4325                4330                4335

Ser Ser Ala Asn Arg Arg Ala Gly Ser Ser Ser Gly Ser Gly Val
    4340                4345                4350

Gln Ser Ala Ala Ala Ser Gly Gln Gly Gly Tyr Glu Ser Ile Phe
    4355                4360                4365

Thr Ala Lys His Leu Asp Phe Asn Gln Ser His Ser Tyr Tyr Tyr
    4370                4375                4380

Tyr

<210> SEQ ID NO 13
<211> LENGTH: 554
<212> TYPE: PRT
<213> ORGANISM: Mus musculus

<400> SEQUENCE: 13

Met Ser Ala Leu Leu Glu Ser Ile Thr Ser Met Ile Glu Ile Phe Gln
1               5                   10                  15

Gln Tyr Ser Thr Ser Asp Lys Glu Glu Glu Thr Leu Ser Lys Glu Glu
            20                  25                  30

Leu Lys Glu Leu Leu Glu Gly Gln Leu Gln Ala Val Leu Lys Asn Pro
        35                  40                  45

Asp Asp Gln Asp Ile Ala Glu Val Phe Met Gln Met Leu Asp Val Asp
    50                  55                  60

His Asp Asp Lys Leu Asp Phe Ala Glu Tyr Leu Leu Val Leu Lys
65                  70                  75                  80

Leu Ala Lys Ala Tyr Tyr Glu Ala Ser Lys Asn Glu Ser Phe Gln Thr
                85                  90                  95

His Gly Ser Asn Gly Arg Ser Lys Thr Asp Tyr Lys Gly Leu Glu Glu
            100                 105                 110

Glu Gly Glu Glu Gly Asn Glu Gln Asn Leu Arg Arg Arg His Gly Gly
        115                 120                 125

Thr Asp Gly Lys Arg Lys Ser Asp Arg Thr Arg Ser Pro Asn Gly Lys
130                 135                 140

Arg Gly Lys Arg Gln Glu Ser Arg Cys Arg Ser Glu Gly Lys Asp Lys
145                 150                 155                 160

His Arg Arg Glu Pro Glu Lys His Arg His Gln Gln Asp Ser Lys Arg
                165                 170                 175

Lys Gln Arg His Gly Ser Gly Ser Thr Glu Arg Lys Asp Asn Arg Asn
            180                 185                 190

Lys Lys Asn Arg Gln Ser Lys Glu Arg Asn Tyr Asp Glu Ile Tyr Asp
        195                 200                 205

Asn Gly Lys Tyr Asn Glu Asp Trp Glu Ala Ser Tyr Asn Cys Tyr
    210                 215                 220

Tyr Lys Thr Gln Asn Thr Thr Leu Asp Gln Arg Glu Gly Asn Arg Arg
225                 230                 235                 240

Pro Arg Ala Asp Ser Gln Lys Glu Pro Gln Ser Phe His Gly Gln Ala

```
                245                 250                 255
Asp Asn Ser Asp Ser Glu Gly Gly Arg Gln Gln Ser His Ser Lys Pro
            260                 265                 270

Ser Pro Val Arg Ala Asp Gln Arg Arg Ser Arg Ala Gly Gln Ala Gly
        275                 280                 285

Ser Ser Lys Val Ser Ala Arg Ser Gly Ser Gly Arg Gly Gln Ser
    290                 295                 300

Pro Asp Gly Ser Gly Arg Ser Ser Asn Arg Arg Asp Arg Pro Arg Gln
305                 310                 315                 320

Pro Ser Pro Ser Gln Ser Ser Asp Ser Gln Val His Ser Gly Val Gln
            325                 330                 335

Val Glu Gly Arg Arg Gly Gln Ser Ser Ala Asn Arg Arg Ala Gly
        340                 345                 350

Ser Ser Ser Gly Ser Gly Val Gln Gly Ala Ser Ala Gly Gly Leu Ala
    355                 360                 365

Ala Asp Ala Ser Arg Arg Thr Gly Ala Leu Gln Gly Gln Ala Ser Ala
370                 375                 380

Gln Gly Arg Ala Gly Ser Gln Gly Gln Ala Gln Gly Arg Val Gly Ser
385                 390                 395                 400

Ser Ala Asp Arg Gln Gly Arg Arg Gly Val Ser Glu Ser Gln Ala Ser
            405                 410                 415

Asp Ser Glu Gly Gln Ser Asp Phe Ser Glu Gly Gln Ala Val Gly Ala
        420                 425                 430

His Arg Gln Ser Gly Ala Gly Gln Arg His Glu Gln Arg Ser Ser Arg
    435                 440                 445

Gly Gln Tyr Gly Ser Gly Phe Tyr Pro Val Tyr Tyr Tyr Glu Gln
    450                 455                 460

Glu His Ser Glu Glu Ser Asp Ser Gln His Gly His Gln His Glu
465                 470                 475                 480

Gln Gln Arg Gly His Gln His Gln His Gln His Glu His Glu Gln Pro
            485                 490                 495

Glu Ser Gly His Arg Gln Gln Gln Ser Ser Gly Arg Gly His Gln Gly
        500                 505                 510

Ala His Gln Glu Gln Gly Arg Asp Ser Ala Arg Ser Arg Gly Ser Asn
    515                 520                 525

Gln Gly His Ser Ser Arg His Gln Ala Asp Ser Pro Arg Val Ser
    530                 535                 540

Val Arg Ser Gly Ser Gly Gly Arg Gly Gln
545                 550

<210> SEQ ID NO 14
<211> LENGTH: 336
<212> TYPE: PRT
<213> ORGANISM: Mus musculus

<400> SEQUENCE: 14

Pro Asp Gly Ser Gly Arg Ser Ser Asn Arg Arg Asp Arg Pro Arg Gln
1               5                   10                  15

Leu Ser Pro Ser Gln Ser Ser Asp Ser Gln Val His Ser Gly Val Gln
            20                  25                  30

Val Glu Gly Arg Arg Gly His Ser Ser Ala Asn Arg Arg Ala Gly
        35                  40                  45

Ser Ser Ser Gly Ser Gly Val Gln Gly Ala Ser Ala Gly Gly Leu Ala
    50                  55                  60
```

```
Ala Asp Ala Ser Arg Arg Ser Gly Ala Arg Gln Gly Gln Ala Ser Ala
 65                  70                  75                  80

Gln Gly Arg Ala Gly Ser Gln Gly Gln Ala Gln Gly Arg Val Ser Ser
                 85                  90                  95

Ser Ala Asp Arg Gln Gly Arg Arg Gly Val Ser Glu Ser Arg Ala Ser
            100                 105                 110

Asp Ser Glu Gly His Ser Asp Phe Ser Glu Gly Gln Ala Val Gly Ala
            115                 120                 125

His Arg Gln Ser Gly Ala Gly Gln Arg His Glu Gln Arg Ser Ser Arg
        130                 135                 140

Gly Gln His Gly Ser Gly Tyr Tyr Tyr Glu Gln Glu His Ser Glu Glu
145                 150                 155                 160

Glu Ser Asp Ser Gln His Gln His Gly His Gln His Glu Gln Gln Arg
            165                 170                 175

Gly His Gln His Gln His Gln His Gln His Glu His Glu Gln Pro Glu
        180                 185                 190

Ser Gly His Arg Gln Gln Ser Ser Gly Arg Gly His Gln Gly Ala
        195                 200                 205

His Gln Glu Gln Gly Arg Asp Ser Ala Arg Pro Arg Gly Ser Asn Gln
210                 215                 220

Gly His Ser Ser Ser Arg His Gln Ala Asp Ser Pro Arg Val Ser Ala
225                 230                 235                 240

Arg Ser Gly Ser Gly Gly Arg Gly Gln Ser Pro Asp Ala Ser Gly Arg
                245                 250                 255

Ser Ser Asn Arg Arg Asp Arg Pro Arg Gln Pro Ser Pro Ser Gln Ser
            260                 265                 270

Ser Asp Ser Gln Val His Ser Gly Val Gln Val Glu Ala Gln Arg Gly
        275                 280                 285

Gln Ser Ser Ser Ala Asn Arg Arg Ala Gly Ser Ser Gly Ser Gly
        290                 295                 300

Val Gln Gly Ala Ala Ala Ser Gly Gln Gly Gly Tyr Glu Ser Ile Phe
305                 310                 315                 320

Thr Ala Lys His Leu Asp Phe Asn Gln Ser His Ser Tyr Tyr Tyr Tyr
                325                 330                 335

<210> SEQ ID NO 15
<211> LENGTH: 250
<212> TYPE: PRT
<213> ORGANISM: Mus musculus

<400> SEQUENCE: 15

Gly Gly Leu Ala Ala Asp Ala Ser Arg Arg Ser Gly Ala Leu Gln Gly
1               5                   10                  15

Gln Ala Ser Ala Gln Gly Arg Ala Gly Ser Gln Gly Gln Ala Gln Gly
                20                  25                  30

Arg Val Gly Ser Ser Ala Asp Arg Gln Gly Arg Arg Gly Val Ser Glu
            35                  40                  45

Ser Gln Ala Ser Asp Ser Glu Gly His Ser Asp Phe Ser Glu Gly Gln
        50                  55                  60

Ala Val Gly Ala His Arg Gln Ser Gly Ala Gly Gln Arg His Glu Gln
65                  70                  75                  80

Arg Ser Ser Arg Gly Gln His Gly Ser Gly Tyr Tyr Tyr Glu Gln Glu
                85                  90                  95

His Ser Glu Glu Glu Ser Asp Ser Gln His Gln His Gly His Gln His
            100                 105                 110
```

```
Glu Gln Gln Arg Gly His Gln His Gln His Gln His Glu His
        115                 120                 125

Glu Gln Pro Glu Ser Gly His Arg Gln Gln Ser Ser Gly Arg Gly
    130                 135                 140

His Gln Gly Ala His Gln Glu Gln Gly Arg Asp Ser Ala Arg Ser Arg
145                 150                 155                 160

Gly Ser Asn Gln Gly His Ser Ser Arg His Gln Ala Asp Ser Pro
                165                 170                 175

Arg Val Ser Ala Arg Ser Gly Ser Gly Arg Gly Gln Ser Pro Asp
            180                 185                 190

Ala Ser Gly Arg Ser Ser Asn Arg Arg Asp Arg Pro Arg Gln Pro Ser
        195                 200                 205

Pro Ser Gln Ser Ser Asp Ser Gln Val His Ser Gly Val Gln Val Glu
    210                 215                 220

Gly Arg Arg Gly Gln Ser Ser Ala Asn Arg Arg Ala Gly Ser Ser
225                 230                 235                 240

Ser Ser Ser Gly Val Gln Gly Ala Ser Ala
                245                 250

<210> SEQ ID NO 16
<211> LENGTH: 2642
<212> TYPE: PRT
<213> ORGANISM: Mus musculus

<400> SEQUENCE: 16

Met Ser Thr Asn Ser Pro Ser Pro Ala Thr Gly Ser Ser Ser Ser Ala
1               5                   10                  15

Asp Ser Pro Arg Val Ser Ala Arg Ser Gly Ser Gly Gly Arg Gly Gln
                20                  25                  30

Ser Pro Asp Ala Ser Gly Arg Ser Ser Asn Arg Arg Asp Arg Pro Arg
            35                  40                  45

Gln Pro Ser Pro Ser Gln Ser Ser Asp Ser Gln Val His Ser Gly Val
    50                  55                  60

Gln Val Glu Gly Arg Arg Gly Gln Ser Ser Ala Asn Arg Arg Ala
65                  70                  75                  80

Gly Ser Ser Ser Gly Ser Gly Val Gln Gly Ala Ser Ala Gly Gly Leu
                85                  90                  95

Ala Ala Asp Ala Ser Arg Arg Ser Gly Ala Arg Gln Gly Gln Ala Ser
            100                 105                 110

Ala Gln Gly Arg Ala Gly Ser Gln Gly Gln Ala Gln Gly Arg Val Gly
        115                 120                 125

Ser Ser Ala Asp Arg Gln Gly Arg Arg Gly Val Ser Glu Ser Gln Ala
    130                 135                 140

Ser Asp Ser Glu Gly His Ser Asp Phe Ser Glu Gly Gln Ala Val Gly
145                 150                 155                 160

Ala His Arg Gln Ser Gly Ala Gly Gln Arg His Glu Gln Arg Ser Ser
                165                 170                 175

Arg Gly Gln His Gly Ser Gly Phe Tyr Pro Val Tyr Tyr Tyr Glu
            180                 185                 190

Gln Glu His Ser Glu Glu Ser Asp Ser Gln His Gln His Gly His
        195                 200                 205

Gln His Glu Gln Gln Arg Gly His Gln His Gln His Gln His
    210                 215                 220

Glu His Glu Gln Pro Glu Ser Gly His Arg Gln Gln Ser Ser Gly
```

```
            225                 230                 235                 240
        Arg Gly His Gln Gly Ala His Gln Glu Gln Gly Arg Asp Ser Ala Arg
                        245                 250                 255

Ser Arg Gly Ser Asn Gln Gly His Ser Ser Ser Arg His Gln Ala Asp
                        260                 265                 270

Ser Pro Arg Val Ser Ala Arg Ser Gly Gly Arg Gly Gln Ser
                        275                 280                 285

Pro Asp Ala Ser Gly Arg Ser Ser Asn Arg Arg Asp Arg Pro Arg Gln
        290                 295                 300

Pro Ser Pro Ser Gln Ser Ser Asp Ser Gln Val His Ser Gly Val Gln
        305                 310                 315                 320

Val Glu Gly Arg Arg Gly Gln Ser Ser Ala Asn Arg Arg Ala Gly
                        325                 330                 335

Ser Ser Ser Gly Ser Gly Val Gln Gly Ala Ser Ala Gly Gly Leu Ala
                        340                 345                 350

Ala Asp Ala Ser Arg Arg Ser Gly Ala Arg Gln Gly Gln Ala Ser Ala
                        355                 360                 365

Gln Gly Arg Ala Gly Ser Gln Gly Gln Ala Gly Arg Val Gly Ser
                        370                 375                 380

Ser Ala Asp Arg Gln Gly Arg Arg Gly Val Ser Glu Ser Gln Ala Ser
        385                 390                 395                 400

Asp Ser Glu Gly His Ser Asp Phe Ser Glu Gly Gln Ala Val Gly Ala
                        405                 410                 415

His Arg Gln Ser Gly Ala Gly Gln Arg His Glu Gln Arg Ser Ser Arg
                        420                 425                 430

Gly Gln His Gly Ser Gly Tyr Tyr Tyr Glu Gln Glu His Ser Glu Glu
                        435                 440                 445

Glu Ser Asp Ser Gln His Gln His Ser His Gln His Glu Gln Gln Arg
                        450                 455                 460

Gly His Gln His Gln His Gln His Gln His Glu His Glu Gln Pro Glu
        465                 470                 475                 480

Ser Gly His Arg Gln Gln Gln Phe Ser Gly Arg Gly His Gln Gly Ala
                        485                 490                 495

His Gln Glu Gln Gly Arg Asp Ser Ala Arg Ser Arg Gly Ser Asn Gln
                        500                 505                 510

Gly His Ser Ser Ser Arg His Gln Ala Asp Ser Pro Arg Val Ser Ala
                        515                 520                 525

Arg Ser Gly Ser Gly Gly Arg Gly Gln Ser Pro Asp Ala Ser Gly Arg
                        530                 535                 540

Ser Ser Asn Arg Arg Asp Arg Pro Arg Gln Pro Ser Pro Ser Gln Ser
        545                 550                 555                 560

Ser Asp Ser Gln Val His Ser Gly Val Gln Val Glu Gly Arg Arg Gly
                        565                 570                 575

Gln Ser Ser Ser Ala Asn Arg Arg Ala Gly Ser Ser Ser Gly Ser Gly
                        580                 585                 590

Val Gln Gly Ala Ser Ala Gly Gly Leu Ala Ala Asp Ala Ser Arg Arg
                        595                 600                 605

Ser Gly Ala Arg Gln Gly Gln Ala Ser Ala Gln Gly Arg Ala Gly Ser
                        610                 615                 620

Gln Gly Gln Ala Gln Gly Arg Val Gly Ser Ser Ala Asp Arg Gln Gly
        625                 630                 635                 640

Arg Arg Gly Val Ser Glu Ser Gln Ala Ser Asp Ser Glu Gly His Ser
                        645                 650                 655
```

-continued

```
Asp Phe Ser Glu Gly Gln Ala Val Gly Ala His Arg Gln Ser Gly Ala
                660                 665                 670

Gly Gln Arg His Glu Gln Arg Ser Ser Arg Gly Gln His Gly Ser Gly
        675                 680                 685

Phe Tyr Pro Val Tyr Tyr Tyr Glu Gln Glu His Ser Glu Glu Glu
690                 695                 700

Ser Asp Ser Gln His Gln His Gly His Gln His Glu Gln Gln Arg Gly
705                 710                 715                 720

His Gln His Gln His Gln His Gln His Glu His Glu Gln Pro Glu Ser
                725                 730                 735

Gly His Arg Gln Gln Ser Ser Arg Gly His Gln Gly Ala His
                740                 745                 750

Gln Glu Gln Gly Arg Asp Ser Ala Arg Ser Arg Gly Ser Asn Gln Gly
                755                 760                 765

His Ser Ser Ser Arg His Gln Ala Asp Ser Pro Arg Val Ser Ala Arg
                770                 775                 780

Ser Gly Ser Gly Gly Arg Gly Gln Ser Pro Asp Ala Ser Gly Arg Ser
785                 790                 795                 800

Ser Asn Arg Arg Asp Arg Pro Arg Gln Pro Ser Pro Ser Gln Ser Ser
                805                 810                 815

Asp Ser Gln Val His Ser Gly Val Gln Val Glu Gly Arg Arg Gly Gln
                820                 825                 830

Ser Ser Ser Ala Asn Arg Arg Ala Gly Ser Ser Gly Ser Gly Val
                835                 840                 845

Gln Gly Ala Ser Ala Gly Gly Leu Ala Ala Asp Ala Ser Arg Arg Ser
850                 855                 860

Gly Ala Arg Gln Gly Gln Ala Ser Ala Gln Gly Arg Ala Gly Ser Gln
865                 870                 875                 880

Gly Gln Ala Gln Gly Arg Val Gly Ser Ser Ala Asp Arg Gln Gly Arg
                885                 890                 895

Arg Gly Val Ser Glu Ser Gln Ala Ser Asp Ser Glu Gly His Ser Asp
                900                 905                 910

Phe Ser Glu Gly Gln Ala Val Gly Ala His Arg Gln Ser Gly Ala Gly
        915                 920                 925

Gln Arg His Glu Gln Arg Ser Ser Arg Ser Gln His Gly Ser Gly Tyr
        930                 935                 940

Tyr Tyr Glu Gln Glu His Ser Glu Glu Glu Ser Asp Ser Gln His Gln
945                 950                 955                 960

His Ser His Gln His Glu Gln Gln Arg Gly His Gln His Gln His Gln
                965                 970                 975

His Gln His Glu His Glu Gln Pro Glu Ser Gly His Arg Gln Gln Gln
                980                 985                 990

Ser Ser Gly Arg Gly Asn Gln Gly Ala His Gln Glu Gln Gly Arg Asp
        995                 1000                1005

Ser Ala Arg Ser Arg Gly Ser Asn Gln Gly His Ser Ser Ser Arg
    1010                1015                1020

His Gln Ala Asp Ser Pro Arg Val Ser Ala Arg Ser Gly Ser Gly
    1025                1030                1035

Gly Arg Gly Gln Ser Pro Asp Ala Ser Gly Arg Ser Ser Asn Arg
    1040                1045                1050

Arg Asp Arg Pro Arg Gln Pro Ser Pro Ser Gln Ser Ser Asp Ser
    1055                1060                1065
```

```
His Val His Ser Gly Val Gln Val Glu Gly Arg Arg Gly Gln Ser
    1070            1075            1080

Ser Ser Ala Asn Arg Arg Ala Gly Ser Ser Gly Ser Gly Val
    1085            1090            1095

Gln Gly Ala Ser Ala Gly Gly Leu Ala Ala Asp Ala Ser Arg Arg
    1100            1105            1110

Ser Gly Ala Arg Gln Gly Gln Ala Ser Ala Gln Gly Arg Ala Gly
    1115            1120            1125

Ser Gln Gly Gln Ala Gln Gly Arg Val Gly Ser Ser Ala Asp Arg
    1130            1135            1140

Gln Gly Arg Arg Gly Val Ser Glu Ser Gln Ala Ser Asp Ser Glu
    1145            1150            1155

Gly His Ser Asp Phe Ser Glu Gly Gln Ala Val Gly Ala His Arg
    1160            1165            1170

Gln Ser Gly Ala Gly Gln Arg His Glu Gln Arg Ser Ser Arg Gly
    1175            1180            1185

Gln His Gly Ser Gly Phe Tyr Pro Val Tyr Tyr Tyr Tyr Glu Gln
    1190            1195            1200

Glu His Ser Glu Glu Glu Ser Asp Ser Gln His Gln His Gly His
    1205            1210            1215

Gln His Glu Gln Gln Arg Gly His Gln His Gln His Gln His Gln
    1220            1225            1230

His Glu His Glu Gln Pro Glu Ser Gly His Arg Gln Gln Gln Ser
    1235            1240            1245

Ser Gly Arg Gly His Gln Gly Ala His Gln Glu Gln Gly Arg Asp
    1250            1255            1260

Ser Ala Arg Ser Arg Gly Ser Asn Gln Gly His Ser Ser Ser Arg
    1265            1270            1275

His Gln Ala Asp Ser Pro Arg Val Ser Ala Arg Ser Gly Ser Gly
    1280            1285            1290

Gly Arg Gly Gln Ser Pro Asp Ala Ser Gly Arg Ser Ser Asn Arg
    1295            1300            1305

Arg Asp Arg Ser Arg Gln Pro Ser Pro Ser Gln Ser Ser Asp Ser
    1310            1315            1320

Gln Val His Ser Gly Val Gln Val Glu Gly Arg Arg Gly Gln Ser
    1325            1330            1335

Ser Ser Ala Asn Arg Arg Ala Gly Ser Ser Gly Ser Gly Val
    1340            1345            1350

Gln Gly Ala Ser Ala Gly Gly Leu Ala Ala Asp Ala Ser Arg Arg
    1355            1360            1365

Ser Gly Ala Arg Gln Gly Gln Ala Ser Ala Gln Gly Arg Ala Gly
    1370            1375            1380

Ser Gln Gly Gln Ala Gln Gly Arg Val Gly Ser Ser Ala Asp Arg
    1385            1390            1395

Gln Gly Arg Arg Gly Val Ser Glu Ser Gln Ala Ser Asp Ser Glu
    1400            1405            1410

Gly His Ser Asp Phe Ser Glu Gly Gln Ala Val Gly Ala His Arg
    1415            1420            1425

Gln Ser Gly Ala Gly Gln Arg His Glu Gln Arg Ser Ser Arg Gly
    1430            1435            1440

Gln His Gly Ser Gly Phe Tyr Pro Val Tyr Tyr Tyr Tyr Glu Gln
    1445            1450            1455

Glu His Ser Glu Glu Glu Ser Asp Ser Gln His Gln His Gly His
```

```
            1460                1465                1470

Gln His Glu Gln Gln Arg Gly His Gln His Gln His Glu
    1475                1480                1485

His Glu Gln Pro Glu Ser Gly His Arg Gln Gln Ser Ser Gly
    1490                1495                1500

Arg Gly His Gln Gly Ala His Gln Glu Gln Gly Arg Asp Ser Ala
    1505                1510                1515

Arg Ser Arg Gly Ser Asn Gln Gly His Ser Ser Arg His Gln
    1520                1525                1530

Ala Asp Ser Pro Arg Val Ser Ala Arg Ser Gly Ser Gly Gly Arg
    1535                1540                1545

Gly Gln Ser Pro Asp Ala Ser Gly Arg Ser Ser Asn Arg Arg Asp
    1550                1555                1560

Arg Pro Arg Gln Pro Ser Pro Ser Gln Ser Ser Asp Ser Gln Val
    1565                1570                1575

His Ser Gly Val Gln Val Glu Gly Arg Arg Gly Gln Ser Ser Ser
    1580                1585                1590

Ala Asn Arg Arg Ala Gly Ser Ser Ser Gly Ser Gly Val Gln Gly
    1595                1600                1605

Ala Ser Ala Gly Gly Leu Ala Ala Asp Ala Ser Arg Arg Ser Gly
    1610                1615                1620

Ala Leu Gln Gly Gln Ala Ser Ala Gln Gly Arg Ala Gly Ser Gln
    1625                1630                1635

Gly Gln Ala Gln Gly Arg Val Gly Ser Ser Ala Asp Arg Gln Gly
    1640                1645                1650

Arg Arg Gly Val Ser Glu Ser Gln Ala Ser Asp Ser Glu Gly His
    1655                1660                1665

Ser Asp Phe Ser Glu Gly Gln Ala Val Gly Ala His Arg Gln Ser
    1670                1675                1680

Gly Ala Gly Gln Arg His Glu Gln Arg Ser Ser Arg Gly Gln His
    1685                1690                1695

Gly Ser Gly Tyr Tyr Tyr Glu Gln Glu His Ser Glu Glu Glu Ser
    1700                1705                1710

Asp Ser Gln His Gln His Gly His Gln His Glu Gln Gln Arg Gly
    1715                1720                1725

His Gln His Gln His Gln His Gln His Glu His Glu Gln Pro Glu
    1730                1735                1740

Ser Gly His Arg Gln Gln Ser Ser Gly Arg Gly His Gln Gly
    1745                1750                1755

Ala His Gln Glu Gln Gly Arg Asp Ser Ala Arg Ser Arg Gly Ser
    1760                1765                1770

Asn Gln Gly His Ser Ser Ser Arg His Gln Ala Asp Ser Pro Arg
    1775                1780                1785

Val Ser Ala Arg Ser Gly Ser Gly Gly Arg Gly Gln Ser Pro Asp
    1790                1795                1800

Ala Ser Gly Arg Ser Ser Asn Arg Arg Asp Arg Pro Arg Gln Pro
    1805                1810                1815

Ser Pro Ser Gln Ser Ser Asp Ser Gln Val His Ser Gly Val Gln
    1820                1825                1830

Val Glu Gly Arg Arg Gly Gln Ser Ser Ser Ala Asn Arg Arg Ala
    1835                1840                1845

Gly Ser Ser Ser Gly Ser Gly Val Gln Gly Ala Ser Ala Gly Gly
    1850                1855                1860
```

```
Leu Ala Ala Asp Ala Ser Arg Arg Ser Gly Ala Arg Gln Gly Gln
        1865                1870                1875

Ala Ser Ala Gln Gly Arg Ala Gly Ser Gln Gly Gln Ala Gln Gly
        1880                1885                1890

Arg Val Gly Ser Ser Ala Asp Arg Gln Gly Arg Arg Gly Val Ser
        1895                1900                1905

Gly Ser Gln Ala Ser Asp Ser Glu Gly His Ser Asp Phe Ser Glu
        1910                1915                1920

Gly Gln Ala Val Gly Ala His Arg Gln Ser Gly Ala Gly Gln Arg
        1925                1930                1935

His Glu Gln Arg Ser Ser Arg Gly Gln His Gly Ser Gly Tyr Tyr
        1940                1945                1950

Tyr Glu Gln Glu His Ser Glu Glu Ser Asp Ser Gln His Gln
        1955                1960                1965

His Gly His Gln His Glu Gln Gln Arg Gly His Gln His Gln His
        1970                1975                1980

Gln His Gln His Glu His Glu Gln Pro Glu Ser Gly His Arg Gln
        1985                1990                1995

Gln Gln Phe Ser Gly Arg Gly His Gln Gly Ala His Gln Glu Gln
        2000                2005                2010

Gly Arg Asp Ser Ala Arg Ser Arg Gly Ser Asn Gln Gly His Ser
        2015                2020                2025

Ser Ser Arg His Gln Ala Asp Ser Pro Arg Val Ser Ala Arg Ser
        2030                2035                2040

Gly Ser Gly Gly Arg Gly Gln Ser Pro Asp Ala Ser Gly Arg Ser
        2045                2050                2055

Ser Asn Arg Arg Asp Arg Pro Arg Gln Pro Ser Pro Ser Gln Ser
        2060                2065                2070

Ser Asp Ser Gln Val His Ser Gly Val Gln Val Glu Gly Arg Arg
        2075                2080                2085

Gly Gln Ser Ser Ser Ala Asn Arg Arg Ala Gly Ser Ser Ser Ser
        2090                2095                2100

Ser Gly Val Gln Gly Ala Ser Ala Gly Gly Leu Ala Ala Asp Ala
        2105                2110                2115

Ser Arg Arg Ser Gly Ala Arg Gln Gly Gln Ala Ser Ala Gln Gly
        2120                2125                2130

Arg Ala Gly Ser Gln Gly Gln Ala Gln Gly Arg Val Gly Ser Ser
        2135                2140                2145

Ala Asp Arg Gln Gly Arg Arg Gly Val Ser Glu Ser Gln Ala Ser
        2150                2155                2160

Asp Ser Glu Gly His Ser Asp Phe Ser Glu Gly Gln Ala Val Gly
        2165                2170                2175

Ala His Arg Gln Ser Gly Ala Gly Gln Arg His Glu Gln Arg Ser
        2180                2185                2190

Ser Arg Gly Gln His Gly Ser Gly Phe Tyr Pro Val Tyr Tyr Tyr
        2195                2200                2205

Tyr Glu Gln Glu His Ser Glu Glu Ser Asp Ser Gln His Gln
        2210                2215                2220

His Gly His Gln His Glu Gln Gln Arg Gly His Gln His Gln His
        2225                2230                2235

Gln His Gln His Glu His Glu Gln Pro Glu Ser Gly His Arg Gln
        2240                2245                2250
```

```
Gln Gln Phe Ser Gly Arg Gly His Gln Gly Ala His Gln Glu Gln
    2255                2260                2265

Gly Arg Asp Ser Ala Arg Ser Arg Gly Ser Asn Gln Gly His Ser
    2270                2275                2280

Ser Ser Arg His Gln Ala Asp Ser Pro Arg Val Ser Ala Arg Ser
    2285                2290                2295

Gly Ser Gly Gly Arg Gly Gln Ser Pro Asp Ala Ser Gly Arg Ser
    2300                2305                2310

Ser Asn Arg Arg Asp Arg Pro Arg Gln Pro Ser Pro Ser Gln Ser
    2315                2320                2325

Ser Asp Ser Gln Val His Ser Gly Val Gln Val Glu Gly Arg Arg
    2330                2335                2340

Gly Gln Ser Ser Ser Ala Asn Arg Arg Ala Gly Ser Ser Ser Gly
    2345                2350                2355

Ser Gly Val Gln Gly Ala Ser Ala Gly Gly Leu Ala Ala Asp Ala
    2360                2365                2370

Ser Arg Arg Ser Gly Ala Arg Gln Gly Gln Ala Ser Ala Gln Gly
    2375                2380                2385

Arg Ala Gly Ser Gln Gly Gln Ala Gln Gly Arg Val Gly Ser Ser
    2390                2395                2400

Ala Asp Arg Gln Gly Arg Arg Gly Val Ser Glu Ser Gln Ala Ser
    2405                2410                2415

Asp Ser Glu Gly His Ser Asp Phe Ser Glu Gly Gln Ala Val Gly
    2420                2425                2430

Ala His Arg Gln Ser Gly Ala Gly Gln Arg His Glu Gln Arg Ser
    2435                2440                2445

Ser Arg Gly Gln His Gly Ser Gly Tyr Tyr Tyr Glu Gln Glu His
    2450                2455                2460

Ser Glu Glu Glu Ser Asp Ser Gln His Gln Gly His Gln His
    2465                2470                2475

Glu Gln Gln Arg Gly His Gln His Gln His Gln His Gln His Glu
    2480                2485                2490

His Glu Gln Pro Glu Ser Gly His Arg Gln Gln Gln Ser Ser Gly
    2495                2500                2505

Arg Gly His Gln Gly Ala His Gln Glu Gln Gly Arg Asp Ser Ala
    2510                2515                2520

Arg Ser Arg Gly Ser Asn Gln Gly His Ser Ser Ser Arg His Gln
    2525                2530                2535

Ala Asp Ser Pro Arg Val Ser Ala Arg Ser Gly Ser Gly Gly Arg
    2540                2545                2550

Gly Gln Ser Pro Asp Gly Ser Gly Arg Ser Ser Asn Arg Arg Asp
    2555                2560                2565

Arg Pro Arg Gln Pro Ser Ala Ser Gln Ser Ser Asp Ser Gln Val
    2570                2575                2580

His Ser Gly Val Gln Val Glu Ala Gln Arg Gly Gln Ser Ser Ser
    2585                2590                2595

Ala Asn Arg Arg Ala Gly Ser Ser Gly Ser Gly Val Gln Ser
    2600                2605                2610

Ala Ala Ala Ser Gly Gln Gly Gly Tyr Glu Ser Ile Phe Thr Ala
    2615                2620                2625

Lys His Leu Asp Phe Asn Gln Ser His Ser Tyr Tyr Tyr Tyr
    2630                2635                2640
```

```
<210> SEQ ID NO 17
<211> LENGTH: 336
<212> TYPE: PRT
<213> ORGANISM: Mus musculus

<400> SEQUENCE: 17

Pro Asp Gly Ser Gly Arg Ser Ser Asn Arg Arg Asp Arg Pro Arg Gln
1               5                   10                  15

Leu Ser Pro Ser Gln Ser Ser Asp Ser Gln Val His Ser Gly Val Gln
            20                  25                  30

Val Glu Gly Arg Arg Gly His Ser Ser Ala Asn Arg Arg Ala Gly
        35                  40                  45

Ser Ser Ser Gly Ser Gly Val Gln Gly Ala Ser Ala Gly Gly Leu Ala
50                  55                  60

Ala Asp Ala Ser Arg Arg Ser Gly Ala Arg Gln Gly Gln Ala Ser Ala
65                  70                  75                  80

Gln Gly Arg Ala Gly Ser Gln Gly Gln Ala Gln Gly Arg Val Ser Ser
                85                  90                  95

Ser Ala Asp Arg Gln Gly Arg Arg Gly Val Ser Glu Ser Arg Ala Ser
            100                 105                 110

Asp Ser Glu Gly His Ser Asp Phe Ser Glu Gly Gln Ala Val Gly Ala
        115                 120                 125

His Arg Gln Ser Gly Ala Gly Gln Arg His Glu Gln Arg Ser Ser Arg
130                 135                 140

Gly Gln His Gly Ser Gly Tyr Tyr Tyr Glu Gln Glu His Ser Glu Glu
145                 150                 155                 160

Glu Ser Asp Ser Gln His Gln His Gly His Gln His Glu Gln Arg
                165                 170                 175

Gly His Gln His Gln His Gln His Gln His Glu His Glu Gln Pro Glu
            180                 185                 190

Ser Gly His Arg Gln Gln Ser Ser Gly Arg Gly His Gln Gly Ala
        195                 200                 205

His Gln Glu Gln Gly Arg Asp Ser Ala Arg Pro Arg Gly Ser Asn Gln
210                 215                 220

Gly His Ser Ser Ser Arg His Gln Ala Asp Ser Pro Arg Val Ser Ala
225                 230                 235                 240

Arg Ser Gly Ser Gly Arg Gly Gln Ser Pro Asp Ala Ser Gly Arg
                245                 250                 255

Ser Ser Asn Arg Arg Asp Arg Pro Arg Gln Pro Ser Pro Ser Gln Ser
            260                 265                 270

Ser Asp Ser Gln Val His Ser Gly Val Gln Val Glu Ala Gln Arg Gly
        275                 280                 285

Gln Ser Ser Ala Asn Arg Arg Ala Gly Ser Ser Gly Ser Gly
290                 295                 300

Val Gln Gly Ala Ala Ser Gly Gln Gly Gly Tyr Glu Ser Ile Phe
305                 310                 315                 320

Thr Ala Lys His Leu Asp Phe Asn Gln Ser His Ser Tyr Tyr Tyr Tyr
                325                 330                 335

<210> SEQ ID NO 18
<211> LENGTH: 357
<212> TYPE: PRT
<213> ORGANISM: Mus musculus

<400> SEQUENCE: 18

Met Ser Ala Leu Leu Glu Ser Ile Thr Ser Met Ile Glu Ile Phe Gln
```

```
            1               5                  10                 15
          Gln Tyr Ser Thr Ser Asp Lys Glu Glu Thr Leu Ser Lys Glu Glu
                          20                 25                 30

Leu Lys Glu Leu Leu Glu Gly Gln Leu Gln Ala Val Leu Lys Asn Pro
                          35                 40                 45

Asp Gln Asp Ile Ala Glu Val Phe Met Gln Met Leu Asp Val Asp
              50                 55                 60

His Asp Asp Lys Leu Asp Phe Ala Glu Tyr Leu Leu Leu Val Leu Lys
          65                  70                 75                 80

Leu Ala Lys Ala Tyr Tyr Glu Ala Ser Lys Asn Glu Ser Phe Gln Thr
                          85                 90                 95

His Gly Ser Asn Gly Arg Ser Lys Thr Asp Tyr Lys Gly Leu Glu Glu
                          100                105                110

Glu Gly Glu Gly Asn Lys Gln Asn Leu Arg Arg Arg His Gly Gly
                          115                120                125

Thr Asp Gly Lys Arg Lys Ser Asp Arg Thr Arg Ser Pro Asn Gly Lys
              130                135                140

Arg Gly Lys Arg Gln Glu Ser Arg Cys Arg Ser Glu Gly Lys Asp Lys
          145                 150                155                160

His Arg Arg Glu Pro Glu Lys His Arg His Gln Gln Asp Ser Lys Arg
                          165                170                175

Lys Gln Arg His Gly Ser Gly Ser Thr Glu Lys Asp Asn Arg Asn
                          180                185                190

Lys Lys Asn Arg Gln Ser Lys Glu Arg Asn Tyr Asp Glu Ile Tyr Asp
                          195                200                205

Asn Gly Lys Tyr Asn Glu Asp Trp Glu Ala Ser Tyr Asn Asn Cys Tyr
              210                215                220

Tyr Lys Thr Gln Asn Thr Thr Leu Asp Gln Arg Glu Gly Asn Arg Arg
          225                 230                235                240

Pro Arg Ala Asp Ser Gln Lys Glu Pro Gln Ser Ser His Gly Gln Ala
                          245                250                255

Asp Asn Ser Asp Ser Glu Gly Gly Arg Gln Gln Ser His Ser Lys Pro
                          260                265                270

Ser Pro Val Arg Ala Asp Gln Arg Ser Arg Ala Gly Gln Ala Gly
                          275                280                285

Ser Ser Lys Val Ser Ala Arg Ser Gly Ser Gly Arg Gly Gln Ser
                          290                295                300

Pro Asp Gly Ser Gly Arg Ser Ser Asn Arg Arg Asp Arg Pro Arg Gln
          305                 310                315                320

Pro Ser Pro Ser Gln Ser Ser Asp Ser Gln Val His Ser Gly Val Gln
                          325                330                335

Val Glu Gly Arg Arg Gly Gln Ser Ser Ala Asn Arg Arg Ala Gly
                          340                345                350

Ser Ser Ser Gly Ser
                          355

<210> SEQ ID NO 19
<211> LENGTH: 366
<212> TYPE: PRT
<213> ORGANISM: Rattus norvegicus

<400> SEQUENCE: 19

Met Ser Thr Leu Leu Glu Ser Ile Thr Ser Met Ile Asp Ile Phe Gln
1               5                   10                  15
```

```
Gln Tyr Ser Asn Asn Asp Lys Glu Glu Thr Leu Ser Lys Glu Glu
            20                  25                  30

Leu Lys Glu Leu Leu Glu Gly Glu Leu Gln Ala Val Leu Lys Asn Pro
        35                  40                  45

Asn Asp Gln Asp Ile Ala Glu Val Phe Met Gln Met Leu Asp Val Asp
    50                  55                  60

His Asp Asp Lys Ile Asp Phe Thr Glu Tyr Leu Leu Met Val Leu Lys
65                  70                  75                  80

Leu Ala Gln Ala Tyr Tyr Glu Thr Ser Lys Lys Arg Arg Ser Gln Thr
                85                  90                  95

Lys Glu Ser Gly Lys Arg Asn Glu His Asp Tyr Lys Gly Tyr Glu Glu
            100                 105                 110

Arg Arg Glu Lys Val Gln Arg His Arg Arg Asn Ser Gly Thr
        115                 120                 125

Asp Gly Lys Gln Glu Asn Glu Arg Ser Lys Ser Pro Arg Gly Arg Gly
    130                 135                 140

Asn Lys Arg Arg Gly Ser Ser Thr Ile Ser Glu Glu Ser Asp Thr Asn
145                 150                 155                 160

Arg Asn Ser Asp Thr Glu Asn Lys Arg His His His Gly Ser Asn Arg
                165                 170                 175

Arg Gln Arg Arg Gly Ser Asn Ser Ser Asp Arg Lys Glu Thr Arg Ser
            180                 185                 190

Lys Lys His Arg Glu Val Lys Glu Arg Asn Ala Gly Ile Tyr Asn Asp
        195                 200                 205

Gly Lys Asp Gly Gln Asp Trp Glu Val Asn Tyr Glu Asn Cys Tyr Tyr
    210                 215                 220

Lys Thr Glu Glu Ser Asn Arg Glu Gln Arg Glu Gly Arg Asn His Lys
225                 230                 235                 240

Thr Lys Glu Ser His Ser Glu Ser Glu Ala Ser Gly Gly Gln Ala Gly
                245                 250                 255

Arg Arg Gly Thr Ala Ala Thr Arg His Thr Ser Arg Pro Glu Gln Ser
            260                 265                 270

Pro Asp Thr Ala Gly Arg Thr Gly Ser Ser Arg Gly Gln Gln Ser Ala
    275                 280                 285

Gln Arg His Ala Asp Ser Thr Pro Gly Ser Thr Arg Thr Gly Ser Arg
    290                 295                 300

Gly Arg Gly Glu Ser Pro Ala Gly Gln Gln Ser Pro Asp Arg Ala Arg
305                 310                 315                 320

His Ile Glu Ser Arg Arg Gly Arg Thr Arg Glu Ala Ser Ala Ser Gln
                325                 330                 335

Ser Ser Asp Ser Glu Gly His Ser Gly Ala His Ala Gly Ile Gly Gln
            340                 345                 350

Gly Gln Thr Ser Thr Thr His Arg Arg Ala Gly Ser Ser Ser
        355                 360                 365

<210> SEQ ID NO 20
<211> LENGTH: 3088
<212> TYPE: PRT
<213> ORGANISM: Pan troglodytes

<400> SEQUENCE: 20

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30
```

```
Leu Lys Glu Leu Leu Glu Lys Glu Phe Arg Gln Ile Leu Lys Asn Pro
            35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His His Asp Lys His Glu Asp
                100                 105                 110

Asn Lys Gln Glu Glu Asn Lys Glu Asn Arg Lys Arg Pro Ser Ser Leu
                115                 120                 125

Glu Arg Arg Asn Asn Arg Lys Gly Asn Lys Gly Arg Ser Lys Ser Pro
            130                 135                 140

Arg Glu Thr Gly Gly Lys Arg His Glu Ser Ser Ser Glu Lys Lys Glu
145                 150                 155                 160

Arg Lys Gly Tyr Ser Pro Thr His Arg Glu Glu Tyr Gly Lys Asn
                165                 170                 175

His His Asn Ser Ser Lys Lys Gln Lys Asn Lys Thr Glu Asn Thr Arg
                180                 185                 190

Leu Glu Asp Asn Arg Lys Arg Leu Ser Glu Arg Leu Glu Glu Lys Glu
            195                 200                 205

Asp Asn Glu Glu Gly Gly Tyr Asp Tyr Glu Asn Thr Gly Arg Met Thr
    210                 215                 220

Gln Lys Trp Ile Gln Ser Gly His Ile Ala Thr Tyr Tyr Thr Ile Gln
225                 230                 235                 240

Asp Glu Ala Tyr Asp Thr Thr Asp Asn Leu Leu Glu Glu Asn Lys Ile
                245                 250                 255

Tyr Glu Arg Ser Arg Ser Ser Asp Asp Lys Ser Ser Ser Gln Val Asn
                260                 265                 270

Arg Ser Arg His Glu Asn Thr Ser Gln Val Pro Leu Gln Glu Ser Arg
            275                 280                 285

Thr Arg Lys Arg Arg Gly Ser Arg Val Ser Gln Asp Arg Asp Ser Glu
    290                 295                 300

Gly His Ser Glu Asp Ser Glu Arg His Ser Gly Ser Ala Ser Arg Asn
305                 310                 315                 320

His Pro Gly Ser Ala Arg Gln Gln Ser Arg Asp Gly Ser Arg His Pro
                325                 330                 335

Arg Ser His Asp Glu Asp Arg Ala Ser His Gly His Ser Ala Asp Ser
                340                 345                 350

Ser Arg Gln Ser Gly Thr Arg His Ala Glu Thr Ser Ser Arg Gly Gln
            355                 360                 365

Thr Ala Ser Ser His Glu Gln Ala Arg Ser Ser Pro Gly Glu Arg His
    370                 375                 380

Gly Ser Arg His Gln Gln Ser Ala Asp Ser Ser Arg His Ser Ala Thr
385                 390                 395                 400

Gly Arg Gly Gln Ala Ser Ser Ala Val Ser Asp Arg Gly Pro Arg Gly
                405                 410                 415

Ser Ser Gly Ser Gln Ala Ser Asp Ser Glu Gly His Ser Glu Asn Ser
                420                 425                 430

Asp Thr Gln Ser Val Ser Gly His Gly Lys Ala Gly Pro Arg Gln Gln
                435                 440                 445
```

```
Ser His Gln Glu Ser Ala Arg Gly Arg Ser Gly Glu Arg Ser Gly His
450                 455                 460

Ser Gly Ser Phe Leu Tyr Gln Val Ser Thr His Glu Gln Ser Asp Ser
465                 470                 475                 480

Ala His Gly Arg Thr Gly Thr Ser Thr Gly Gly Arg Gln Gly Ser His
                485                 490                 495

His Glu Gln Ala Arg Asp Ser Ser Arg His Ser Ala Ser Gln Glu Gly
            500                 505                 510

Gln Asp Thr Ile Arg Gly His Pro Gly Ser Ser Arg Gly Gly Arg Gln
            515                 520                 525

Gly Ser His His Glu Gln Leu Val Asn Arg Ser Gly His Ser Gly Ser
530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
                565                 570                 575

Ser Gly Asp Gly Ser Arg His Ser Gly Ser Arg His His Glu Ala Ser
            580                 585                 590

Ser Gln Ala Asp Ser Ser Arg His Ser Gln Val Gly Gln Gly Gln Ser
    595                 600                 605

Ser Gly Pro Arg Thr Ser Ser His Gln Gly Ser Ser Val Ser Gln Asp
    610                 615                 620

Ser Asp Ser Glu Gly His Ser Glu Asp Ser Glu Arg Trp Ser Gly Ser
625                 630                 635                 640

Ala Ser Arg Asn His His Gly Ser Ala Arg Glu Gln Ser Arg Asp Gly
                645                 650                 655

Ser Arg His Pro Arg Ser His His Glu Asp Arg Ala Gly His Gly His
                660                 665                 670

Ser Ala Asp Ser Ser Arg Gln Ser Gly Thr Arg His Thr Glu Ser Ser
            675                 680                 685

Ser Arg Gly Gln Ala Val Ser Ser His Glu Gln Ala Arg Ser Ser Pro
            690                 695                 700

Gly Glu Arg His Gly Ser Arg His Gln Gln Ser Ala Asp Ser Ser Arg
705                 710                 715                 720

His Ser Gly Ile Gly His Gly Gln Ala Ser Ser Ala Val Arg Asp Ser
                725                 730                 735

Gly His Arg Gly Ser Ser Gly Ser Gln Ala Ile Asp Ser Glu Gly His
            740                 745                 750

Ser Glu Asp Ser Asp Thr Gln Ser Val Ser Ser His Gly Gln Ala Gly
            755                 760                 765

Pro His Gln Gln Ser His Lys Glu Ser Ala Arg Gly Gln Ser Gly Glu
    770                 775                 780

Ser Ser Gly Arg Ser Gly Ser Phe Leu Tyr Gln Val Ser Ser His Glu
785                 790                 795                 800

Gln Ser Glu Ser Thr Tyr Gly Gln Thr Ala Pro Ser Thr Gly Gly Arg
            805                 810                 815

Gln Gly Ser Arg His Glu Gln Ala Arg Asn Ser Ser Arg His Ser Ala
                820                 825                 830

Ser Gln Asp Gly Gln Asp Thr Ile Arg Gly His Pro Gly Ser Ser Arg
    835                 840                 845

Gly Gly Arg Gln Gly Ser Tyr His Glu Gln Ser Val Asp Arg Ser Gly
850                 855                 860

His Ser Gly Tyr His His Ser His Thr Thr Pro Gln Gly Arg Ser Asp
```

```
                865                 870                 875                 880
           Ala Ser His Gly Gln Ser Gly Pro Arg Ser Ala Ser Arg Gln Thr Arg
                             885                 890                 895

Asn Glu Glu Gln Ser Gly Asp Gly Ser Arg His Ser Gly Ser Arg His
                         900                 905                 910

His Glu Pro Ser Thr Arg Ala Ser Ser Arg His Ser Gln Val Gly
                     915                 920                 925

Gln Gly Glu Ser Ala Val Ser Lys Thr Ser Arg Arg Gln Gly Ser Ser
           930                 935                 940

Val Ser Gln Asp Arg Asp Ser Glu Gly His Ser Glu Asp Ser Glu Arg
           945                 950                 955                 960

Gln Ser Glu Ser Ala Ser Arg Asn His Tyr Gly Ser Ala Arg Glu Gln
                         965                 970                 975

Ser Arg His Gly Ser Arg Asn Pro Arg Ser His Gln Glu Asp Arg Ala
                     980                 985                 990

Ser His Gly His Ser Ala Glu Ser  Ser Arg Gln Ser Gly  Thr His His
                     995                 1000                1005

Ala Glu  Thr Ser Ser His Gly  Gln Ala Ala Ser  Gln Glu Gln
           1010                1015                1020

Ala Arg  Ser Ser Arg Gly Glu  Arg His Gly Ser Arg  His Gln Gln
           1025                1030                1035

Ser Ala Asp Ser Ser Thr Asp  Ser Gly Thr Gly Gly  Arg Gln Ala
           1040                1045                1050

Ser Ser  Val Val Gly Asp Ser  Gly Asn Arg Gly Ser  Ser Gly Ser
           1055                1060                1065

Gln Ala Ser Asp Ser Glu Gly  His Ser Glu Asp Ser  Asp Thr Gln
           1070                1075                1080

Ser Val  Ser Ala His Gly Gln  Ala Gly Pro Arg Gln  Gln Ser His
           1085                1090                1095

Gln Glu  Ser Thr Arg Gly Gln  Ser Gly Glu Arg Ser  Gly Arg Ser
           1100                1105                1110

Gly Ser  Phe Leu Tyr Gln Val  Ser Thr His Glu Gln  Ser Glu Ser
           1115                1120                1125

Ala His  Gly Arg Thr Gly Pro  Ser Thr Gly Gly Arg  Gln Arg Ser
           1130                1135                1140

Arg His  Glu Gln Ala Arg Asp  Ser Ser Arg His Ser  Ala Ser Gln
           1145                1150                1155

Glu Ser  Gln Asp Ile Ile His  Ala His Pro Gly Ser  Ser Arg Gly
           1160                1165                1170

Gly Arg  Gln Gly Ser His Tyr  Glu Gln Ser Val Asp  Arg Ser Gly
           1175                1180                1185

His Ser  Gly Ser His His Ser  His Thr Thr Ser Gln  Glu Arg Ser
           1190                1195                1200

Asn Ala  Ser His Gly Gln Ser  Gly Ser Arg Ser Ala  Ser Arg Gln
           1205                1210                1215

Thr Arg  Asn Glu Glu Gln Ser  Gly Asp Gly Ser Arg  His Ser Gly
           1220                1225                1230

Ser Arg  His His Glu Ala Ser  Ser Arg Ala Asp Ser  Ser Arg His
           1235                1240                1245

Ser Gln  Val Gly Gln Gly Gln  Ser Ser Gly Pro Arg  Thr Ser Arg
           1250                1255                1260

Asn Gln  Gly Ser Ser Val Ser  Gln Asp Ser Asp Ser  Gln Gly His
           1265                1270                1275
```

```
Ser Glu Asp Ser Glu Arg Trp Ser Gly Ser Ala Ser  Arg Asn His
    1280            1285                1290

His Gly Ser Ala Trp Glu Gln Ser Arg Asp Gly Ser  Arg His Pro
    1295            1300                1305

Gly Ser His Gln Glu Asp Arg Ala Gly His Gly His  Ser Ala Asp
    1310            1315                1320

Ser Ser Arg Gln Ser Gly Thr His His Thr Glu Ser  Ser Ser Arg
    1325            1330                1335

Gly Gln Ala Ala Ser Ser His Glu His Ala Arg Ser  Ser Ala Gly
    1340            1345                1350

Glu Arg His Gly Ser His His Gln Gln Ser Ala Asp  Ser Ser Arg
    1355            1360                1365

His Ser Gly Ile Gly His Gly Gln Ala Ser Ser Ala  Val Arg Asp
    1370            1375                1380

Ser Gly His Arg Gly Ser Ser Gly Ser Gln Ala Ser  Asp Ser Glu
    1385            1390                1395

Gly His Ser Glu Asp Ser Asp Thr Gln Ser Leu Ser  Ala His Gly
    1400            1405                1410

Gln Ala Gly Pro His Gln Gln Ser His Gln Glu Ser  Thr Arg Gly
    1415            1420                1425

Arg Ser Ala Glu Arg Ser Gly Arg Ser Gly Ser Phe  Leu Tyr Gln
    1430            1435                1440

Val Ser Thr His Glu Gln Ser Glu Ser Ala His Gly  Arg Thr Gly
    1445            1450                1455

Thr Ser Thr Gly Gly Arg Lys Arg Ser Leu His Glu  Gln Ala Arg
    1460            1465                1470

Asp Ser Ser Arg His Ser Val Ser Gln Glu Gly Gln  Asp Thr Ile
    1475            1480                1485

His Gly His Ala Gly Ser Ser Ser Gly Gly Arg Gln  Gly Ser His
    1490            1495                1500

Tyr Glu Gln Leu Val Asp Arg Ser Gly His Ser Gly  Ser His His
    1505            1510                1515

Ser His Thr Thr Ser Gln Gly Arg Ser Asp Ala Tyr  His Gly Gln
    1520            1525                1530

Ser Gly Ser Arg Ser Ala Ser Arg Gln Thr His Asn  Asp Glu Gln
    1535            1540                1545

Ser Gly Asp Gly Phe Arg His Ser Gly Ser His His  His Glu Ala
    1550            1555                1560

Ser Ser Arg Ala Asp Ser Ser Arg His Ser Gln Val  Gly Gln Gly
    1565            1570                1575

Gln Ser Glu Gly Pro Arg Thr Ser Arg His Arg Glu  Ser Ser Val
    1580            1585                1590

Ser Gln Asp Ser Asp Ser Glu Gly His Ser Glu Asp  Ser Glu Arg
    1595            1600                1605

Trp Ser Gly Ser Ala Ser Arg Asn His His Gly Ser  Ala Arg Glu
    1610            1615                1620

Gln Ser Arg Asp Gly Ser Arg His Pro Arg Ser His  His Glu Asp
    1625            1630                1635

Arg Ala Gly His Gly His Ser Ala Asp Ser Ser Arg  Gln Ser Gly
    1640            1645                1650

Thr Arg His Thr Gln Thr Ser Ser Gly Gly Gln Ala  Ala Ser Ser
    1655            1660                1665
```

```
His Glu Gln Gly Arg Ser Ser Ala Gly Glu Arg His Gly Ser Arg
1670                1675                1680

His Gln Gln Ser Ala Asp Ser Arg His Ser Gly Ile Gly His
1685                1690                1695

Gly Gln Ala Ser Ser Ala Val Arg Asp Ser Gly His Arg Gly Tyr
1700                1705                1710

Ser Gly Ser Gln Ala Ser Asp Ser Glu Gly His Ser Glu Asp Ser
1715                1720                1725

Asp Thr Gln Ser Val Ser Ala His Gly Gln Ala Gly Ser His Gln
1730                1735                1740

Gln Ser His Gln Glu Ser Ala Arg Gly Arg Ser Gly Glu Arg Ser
1745                1750                1755

Gly Arg Ser Gly Ser Phe Leu Tyr Gln Val Ser Thr His Glu Gln
1760                1765                1770

Ser Glu Ser Ser His Gly Trp Thr Gly Pro Ser Thr Arg Gly Arg
1775                1780                1785

Gln Gly Ser Arg His Glu Gln Ala Gln Asp Ser Arg His Ser
1790                1795                1800

Ala Ser Gln Glu Gly Gln Asp Thr Ile Arg Gly His Pro Gly Pro
1805                1810                1815

Ser Arg Gly Gly Arg Gln Gly Tyr His His Glu Gln Ser Val Asp
1820                1825                1830

Ser Ser Gly His Ser Gly Ser His His Ser His Ile Thr Ser Gln
1835                1840                1845

Gly Ser Ser His Ala Ser His Gly Gln Ser Gly Ser Arg Ser Ala
1850                1855                1860

Ser Arg Thr Thr Arg Asn Asp Glu Gln Ser Val Asp Gly Ser Arg
1865                1870                1875

His Ser Gly Ser Arg His His Glu Ala Ser Thr His Ala Asp Ile
1880                1885                1890

Ser Arg His Ser Gln Ala Gly Gln Gly Gln Ser Glu Gly Ser Arg
1895                1900                1905

Thr Ser Arg Arg Gln Gly Ser Ser Val Ser Gln Asp Ser Asp Ser
1910                1915                1920

Glu Gly His Ser Glu Asp Ser Glu Arg Trp Ser Gly Ser Ala Ser
1925                1930                1935

Arg Asn His Arg Gly Ser Ala Gln Glu Gln Ser Arg Asp Gly Ser
1940                1945                1950

Arg His Pro Arg Ser His His Glu Asp Arg Ala Gly His Gly His
1955                1960                1965

Ser Ala Asp Ser Ser Arg Gln Ser Gly Thr His His Ala Glu Thr
1970                1975                1980

Ser Ser Gly Gly Gln Ala Ala Ser Ser Arg Glu Gln Ala Arg Ser
1985                1990                1995

Ser Pro Gly Glu Arg His Gly Ser Arg His Gln Gln Ser Ala Asp
2000                2005                2010

Ser Ser Arg His Ser Gly Ile Arg Arg Gly Gln Ala Ser Ser Ala
2015                2020                2025

Val Arg Asp Ser Gly His Trp Gly Ser Ser Gly Ser Gln Ala Ser
2030                2035                2040

Asp Ser Glu Gly His Ser Glu Ser Asp Thr Gln Ser Val Ser
2045                2050                2055

Gly His Gly Gln Asp Gly Pro His Gln Gln Ser His Gln Glu Ser
```

```
                    2060                2065                2070

Ala Arg Asp Arg Ser Gly Gly Arg Ser Gly Arg Ser Gly Ser Phe
    2075                2080                2085

Leu Tyr Gln Val Ser Thr His Glu Gln Ser Glu Ser Thr His Gly
    2090                2095                2100

Gln Thr Gly Thr Ser Thr Gly Gly Arg Gln Gly Ser His His Glu
    2105                2110                2115

Gln Ala Arg Asp Ser Ser Arg His Ser Ala Ser Gln Glu Gly Gln
    2120                2125                2130

Asp Thr Ile His Ala His Pro Gly Ser Ser Arg Gly Gly Arg Gln
    2135                2140                2145

Gly Ser His His Glu Gln Ser Val Asp Thr Ser Gly His Ser Gly
    2150                2155                2160

Ser His His Ser His Thr Thr Ser Gln Gly Arg Ser Asp Ala Ser
    2165                2170                2175

His Gly Gln Ser Gly Ser Arg Ser Ala Ser Arg Gln Thr Arg Asn
    2180                2185                2190

Asp Glu Gln Ser Gly Asp Gly Ser Arg His Ser Gly Ser His His
    2195                2200                2205

His Glu Ala Phe Thr Gln Ala Asp Ser Ser Arg His Ser Gln Ser
    2210                2215                2220

Gly Gln Gly Glu Ser Ala Gly Ser Arg Arg Ser Arg Arg Gln Gly
    2225                2230                2235

Ser Ser Val Ser Gln Asp Ser Asp Ser Gln Gly His Ser Glu Asp
    2240                2245                2250

Ser Glu Arg Trp Ser Gly Ser Ala Ser Arg Asn Gln His Gly Ser
    2255                2260                2265

Ala Arg Glu Gln Ser Arg Asp Gly Ser Arg His Pro Gly Ser His
    2270                2275                2280

Gln Glu Asp Arg Ala Gly His Gly His Ser Ala Asp Ser Ser Arg
    2285                2290                2295

Gln Ser Gly Thr Arg His Thr Glu Ser Ser Ser Arg Gly Gln Ala
    2300                2305                2310

Ala Ser Ser His Glu Gln Ala Arg Ser Ser Ala Gly Glu Arg His
    2315                2320                2325

Gly Ser Arg His Gln Leu Gln Ser Ala Asp Ser Ser Arg His Ser
    2330                2335                2340

Gly Ile Gly His Gly Gln Ala Ser Ser Ala Val Arg Asp Ser Gly
    2345                2350                2355

His Arg Gly Ser Ser Gly Ser Gln Ala Ile Asp Ser Glu Gly His
    2360                2365                2370

Ser Glu Asp Ser Asp Thr Gln Ser Val Ser Ala Gln Gly Gln Ala
    2375                2380                2385

Gly Pro His Gln Arg Ser His Lys Glu Ser Ala Arg Gly Gln Ser
    2390                2395                2400

Gly Glu Ser Ser Gly Arg Ser Gly Ser Phe Leu Tyr Gln Val Ser
    2405                2410                2415

Thr His Glu Gln Pro Glu Ser Thr His Gly Gln Ser Ala Pro Ser
    2420                2425                2430

Thr Gly Gly Arg Gln Gly Ser His His Asp Gln Ala Gln Asp Ser
    2435                2440                2445

Ser Arg His Ser Ala Ser Gln Glu Gly Gln Asp Thr Ile Arg Gly
    2450                2455                2460
```

```
His Pro Gly Pro Ser Arg Gly Gly Arg Gln Gly Ser His His Lys
    2465            2470                2475

Gln Ser Val Asp Arg Ser Gly His Ser Gly Ser His His Ser His
    2480            2485                2490

Thr Thr Ser Gln Gly Arg Ser Asp Ala Ser Arg Gly Gln Ser Gly
    2495            2500                2505

Ser Arg Ser Ala Ser Arg Gln Thr His Asp Lys Glu Gln Ser Gly
    2510            2515                2520

Asp Gly Ser Arg His Ser Gly Ser Arg His His Glu Ala Ser Ser
    2525            2530                2535

Trp Ala Asp Ser Ser Arg His Ser Gln Ala Gly Gln Gly Gln Ser
    2540            2545                2550

Glu Gly Ser Arg Thr Ser Arg Arg Gln Gly Ser Ser Phe Ser Gln
    2555            2560                2565

Asp Ser Asp Ser Glu Gly His Ser Glu Asp Ser Glu Arg Arg Ser
    2570            2575                2580

Gly Ser Ala Ser Arg Asn His Arg Gly Ser Ala Gln Glu Gln Ser
    2585            2590                2595

Arg Asp Gly Ser Arg His Pro Arg Ser His His Glu Asp Arg Ala
    2600            2605                2610

Gly His Gly His Ser Ala Asp Ser Ser Arg Gln Ser Gly Thr His
    2615            2620                2625

His Ala Gln Asn Ser Ser Gly Gly Gln Ala Ala Ser Phe His Glu
    2630            2635                2640

Gln Ala Arg Ser Ser Ala Gly Glu Arg His Gly Ser His His Gln
    2645            2650                2655

Gln Ser Ala Asp Ser Ser Arg His Ser Gly Ile Gly His Gly Gln
    2660            2665                2670

Ala Ser Ser Ala Val Arg Asp Ser Gly His Arg Gly Ser Ser Gly
    2675            2680                2685

Ser Gln Ala Ser Asp Ser Glu Gly His Ser Glu Asp Ser Asp Thr
    2690            2695                2700

Gln Ser Val Ser Ala His Gly Gln Ala Gly Pro His Gln Gln Ser
    2705            2710                2715

His Gln Glu Ser Thr Arg Gly Arg Ser Ala Glu Arg Ser Gly Arg
    2720            2725                2730

Ser Gly Ser Phe Leu Tyr Gln Val Ser Thr His Glu Gln Ser Glu
    2735            2740                2745

Ser Ala His Gly Arg Thr Gly Pro Ser Thr Gly Gly Arg Gln Gly
    2750            2755                2760

Ser Arg His Glu Gln Ala Arg Asp Ser Ser Arg His Ser Ala Ser
    2765            2770                2775

Gln Glu Gly Gln Asp Thr Ile His Gly His Pro Gly Ser Arg Arg
    2780            2785                2790

Gly Gly Arg Gln Gly Ser Tyr His Glu Gln Ser Val Asp Arg Ser
    2795            2800                2805

Gly His Ser Gly Ser His His Ser His Thr Thr Ser Gln Gly Arg
    2810            2815                2820

Ser Asp Ala Ser His Gly Gln Ser Gly Ser Arg Ser Ala Ser Arg
    2825            2830                2835

Gln Thr Arg Asn Glu Gln Gln Ser Gly Asp Gly Ser Arg His Ser
    2840            2845                2850
```

```
Gly Ser Ser His His Glu Ala Ser Thr Gln Ala Asp Ser Ser Arg
    2855                2860                2865

His Ser Gln Ser Gly Gln Gly Glu Ser Ala Gly Ser Arg Arg Ser
    2870                2875                2880

Arg Arg Gln Gly Ser Ser Val Ser Gln Asp Ser Asp Ser Glu Ala
    2885                2890                2895

Tyr Pro Glu Asp Ser Glu Arg Arg Ser Glu Ser Ala Ser Arg Asn
    2900                2905                2910

Arg His Gly Ser Ser Arg Glu Gln Ser Arg Asp Gly Ser Arg His
    2915                2920                2925

Pro Gly Ser Ser His Arg Asp Thr Thr Arg His Val Gln Ser Ser
    2930                2935                2940

Pro Val Gln Ser Asp Ser Ser Thr Ala Lys Glu His Gly His Phe
    2945                2950                2955

Ser Ser Leu Ser Gln Asp Ser Ala Tyr Arg Ser Gly Ile Gln Ser
    2960                2965                2970

Arg Gly Ser Pro His Ser Ser Ser Ser Tyr His Tyr Gln Ser Glu
    2975                2980                2985

Gly Thr Glu Arg Gln Lys Gly Gln Ser Gly Leu Val Trp Arg His
    2990                2995                3000

Gly Ser Tyr Gly Ser Ala Asp Tyr Asp Tyr Gly Glu Ser Gly Phe
    3005                3010                3015

Arg His Ser Gln His Gly Ser Val Ser Tyr Asn Ser Asn Pro Val
    3020                3025                3030

Val Phe Lys Glu Arg Ser Asp Ile Cys Lys Ala Ser Ala Phe Gly
    3035                3040                3045

Lys Asp His Pro Arg Tyr Tyr Ala Thr Tyr Ile Asn Lys Asp Pro
    3050                3055                3060

Gly Leu Cys Gly His Ser Ser Asp Ile Ser Lys Gln Leu Gly Phe
    3065                3070                3075

Ser Gln Ser Gln Arg Tyr Tyr Tyr Tyr Glu
    3080                3085

<210> SEQ ID NO 21
<211> LENGTH: 2764
<212> TYPE: PRT
<213> ORGANISM: Pan troglodytes

<400> SEQUENCE: 21

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Gln Ile Leu Lys Asn Pro
        35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His Asp Lys His Glu Asp
            100                 105                 110

Asn Lys Gln Glu Glu Asn Lys Glu Asn Arg Lys Arg Pro Ser Ser Leu
        115                 120                 125
```

-continued

```
Glu Arg Arg Asn Asn Arg Lys Gly Asn Lys Gly Arg Ser Lys Ser Pro
            130                 135                 140
Arg Glu Thr Gly Gly Lys Arg His Glu Ser Ser Glu Lys Lys Glu
145                 150                 155                 160
Arg Lys Gly Tyr Ser Pro Thr His Arg Glu Glu Tyr Gly Lys Asn
                165                 170                 175
His His Asn Ser Ser Lys Lys Gln Lys Asn Lys Thr Glu Asn Thr Arg
            180                 185                 190
Leu Glu Asp Asn Arg Lys Arg Leu Ser Glu Arg Leu Glu Glu Lys Glu
            195                 200                 205
Asp Asn Glu Glu Gly Gly Tyr Asp Tyr Glu Asn Thr Gly Arg Met Thr
210                 215                 220
Gln Lys Trp Ile Gln Ser Gly His Ile Ala Thr Tyr Tyr Thr Ile Gln
225                 230                 235                 240
Asp Glu Ala Tyr Asp Thr Thr Asp Asn Leu Leu Glu Glu Asn Lys Ile
                245                 250                 255
Tyr Glu Arg Ser Arg Ser Ser Asp Asp Lys Ser Ser Ser Gln Val Asn
                260                 265                 270
Arg Ser Arg His Glu Asn Thr Ser Gln Val Pro Leu Gln Glu Ser Arg
            275                 280                 285
Thr Arg Lys Arg Arg Gly Ser Arg Val Ser Gln Asp Arg Asp Ser Glu
290                 295                 300
Gly His Ser Glu Asp Ser Glu Arg His Ser Gly Ser Ala Ser Arg Asn
305                 310                 315                 320
His Pro Gly Ser Ala Arg Gln Gln Ser Arg Asp Gly Ser Arg His Pro
                325                 330                 335
Arg Ser His Asp Glu Asp Arg Ala Ser His Gly His Ser Ala Asp Ser
            340                 345                 350
Ser Arg Gln Ser Gly Thr Arg His Ala Glu Thr Ser Ser Arg Gly Gln
            355                 360                 365
Thr Ala Ser Ser His Glu Gln Ala Arg Ser Ser Pro Gly Glu Arg His
370                 375                 380
Gly Ser Arg His Gln Gln Ser Ala Asp Ser Ser Arg His Ser Ala Thr
385                 390                 395                 400
Gly Arg Gly Gln Ala Ser Ser Ala Val Ser Asp Arg Gly Pro Arg Gly
                405                 410                 415
Ser Ser Gly Ser Gln Ala Ser Asp Ser Glu Gly His Ser Glu Asn Ser
            420                 425                 430
Asp Thr Gln Ser Val Ser Gly His Gly Lys Ala Gly Pro Arg Gln Gln
            435                 440                 445
Ser His Gln Glu Ser Ala Arg Gly Arg Ser Gly Glu Arg Ser Gly His
450                 455                 460
Ser Gly Ser Phe Leu Tyr Gln Val Ser Thr His Glu Gln Ser Asp Ser
465                 470                 475                 480
Ala His Gly Arg Thr Gly Thr Ser Thr Gly Gly Arg Gln Gly Ser His
                485                 490                 495
His Glu Gln Ala Arg Asp Ser Ser Arg His Ser Ala Ser Gln Glu Gly
            500                 505                 510
Gln Asp Thr Ile Arg Gly His Pro Gly Ser Arg Gly Gly Arg Gln
            515                 520                 525
Gly Ser His His Glu Gln Leu Val Asn Arg Ser Gly His Ser Gly Ser
530                 535                 540
```

-continued

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
                565                 570                 575

Ser Gly Asp Gly Ser Arg His Ser Gly Ser Arg His His Glu Ala Ser
            580                 585                 590

Ser Gln Ala Asp Ser Ser Arg His Ser Gln Val Gly Gln Gly Gln Ser
        595                 600                 605

Ser Gly Pro Arg Thr Ser Ser His Gln Gly Ser Ser Val Ser Gln Asp
    610                 615                 620

Ser Asp Ser Glu Gly His Ser Glu Asp Ser Glu Arg Trp Ser Gly Ser
625                 630                 635                 640

Ala Ser Arg Asn His His Gly Ser Ala Arg Glu Gln Ser Arg Asp Gly
                645                 650                 655

Ser Arg His Pro Arg Ser His His Glu Asp Arg Ala Gly His Gly His
            660                 665                 670

Ser Ala Asp Ser Ser Arg Gln Ser Gly Thr Arg His Thr Glu Ser Ser
        675                 680                 685

Ser Arg Gly Gln Ala Val Ser Ser His Glu Gln Ala Arg Ser Ser Pro
    690                 695                 700

Gly Glu Arg His Gly Ser Arg His Gln Gln Ser Ala Asp Ser Ser Arg
705                 710                 715                 720

His Ser Gly Ile Gly His Gly Gln Ala Ser Ala Val Arg Asp Ser
                725                 730                 735

Gly His Arg Gly Ser Ser Gly Ser Gln Ala Ile Asp Ser Glu Gly His
            740                 745                 750

Ser Glu Asp Ser Asp Thr Gln Ser Val Ser Ser His Gly Gln Ala Gly
        755                 760                 765

Pro His Gln Gln Ser His Lys Glu Ser Ala Arg Gly Gln Ser Gly Glu
    770                 775                 780

Ser Ser Gly Arg Ser Gly Ser Phe Leu Tyr Gln Val Ser Ser His Glu
785                 790                 795                 800

Gln Ser Glu Ser Thr Tyr Gly Gln Thr Ala Pro Ser Thr Gly Gly Arg
                805                 810                 815

Gln Gly Ser Arg His Glu Gln Ala Arg Asn Ser Ser Arg His Ser Ala
            820                 825                 830

Ser Gln Asp Gly Gln Asp Thr Ile Arg Gly His Pro Gly Ser Ser Arg
        835                 840                 845

Gly Gly Arg Gln Gly Ser Tyr His Glu Gln Ser Val Asp Arg Ser Gly
    850                 855                 860

His Ser Gly Tyr His His Ser His Thr Thr Pro Gln Gly Arg Ser Asn
865                 870                 875                 880

Ala Ser His Gly Gln Ser Gly Ser Arg Ser Ala Ser Arg Gln Thr Arg
                885                 890                 895

Asn Glu Glu Gln Ser Gly Asp Gly Ser Arg His Ser Gly Ser Arg His
            900                 905                 910

His Glu Ala Ser Ser Arg Ala Asp Ser Ser Arg His Ser Gln Val Gly
        915                 920                 925

Gln Gly Gln Ser Ser Gly Pro Arg Thr Ser Arg Asn Gln Gly Ser Ser
    930                 935                 940

Val Ser Gln Asp Ser Asp Ser Gln Gly His Ser Glu Asp Ser Glu Arg
945                 950                 955                 960

Trp Ser Gly Ser Ala Ser Arg Asn His His Gly Ser Ala Trp Glu Gln

-continued

```
                965                 970                 975
Ser Arg Asp Gly Ser Arg His Pro Gly Ser His Gln Glu Asp Arg Ala
                    980                 985                 990
Gly His Gly His Ser Ala Asp Ser  Ser Arg Gln Ser Gly  Thr His His
            995                 1000                1005
Thr Glu  Ser Ser Ser Arg Gly  Gln Ala Ala Ser  His Glu His
    1010                1015                1020
Ala Arg  Ser Ser Ala Gly Glu  Arg His Gly Ser  His Gln Gln
    1025                1030                1035
Ser Ala  Asp Ser Ser Arg His  Ser Gly Ile Gly  His Gly Gln Ala
    1040                1045                1050
Ser Ser  Ala Val Arg Asp Ser  Gly His Arg Gly  Ser  Ser Gly Ser
    1055                1060                1065
Gln Ala  Ser Asp Ser Glu Gly  His Ser Glu Asp  Ser  Asp Thr Gln
    1070                1075                1080
Ser Leu  Ser Ala His Gly Gln  Ala Gly Pro His  Gln  Gln Ser His
    1085                1090                1095
Gln Glu  Ser Thr Arg Gly Arg  Ser Ala Glu Arg  Ser  Gly Arg Ser
    1100                1105                1110
Gly Ser  Phe Leu Tyr Gln Val  Ser Thr His Glu  Gln  Ser Glu Ser
    1115                1120                1125
Ala His  Gly Arg Thr Gly Thr  Ser Thr Gly Gly  Arg  Lys Arg Ser
    1130                1135                1140
Leu His  Glu Gln Ala Arg Asp  Ser Ser Arg His  Ser  Val Ser Gln
    1145                1150                1155
Glu Gly  Gln Asp Thr Ile His  Gly His Ala Gly  Ser  Ser Ser Gly
    1160                1165                1170
Gly Arg  Gln Gly Ser His Tyr  Glu Gln Leu Val  Asp  Arg Ser Gly
    1175                1180                1185
His Ser  Gly Ser His His Ser  His Thr Thr Ser  Gln  Gly Arg Ser
    1190                1195                1200
Asp Ala  Tyr His Gly Gln Ser  Gly Ser Arg Ser  Ala  Ser Arg Gln
    1205                1210                1215
Thr His  Asn Asp Glu Gln Ser  Gly Asp Gly Phe  Arg  His Ser Gly
    1220                1225                1230
Ser His  His His Glu Ala Ser  Ser Arg Ala Asp  Ser  Ser Arg His
    1235                1240                1245
Ser Gln  Val Gly Gln Gly Gln  Ser Glu Gly Pro  Arg  Thr Ser Arg
    1250                1255                1260
His Arg  Glu Ser Ser Val Ser  Gln Asp Ser Asp  Ser  Glu Gly His
    1265                1270                1275
Ser Glu  Asp Ser Glu Arg Trp  Ser Gly Ser Ala  Ser  Arg Asn His
    1280                1285                1290
His Gly  Ser Ala Arg Glu Gln  Ser Arg Asp Gly  Ser  Arg His Pro
    1295                1300                1305
Arg Ser  His His Glu Asp Arg  Ala Gly His Gly  His  Ser Ala Asp
    1310                1315                1320
Ser Ser  Arg Gln Ser Gly Thr  Arg His Thr Gln  Thr  Ser Ser Gly
    1325                1330                1335
Gly Gln  Ala Ala Ser Ser His  Glu Gln Gly Arg  Ser  Ser Ala Gly
    1340                1345                1350
Glu Arg  His Gly Ser Arg His  Gln Gln Ser Ala  Asp  Ser Ser Arg
    1355                1360                1365
```

-continued

```
His Ser Gly Ile Gly His Gly Gln Ala Ser Ser Ala Val Arg Asp
    1370            1375                1380
Ser Gly His Arg Gly Tyr Ser Gly Ser Gln Ala Ser Asp Ser Glu
    1385            1390                1395
Gly His Ser Glu Asp Ser Asp Thr Gln Ser Val Ser Ala His Gly
    1400            1405                1410
Gln Ala Gly Ser His Gln Gln Ser His Gln Glu Ser Ala Arg Gly
    1415            1420                1425
Arg Ser Gly Glu Arg Ser Gly Arg Ser Gly Ser Phe Leu Tyr Gln
    1430            1435                1440
Val Ser Thr His Glu Gln Ser Glu Ser Ser His Gly Trp Thr Gly
    1445            1450                1455
Pro Ser Thr Arg Gly Arg Gln Gly Ser Arg His Glu Gln Ala Gln
    1460            1465                1470
Asp Ser Ser Arg His Ser Ala Ser Gln Glu Gly Gln Asp Thr Ile
    1475            1480                1485
Arg Gly His Pro Gly Pro Ser Arg Gly Gly Arg Gln Gly Tyr His
    1490            1495                1500
His Glu Gln Ser Val Asp Ser Ser Gly His Ser Gly Ser His His
    1505            1510                1515
Ser His Ile Thr Ser Gln Gly Ser Ser His Ala Ser His Gly Gln
    1520            1525                1530
Ser Gly Ser Arg Ser Ala Ser Arg Thr Thr Arg Asn Asp Glu Gln
    1535            1540                1545
Ser Val Asp Gly Ser Arg His Ser Gly Ser Arg His His Glu Ala
    1550            1555                1560
Ser Thr His Ala Asp Ile Ser Arg His Ser Gln Ala Gly Gln Gly
    1565            1570                1575
Gln Ser Glu Gly Ser Arg Thr Ser Arg Arg Gln Gly Ser Ser Val
    1580            1585                1590
Ser Gln Asp Ser Asp Ser Glu Gly His Ser Glu Asp Ser Glu Arg
    1595            1600                1605
Trp Ser Gly Ser Ala Ser Arg Asn His Arg Gly Ser Ala Gln Glu
    1610            1615                1620
Gln Ser Arg Asp Gly Ser Arg His Pro Arg Ser His His Glu Asp
    1625            1630                1635
Arg Ala Gly His Gly His Ser Ala Asp Ser Ser Arg Gln Ser Gly
    1640            1645                1650
Thr His His Ala Glu Thr Ser Ser Gly Gly Gln Ala Ala Ser Ser
    1655            1660                1665
Arg Glu Gln Ala Arg Ser Ser Pro Gly Glu Arg His Gly Ser Arg
    1670            1675                1680
His Gln Gln Ser Ala Asp Ser Ser Arg His Ser Gly Ile Arg Arg
    1685            1690                1695
Gly Gln Ala Ser Ser Ala Val Arg Asp Ser Gly His Trp Gly Ser
    1700            1705                1710
Ser Gly Ser Gln Ala Ser Asp Ser Glu Gly His Ser Glu Glu Ser
    1715            1720                1725
Asp Thr Gln Ser Val Ser Gly His Gly Gln Asp Gly Pro His Gln
    1730            1735                1740
Gln Ser His Gln Glu Ser Ala Arg Asp Arg Ser Gly Gly Arg Ser
    1745            1750                1755
```

```
Gly Arg Ser Gly Ser Phe Leu Tyr Gln Val Ser Thr His Glu Gln
    1760                1765                1770

Ser Glu Ser Thr His Gly Gln Thr Gly Thr Ser Thr Gly Gly Arg
    1775                1780                1785

Gln Gly Ser His His Glu Gln Ala Arg Asp Ser Ser Arg His Ser
    1790                1795                1800

Ala Ser Gln Glu Gly Gln Asp Thr Ile His Ala His Pro Gly Ser
    1805                1810                1815

Ser Arg Gly Gly Arg Gln Gly Ser His His Glu Gln Ser Val Asp
    1820                1825                1830

Thr Ser Gly His Ser Gly Ser His His Ser His Thr Thr Ser Gln
    1835                1840                1845

Gly Arg Ser Asp Ala Ser His Gly Gln Ser Gly Ser Arg Ser Ala
    1850                1855                1860

Ser Arg Gln Thr Arg Asn Asp Glu Gln Ser Gly Asp Gly Ser Arg
    1865                1870                1875

His Ser Gly Ser His His His Glu Ala Phe Thr Gln Ala Asp Ser
    1880                1885                1890

Ser Arg His Ser Gln Ser Gly Gln Gly Glu Ser Ala Gly Ser Arg
    1895                1900                1905

Arg Ser Arg Arg Gln Gly Ser Ser Val Ser Gln Asp Ser Asp Ser
    1910                1915                1920

Gln Gly His Ser Glu Asp Ser Glu Arg Trp Ser Gly Ser Ala Ser
    1925                1930                1935

Arg Asn Gln His Gly Ser Ala Arg Glu Gln Ser Arg Asp Gly Ser
    1940                1945                1950

Arg His Pro Gly Ser His Gln Glu Asp Arg Ala Gly His Gly His
    1955                1960                1965

Ser Ala Asp Ser Ser Arg Gln Ser Gly Thr Arg His Thr Glu Ser
    1970                1975                1980

Ser Ser Arg Gly Gln Ala Ala Ser Ser His Glu Gln Ala Arg Ser
    1985                1990                1995

Ser Ala Gly Glu Arg His Gly Ser Arg His Gln Leu Gln Ser Ala
    2000                2005                2010

Asp Ser Ser Arg His Ser Gly Ile Gly His Gly Gln Ala Ser Ser
    2015                2020                2025

Ala Val Arg Asp Ser Gly His Arg Gly Ser Ser Gly Ser Gln Ala
    2030                2035                2040

Ile Asp Ser Glu Gly His Ser Glu Asp Ser Asp Thr Gln Ser Val
    2045                2050                2055

Ser Ala Gln Gly Gln Ala Gly Pro His Gln Arg Ser His Lys Glu
    2060                2065                2070

Ser Ala Arg Gly Gln Ser Gly Glu Ser Ser Gly Arg Ser Gly Ser
    2075                2080                2085

Phe Leu Tyr Gln Val Ser Thr His Glu Gln Pro Glu Ser Thr His
    2090                2095                2100

Gly Gln Ser Ala Pro Ser Thr Gly Gly Arg Gln Gly Ser His His
    2105                2110                2115

Asp Gln Ala Gln Asp Ser Ser Arg His Ser Ala Ser Gln Glu Gly
    2120                2125                2130

Gln Asp Thr Ile Arg Gly His Pro Gly Pro Ser Arg Gly Gly Arg
    2135                2140                2145

Gln Gly Ser His His Lys Gln Ser Val Asp Arg Ser Gly His Ser
```

-continued

```
            2150                2155                2160
Gly Ser His His Ser His Thr Thr Ser Gln Gly Arg Ser Asp Ala
            2165                2170                2175
Ser Arg Gly Gln Ser Gly Ser Arg Ser Ala Ser Arg Gln Thr His
            2180                2185                2190
Asp Lys Glu Gln Ser Gly Asp Gly Ser Arg His Ser Gly Ser Arg
            2195                2200                2205
His His Glu Ala Ser Ser Trp Ala Asp Ser Ser Arg His Ser Gln
            2210                2215                2220
Ala Gly Gln Gly Gln Ser Glu Gly Ser Arg Thr Ser Arg Arg Gln
            2225                2230                2235
Gly Ser Ser Phe Ser Gln Asp Ser Asp Ser Glu Gly His Ser Glu
            2240                2245                2250
Asp Ser Glu Arg Arg Ser Gly Ser Ala Ser Arg Asn His Arg Gly
            2255                2260                2265
Ser Ala Gln Glu Gln Ser Arg Asp Gly Ser Arg His Pro Arg Ser
            2270                2275                2280
His His Glu Asp Arg Ala Gly His Gly His Ser Ala Asp Ser Ser
            2285                2290                2295
Arg Gln Ser Gly Thr His His Ala Gln Asn Ser Ser Gly Gly Gln
            2300                2305                2310
Ala Ala Ser Phe His Glu Gln Ala Arg Ser Ser Ala Gly Glu Arg
            2315                2320                2325
His Gly Ser His His Gln Gln Ser Ala Asp Ser Ser Arg His Ser
            2330                2335                2340
Gly Ile Gly His Gly Gln Ala Ser Ser Ala Val Arg Asp Ser Gly
            2345                2350                2355
His Arg Gly Ser Ser Gly Ser Gln Ala Ser Asp Ser Glu Gly His
            2360                2365                2370
Ser Glu Asp Ser Asp Thr Gln Ser Val Ser Ala His Gly Gln Ala
            2375                2380                2385
Gly Pro His Gln Gln Ser His Gln Glu Ser Thr Arg Gly Arg Ser
            2390                2395                2400
Ala Glu Arg Ser Gly Arg Ser Gly Ser Phe Leu Tyr Gln Val Ser
            2405                2410                2415
Thr His Glu Gln Ser Glu Ser Ala His Gly Arg Thr Gly Pro Ser
            2420                2425                2430
Thr Gly Gly Arg Gln Gly Ser Arg His Glu Gln Ala Arg Asp Ser
            2435                2440                2445
Ser Arg His Ser Ala Ser Gln Glu Gly Gln Asp Thr Ile His Gly
            2450                2455                2460
His Pro Gly Ser Arg Arg Gly Gly Arg Gln Gly Ser Tyr His Glu
            2465                2470                2475
Gln Ser Val Asp Arg Ser Gly His Ser Gly Ser His His Ser His
            2480                2485                2490
Thr Thr Ser Gln Gly Arg Ser Asp Ala Ser His Gly Gln Ser Gly
            2495                2500                2505
Ser Arg Ser Ala Ser Arg Gln Thr Arg Asn Glu Gln Gln Ser Gly
            2510                2515                2520
Asp Gly Ser Arg His Ser Gly Ser Ser His His Glu Ala Ser Thr
            2525                2530                2535
Gln Ala Asp Ser Ser Arg His Ser Gln Ser Gly Gln Gly Glu Ser
            2540                2545                2550
```

Ala Gly Ser Arg Arg Ser Arg Arg Gln Gly Ser Ser Val Ser Gln
            2555                2560                2565

Asp Ser Asp Ser Glu Ala Tyr Pro Glu Asp Ser Glu Arg Arg Ser
    2570                2575                2580

Glu Ser Ala Ser Arg Asn Arg His Gly Ser Ser Arg Glu Gln Ser
    2585                2590                2595

Arg Asp Gly Ser Arg His Pro Gly Ser Ser His Arg Asp Thr Thr
    2600                2605                2610

Arg His Val Gln Ser Ser Pro Val Gln Ser Asp Ser Ser Thr Ala
    2615                2620                2625

Lys Glu His Gly His Phe Ser Ser Leu Ser Gln Asp Ser Ala Tyr
    2630                2635                2640

Arg Ser Gly Ile Gln Ser Arg Gly Ser Pro His Ser Ser Ser Ser
    2645                2650                2655

Tyr His Tyr Gln Ser Glu Gly Thr Glu Arg Gln Lys Gly Gln Ser
    2660                2665                2670

Gly Leu Val Trp Arg His Gly Ser Tyr Gly Ser Ala Asp Tyr Asp
    2675                2680                2685

Tyr Gly Glu Ser Gly Phe Arg His Ser Gln His Gly Ser Val Ser
    2690                2695                2700

Tyr Asn Ser Asn Pro Val Val Phe Lys Glu Arg Ser Asp Ile Cys
    2705                2710                2715

Lys Ala Ser Ala Phe Gly Lys Asp His Pro Arg Tyr Tyr Ala Thr
    2720                2725                2730

Tyr Ile Asn Lys Asp Pro Gly Leu Cys Gly His Ser Ser Asp Ile
    2735                2740                2745

Ser Lys Gln Leu Gly Phe Ser Gln Ser Gln Arg Tyr Tyr Tyr Tyr
    2750                2755                2760

Glu

<210> SEQ ID NO 22
<211> LENGTH: 819
<212> TYPE: PRT
<213> ORGANISM: Bos taurus

<400> SEQUENCE: 22

Met Ser Thr Leu Leu Glu Asn Ile Asn Asp Ile Ile Lys Ile Phe His
1               5                   10                  15

Lys Tyr Ser Lys Thr Asp Lys Glu Thr Asp Thr Leu Ser Glu Lys Glu
            20                  25                  30

Leu Lys Glu Leu Val Glu Val Glu Phe Arg Pro Ile Leu Lys Asn Pro
        35                  40                  45

Gly Asp Pro Asp Thr Ala Glu Val Phe Met Tyr Asn Leu Asp Arg Asp
    50                  55                  60

His Asn Asn Lys Ile Asp Phe Thr Glu Phe Phe Leu Met Val Phe Lys
65                  70                  75                  80

Val Ala Gln Val Tyr Tyr Ser Tyr Thr Gln Arg Gln Asn Leu Gln Arg
                85                  90                  95

Ala Gly Gln Lys Gln Lys Lys Cys Thr Tyr His Tyr Gly Asp Glu Glu
            100                 105                 110

Asp Asp Thr Glu Glu Asp Lys Glu Glu Thr Glu Arg Lys Tyr Ser His
        115                 120                 125

Ser Arg Ser Asp Gly Lys Thr Gln Asp Arg Ser Lys Ser Pro Arg Gly
    130                 135                 140

-continued

```
Arg Gly Lys Lys Arg His Gly Ser Lys Ser Gly Ser Lys Gln Arg Arg
145                 150                 155                 160

Gly Asp Thr Pro Thr Ser Gly Leu Arg His Gly Cys Ser Lys Lys His
                165                 170                 175

Glu Ser Arg Arg Glu Lys Lys Arg Arg Pro Ser Ser Thr Glu Pro Lys
            180                 185                 190

Glu Arg Arg His Met Ser Ser Val Ser Pro Thr Arg Gly Tyr Glu Glu
            195                 200                 205

Lys Glu Glu Glu His Gly Tyr Glu Asn Lys Gly Lys Thr Ser Ala Lys
            210                 215                 220

Cys Ile Gly Ser Glu Tyr Asp Asp Ser Tyr Gln Val Cys Glu Asp Lys
225                 230                 235                 240

Val Thr Thr Asn Phe Gln Pro Ser His Ser Lys Asn Tyr Gly Ser Asn
                245                 250                 255

Ile Thr Lys Gly Arg Asp Thr Glu Gly His Ser Arg Asp Thr Gly Arg
                260                 265                 270

Lys Ser Val Phe Thr His Ala Arg Ser Gly Ser Ser Ser Arg Asn Gln
                275                 280                 285

Asn Gly Ser Val Gln Thr His Thr Gly Asp Asn Ser Thr His Ser Glu
            290                 295                 300

Ser Gln Gln Glu Thr Asn Ser Glu Ser Val His Arg Arg Ser Arg Asn
305                 310                 315                 320

Thr Gly Gln Arg Gln Gly Ser His His Glu Gln Ser Arg Asp Ser Ser
                325                 330                 335

Arg His Ser Gly Thr Arg His Gly Gln Pro Ser Thr Gly Ser Gly Gly
                340                 345                 350

Ser Arg His Arg Glu Ser Ser Val Ser Gln Ala Ser Asp Ser Glu Gly
            355                 360                 365

His Ser Glu Asp Ser Gly Arg Gln Ser Val Thr Thr His Gly Arg Pro
            370                 375                 380

Gly Ser Ser Ser Arg Asn Gln His Gly Ser Ser Gln Gly Gln Thr Gly
385                 390                 395                 400

Asp Ser Ser Arg His Ser Glu Ser His Gln Gly Arg His Ser Asp Ser
                405                 410                 415

Leu Gln Arg Arg Ser Gly Thr Ser Thr Gly Gln Arg Gln Gly Ser His
                420                 425                 430

His Glu Gln Ser Arg Asp Ser Ser Arg His Ser Gly Thr Gln Gln Gly
            435                 440                 445

Gln Thr Ser Thr Gly Ser Gly Ser Ser Arg His Arg Asp Ser Ser Val
            450                 455                 460

Ser Gln Ala Ser Asp Ser Glu Gly His Ser Glu Asp Ser Gly Arg Gln
465                 470                 475                 480

Leu Glu Thr Val Leu Gly Ile Gln Ser Pro Ile Lys Glu Ala Thr Val
                485                 490                 495

Lys Leu Phe Met Lys Gly Gln Asp Pro Ala Arg Gly Lys Gly Arg Gly
                500                 505                 510

Ala Thr Met Ser Ser Gln Gly Thr Ala Pro Asp Thr Leu Glu Leu Asp
            515                 520                 525

Met Asp Lys Ser Gln Leu Asn Leu Glu Met Ala Asp Ile Gly Asn Pro
            530                 535                 540

Val Leu Val Lys Pro Val Thr Val Arg Asp Thr Pro Glu Ile Gln Val
545                 550                 555                 560
```

Gly Ile Leu Arg Gln Leu Met Glu Asp Met Val Pro Ala Gln Gly Thr
                565                 570                 575

Asn Met Asp Pro Pro Met Val Arg Gln Gly Thr Val Ile Gly Thr Gln
            580                 585                 590

Arg Pro Ile Lys Gly Asp Thr Ile Arg Asp Thr Gln Glu Ile Gln Val
        595                 600                 605

Gly Ile Leu Arg Gln Leu Met Glu Asp Leu Val Pro Ala Gln Glu Thr
    610                 615                 620

Asn Met Asp Leu Pro Met Ala Arg Val Glu Thr Val Leu Gly Thr Gln
625                 630                 635                 640

Ser Pro Ile Lys Arg Gly Ile Val Asn Leu Ser Met Glu Gly Gln Asp
                645                 650                 655

Pro Ala Leu Gly Lys Asp Arg Gly Ala Thr Met Ser Ser Gln Glu Thr
            660                 665                 670

Ala Pro Asp Thr Leu Glu Leu Asp Met Gly Lys Pro Gln Leu Asn Leu
        675                 680                 685

Glu Met Ala Asp Ile Gly Asn Pro Val Leu Val Lys Pro Val Thr Val
    690                 695                 700

Arg Asp Thr Pro Glu Ile Gln Val Gly Ile Leu Arg Gln Leu Met Glu
705                 710                 715                 720

Gly Leu Val Gln Ala Gln Glu Thr Asn Met Asp Leu Pro Arg Ala Arg
                725                 730                 735

Gln Glu Thr Val Leu Gly Thr Gln His Ile Ile Lys Gly Gly Thr Val
            740                 745                 750

Asn Leu Ser Met Lys Gly Gln Arg Leu Glu Leu Gly Lys Asp Arg Gly
        755                 760                 765

Ala Thr Met Ser Ser Gln Gly Thr Ala Pro Asp Ser Leu Glu Leu Asp
    770                 775                 780

Met Asp Ile Pro Leu Leu Asp Leu Glu Met Ala Asp Ile Gly Asn Pro
785                 790                 795                 800

Val Leu Val Ser Gln Val Thr Glu Arg Asp Thr Gln Glu Ile Gln Val
                805                 810                 815

Asp Ser Pro

<210> SEQ ID NO 23
<211> LENGTH: 1183
<212> TYPE: PRT
<213> ORGANISM: Macaca mulatta

<400> SEQUENCE: 23

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Gln Lys Glu Phe Arg Pro Ile Leu Lys Asn Pro
        35                  40                  45

Asp Asp Pro Asp Thr Val Glu Val Phe Met His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Gln Asn Leu Pro Ile
                85                  90                  95

Ala Gly His Lys His Arg Lys His Ser His His Asp Lys His Glu Asp
            100                 105                 110

```
Asn Lys Glu Glu Asn Lys Glu Lys Arg Lys Arg Pro Leu Ser Leu
        115                 120                 125
Glu Arg Arg Asn Asn Arg Lys Gly Asn Thr Gly Arg Ser Lys Ser Pro
    130                 135                 140
Arg Glu Arg Gly Gly Lys Arg His Glu Ser Ser Phe Glu Lys Lys Glu
145                 150                 155                 160
Arg Lys Gly Tyr Ser Pro Thr Tyr Glu Glu Glu Tyr Gly Gln Asn
                165                 170                 175
His His Lys Ser Ser Lys Lys Glu Lys Asn Lys Thr Glu Ile Thr Arg
        180                 185                 190
Leu Glu His Glu Gly Lys Arg Ile Ser Glu Arg Pro Glu Lys Lys Glu
        195                 200                 205
Glu Lys Glu Asp Gly Gln Phe Asp Tyr Glu Asn Ala Gly Arg Met Asp
    210                 215                 220
Glu Lys Trp Thr Glu Ser Gly His Ile Ala Ile Tyr His Ala Ile Gln
225                 230                 235                 240
Asp Glu Val Asp Thr Thr Glu Asn Ile Leu Glu Glu Asn Arg Arg
                245                 250                 255
Tyr Glu Thr Ser Arg Ser Pro His Asp Lys Ser Ser Leu Arg Val Asn
                260                 265                 270
Arg Ser Pro Asn Ala Asn Thr Ser Gln Ile Pro Leu Val Glu Pro Arg
        275                 280                 285
Arg Arg Thr Arg Gln Arg Ser Ser Val Ser Gln Asp Ser Asp Ser Glu
    290                 295                 300
Gly His Ser Glu Asp Ser Glu Arg Gln Ser Glu Ser Ala Ser Arg Asn
305                 310                 315                 320
His His Gly Ser Val Arg Glu Gln Ser Arg His Gly Ser Arg His Pro
                325                 330                 335
Gly Ser His His Glu Asp Arg Ala Gly His Gly His Ser Ala Asp Ser
                340                 345                 350
Ser Thr Gln Ser Gly Thr Arg His Thr Glu Thr Ser Ser Arg Gly Gln
        355                 360                 365
Ala Val Ser Ser His Glu Gln Ala Arg Ser Ser Pro Gly Glu Arg His
    370                 375                 380
Gly Ser Arg His Gln Gln Ser Ala Glu Ser Ser Arg His Ser Gly Ile
385                 390                 395                 400
Gly Arg Gly Gln Ala Ser Ser Ala Val Ser Asp Arg Gly His Gln Gly
                405                 410                 415
Pro Ser Gly Ser His Phe Ser Asp Ser Glu Gly His Ser Glu His Ser
                420                 425                 430
Asp Thr Gln Ser Val Ser Gly His Gly Gln Ala Gly Pro His Pro His
        435                 440                 445
Ser His Gln Glu Ser Ala Arg Gly Arg Ser Arg Glu Arg Ser Gly Arg
        450                 455                 460
Ser Gly Ser Phe Leu Tyr Gln Val Ser Thr His Glu Gln Ser Glu Ser
465                 470                 475                 480
Thr His Gly Arg Thr Gly Pro Ser Ser Ala Gly Arg Gln Gly Ser Arg
                485                 490                 495
Asn Glu Gln Ala Arg Asp Ser Ser Arg His Ser Ala Ser His Glu Val
                500                 505                 510
Gln Asp Thr Val His Gly His His Gly Ser Ser Arg Gly Arg Gln
        515                 520                 525
Gly Ser His His Glu Gln Leu Val Asp Ser Ser Gly His Ser Gly Ser
```

```
              530             535             540
His His Ser His Thr Thr Ser Gln Gly Arg Ser Asp Ala Ser Arg Gly
545                 550                 555                 560

Glu Ser Gly Ala Arg Ser Ala Ser Arg Gln Thr Arg His Glu Glu Gln
                565                 570                 575

Ser Gly Asp Gly Ser Arg His Ser Gly Ser Arg His His Glu Ser Ser
                580                 585                 590

Asn Arg Ala Asp Ser Ser Arg His Ala Gln Ser Ser Gln Gly Gln Ser
            595                 600                 605

Ala Gly Phe Arg Thr Ser Thr Arg Arg Gly Ser Ser Val Ser Gln Asp
        610                 615                 620

Ser Asp Ser Glu Gly His Ser Glu Asp Ser Glu Arg Gln Ser Glu Ser
625                 630                 635                 640

Ala Ser Arg Asn His His Gly Ser Val Arg Glu Gln Ser Arg His Gly
                645                 650                 655

Ser Gly His Ser Gly Ser His His Gln Asp Lys Val Gly His Arg Tyr
                660                 665                 670

Ser Gly Asp Ser Ser Arg Gln Ser Gly Thr His His Val Glu Thr Ser
            675                 680                 685

Ser His Gly Gln Ala Ala Ser Ser His Glu Gln Thr Arg Ser Ser Pro
        690                 695                 700

Gly Glu Arg His Gly Ser His His Gln Gln Ser Ala Asp Ser Ser Arg
705                 710                 715                 720

His Ser Gly Thr Gly Arg Gly Gln Ala Ser Ser Ala Val Ser Asp Arg
                725                 730                 735

Gly His Gln Gly Pro Ser Gly Ser His Phe Ser Asp Ser Glu Gly His
                740                 745                 750

Ser Glu His Ser Asp Thr Gln Ser Val Ser Gly Gln Gly Gln Ala Gly
            755                 760                 765

Arg His Pro His Ser His Gln Glu Ser Ala Arg Gly Arg Ser Gly Glu
        770                 775                 780

Arg Ser Gly Arg Ser Gly Ser Phe Val Tyr Gln Val Ser Thr His Glu
785                 790                 795                 800

Gln Ser Glu Ser Thr His Gly Arg Thr Gly Pro Ser Thr Gly Gly Arg
                805                 810                 815

Gln Gly Ser Arg Asn Glu Gln Ala Arg Asp Ser Ser Arg His Ser Val
            820                 825                 830

Ser His Glu Gly Gln Asp Thr Ile His Gly His His Gly Ser Ser Arg
        835                 840                 845

Gly Gly Arg Gln Gly Ser His His Glu Gln Ser Val Asp Ser Ser Gly
    850                 855                 860

His Ser Gly Ser His His Ser His Thr Thr Ser Gln Gly Arg Ser Asp
865                 870                 875                 880

Ala Ser Arg Gly Glu Ser Gly Ala Arg Ser Ala Ser Arg Gln Thr Arg
                885                 890                 895

His Glu Glu Gln Ser Gly Asp Gly Ser Arg His Ser Gly Ser Arg His
            900                 905                 910

His Glu Ala Ser Asn Arg Ala Asp Ser Ser Arg His Ala Gln Ser Gly
        915                 920                 925

Gln Gly Gln Ser Ala Gly Phe Arg Thr Ser Thr Arg Arg Gly Ser Ser
    930                 935                 940

Val Ser Gln Asp Ser Asp Ser Glu Gly His Ser Glu Asp Ser Glu Arg
945                 950                 955                 960
```

```
Gln Ser Glu Ser Ala Ser Arg Asn His His Gly Ser Val Arg Glu Gln
                965                 970                 975

Ser Arg His Gly Ser Arg His Pro Gly Ser His His Glu Asp Arg Ala
            980                 985                 990

Gly His Gly His Ser Ala Asp Ser  Ser Arg Gln Ser Gly  Thr Arg His
            995                 1000                1005

Thr Glu  Thr Ser Ser Arg Gly  Gln Ala Val Ser Ser  His Glu Gln
    1010                1015                1020

Ala Arg  Ser Ser Pro Gly Glu  Arg His Gly Ser Arg  His Gln Gln
    1025                1030                1035

Ser Ala  Glu Ser Ser Arg His  Ser Gly Ile Gly Arg  Gly Gln Ala
    1040                1045                1050

Ser Ser  Ala Val Ser Asp Arg  Gly His Gln Gly Pro  Ser Gly Ser
    1055                1060                1065

His Phe  Ser Asp Ser Glu Gly  His Ser Glu His Ser  Asp Thr Gln
    1070                1075                1080

Ser Val  Ser Gly His Gly Gln  Ala Gly Pro His Pro  His Ser His
    1085                1090                1095

Gln Glu  Ser Ala Arg Gly Arg  Ser Gly Glu Arg Ser  Gly Arg Ser
    1100                1105                1110

Gly Ser  Phe Leu Tyr Gln Val  Ser Thr His Glu Gln  Ser Glu Ser
    1115                1120                1125

Thr His  Gly Arg Thr Gly Pro  Ser Ser Ala Gly Arg  Gln Gly Ser
    1130                1135                1140

Arg Asn  Glu Gln Ala Arg Asp  Ser Ser Arg His Ser  Ala Ser His
    1145                1150                1155

Glu Val  Gln Asp Thr Val His  Gly His His Gly Ser  Ser Arg Gly
    1160                1165                1170

Gly Arg  Gln Gly Ser His His  Glu Gln Ser
    1175                1180

<210> SEQ ID NO 24
<211> LENGTH: 2265
<212> TYPE: PRT
<213> ORGANISM: Macaca mulatta

<400> SEQUENCE: 24

Met Thr Asp Leu Leu Arg Ser Val Val Thr Val Ile Asp Val Phe Tyr
1               5                   10                  15

Lys Tyr Thr Lys Gln Asp Gly Glu Cys Gly Thr Leu Ser Lys Asp Glu
                20                  25                  30

Leu Lys Glu Leu Leu Glu Lys Glu Phe His Pro Val Leu Lys Asn Pro
            35                  40                  45

Asp Asp Pro Asp Thr Val Asp Val Ile Met His Met Leu Asp Arg Asp
    50                  55                  60

His Asp Arg Arg Leu Asp Phe Thr Glu Phe Leu Leu Met Ile Phe Lys
65                  70                  75                  80

Leu Thr Met Ala Cys Asn Lys Val Leu Ser Lys Glu Tyr Cys Lys Ala
                85                  90                  95

Ser Gly Ser Lys Lys His Arg Arg Gly His Arg His Gln Glu Glu Glu
                100                 105                 110

Ser Glu Thr Glu Glu Asp Glu Glu Asp Thr Pro Glu His Lys Ser Gly
            115                 120                 125

Tyr Arg His Ser Ser Trp Ser Glu Gly Glu Glu His Gly Tyr Ser Ser
```

```
                130                 135                 140
Gly His Ser Arg Gly Thr Val Lys Arg Arg His Gly Ser Asn Ser Arg
145                 150                 155                 160

Arg Leu Gly Arg Gln Gly His Leu Ser Ser Ser Gly Asn Gln Glu Arg
                165                 170                 175

Ser Gln Lys Arg Tyr His Arg Ser Ser Ser Gly His Ser Trp Ser Ser
                180                 185                 190

Gly Lys Glu Arg His Gly Phe Ser Ser Gly Glu Leu Arg Glu Arg Ile
                195                 200                 205

Asn Lys Ser His Val Ser Pro Ser Arg Glu Phe Gly Glu Glu Tyr Glu
                210                 215                 220

Ser Gly Ser Gly Ser Lys Ser Trp Glu Arg Lys Gly His Gly Gly Leu
225                 230                 235                 240

Ser Cys Gly Leu Glu Ile Ser Gly His Glu Ser Asn Ser Thr Gln Ser
                245                 250                 255

Arg Ser Ser Gly Gln Lys Leu Gly Ser Ser Arg Ser Cys Ser Gly Asp
                260                 265                 270

Ser Arg Arg Arg Ser His Ala Cys Gly Tyr Ser Asn Ser Ser Gly Cys
                275                 280                 285

Gly Arg Pro Gln Asn Ala Ser Asn Ser Cys Gln Ser His Arg Phe Gly
                290                 295                 300

Gly Gln Val Asn Gln Ser Ser Tyr Ile Gln Ser Gly Cys Gln Ser Gly
305                 310                 315                 320

Ile Asn Gly Glu Gln Gly His Asp Cys Val Ser Gly Gly Gln Pro Ser
                325                 330                 335

Gly Cys Gly Gln Pro Glu Ser Asn Ser Cys Ser Gln Ser Tyr Ser Gln
                340                 345                 350

Arg Gly Tyr Gly Ala Arg Glu Asn Gly Gln Pro Gln Asn Cys Gly Gly
                355                 360                 365

Gln Gln Arg Thr Gly Ser Ser Gln Ser Ser Phe Cys Gly Gln Tyr Glu
                370                 375                 380

Ser Gly Gly Ser Gln Ser Cys Ser Asn Gly Gln His Glu His Gly Ser
385                 390                 395                 400

Cys Gly Arg Phe Ser Asn Ser Ser Ser Asn Glu Phe Ser Lys Cys
                405                 410                 415

Gly Lys His Arg Ser Gly Ser Gly Gln Phe Thr Ser Cys Glu Gln His
                420                 425                 430

Gly Thr Gly Leu Ser Gln Ser Ser Gly Phe Glu Gln Gln Val Ala Gly
                435                 440                 445

Ser Ser Gln Thr Cys Ser Gln Tyr Gly Ser Arg Ser Ser Gln Ser Ser
450                 455                 460

Gly Tyr Asp Glu His Gly Ser Ser Ser Gly Lys Thr Ser Gly Phe Gly
465                 470                 475                 480

Gln His Arg Ser Gly Ser Gly His Ser Ser Gly Phe Gln His Gly
                485                 490                 495

Ser Gly Ser Gly Gln Ser Phe Gly Phe Gly Gln His Gly Ser Gly Ser
                500                 505                 510

Gly Gln Ser Ser Gly Phe Gly Gln His Glu Ser Arg Ser Cys Gln Ser
                515                 520                 525

Ser Tyr Gly Gln His Gly Ser Gly Ser Ser Gly Ser Ser Gly Tyr Gly
                530                 535                 540

Gln His Ala Ser Arg Gln Thr Ser Gly Phe Gly Gln His Gly Leu Gly
545                 550                 555                 560
```

```
Ser Gly Gln Ser Thr Gly Phe Gly Gln Tyr Gly Ser Gly Ser Gly Gln
                565                 570                 575

Ser Ser Gly Phe Gly Gln His Gly Ser Gly Ser Gln Ser Ser Gly
            580                 585                 590

Phe Gly Gln His Glu Ser Arg Ser Gly Gln Ser Ser Tyr Gly Gln His
        595                 600                 605

Ser Ser Ser Ser Ser Gln Ser Ser Gly Tyr Gly Gln His Gly Ser Arg
            610                 615                 620

Gln Thr Ser Gly Phe Gly Gln His Gly Ser Gly Ser Gly Gln Ser Thr
625                 630                 635                 640

Gly Phe Gly Gln Tyr Gly Ser Ser Leu Gly Gln Ser Ser Gly Phe Gly
            645                 650                 655

Gln His Gly Ser Gly Ser Gly Gln Ser Ser Gly Phe Gly Gln His Glu
            660                 665                 670

Ser Thr Ser Gly Gln Ser Ser Tyr Gly Gln His Gly Phe Gly Ser Ser
            675                 680                 685

Gln Ser Ser Gly Cys Gly Gln His Gly Leu Ser Ser Gly Gln Thr Ser
            690                 695                 700

Gly Phe Gly Gln His Glu Leu Ser Ser Gly Gln Ser Ser Ser Phe Gly
705                 710                 715                 720

Gln His Gly Ser Gly Ser Gly Gln Ser Ser Gly Phe Arg Gln His Glu
            725                 730                 735

Ser Gly Ser Gly Gln Ser Ser Gly Phe Gly Gln His Glu Ser Arg Ser
            740                 745                 750

His Gln Ser Ser Tyr Gly Pro His Gly Ser Gly Ser Gly Gln Ser Ser
            755                 760                 765

Gly Tyr Gly Gln His Gly Ser Ser Ser Gly Gln Thr Ser Gly Phe Gly
            770                 775                 780

Gln Gln Gly Ser Ser Ser Gln Tyr Ser Gly Phe Gly Gln His Gly
785                 790                 795                 800

Ser Gly Leu Gly Gln Ser Ser Gly Phe Gly Gln His Gly Thr Gly Ser
            805                 810                 815

Gly Gln Phe Ser Gly Phe Gly Gln His Glu Ser Arg Ser His Gln Ser
            820                 825                 830

Ser Tyr Gly Gln His Gly Ser Gly Ser Ser Gln Ser Ser Gly Tyr Gly
            835                 840                 845

Gln His Gly Ser Ser Ser Gly His Thr Thr Gly Phe Gly Gln His Arg
            850                 855                 860

Ser Ser Ser Gly Gln Tyr Gly Ser Phe Gly Gln His Gly Ser Gly Leu
865                 870                 875                 880

Gly Gln Ser Ser Gly Phe Gly Gln His Gly Thr Gly Ser Gly Gln Ser
            885                 890                 895

Ser Gly Phe Gly Gln His Glu Ser Arg Ser His Gln Ser Ser Tyr Gly
            900                 905                 910

Gln His Gly Ser Gly Ser Ser Gln Ser Ser Tyr Gly Gln His Gly
            915                 920                 925

Ser Ser Ser Gly Gln Thr Ser Gly Phe Gly Gln His Arg Ser Gly Ser
            930                 935                 940

Gly Gln Ser Ser Gly Phe Gly Gln Tyr Gly Leu Gly Ser Gly Gln Ser
945                 950                 955                 960

Ser Gly Phe Gly Gln His Gly Ser Gly Thr Gly Gln Ser Ser Gly Phe
            965                 970                 975
```

```
Ala Arg His Glu Tyr Arg Ser Gly Gln Ser Ser Tyr Gly Gln His Gly
            980                 985                 990

Thr Gly Ser Ser Gln Ser Ser Gly Cys Gly Gln Arg Glu  Ser Gly Ser
        995                 1000                1005

Gly Pro Thr Thr Gly Phe Gly Gln His Val Ser Gly  Ser Asp Asn
    1010                1015                1020

Phe Ser Ser Ser Gly Gln His Ile Ser Gly Ser Asp  Gln Ser Thr
    1025                1030                1035

Gly Phe Gly Gln Tyr Gly Ser Gly Ser Gly Gln Ser  Thr Gly Leu
    1040                1045                1050

Gly Gln Val Glu Ser Gln Gln Val Ala Ser Gly Ser  Thr Val His
    1055                1060                1065

Gly Arg Gln Glu Thr Thr His Gly Gln Thr Ile Asn  Thr Ala Arg
    1070                1075                1080

His Ser Gln Ser Gly Gln Gly Gln Ser Thr Gln Thr  Gly Ser Arg
    1085                1090                1095

Val Ser Arg Arg Arg Ser Ser Gln Ser Glu Asn Ile  Asp Ser
    1100                1105                1110

Glu Val His Ser Arg Val Ser His Arg His Ser Glu  His Ile Asp
    1115                1120                1125

Thr Gln Val Gly Ser His Tyr Pro Glu Ser Gly Ser  Thr Val His
    1130                1135                1140

Arg Arg Gln Gly Thr Thr His Gly Gln Arg Gly Asp  Thr Thr Arg
    1145                1150                1155

His Ser His Ser Gly His Gly Gln Ser Thr Gln Thr  Gly Ser Arg
    1160                1165                1170

Thr Thr Gly Arg Gln Arg Phe Ser His Ser Asp Ala  Thr Asp Ser
    1175                1180                1185

Glu Val His Ser Gly Val Ser His Arg Pro His Ser  Gln Glu His
    1190                1195                1200

Thr His Gly Gln Asp Gly Ser Gln Leu Gly Glu Ser  Gln Ser Thr
    1205                1210                1215

Val His Glu Arg His Glu Thr Thr Tyr Gly Gln Thr  Gly Asp Ala
    1220                1225                1230

Thr Gly His Gly Tyr Ser Gly His Gly Gln Ser Thr  Gln Ile Gly
    1235                1240                1245

Ser Arg Thr Ser Gly Arg Arg Gly Ser Gly His Ser  Glu Ser Ser
    1250                1255                1260

Asp Thr Glu Val His Ser Gly Gly Ser His Arg Pro  His Ser Gln
    1265                1270                1275

Glu Gln Thr His Gly Gln Ala Arg Ser Gln His Gly  Glu Ser Arg
    1280                1285                1290

Ser Thr Val His Glu Arg His Gly Thr Thr His Gly  Gln Thr Gly
    1295                1300                1305

Asp Thr Thr Arg Tyr Ala His Tyr His Asn Gly Gln  Ser Ala Gln
    1310                1315                1320

Arg Gly Ser Arg Thr Thr Gly Arg Gly Ser Gly His  Ser Glu Tyr
    1325                1330                1335

Ser Asp Ser Glu Leu Tyr Ser Gly Gly Ser His Thr  Tyr Ser Gly
    1340                1345                1350

His Thr His Gly Gln Ala Gly Ser Gln His Gly Glu  Ser Asp Ser
    1355                1360                1365

Ile Val His Glu Arg Tyr Gly Thr Thr His Gly Gln  Thr Gly Asp
```

```
            1370              1375              1380
Thr Thr Arg His Ala His Tyr Ser His Gly Gln Ser Lys Gln Arg
    1385              1390              1395
Gly Ser Arg Thr Thr Gly Arg Arg Gly Ser Gly His Ser Glu Tyr
    1400              1405              1410
Ser Asp Ser Glu Gly His Ser Gly Gly Ser His Thr His Ser Gly
    1415              1420              1425
His Thr His Gly His Thr His Gly Gln Ala Gly Ser Gln His Gly
    1430              1435              1440
Glu Ser Gly Ser Ser Gly His Gly Gly Gln Gly Thr Thr His Gly
    1445              1450              1455
Gln Thr Gly Asp Thr Thr Arg His Ala His Tyr Gly His Gly Gln
    1460              1465              1470
Ser Thr Gln Arg Gly Ser Arg Thr Ala Gly Arg Arg Gly Ser Gly
    1475              1480              1485
His Ser Glu Tyr Ser Asp Ser Glu Gly His Ser Gly Val Ser His
    1490              1495              1500
Thr His Ser Gly His Thr His Gly Gln Ala Gly Ser Gln His Gly
    1505              1510              1515
Glu Ser Glu Ser Thr Val His Glu Arg Gln Gln Thr Thr His Gly
    1520              1525              1530
Gln Thr Gly Asp Thr Thr Arg His Ala His Tyr Gly His Gly Gln
    1535              1540              1545
Ser Thr Gln Thr Gly Ser Arg Thr Thr Gly Arg Arg Gly Ser Gly
    1550              1555              1560
His Ser Glu Tyr Ser Asp Ser Glu Gly His Ser Gly Val Ser His
    1565              1570              1575
Thr His Ser Gly His Thr His Gly Gln Ala Arg Ser Gln His Gly
    1580              1585              1590
Glu Ser Gly Ser Ala Ile His Gly Arg Gln Gly Thr Ile His Gly
    1595              1600              1605
Gln Thr Gly Asp Thr Thr Arg His Gly Gln Ser Gly His Gly Gln
    1610              1615              1620
Ser Thr Gln Thr Gly Ser Arg Thr Thr Gly Arg Arg Gly Ser Gly
    1625              1630              1635
His Ser Glu Tyr Ser Asp Ser Glu Gly His Ser Gly Gly Ser His
    1640              1645              1650
Thr His Ser Gly His Thr His Gly Gln Ala Gly Ser Gln His Gly
    1655              1660              1665
Glu Ser Gly Ser Thr Val His Gly Arg Gln Gly Thr Ile His Gly
    1670              1675              1680
Gln Thr Gly Asp Thr Thr Arg His Gly Gln Ser Gly His Gly Gln
    1685              1690              1695
Ser Ile Glu Thr Gly Ser Arg Thr Thr Gly Arg Arg Gly Ser Gly
    1700              1705              1710
His Ser Glu Tyr Ser Asp Ser Glu Gly His Ser Gly Val Ser His
    1715              1720              1725
Thr His Ser Gly His Thr His Gly Gln Ala Gly Ser Gln His Gly
    1730              1735              1740
Glu Ser Glu Ser Thr Val His Glu Arg Gln Gln Thr Thr His Gly
    1745              1750              1755
Gln Thr Gly Asp Ile Thr Glu His Gly His Ser Ser His Gly Gln
    1760              1765              1770
```

```
Thr Thr Gln Thr Gly Ser Arg  Thr Thr Gly Arg Arg  Gly Ser Gly
1775                1780                 1785

His Ser Glu Tyr Ser Asp Ser  Glu Trp His Ser Gly  Gly Ser His
    1790                1795                 1800

Thr His Ser Gly His Thr His  Gly Gln Ala Gly Phe  Gln His Gly
    1805                1810                 1815

Glu Ser Gly Ser Ala Val His  Gly Arg Gln Gly Thr  Ile His Gly
    1820                1825                 1830

Gln Thr Gly Asp Thr Thr Arg  His Gly Gln Ser Gly  His Gly Glu
    1835                1840                 1845

Ser Ile Gln Thr Gly Ser Arg  Thr Ile Gly Arg Arg  Gly Ser Gly
    1850                1855                 1860

His Ser Glu Tyr Ser Asp Ser  Glu Gly His Ser Gly  Ile Ser His
    1865                1870                 1875

Thr His Ser Gly His Thr His  Gly Gln Ala Gly Ser  Gln His Gly
    1880                1885                 1890

Glu Ser Gly Ser Ser Gly His  Gly Arg Gln Gly Thr  Ala His Gly
    1895                1900                 1905

Gln Thr Gly Asp Thr Thr Arg  His Ala His Tyr Asp  His Gly Gln
    1910                1915                 1920

Ser Thr Gln Arg Gly Ser Arg  Thr Ala Gly Arg Arg  Gly Ser Gly
    1925                1930                 1935

His Ser Glu Tyr Ser Asp Ser  Glu Gly His Ser Gly  Val Ser His
    1940                1945                 1950

Thr His Ser Gly His Thr His  Gly Gln Ala Gly Ser  Gln His Gly
    1955                1960                 1965

Glu Ser Gly Ala Ala Val His  Gly Arg Gln Gly Ile  Ile His Gly
    1970                1975                 1980

Gln Thr Gly Asp Thr Thr Arg  His Gly Gln Ser Gly  Gln Gly Gln
    1985                1990                 1995

Ser Thr Gln Arg Gly Ser Arg  Thr Thr Gly Arg Arg  Gly Ser Gly
    2000                2005                 2010

His Ser Glu Tyr Ser Asp Ser  Val Gly His Ser Gly  Val Ser His
    2015                2020                 2025

Thr His Ser Gly His Thr His  Gly Leu Ala Gly Ser  Gln His Gly
    2030                2035                 2040

Glu Ser Gly Ser Ser Gly His  Gly Arg Gln Gly Thr  Leu His Gly
    2045                2050                 2055

Gln Thr Gly Asp Thr Thr Arg  His Ala His Tyr Gly  His Gly Gln
    2060                2065                 2070

Ser Thr Gln Arg Gly Ser Arg  Thr Ala Gly Arg Arg  Gly Ser Gly
    2075                2080                 2085

His Ser Glu Tyr Ser Asp Ser  Glu Trp His Ser Gly  Gly Ser His
    2090                2095                 2100

Thr His Ser Gly His Thr His  Gly Gln Ala Gly Ser  Gln His Gly
    2105                2110                 2115

Glu Ser Gly Ser Ala Val His  Gly Arg Gln Gly Thr  Ile His Gly
    2120                2125                 2130

Gln Thr Gly Asp Thr Thr Arg  His Gly Gln Ser Gly  His Gly Gln
    2135                2140                 2145

Ser Thr Gln Ile Gly Pro His  Ser Ser Ser Ser Tyr  Asn Tyr His
    2150                2155                 2160
```

```
Ser Glu  Gly Thr Glu Arg Glu  Arg Gly Gln Ser  Gly Leu Val Trp
    2165             2170              2175

Arg His  Gly Ser Tyr Gly Ser  Ala Asp Tyr Asp  Tyr Gly Glu Ser
    2180             2185              2190

Arg Phe  Arg His Ser Gln His  Gly Ser Val Ser  Tyr Asn Ser Asn
    2195             2200              2205

Pro Val  Val Phe Lys Glu Arg  Ser Asp Ile Arg  Lys Ala Ser Ala
    2210             2215              2220

Phe Gly  Glu Asp His Pro Arg  Tyr Tyr Ala Arg  Tyr Val Asn Arg
    2225             2230              2235

Gln Pro  Gly Leu Tyr Arg His  Ser Ser Asp Ile  Ser Lys Gln Leu
    2240             2245              2250

Gly Phe  Ser Gln Ser Gln Arg  Tyr Tyr Tyr Tyr  Glu
    2255             2260              2265

<210> SEQ ID NO 25
<211> LENGTH: 12
<212> TYPE: PRT
<213> ORGANISM: Unknown
<220> FEATURE:
<223> OTHER INFORMATION: Description of Unknown:
      Human or Mouse filaggrin sequence

<400> SEQUENCE: 25

Ser Gly Ser Gln Ala Ser Asp Ser Glu Gly His Ser
1               5                   10

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (18)..(18)
<223> OTHER INFORMATION: Any amino acid

<400> SEQUENCE: 26

Gln Ser Gly Glu Xaa Ser Gly Arg Ser Xaa Ser Phe Leu Tyr Gln Val
1               5                   10                  15

Ser Xaa His Glu Gln Ser Glu Ser
            20

<210> SEQ ID NO 27
<211> LENGTH: 345
<212> TYPE: PRT
<213> ORGANISM: Homo sapiens

<400> SEQUENCE: 27

Gln Ser Gly Glu Ser Ser Gly Arg Ser Arg Ser Phe Leu Tyr Gln Val
1               5                   10                  15

Ser Ser His Glu Gln Ser Glu Ser Thr His Gly Gln Thr Ala Pro Ser
            20                  25                  30

Thr Gly Gly Arg Gln Gly Ser Arg His Glu Gln Ala Arg Asn Ser Ser
```

```
            35                  40                  45
Arg His Ser Ala Ser Gln Asp Gly Gln Asp Thr Ile Arg Gly His Pro
 50                  55                  60
Gly Ser Ser Arg Gly Gly Arg Gln Gly Ser Tyr His Glu Gln Ser Val
 65                  70                  75                  80
Asp Arg Ser Gly His Ser Gly Tyr His His Ser His Thr Thr Pro Gln
                 85                  90                  95
Gly Arg Ser Asp Ala Ser His Gly Gln Ser Gly Pro Arg Ser Ala Ser
                100                 105                 110
Arg Gln Thr Arg Asn Glu Glu Gln Ser Gly Asp Gly Ser Arg His Ser
                115                 120                 125
Gly Ser Arg His His Glu Pro Ser Thr Arg Ala Gly Ser Ser Arg His
            130                 135                 140
Ser Gln Val Gly Gln Gly Glu Ser Ala Gly Ser Lys Thr Ser Arg Arg
145                 150                 155                 160
Gln Gly Ser Ser Val Ser Gln Asp Arg Asp Ser Glu Gly His Ser Glu
                165                 170                 175
Asp Ser Glu Arg Arg Ser Glu Ser Ala Ser Arg Asn His Tyr Gly Ser
                180                 185                 190
Ala Arg Glu Gln Ser Arg His Gly Ser Arg Asn Pro Arg Ser His Gln
            195                 200                 205
Glu Asp Arg Ala Ser His Gly His Ser Ala Glu Ser Ser Arg Gln Ser
210                 215                 220
Gly Thr Arg His Ala Glu Thr Ser Ser Gly Gly Gln Ala Ala Ser Ser
225                 230                 235                 240
Gln Glu Gln Ala Arg Ser Ser Pro Gly Glu Arg His Gly Ser Arg His
                245                 250                 255
Gln Gln Ser Ala Asp Ser Ser Thr Asp Ser Gly Thr Gly Arg Arg Gln
            260                 265                 270
Asp Ser Ser Val Val Gly Asp Ser Gly Asn Arg Gly Ser Ser Gly Ser
275                 280                 285
Gln Ala Ser Asp Ser Glu Gly His Ser Glu Glu Ser Asp Thr Gln Ser
            290                 295                 300
Val Ser Ala His Gly Gln Ala Gly Pro His Gln Gln Ser His Gln Glu
305                 310                 315                 320
Ser Thr Arg Gly Gln Ser Gly Glu Arg Ser Gly Arg Ser Gly Ser Phe
                325                 330                 335
Leu Tyr Gln Val Ser Thr His Glu Gln
            340                 345

<210> SEQ ID NO 28
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Ser Gly Glu Ser Ser Gly Arg Ser Arg Ser Phe Leu Tyr Gln Val
1                   5                  10                  15
Ser Ser His Glu Gln Ser Glu Ser Thr His Gly Gln Thr Ala Pro Ser
                 20                  25                  30
Thr Gly Gly Arg Gln Gly Ser Arg His Glu Gln Ala Arg Asn Ser Ser
            35                  40                  45
```

-continued

```
Arg His Ser Ala Ser Gln Asp Gly Gln Asp Thr Ile Arg Gly His Pro
 50                  55                  60

Gly Ser Ser Arg Gly Gly Arg Gln Gly Ser Tyr His Glu Gln Ser Val
 65                  70                  75                  80

Asp Arg Ser Gly His Ser Gly Tyr His His Ser His Thr Thr Pro Gln
                 85                  90                  95

Gly Arg Ser Asp Ala Ser His Gly Gln Ser Gly Pro Arg Ser Ala Ser
                100                 105                 110

Arg Gln Thr Arg Asn Glu Glu Gln Ser Gly Asp Gly Ser Arg His Ser
            115                 120                 125

Gly Ser Arg His His Glu Pro Ser Thr Arg Ala Gly Ser Ser Arg His
130                 135                 140

Ser Gln Val Gly Gln Gly Glu Ser Ala Gly Ser Lys Thr Ser Arg Arg
145                 150                 155                 160

Gln Gly Ser Ser Val Ser Gln Asp Arg Asp Ser Glu Gly His Ser Glu
                165                 170                 175

Asp Ser Glu Arg Arg Ser Glu Ser Ala Ser Arg Asn His Tyr Gly Ser
            180                 185                 190

Ala Arg Glu Gln Ser Arg His Gly Ser Arg Asn Pro Arg Ser His Gln
            195                 200                 205

Glu Asp Arg Ala Ser His Gly His Ser Ala Glu Ser Ser Arg Gln Ser
210                 215                 220

Gly Thr Arg His Ala Glu Thr Ser Ser Gly Gly Gln Ala Ala Ser Ser
225                 230                 235                 240

Gln Glu Gln Ala Arg Ser Ser Pro Gly Glu Arg His Gly Ser Arg His
                245                 250                 255

Gln Gln Ser Ala Asp Ser Ser Thr Asp Ser Gly Thr Gly Arg Arg Gln
            260                 265                 270

Asp Ser Ser Val Val Gly Asp Ser Gly Asn Arg Gly Ser Ser Gly Ser
            275                 280                 285

Gln Ala Ser Asp Ser Glu Gly His Ser Glu Glu Ser Asp Thr Gln Ser
290                 295                 300

Val Ser Ala His Gly Gln Ala Gly Pro His Gln Gln Ser His Gln Glu
305                 310                 315                 320

Ser Thr Arg Gly Gln Ser Gly Glu Arg Ser Gly Arg Ser Gly Ser Phe
                325                 330                 335

Leu Tyr Gln Val Ser Thr His Glu Gln
            340                 345

<210> SEQ ID NO 29
<211> LENGTH: 7
<212> TYPE: PRT
<213> ORGANISM: Unknown
<220> FEATURE:
<223> OTHER INFORMATION: Description of Unknown:
      filaggrin sequence

<400> SEQUENCE: 29

Gln Ser Gly Glu Ser Ser Gly
1               5

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 30
gaagtgcggt tcaacaccct ccg                                              23

<210> SEQ ID NO 31
<211> LENGTH: 15
<212> TYPE: DNA
<213> ORGANISM: Unknown
<220> FEATURE:
<223> OTHER INFORMATION: Description of Unknown:
      operational taxonomic unit sequence

<400> SEQUENCE: 31
gatacagaga tgcat                                                       15

<210> SEQ ID NO 32
<211> LENGTH: 15
<212> TYPE: DNA
<213> ORGANISM: Unknown
<220> FEATURE:
<223> OTHER INFORMATION: Description of Unknown:
      operational taxonomic unit sequence

<400> SEQUENCE: 32
gatacagtga tgcat                                                       15

<210> SEQ ID NO 33
<211> LENGTH: 15
<212> TYPE: DNA
<213> ORGANISM: Unknown
<220> FEATURE:
<223> OTHER INFORMATION: Description of Unknown:
      operational taxonomic unit sequence

<400> SEQUENCE: 33
gatacagtag atgca                                                       15

<210> SEQ ID NO 34
<211> LENGTH: 15
<212> TYPE: DNA
<213> ORGANISM: Unknown
<220> FEATURE:
<223> OTHER INFORMATION: Description of Unknown:
      operational taxonomic unit sequence

<400> SEQUENCE: 34
taccagattt acata                                                       15

<210> SEQ ID NO 35
<211> LENGTH: 14
<212> TYPE: DNA
<213> ORGANISM: Unknown
<220> FEATURE:
<223> OTHER INFORMATION: Description of Unknown:
      operational taxonomic unit sequence

<400> SEQUENCE: 35
taccagatta cata                                                        14

<210> SEQ ID NO 36
<211> LENGTH: 14
<212> TYPE: DNA
<213> ORGANISM: Unknown
<220> FEATURE:
<223> OTHER INFORMATION: Description of Unknown:
      operational taxonomic unit sequence
```

```
<400> SEQUENCE: 36
caggtaggat aata                                                        14

<210> SEQ ID NO 37
<211> LENGTH: 15
<212> TYPE: DNA
<213> ORGANISM: Unknown
<220> FEATURE:
<223> OTHER INFORMATION: Description of Unknown:
      operational taxonomic unit sequence

<400> SEQUENCE: 37
caggtaggat aatta                                                       15

<210> SEQ ID NO 38
<211> LENGTH: 15
<212> TYPE: DNA
<213> ORGANISM: Unknown
<220> FEATURE:
<223> OTHER INFORMATION: Description of Unknown:
      operational taxonomic unit sequence

<400> SEQUENCE: 38
caggtaggat aaata                                                       15

<210> SEQ ID NO 39
<211> LENGTH: 13
<212> TYPE: DNA
<213> ORGANISM: Unknown
<220> FEATURE:
<223> OTHER INFORMATION: Description of Unknown:
      operational taxonomic unit sequence

<400> SEQUENCE: 39
caggtaggaa ata                                                         13

<210> SEQ ID NO 40
<211> LENGTH: 14
<212> TYPE: DNA
<213> ORGANISM: Unknown
<220> FEATURE:
<223> OTHER INFORMATION: Description of Unknown:
      operational taxonomic unit sequence

<400> SEQUENCE: 40
gattacagat taca                                                        14

<210> SEQ ID NO 41
<211> LENGTH: 15
<212> TYPE: DNA
<213> ORGANISM: Unknown
<220> FEATURE:
<223> OTHER INFORMATION: Description of Unknown:
      operational taxonomic unit sequence

<400> SEQUENCE: 41
gattacagat ttaca                                                       15

<210> SEQ ID NO 42
<211> LENGTH: 15
<212> TYPE: DNA
<213> ORGANISM: Unknown
<220> FEATURE:
<223> OTHER INFORMATION: Description of Unknown:
      operational taxonomic unit sequence

<400> SEQUENCE: 42
```
gattacagaa ttaca							15

<210> SEQ ID NO 43
<211> LENGTH: 328
<212> TYPE: PRT
<213> ORGANISM: Homo sapiens

<400> SEQUENCE: 43

Ser Leu Tyr Gln Val Ser Thr His Glu Gln Pro Asp Ser Ala His Gly
1               5                   10                  15

Arg Thr Gly Thr Ser Thr Gly Gly Arg Gln Gly Ser His His Glu Gln
            20                  25                  30

Ala Arg Asp Ser Ser Arg His Ser Ala Ser Gln Glu Gly Gln Asp Thr
        35                  40                  45

Ile Arg Gly His Pro Gly Ser Ser Arg Gly Gly Arg Gln Gly Ser His
    50                  55                  60

His Glu Gln Ser Val Asn Arg Ser Gly His Ser Gly Ser His His Ser
65                  70                  75                  80

His Thr Thr Ser Gln Gly Arg Ser Asp Ala Ser His Gly Gln Ser Gly
                85                  90                  95

Ser Arg Ser Ala Ser Arg Gln Thr Arg Asn Glu Glu Gln Ser Gly Asp
            100                 105                 110

Gly Thr Arg His Ser Gly Ser Arg His His Glu Ala Ser Ser Gln Ala
        115                 120                 125

Asp Ser Ser Arg His Ser Gln Val Gly Gln Gly Gln Ser Ser Gly Pro
    130                 135                 140

Arg Thr Ser Arg Asn Gln Gly Ser Ser Val Ser Gln Asp Ser Asp Ser
145                 150                 155                 160

Gln Gly His Ser Glu Asp Ser Glu Arg Trp Ser Gly Ser Ala Ser Arg
                165                 170                 175

Asn His His Gly Ser Ala Gln Glu Gln Ser Arg Asp Gly Ser Arg His
            180                 185                 190

Pro Arg Ser His His Glu Asp Arg Ala Gly His Gly His Ser Ala Asp
        195                 200                 205

Ser Ser Arg Lys Ser Gly Thr Arg His Thr Gln Asn Ser Ser Ser Gly
    210                 215                 220

Gln Ala Ala Ser Ser His Glu Gln Ala Arg Ser Ser Ala Gly Glu Arg
225                 230                 235                 240

His Gly Ser Arg His Gln Leu Gln Ser Ala Asp Ser Ser Arg His Ser
                245                 250                 255

Gly Thr Gly His Gly Gln Ala Ser Ser Ala Val Arg Asp Ser Gly His
            260                 265                 270

Arg Gly Ser Ser Gly Ser Gln Ala Thr Asp Ser Glu Gly His Ser Glu
        275                 280                 285

Asp Ser Asp Thr Gln Ser Val Ser Gly His Gly Gln Ala Gly His His
    290                 295                 300

Gln Gln Ser His Gln Glu Ser Ala Arg Asp Arg Ser Gly Glu Arg Ser
305                 310                 315                 320

Arg Arg Ser Gly Ser Phe Leu Tyr
                325

<210> SEQ ID NO 44
<211> LENGTH: 327
<212> TYPE: PRT
<213> ORGANISM: Homo sapiens

<400> SEQUENCE: 44

```
Phe Leu Tyr Gln Val Ser Thr His Lys Gln Ser Glu Ser Ser His Gly
1               5                   10                  15

Trp Thr Gly Pro Ser Thr Gly Val Arg Gln Gly Ser His His Glu Gln
            20                  25                  30

Ala Arg Asp Asn Ser Arg His Ser Ala Ser Gln Asp Gly Gln Asp Thr
        35                  40                  45

Ile Arg Gly His Pro Gly Ser Ser Arg Gly Arg Gln Gly Ser His
    50                  55                  60

His Glu Gln Ser Val Asp Arg Ser Gly His Ser Gly Ser His His Ser
65                  70                  75                  80

His Thr Thr Ser Gln Gly Arg Ser Asp Ala Ser Arg Gly Gln Ser Gly
                85                  90                  95

Ser Arg Ser Ala Ser Arg Thr Thr Arg Asn Glu Gln Ser Arg Asp
            100                 105                 110

Gly Ser Arg His Ser Gly Ser Arg His His Glu Ala Ser Ser His Ala
            115                 120                 125

Asp Ile Ser Arg His Ser Gln Ala Gly Gln Gly Gln Ser Glu Gly Ser
    130                 135                 140

Arg Thr Ser Arg Arg Gln Gly Ser Ser Val Ser Gln Asp Ser Asp Ser
145                 150                 155                 160

Glu Gly His Ser Glu Asp Ser Glu Arg Trp Ser Gly Ser Ala Ser Arg
                165                 170                 175

Asn His Arg Gly Ser Ala Gln Glu Gln Ser Arg His Gly Ser Arg His
            180                 185                 190

Pro Arg Ser His His Glu Asp Arg Ala Gly His Gly His Ser Ala Asp
        195                 200                 205

Ser Ser Arg Gln Ser Gly Thr Pro His Ala Glu Thr Ser Ser Gly Gly
    210                 215                 220

Gln Ala Ala Ser Ser His Glu Gln Ala Arg Ser Ser Pro Gly Glu Arg
225                 230                 235                 240

His Gly Ser Arg His Gln Gln Ser Ala Asp Ser Ser Arg His Ser Gly
                245                 250                 255

Ile Pro Arg Arg Gln Ala Ser Ser Ala Val Arg Asp Ser Gly His Trp
            260                 265                 270

Gly Ser Ser Gly Ser Gln Ala Ser Asp Ser Glu Gly His Ser Glu Glu
        275                 280                 285

Ser Asp Thr Gln Ser Val Ser Gly His Gly Gln Asp Gly Pro His Gln
    290                 295                 300

Gln Ser His Gln Glu Ser Ala Arg Asp Trp Ser Gly Arg Ser Gly
305                 310                 315                 320

Arg Ser Gly Ser Phe Ile Tyr
                325
```

<210> SEQ ID NO 45
<211> LENGTH: 327
<212> TYPE: PRT
<213> ORGANISM: Homo sapiens

<400> SEQUENCE: 45

```
Phe Ile Tyr Gln Val Ser Thr His Glu Gln Ser Glu Ser Ala His Gly
1               5                   10                  15

Arg Thr Arg Thr Ser Thr Gly Arg Arg Gln Gly Ser His His Glu Gln
            20                  25                  30
```

-continued

```
Ala Arg Asp Ser Ser Arg His Ser Ala Ser Gln Glu Gly Gln Asp Thr
        35                  40                  45

Ile Arg Ala His Pro Gly Ser Arg Gly Gly Arg Gln Gly Ser His
 50                  55                  60

His Glu Gln Ser Val Asp Arg Ser Gly His Ser Gly Ser His His Ser
 65                  70                  75                  80

His Thr Thr Ser Gln Gly Arg Ser Asp Ala Ser His Gly Gln Ser Gly
                85                  90                  95

Ser Arg Ser Ala Ser Arg Gln Thr Arg Lys Asp Lys Gln Ser Gly Asp
            100                 105                 110

Gly Ser Arg His Ser Gly Ser Arg His His Glu Ala Ala Ser Trp Ala
            115                 120                 125

Asp Ser Ser Arg His Ser Gln Val Gly Gln Glu Gln Ser Ser Gly Ser
        130                 135                 140

Arg Thr Ser Arg His Gln Gly Ser Ser Val Ser Gln Asp Ser Asp Ser
145                 150                 155                 160

Glu Arg His Ser Asp Asp Ser Glu Arg Leu Ser Gly Ser Ala Ser Arg
                165                 170                 175

Asn His His Gly Ser Ser Arg Glu Gln Ser Arg Asp Gly Ser Arg His
            180                 185                 190

Pro Gly Phe His Gln Glu Asp Arg Ala Ser His Gly His Ser Ala Asp
        195                 200                 205

Ser Ser Arg Gln Ser Gly Thr His His Thr Glu Ser Ser His Gly
    210                 215                 220

Gln Ala Val Ser Ser His Glu Gln Ala Arg Ser Ser Pro Gly Glu Arg
225                 230                 235                 240

His Gly Ser Arg His Gln Gln Ser Ala Asp Ser Ser Arg His Ser Gly
                245                 250                 255

Ile Gly His Arg Gln Ala Ser Ser Ala Val Arg Asp Ser Gly His Arg
            260                 265                 270

Gly Ser Ser Gly Ser Gln Val Thr Asn Ser Glu Gly His Ser Glu Asp
        275                 280                 285

Ser Asp Thr Gln Ser Val Ser Ala His Gly Ala Gly Pro His Gln
    290                 295                 300

Gln Ser His Lys Glu Ser Ala Arg Gly Gln Ser Gly Glu Ser Ser Gly
305                 310                 315                 320

Arg Ser Arg Ser Phe Leu Tyr
                325

<210> SEQ ID NO 46
<211> LENGTH: 327
<212> TYPE: PRT
<213> ORGANISM: Homo sapiens

<400> SEQUENCE: 46

Phe Leu Tyr Gln Val Ser Ser His Glu Gln Ser Glu Ser Thr His Gly
 1               5                  10                  15

Gln Thr Ala Pro Ser Thr Gly Gly Arg Gln Gly Ser Arg His Glu Gln
                20                  25                  30

Ala Arg Asn Ser Ser Arg His Ser Ala Ser Gln Asp Gly Gln Asp Thr
            35                  40                  45

Ile Arg Gly His Pro Gly Ser Ser Arg Gly Gly Arg Gln Gly Ser Tyr
        50                  55                  60

His Glu Gln Ser Val Asp Arg Ser Gly His Ser Gly Tyr His His Ser
```

```
                65                  70                  75                  80
        His Thr Thr Pro Gln Gly Arg Ser Asp Ala Ser His Gly Gln Ser Gly
                            85                  90                  95
        Pro Arg Ser Ala Ser Arg Gln Thr Arg Asn Glu Glu Gln Ser Gly Asp
                        100                 105                 110
        Gly Ser Arg His Ser Gly Ser Arg His His Glu Pro Ser Thr Arg Ala
                        115                 120                 125
        Gly Ser Ser Arg His Ser Gln Val Gly Gln Gly Glu Ser Ala Gly Ser
                    130                 135                 140
        Lys Thr Ser Arg Arg Gln Gly Ser Ser Val Ser Gln Asp Arg Asp Ser
        145                 150                 155                 160
        Glu Gly His Ser Glu Asp Ser Glu Arg Arg Ser Glu Ser Ala Ser Arg
                            165                 170                 175
        Asn His Tyr Gly Ser Ala Arg Glu Gln Ser Arg His Gly Ser Arg Asn
                        180                 185                 190
        Pro Arg Ser His Gln Glu Asp Arg Ala Ser His Gly His Ser Ala Glu
                        195                 200                 205
        Ser Ser Arg Gln Ser Gly Thr Arg His Ala Glu Thr Ser Ser Gly Gly
                    210                 215                 220
        Gln Ala Ala Ser Ser Gln Glu Gln Ala Arg Ser Ser Pro Gly Glu Arg
        225                 230                 235                 240
        His Gly Ser Arg His Gln Gln Ser Ala Asp Ser Ser Thr Asp Ser Gly
                            245                 250                 255
        Thr Gly Arg Arg Gln Asp Ser Ser Val Val Gly Asp Ser Gly Asn Arg
                        260                 265                 270
        Gly Ser Ser Gly Ser Gln Ala Ser Asp Ser Glu Gly His Ser Glu Glu
                    275                 280                 285
        Ser Asp Thr Gln Ser Val Ser Ala His Gly Gln Ala Gly Pro His Gln
                290                 295                 300
        Gln Ser His Gln Glu Ser Thr Arg Gly Gln Ser Gly Glu Arg Ser Gly
        305                 310                 315                 320
        Arg Ser Gly Ser Phe Leu Tyr
                        325

<210> SEQ ID NO 47
<211> LENGTH: 328
<212> TYPE: PRT
<213> ORGANISM: Homo sapiens

<400> SEQUENCE: 47

Phe Leu Tyr Gln Val Ser Thr His Glu Gln Ser Glu Ser Ala His Gly
        1               5                   10                  15
        Arg Thr Gly Pro Ser Thr Gly Gly Arg Gln Arg Ser Arg His Glu Gln
                        20                  25                  30
        Ala Arg Asp Ser Ser Arg His Ser Ala Ser Gln Glu Gly Gln Asp Thr
                    35                  40                  45
        Ile Arg Gly His Pro Gly Ser Ser Arg Gly Gly Arg Gln Gly Ser His
                50                  55                  60
        Tyr Glu Gln Ser Val Asp Ser Ser Gly His Ser Gly Ser His His Ser
        65                  70                  75                  80
        His Thr Thr Ser Gln Glu Arg Ser Asp Val Ser Arg Gly Gln Ser Gly
                            85                  90                  95
        Ser Arg Ser Val Ser Arg Gln Thr Arg Asn Glu Lys Gln Ser Gly Asp
                        100                 105                 110
```

```
Gly Ser Arg His Ser Gly Arg His His Glu Ala Ser Ser Arg Ala
            115                 120                 125

Asp Ser Ser Arg His Ser Gln Val Gly Gln Gly Ser Ser Gly Pro
130                 135                 140

Arg Thr Ser Arg Asn Gln Gly Ser Ser Val Ser Gln Asp Ser Asp Ser
145                 150                 155                 160

Gln Gly His Ser Glu Asp Ser Glu Arg Trp Ser Gly Ser Ala Ser Arg
                    165                 170                 175

Asn His Leu Gly Ser Ala Trp Glu Gln Ser Arg Asp Gly Ser Arg His
            180                 185                 190

Pro Gly Ser His His Glu Asp Arg Ala Gly His Gly His Ser Ala Asp
            195                 200                 205

Ser Ser Arg Gln Ser Gly Thr Arg His Thr Glu Ser Ser Ser Arg Gly
210                 215                 220

Gln Ala Ala Ser Ser His Glu Gln Ala Arg Ser Ser Ala Gly Glu Arg
225                 230                 235                 240

His Gly Ser His His Gln Leu Gln Ser Ala Asp Ser Ser Arg His Ser
                    245                 250                 255

Gly Ile Gly His Gly Gln Ala Ser Ser Ala Val Arg Asp Ser Gly His
            260                 265                 270

Arg Gly Tyr Ser Gly Ser Gln Ala Ser Asp Ser Glu Gly His Ser Glu
            275                 280                 285

Asp Ser Asp Thr Gln Ser Val Ser Ala Gln Gly Lys Ala Gly Pro His
            290                 295                 300

Gln Gln Ser His Lys Glu Ser Ala Arg Gly Gln Ser Gly Glu Ser Ser
305                 310                 315                 320

Gly Arg Ser Gly Ser Phe Leu Tyr
                325

<210> SEQ ID NO 48
<211> LENGTH: 327
<212> TYPE: PRT
<213> ORGANISM: Homo sapiens

<400> SEQUENCE: 48

Phe Leu Tyr Gln Val Ser Thr His Glu Gln Ser Glu Ser Thr His Gly
1               5                   10                  15

Gln Ser Ala Pro Ser Thr Gly Gly Arg Gln Gly Ser His Tyr Asp Gln
            20                  25                  30

Ala Gln Asp Ser Ser Arg His Ser Ala Ser Gln Glu Gly Gln Asp Thr
            35                  40                  45

Ile Arg Gly His Pro Gly Pro Ser Arg Gly Gly Arg Gln Gly Ser His
50                  55                  60

Gln Glu Gln Ser Val Asp Arg Ser Gly His Ser Gly His His Ser
65                  70                  75                  80

His Thr Thr Ser Gln Gly Arg Ser Asp Ala Ser Arg Gly Gln Ser Gly
                85                  90                  95

Ser Arg Ser Ala Ser Arg Lys Thr Tyr Asp Lys Glu Gln Ser Gly Asp
            100                 105                 110

Gly Ser Arg His Ser Gly Ser His His Glu Ala Ser Ser Trp Ala
            115                 120                 125

Asp Ser Ser Arg His Ser Leu Val Gly Gln Gly Gln Ser Ser Gly Pro
130                 135                 140

Arg Thr Ser Arg Pro Arg Gly Ser Ser Val Ser Gln Asp Ser Asp Ser
145                 150                 155                 160
```

Glu Gly His Ser Glu Asp Ser Glu Arg Arg Ser Gly Ser Ala Ser Arg
                165                 170                 175

Asn His His Gly Ser Ala Gln Glu Gln Ser Arg Asp Gly Ser Arg His
            180                 185                 190

Pro Arg Ser His His Glu Asp Arg Ala Gly His Gly His Ser Ala Glu
            195                 200                 205

Ser Ser Arg Gln Ser Gly Thr His His Ala Glu Asn Ser Ser Gly Gly
            210                 215                 220

Gln Ala Ala Ser Ser His Glu Gln Ala Arg Ser Ser Ala Gly Glu Arg
225                 230                 235                 240

His Gly Ser His His Gln Gln Ser Ala Asp Ser Ser Arg His Ser Gly
            245                 250                 255

Ile Gly His Gly Gln Ala Ser Ser Ala Val Arg Asp Ser Gly His Arg
            260                 265                 270

Gly Ser Ser Gly Ser Gln Ala Ser Asp Ser Glu Gly His Ser Glu Asp
            275                 280                 285

Ser Asp Thr Gln Ser Val Ser Ala His Gly Gln Ala Gly Pro His Gln
            290                 295                 300

Gln Ser His Gln Glu Ser Thr Arg Gly Arg Ser Ala Gly Arg Ser Gly
305                 310                 315                 320

Arg Ser Gly Ser Phe Leu Tyr
            325

<210> SEQ ID NO 49
<211> LENGTH: 327
<212> TYPE: PRT
<213> ORGANISM: Homo sapiens

<400> SEQUENCE: 49

Phe Leu Tyr Gln Val Ser Thr His Glu Gln Ser Glu Ser Ala His Gly
1               5                   10                  15

Arg Thr Gly Thr Ser Thr Gly Gly Arg Gln Gly Ser His His Lys Gln
            20                  25                  30

Ala Arg Asp Ser Ser Arg His Ser Thr Ser Gln Glu Gly Gln Asp Thr
            35                  40                  45

Ile His Gly His Pro Gly Ser Ser Ser Gly Gly Arg Gln Gly Ser His
        50                  55                  60

Tyr Glu Gln Leu Val Asp Arg Ser Gly His Ser Gly Ser His His Ser
65                  70                  75                  80

His Thr Thr Ser Gln Gly Arg Ser Asp Ala Ser His Gly His Ser Gly
            85                  90                  95

Ser Arg Ser Ala Ser Arg Gln Thr Arg Asn Asp Glu Gln Ser Gly Asp
            100                 105                 110

Gly Ser Arg His Ser Gly Ser Arg His His Glu Ala Ser Ser Arg Ala
            115                 120                 125

Asp Ser Ser Gly His Ser Gln Val Gly Gln Gly Gln Ser Glu Gly Pro
            130                 135                 140

Arg Thr Ser Arg Asn Trp Gly Ser Ser Phe Ser Gln Asp Ser Asp Ser
145                 150                 155                 160

Gln Gly His Ser Glu Asp Ser Glu Arg Trp Ser Gly Ser Ala Ser Arg
            165                 170                 175

Asn His His Gly Ser Ala Gln Glu Gln Leu Arg Asp Gly Ser Arg His
            180                 185                 190

Pro Arg Ser His Gln Glu Asp Arg Ala Gly His Gly His Ser Ala Asp

```
        195                 200                 205
Ser Ser Arg Gln Ser Gly Thr Arg His Thr Gln Thr Ser Ser Gly Gly
210                 215                 220

Gln Ala Ala Ser Ser His Glu Gln Ala Arg Ser Ser Ala Gly Glu Arg
225                 230                 235                 240

His Gly Ser His His Gln Gln Ser Ala Asp Ser Ser Arg His Ser Gly
                245                 250                 255

Ile Gly His Gly Gln Ala Ser Ser Ala Val Arg Asp Ser Gly His Arg
            260                 265                 270

Gly Tyr Ser Gly Ser Gln Ala Ser Asp Asn Glu Gly His Ser Glu Asp
        275                 280                 285

Ser Asp Thr Gln Ser Val Ser Ala His Gly Gln Ala Gly Ser His Gln
290                 295                 300

Gln Ser His Gln Glu Ser Ala Arg Gly Arg Ser Gly Glu Thr Ser Gly
305                 310                 315                 320

His Ser Gly Ser Phe Leu Tyr
                325
```

<210> SEQ ID NO 50
<211> LENGTH: 327
<212> TYPE: PRT
<213> ORGANISM: Homo sapiens

<400> SEQUENCE: 50

```
Phe Leu Tyr Gln Val Ser Thr His Glu Gln Ser Glu Ser Ser His Gly
1               5                   10                  15

Trp Thr Gly Pro Ser Thr Arg Gly Arg Gln Gly Ser Arg His Glu Gln
            20                  25                  30

Ala Gln Asp Ser Ser Arg His Ser Ala Ser Gln Asp Gly Gln Asp Thr
        35                  40                  45

Ile Arg Gly His Pro Gly Ser Ser Arg Gly Arg Gln Gly Tyr His
    50                  55                  60

His Glu His Ser Val Asp Ser Ser Gly His Ser Gly Ser His His Ser
65                  70                  75                  80

His Thr Thr Ser Gln Gly Arg Ser Asp Ala Ser Arg Gly Gln Ser Gly
                85                  90                  95

Ser Arg Ser Ala Ser Arg Thr Thr Arg Asn Glu Glu Gln Ser Gly Asp
            100                 105                 110

Gly Ser Arg His Ser Gly Ser Arg His His Glu Ala Ser Thr His Ala
        115                 120                 125

Asp Ile Ser Arg His Ser Gln Ala Val Gln Gly Gln Ser Glu Gly Ser
    130                 135                 140

Arg Arg Ser Arg Arg Gln Gly Ser Ser Val Ser Gln Asp Ser Asp Ser
145                 150                 155                 160

Glu Gly His Ser Glu Asp Ser Glu Arg Trp Ser Gly Ser Ala Ser Arg
                165                 170                 175

Asn His His Gly Ser Ala Gln Glu Gln Leu Arg Asp Gly Ser Arg His
            180                 185                 190

Pro Arg Ser His Gln Glu Asp Arg Ala Gly His Gly His Ser Ala Asp
        195                 200                 205

Ser Ser Arg Gln Ser Gly Thr Arg His Thr Gln Thr Ser Ser Gly Gly
    210                 215                 220

Gln Ala Ala Ser Ser His Glu Gln Ala Arg Ser Ser Ala Gly Glu Arg
225                 230                 235                 240
```

His Gly Ser His His Gln Gln Ser Ala Asp Ser Ser Arg His Ser Gly
             245                 250                 255

Ile Gly His Gly Gln Ala Ser Ser Ala Val Arg Asp Ser Gly His Arg
        260                 265                 270

Gly Tyr Ser Gly Ser Gln Ala Ser Asp Asn Glu Gly His Ser Glu Asp
            275                 280                 285

Ser Asp Thr Gln Ser Val Ser Ala His Gly Gln Ala Gly Ser His Gln
        290                 295                 300

Gln Ser His Gln Glu Ser Ala Arg Gly Arg Ser Gly Glu Thr Ser Gly
305                 310                 315                 320

His Ser Gly Ser Phe Leu Tyr
            325

<210> SEQ ID NO 51
<211> LENGTH: 327
<212> TYPE: PRT
<213> ORGANISM: Homo sapiens

<400> SEQUENCE: 51

Phe Leu Tyr Gln Val Ser Thr His Glu Gln Ser Glu Ser Ser His Gly
1               5                   10                  15

Trp Thr Gly Pro Ser Thr Arg Gly Arg Gln Gly Ser Arg His Glu Gln
            20                  25                  30

Ala Gln Asp Ser Ser Arg His Ser Ala Ser Gln Tyr Gly Gln Asp Thr
        35                  40                  45

Ile Arg Gly His Pro Gly Ser Ser Arg Gly Gly Arg Gln Gly Tyr His
    50                  55                  60

His Glu His Ser Val Asp Ser Ser Gly His Ser Gly Ser His His Ser
65                  70                  75                  80

His Thr Thr Ser Gln Gly Arg Ser Asp Ala Ser Arg Gly Gln Ser Gly
                85                  90                  95

Ser Arg Ser Ala Ser Arg Thr Thr Arg Asn Glu Glu Gln Ser Gly Asp
            100                 105                 110

Ser Ser Arg His Ser Val Ser Arg His His Glu Ala Ser Thr His Ala
        115                 120                 125

Asp Ile Ser Arg His Ser Gln Ala Val Gln Gly Gln Ser Glu Gly Ser
    130                 135                 140

Arg Arg Ser Arg Arg Gln Gly Ser Ser Val Ser Gln Asp Ser Asp Ser
145                 150                 155                 160

Glu Gly His Ser Glu Asp Ser Glu Arg Trp Ser Gly Ser Ala Ser Arg
                165                 170                 175

Asn His Arg Gly Ser Val Gln Glu Gln Ser Arg His Gly Ser Arg His
            180                 185                 190

Pro Arg Ser His His Glu Asp Arg Ala Gly His Gly His Ser Ala Asp
        195                 200                 205

Arg Ser Arg Gln Ser Gly Thr Arg His Ala Glu Thr Ser Ser Gly Gly
    210                 215                 220

Gln Ala Ala Ser Ser His Glu Gln Ala Arg Ser Ser Pro Gly Glu Arg
225                 230                 235                 240

His Gly Ser Arg His Gln Gln Ser Ala Asp Ser Ser Arg His Ser Gly
                245                 250                 255

Ile Pro Arg Gly Gln Ala Ser Ser Ala Val Arg Asp Ser Arg His Trp
            260                 265                 270

Gly Ser Ser Gly Ser Gln Ala Ser Asp Ser Glu Gly His Ser Glu Glu
        275                 280                 285

```
Ser Asp Thr Gln Ser Val Ser Gly His Gly Gln Ala Gly Pro His Gln
        290                 295                 300

Gln Ser His Gln Glu Ser Ala Arg Asp Arg Ser Gly Gly Arg Ser Gly
305                 310                 315                 320

Arg Ser Gly Ser Phe Leu Tyr
                325

<210> SEQ ID NO 52
<211> LENGTH: 327
<212> TYPE: PRT
<213> ORGANISM: Homo sapiens

<400> SEQUENCE: 52

Phe Leu Tyr Gln Val Ser Thr His Glu Gln Ser Glu Ser Ala His Gly
1               5                   10                  15

Arg Thr Arg Thr Ser Thr Gly Arg Arg Gln Gly Ser His His Glu Gln
            20                  25                  30

Ala Arg Asp Ser Ser Arg His Ser Ala Ser Gln Glu Gly Gln Asp Thr
        35                  40                  45

Ile Arg Gly His Pro Gly Ser Ser Arg Arg Gly Arg Gln Gly Ser His
    50                  55                  60

Tyr Glu Gln Ser Val Asp Arg Ser Gly His Ser Gly His His Ser
65                  70                  75                  80

His Thr Thr Ser Gln Gly Arg Ser Asp Ala Ser Arg Gly Gln Ser Gly
                85                  90                  95

Ser Arg Ser Ala Ser Arg Gln Thr Arg Asn Asp Glu Ser Gly Asp
            100                 105                 110

Gly Ser Arg His Ser Trp Ser His His His Glu Ala Ser Thr Gln Ala
        115                 120                 125

Asp Ser Ser Arg His Ser Gln Ser Gly Gln Gly Gln Ser Ala Gly Pro
    130                 135                 140

Arg Thr Ser Arg Asn Gln Gly Ser Ser Val Ser Gln Asp Ser Asp Ser
145                 150                 155                 160

Gln Gly His Ser Glu Asp Ser Glu Arg Trp Ser Gly Ser Ala Ser Arg
                165                 170                 175

Asn His Arg Gly Ser Ala Gln Glu Gln Ser Arg Asp Gly Ser Arg His
            180                 185                 190

Pro Thr Ser His His Glu Asp Arg Ala Gly His Gly His Ser Ala Glu
        195                 200                 205

Ser Ser Arg Gln Ser Gly Thr His His Ala Glu Asn Ser Ser Gly Gly
    210                 215                 220

Gln Ala Ala Ser Ser His Glu Gln Ala Arg Ser Ser Ala Gly Glu Arg
225                 230                 235                 240

His Gly Ser His His Gln Gln Ser Ala Asp Ser Ser Arg His Ser Gly
                245                 250                 255

Ile Gly His Gly Gln Ala Ser Ser Ala Val Arg Asp Ser Gly His Arg
            260                 265                 270

Gly Ser Ser Gly Ser Gln Ala Ser Asp Ser Glu Gly His Ser Glu Asp
        275                 280                 285

Ser Asp Thr Gln Ser Val Ser Ala His Gly Gln Ala Gly Pro His Gln
    290                 295                 300
```

-continued

```
Gln Ser His Gln Glu Ser Thr Arg Gly Arg Ser Ala Gly Arg Ser Gly
305                 310                 315                 320
Arg Ser Gly Ser Phe Leu Tyr
                325
```